(12) United States Patent
Nakajima

(10) Patent No.: US 7,888,058 B2
(45) Date of Patent: *Feb. 15, 2011

(54) TRANSFORMED CELL WITH ENHANCED SENSITIVITY TO ANTIFUNGAL COMPOUND AND USE THEREOF

(75) Inventor: Hiroki Nakajima, Hyogo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/794,105

(22) Filed: Jun. 4, 2010

(65) Prior Publication Data

US 2010/0291607 A1 Nov. 18, 2010

Related U.S. Application Data

(62) Division of application No. 12/272,705, filed on Nov. 17, 2008, now Pat. No. 7,759,084, which is a division of application No. 10/697,036, filed on Oct. 31, 2003, now Pat. No. 7,452,688.

(30) Foreign Application Priority Data

Oct. 31, 2002 (JP) ............................. 2002-317736

(51) Int. Cl.
*C12Q 1/48* (2006.01)
*C12N 1/20* (2006.01)
*C12N 9/20* (2006.01)
*C07H 21/04* (2006.01)

(52) U.S. Cl. .................. 435/15; 435/252.3; 435/194; 536/23.2

(58) Field of Classification Search ............... 435/194, 435/252.3, 15; 536/23.2
See application file for complete search history.

(56) References Cited

U.S. PATENT DOCUMENTS

5,939,306 A 8/1999 Alex et al.

FOREIGN PATENT DOCUMENTS

WO WO 98/44148 10/1998

OTHER PUBLICATIONS

Alex, Lisa et al., "Hyphal development in *Neurospora crassa*: Involvement of a two-component histidine kinase" Proc. Natl. Acd. Sci. USA (1996) 93:3416-3421.
Schumacher, Marc, etal., The Osmotic-1 Locus of *Neurospora crassa* Encodes a Putative Histidine Kinase Similar to Osmosensors of Bacteria and Yeast, Current Microbiology (1997) 34:340-347.
Oshima, Michiyo et al., "A Point Mutation in the Two-Component Histidine Kinase *BcOS-1* Gene Confers Dicarboximide Resistance in Field Isolates of *Botrytis cinerea*" Phytopathology (2002) 92:75-80.
Fujimura, Makoto et al, "Sensitivity to Phenylpyrrole Fungicides and Abnormal Glycerol Accumulation in *Os* and *Cut* Mutant Strains of *Neuropora crassa*" J. Pesticide Sci (2000) 25:31-36.
Fujimura, Makoto et al., "Fungicide Resistance and Osmotic Stress Sensitivity in *os* Mutants of *Neurospora crassa*"Pesticide Biochem. Physiol. (2000) 67:125-133.
Maeda, Tatsuya et al, A two-component system that regulates an osmosensing MAP kinase cascade in yeast, Nature (1994) 369:242-245.
Aoyama, Keisuke et al., "Genetic Analysis of the His-to-Asp Phosphorelay Implicated in Mitotic Cell Cycle Control: Involvement of Histidine-Kinase Genes of *Schizosaccharomyces pombe*" Biosci. Biotechnol. Biochem. (2001) 65:2347-2352.
Yamada, Hisami et al., "The Arabidopsis AHK4 Histidine Kinase is a Cytokinin-Binding Receptor that Transduces Cytokinin Signals Across the Membrane," Plant Cell Physiol. (2001) 42:107-113.
Freeman, Jeremy et al., A genetic analysis of the functions of LuxN: a two-component hybrid sensor kinase that regulates quorum sensing in *Vibrio harveyi* Mol. Microbiol. (2000) 35:139-149.
Inoue, Tsutomu et al., Identification of CRE1 as a cytokinin receptor from *Arabidopsis* Nature (2001) 409:1060-1063.
Srikantha, Thyagarajan et al, "The two-component hybrid kinase regulator *CaNIK1* of *Candida albicans*, "Microbiology (1998) 144:2715-2729.
Nagahashi, Shigehisa et al, "Isolation of *CaSLNI* and *CaNIK1*, the genes for osmosensing histidine kinase homologues, from the pathogenic fungus *Candida albicans*, "Microbiology (1998) 144:425-432.
Ochiai, Noriyuki et al., Characterization of mutation in the two-component histidine kinase gene that confer fludioxonil resistance and osmotic sensitivity in the *os-1* mutants of *Neurospora crassa*, Pest Management Sci., (2001) 57:437-442.
Miller, Tamara et al, Molecular Dissection of Alleles of the *osmotic-1* Locus of *Neurospora crassa*, Fungi Gen. Biol. (2002) 35:147-155.
GenBank Accession U50263.
GenBank Accession U53189.
GenBank Accession AAB03698.
GenBank Accession AAB01979.
GenBank Accession AF396827.
GenBank Accession AF435964.
GenBank Accession AAL37947.
GenBank Accession AAL30826.
GenBank Accession AB041647.
GenBank Accession BAB40947.

(Continued)

*Primary Examiner*—Maryam Monshipouri
(74) *Attorney, Agent, or Firm*—Sughrue Mion, PLLC

(57) ABSTRACT

The present invention provides a transformed cell in which a polynucleotide having a nucleotide sequence encoding an amino acid sequence of an osmosensing histidine kinase having no transmembrane region is introduced in a functional form into a cell deficient in at least one hybrid-sensor kinase, a method of assaying the antifungal activity of a test substance using the transformed cell, and a method of searching an antifungal compound using the method, and the like.

13 Claims, No Drawings

OTHER PUBLICATIONS

Cui, Wei et al, An osmosensing histidine kinase mediates dicarboximide fungicide resistance in *Botryotinia fuckeliana* (*Botrytic cinerea*), Fung. Gen. Biol (2002) 36:187-198.

Zhang, Yan et al, Osmoregulation and Fungicide Resistance: the *Neurospora crassa os-2* Gene Encodes a *HOG1* Mitogen-Activated Protein Kinase Homologue, Appl. Environ. Microbial (2002 68:532-538 in.

Urao, Takeshi et al, "A Transmembrane Hybrid-Type Histidine Kinase in Arabidopsis Functions as an Osmosensor," The Plant Cell, (1999) 11:1743:1754.

Gen Ban Accession U61838.

GenBank Accession U59310.

Song, Hyun Kyu, Insights into Eukaryotic Multistep Phosphorelay Signal Transduction Revealed by the Crystal Structure of Ypd1p from *Saccharomyces cerevisiae*, J. Mol. Biol. (1999) 293, 753-761.

```
                        SEQUENCE LISTING

<160> NUMBER OF SEQ ID NOS: 90

<210> SEQ ID NO 1
<211> LENGTH: 1315
<212> TYPE: PRT
<213> ORGANISM: Botryotinia fuckeliana

<400> SEQUENCE: 1

Met Glu Asp Ser Thr Ile Ala His Thr Thr Ala Ile Leu Gln Thr Leu
  1               5                  10                  15

Ala Leu Ser Ser Ile Asp Leu Pro Leu Thr Asn Val Tyr Gly Asn Lys
                 20                  25                  30

Gly Ile Arg Leu Pro Gly Ala Asp Thr Ala Glu Lys Leu Ala Leu Glu
             35                  40                  45

Arg Glu Leu Ala Ala Leu Val Ser Arg Val Gln Arg Leu Glu Ala Arg
         50                  55                  60

Ala Ile Thr Val Asn Asn Gln Thr Leu Pro Asp Thr Pro Asn Glu Leu
 65                  70                  75                  80

Gly Ala Pro Ser Ala Phe Ala Asp Val Leu Thr Gly Ala Pro Ser Arg
                 85                  90                  95

Ala Ser Lys Ser Thr Thr Ser Arg Gln Gln Leu Val Asn Ser Leu Leu
            100                 105                 110

Ala Ala Arg Glu Ala Pro Thr Gly Gly Glu Arg Pro Pro Lys Phe Thr
        115                 120                 125

Lys Leu Ser Asp Glu Glu Leu Glu Ala Leu Arg Glu His Val Asp His
    130                 135                 140

Gln Ser Lys Gln Leu Asp Ser Gln Lys Ser Glu Leu Ala Gly Val His
145                 150                 155                 160

Ala Gln Leu Phe Glu Gln Lys Gln Arg Gln Glu Gln Ala Leu Asn Val
                165                 170                 175

Leu Glu Val Glu Arg Val Ala Ala Leu Glu Arg Glu Leu Lys Lys His
            180                 185                 190

Gln Gln Ala Asn Glu Ala Phe Gln Lys Ala Leu Arg Glu Ile Gly Glu
        195                 200                 205

Ile Val Thr Ala Val Ala Arg Gly Asp Leu Ser Lys Lys Val Gln Ile
    210                 215                 220

His Ser Val Glu Met Asp Pro Glu Ile Thr Thr Phe Lys Arg Val Ile
225                 230                 235                 240

Asn Thr Met Met Asp Gln Leu Gln Ile Phe Ser Ser Glu Val Ser Arg
                245                 250                 255

Val Ala Arg Glu Val Gly Thr Glu Gly Ile Leu Gly Gly Gln Ala Lys
            260                 265                 270

Ile Ser Gly Val Asp Gly Thr Trp Lys Glu Leu Thr Asp Asn Val Asn
        275                 280                 285

Val Met Ala Gln Asn Leu Thr Asp Gln Val Arg Glu Ile Ala Ser Val
    290                 295                 300

Thr Thr Ala Val Ala His Gly Asp Leu Thr Gln Lys Ile Glu Arg Pro
305                 310                 315                 320
```

```
Ala Gln Gly Glu Ile Leu Gln Leu Gln Thr Ile Asn Thr Met Val
            325                 330                 335

Asp Gln Leu Arg Thr Phe Ala Ala Glu Val Thr Arg Val Ala Arg Asp
            340                 345                 350

Val Gly Thr Glu Gly Ile Leu Gly Gln Ala Glu Ile Glu Gly Val
            355                 360                 365

Gln Gly Met Trp Asn Thr Leu Ile Val Asn Val Asn Ala Met Ala Asn
            370                 375                 380

Asn Leu Thr Thr Gln Val Arg Asp Ile Ala Ile Val Thr Thr Ala Val
385                 390                 395                 400

Ala Lys Gly Asp Leu Thr Gln Lys Val Gln Ala Glu Cys Lys Gly Glu
                    405                 410                 415

Ile Lys Gln Leu Lys Glu Thr Ile Asn Ser Met Val Asp Gln Leu Gln
                    420                 425                 430

Gln Phe Ala Arg Glu Val Thr Lys Ile Ala Arg Glu Val Gly Thr Glu
            435                 440                 445

Gly Arg Leu Gly Gly Gln Ala Thr Val His Asp Val Glu Gly Thr Trp
            450                 455                 460

Arg Asp Leu Thr Glu Asn Val Asn Gly Met Ala Met Asn Leu Thr Thr
465                 470                 475                 480

Gln Val Arg Glu Ile Ala Lys Val Thr Thr Ala Val Ala Arg Gly Asp
                    485                 490                 495

Leu Thr Lys Lys Ile Glu Val Glu Val Gln Gly Glu Ile Ala Ser Leu
                    500                 505                 510

Lys Asp Thr Ile Asn Thr Met Val Asp Arg Leu Ser Thr Phe Ala Phe
            515                 520                 525

Glu Val Ser Lys Val Ala Arg Glu Val Gly Thr Asp Gly Thr Leu Gly
            530                 535                 540

Gly Gln Ala Gln Val Asp Asn Val Glu Gly Lys Trp Lys Asp Leu Thr
545                 550                 555                 560

Glu Asn Val Asn Thr Met Ala Arg Asn Leu Thr Thr Gln Val Arg Gly
                    565                 570                 575

Ile Ser Thr Val Thr Gln Ala Ile Ala Asn Gly Asp Met Ser Gln Lys
            580                 585                 590

Ile Glu Val Ala Ala Ala Gly Glu Ile Leu Ile Leu Lys Glu Thr Ile
            595                 600                 605

Asn Asn Met Val Asp Arg Leu Ser Ile Phe Ser Asn Glu Val Gln Arg
            610                 615                 620

Val Ala Lys Asp Val Gly Val Asp Gly Lys Met Gly Gly Gln Ala Asp
625                 630                 635                 640

Val Ala Gly Ile Gly Gly Arg Trp Lys Glu Ile Thr Thr Asp Val Asn
                    645                 650                 655

Thr Met Ala Asn Asn Leu Thr Thr Gln Val Arg Ala Phe Gly Asp Ile
                    660                 665                 670

Thr Asn Ala Ala Thr Asp Gly Asp Phe Thr Lys Leu Ile Thr Val Glu
            675                 680                 685

Ala Ser Gly Glu Met Asp Glu Leu Lys Arg Lys Ile Asn Gln Met Val
            690                 695                 700

Tyr Asn Leu Arg Asp Ser Ile Gln Arg Asn Thr Leu Ala Arg Glu Ala
705                 710                 715                 720

Ala Glu Phe Ala Asn Arg Thr Lys Ser Glu Phe Leu Ala Asn Met Ser
                    725                 730                 735
```

```
His Glu Ile Arg Thr Pro Met Asn Gly Ile Ile Gly Met Thr Gln Leu
            740                 745                 750

Thr Leu Asp Thr Asp Leu Thr Gln Tyr Gln Arg Glu Met Leu Asn Ile
            755                 760                 765

Val His Asn Leu Ala Asn Ser Leu Leu Thr Ile Ile Asp Asp Ile Leu
    770                 775                 780

Asp Leu Ser Lys Ile Glu Ala Asn Arg Met Ile Met Glu Glu Ile Pro
785                 790                 795                 800

Tyr Thr Leu Arg Gly Thr Val Phe Asn Ala Leu Lys Thr Leu Ala Val
                805                 810                 815

Lys Ala Asn Glu Lys Phe Leu Asp Leu Thr Tyr Arg Val Asp Ser Ser
            820                 825                 830

Val Pro Asp His Val Val Gly Asp Ser Phe Arg Leu Arg Gln Val Ile
            835                 840                 845

Leu Asn Leu Val Gly Asn Ala Ile Lys Phe Thr Glu His Gly Glu Val
    850                 855                 860

Ser Leu Thr Ile Gln Lys Ala Glu Gln Asp His Cys Ala Pro Asn Glu
865                 870                 875                 880

Tyr Ala Val Glu Phe Cys Val Ser Asp Thr Gly Ile Gly Ile Gln Ala
                885                 890                 895

Asp Lys Leu Asn Leu Ile Phe Asp Thr Phe Gln Gln Ala Asp Gly Ser
            900                 905                 910

Met Thr Arg Lys Phe Gly Gly Thr Gly Leu Gly Leu Ser Ile Ser Lys
            915                 920                 925

Arg Leu Val Asn Leu Met Arg Gly Asp Val Trp Val Lys Ser Gln Tyr
    930                 935                 940

Gly Lys Gly Ser Ser Phe Tyr Phe Thr Cys Thr Val Arg Leu Ala Thr
945                 950                 955                 960

Ser Asp Ile Ser Phe Ile Gln Lys Gln Leu Lys Pro Tyr Gln Gly His
                965                 970                 975

Asn Val Leu Phe Ile Asp Lys Gly Gln Thr Gly His Gly Lys Glu Ile
            980                 985                 990

Ile Thr Met Leu Thr Gln Leu Gly Leu Val Pro Val Val Val Asp Ser
            995                1000                1005

Glu Gln His Thr Ile Leu Leu Gly Asn Gly Arg Thr Lys Glu Lys Ile
   1010                1015                1020

Ala Ser Thr Tyr Asp Val Ile Val Val Asp Ser Ile Glu Ser Ala Arg
   1025                1030                1035                1040

Lys Leu Arg Ser Ile Asp Glu Phe Lys Tyr Ile Pro Ile Val Leu Leu
               1045                1050                1055

Ala Pro Val Ile His Val Ser Leu Lys Ser Ala Leu Asp Leu Gly Ile
           1060                1065                1070

Thr Ser Tyr Met Thr Thr Pro Cys Leu Thr Ile Asp Leu Gly Asn Gly
           1075                1080                1085

Met Ile Pro Ala Leu Glu Asn Arg Ala Ala Pro Ser Leu Ala Asp Asn
   1090                1095                1100

Thr Lys Ser Phe Asp Ile Leu Leu Ala Glu Asp Asn Ile Val Asn Gln
1105                1110                1115                1120

Arg Leu Ala Val Lys Ile Leu Glu Lys Tyr His His Val Val Thr Val
               1125                1130                1135

Val Gly Asn Gly Gln Glu Ala Leu Asp Ala Ile Lys Glu Lys Arg Tyr
           1140                1145                1150
```

```
Asp Val Ile Leu Met Asp Val Gln Met Pro Ile Met Gly Gly Phe Glu
        1155                1160                1165

Ala Thr Ala Lys Ile Arg Glu Tyr Glu Arg Ser Leu Gly Thr Gln Arg
    1170                1175                1180

Thr Pro Ile Ile Ala Leu Thr Ala His Ala Met Leu Gly Asp Arg Glu
1185                1190                1195                1200

Lys Cys Ile Gln Ala Gln Met Asp Glu Tyr Leu Ser Lys Pro Leu Lys
            1205                1210                1215

Gln Asn His Leu Ile Gln Thr Ile Leu Lys Cys Ala Thr Leu Gly Gly
        1220                1225                1230

Ala Leu Leu Glu Lys Gly Arg Glu Val Arg Gln Ser Ala Asn Glu Glu
    1235                1240                1245

Ser Pro Asn Ser Gln Asn Gly Pro Arg Gly Thr Gln His Pro Ala Ser
1250                1255                1260

Ser Pro Thr Pro Ala His Met Arg Pro Ala Ile Glu Pro Arg Ala Tyr
            1265                1270                1275                1280

Thr Thr Thr Gly Pro Ile Asn His Gly Ser Ala Glu Ser Pro Ser Leu
        1285                1290                1295

Val Thr Ala Asp Ala Glu Asp Pro Leu Ala Arg Leu Leu Met Arg Ala
    1300                1305                1310

His Ser Ser
        1315

<210> SEQ ID NO 2
<211> LENGTH: 3948
<212> TYPE: DNA
<213> ORGANISM: Botryotinia fuckeliana
<220> FEATURE:
<221> NAME/KEY: CDS
<222> LOCATION: (1)..(3948)

<400> SEQUENCE: 2 atg gag gat tct aca ata gct cat act act gcg atc ctg caa act ctc     48
Met Glu Asp Ser Thr Ile Ala His Thr Thr Ala Ile Leu Gln Thr Leu
  1               5                  10                  15 gca tta tcg agc atc gat ctt cca ctg acg aat gtt tac ggc aac aag     96
Ala Leu Ser Ser Ile Asp Leu Pro Leu Thr Asn Val Tyr Gly Asn Lys
             20                  25                  30 ggg att agg tta cca ggt gca gat acg gca gag aag ctt gcc ctc gaa    144
Gly Ile Arg Leu Pro Gly Ala Asp Thr Ala Glu Lys Leu Ala Leu Glu
         35                  40                  45 cga gaa ctt gcg gcc ttg gta tcc aga gtc caa aga tta gaa gca agg    192
Arg Glu Leu Ala Ala Leu Val Ser Arg Val Gln Arg Leu Glu Ala Arg
     50                  55                  60 gcg atc aca gtc aat aat caa acc ctg ccc gat acg ccg aat gaa tta    240
Ala Ile Thr Val Asn Asn Gln Thr Leu Pro Asp Thr Pro Asn Glu Leu
 65                  70                  75                  80 gga gcg cca tct gct ttc gca gat gta ctc act ggt gcc cca tcc cga    288
Gly Ala Pro Ser Ala Phe Ala Asp Val Leu Thr Gly Ala Pro Ser Arg
                 85                  90                  95 gcc tca aag agt act aca tcc cga caa cag ctc gta aat tcg ttg ctt    336
Ala Ser Lys Ser Thr Thr Ser Arg Gln Gln Leu Val Asn Ser Leu Leu
            100                 105                 110 gcc gcc aga gaa gcg ccc acc ggc ggt gaa aga cct cct aaa ttt acg    384
Ala Ala Arg Glu Ala Pro Thr Gly Gly Glu Arg Pro Pro Lys Phe Thr
        115                 120                 125 aaa tta agt gac gag gaa ctc gaa gca ctc cgc gaa cat gtc gac cat    432
Lys Leu Ser Asp Glu Glu Leu Glu Ala Leu Arg Glu His Val Asp His
    130                 135                 140
```

-continued

```
caa tcg aaa caa ctc gat agt caa aaa tct gag ctg gcc ggt gta cat        480
Gln Ser Lys Gln Leu Asp Ser Gln Lys Ser Glu Leu Ala Gly Val His
145                 150                 155                 160 gct caa ctg ttt gag cag aag cag aga caa gaa caa gca ctc aac gtt        528
Ala Gln Leu Phe Glu Gln Lys Gln Arg Gln Glu Gln Ala Leu Asn Val
                165                 170                 175 ctt gaa gtc gaa cgc gta gca gct ctc gaa aga gaa ctg aag aag cat        576
Leu Glu Val Glu Arg Val Ala Ala Leu Glu Arg Glu Leu Lys Lys His
            180                 185                 190 caa caa gcc aac gag gct ttc caa aaa gct cta cgg gaa ata gga gag        624
Gln Gln Ala Asn Glu Ala Phe Gln Lys Ala Leu Arg Glu Ile Gly Glu
        195                 200                 205 att gtc aca gct gta gct agg ggt gat ctc agt aag aag gta caa atc        672
Ile Val Thr Ala Val Ala Arg Gly Asp Leu Ser Lys Lys Val Gln Ile
210                 215                 220 cac tcc gtg gag atg gac cct gag att aca act ttc aag cgt gtt att        720
His Ser Val Glu Met Asp Pro Glu Ile Thr Thr Phe Lys Arg Val Ile
225                 230                 235                 240 aat act atg atg gat caa ctt cag ata ttc tct agt gag gtt tct cgt        768
Asn Thr Met Met Asp Gln Leu Gln Ile Phe Ser Ser Glu Val Ser Arg
                245                 250                 255 gta gct aga gag gtc ggc aca gaa ggt att ctc ggt gga caa gcc aag        816
Val Ala Arg Glu Val Gly Thr Glu Gly Ile Leu Gly Gly Gln Ala Lys
            260                 265                 270 att tct ggt gtt gat ggt aca tgg aag gag ttg act gac aat gtc aac        864
Ile Ser Gly Val Asp Gly Thr Trp Lys Glu Leu Thr Asp Asn Val Asn
        275                 280                 285 gtt atg gca caa aat ctc acc gat caa gtc cga gaa att gct tcc gtc        912
Val Met Ala Gln Asn Leu Thr Asp Gln Val Arg Glu Ile Ala Ser Val
290                 295                 300 act act gct gta gct cat gga gat ctc aca caa aag att gag aga cca        960
Thr Thr Ala Val Ala His Gly Asp Leu Thr Gln Lys Ile Glu Arg Pro
305                 310                 315                 320 gcc cag ggt gag ata ctc caa ctg caa caa act atc aat acc atg gtg       1008
Ala Gln Gly Glu Ile Leu Gln Leu Gln Gln Thr Ile Asn Thr Met Val
                325                 330                 335 gat caa ttg aga acg ttc gcc gcc gag gtc acc cgc gta gca aga gat       1056
Asp Gln Leu Arg Thr Phe Ala Ala Glu Val Thr Arg Val Ala Arg Asp
            340                 345                 350 gta gga act gaa ggt att ctt ggg ggt caa gca gaa atc gaa ggc gtc       1104
Val Gly Thr Glu Gly Ile Leu Gly Gly Gln Ala Glu Ile Glu Gly Val
        355                 360                 365 cag ggc atg tgg aac aca ttg ata gtg aac gtc aac gct atg gcc aat       1152
Gln Gly Met Trp Asn Thr Leu Ile Val Asn Val Asn Ala Met Ala Asn
370                 375                 380 aac ctc acc aca caa gtg cgc gat ata gcc att gtc aca aca gct gtc       1200
Asn Leu Thr Thr Gln Val Arg Asp Ile Ala Ile Val Thr Thr Ala Val
385                 390                 395                 400 gca aag gga gac ctg act caa aag gtc caa gca gaa tgt aag ggt gaa       1248
Ala Lys Gly Asp Leu Thr Gln Lys Val Gln Ala Glu Cys Lys Gly Glu
                405                 410                 415 atc aag cag ttg aag gag act ata aat tcc atg gtg gac caa tta caa       1296
Ile Lys Gln Leu Lys Glu Thr Ile Asn Ser Met Val Asp Gln Leu Gln
            420                 425                 430 caa ttt gcg cga gaa gtc acg aag att gct agg gag gtc ggt acc gaa       1344
Gln Phe Ala Arg Glu Val Thr Lys Ile Ala Arg Glu Val Gly Thr Glu
        435                 440                 445 ggt aga ctg ggt gga caa gca aca gtg cat gat gtt gaa ggc act tgg       1392
Gly Arg Leu Gly Gly Gln Ala Thr Val His Asp Val Glu Gly Thr Trp
450                 455                 460
```

```
aga gac ctc acc gaa aat gtg aat ggt atg gcc atg aat ctt acg aca      1440
Arg Asp Leu Thr Glu Asn Val Asn Gly Met Ala Met Asn Leu Thr Thr
465                 470                 475                 480 caa gta cga gag att gca aag gtt acc acc gct gtc gcc aga gga gat      1488
Gln Val Arg Glu Ile Ala Lys Val Thr Thr Ala Val Ala Arg Gly Asp
            485                 490                 495 ttg acc aag aag att gaa gtc gag gtt cag gga gaa atc gct tcg ctg      1536
Leu Thr Lys Lys Ile Glu Val Glu Val Gln Gly Glu Ile Ala Ser Leu
        500                 505                 510 aaa gat acc atc aac acc atg gtg gac aga ctt agt aca ttc gct ttt      1584
Lys Asp Thr Ile Asn Thr Met Val Asp Arg Leu Ser Thr Phe Ala Phe
    515                 520                 525 gag gtt agc aaa gtc gcc agg gag gtc gga act gat ggg act ctt ggt      1632
Glu Val Ser Lys Val Ala Arg Glu Val Gly Thr Asp Gly Thr Leu Gly
530                 535                 540 gga caa gcg caa gtt gat aac gtc gaa gga aag tgg aaa gac ctc act      1680
Gly Gln Ala Gln Val Asp Asn Val Glu Gly Lys Trp Lys Asp Leu Thr
545                 550                 555                 560 gaa aat gtg aac acc atg gcc aga aac ttg act act caa gta cga ggt      1728
Glu Asn Val Asn Thr Met Ala Arg Asn Leu Thr Thr Gln Val Arg Gly
            565                 570                 575 atc tcg act gtt aca caa gct att gcc aat gga gac atg agt cag aag      1776
Ile Ser Thr Val Thr Gln Ala Ile Ala Asn Gly Asp Met Ser Gln Lys
        580                 585                 590 att gag gtt gct gct gcg ggt gaa ata ctc ata cta aag gaa acc ata      1824
Ile Glu Val Ala Ala Ala Gly Glu Ile Leu Ile Leu Lys Glu Thr Ile
    595                 600                 605 aat aac atg gta gac aga ttg agt atc ttc tcc aac gaa gtg caa aga      1872
Asn Asn Met Val Asp Arg Leu Ser Ile Phe Ser Asn Glu Val Gln Arg
610                 615                 620 gtc gcc aaa gat gtg ggt gtg gat ggt aag atg ggt ggc caa gct gac      1920
Val Ala Lys Asp Val Gly Val Asp Gly Lys Met Gly Gly Gln Ala Asp
625                 630                 635                 640 gtt gct ggg att ggc ggc cgt tgg aaa gag atc aca acg gat gtc aat      1968
Val Ala Gly Ile Gly Gly Arg Trp Lys Glu Ile Thr Thr Asp Val Asn
            645                 650                 655 acc atg gct aac aac ttg aca acc caa gtg cgc gcc ttt ggt gat ata      2016
Thr Met Ala Asn Asn Leu Thr Thr Gln Val Arg Ala Phe Gly Asp Ile
        660                 665                 670 act aac gcc gca acc gat ggc gac ttc aca aaa ttg atc act gtc gag      2064
Thr Asn Ala Ala Thr Asp Gly Asp Phe Thr Lys Leu Ile Thr Val Glu
    675                 680                 685 gca tct gga gag atg gat gag ctg aag cga aag atc aac cag atg gtg      2112
Ala Ser Gly Glu Met Asp Glu Leu Lys Arg Lys Ile Asn Gln Met Val
690                 695                 700 tac aat ctg agg gac agt att caa aga aac acc ttg gct agg gag gct      2160
Tyr Asn Leu Arg Asp Ser Ile Gln Arg Asn Thr Leu Ala Arg Glu Ala
705                 710                 715                 720 gcc gaa ttc gcc aat agg acg aag tct gaa ttc ttg gct aac atg tct      2208
Ala Glu Phe Ala Asn Arg Thr Lys Ser Glu Phe Leu Ala Asn Met Ser
            725                 730                 735 cac gag att cga aca cct atg aac ggt atc att ggt atg act cag ttg      2256
His Glu Ile Arg Thr Pro Met Asn Gly Ile Ile Gly Met Thr Gln Leu
        740                 745                 750 aca ctc gac acc gat ctt act caa tat caa cga gaa atg ctc aac att      2304
Thr Leu Asp Thr Asp Leu Thr Gln Tyr Gln Arg Glu Met Leu Asn Ile
    755                 760                 765 gtt cac aac ttg gcc aac agt tta ttg acc atc att gat gat att ctc      2352
Val His Asn Leu Ala Asn Ser Leu Leu Thr Ile Ile Asp Asp Ile Leu
770                 775                 780
```

-continued

| | | |
|---|---|---|
| gat tta tca aag atc gaa gca aac cgt atg atc atg gag gag att cca<br>Asp Leu Ser Lys Ile Glu Ala Asn Arg Met Ile Met Glu Glu Ile Pro<br>785                790                795                800 | 2400 |
| tac act ctt aga gga acc gtc ttc aac gcc ctc aag act ctc gct gtc<br>Tyr Thr Leu Arg Gly Thr Val Phe Asn Ala Leu Lys Thr Leu Ala Val<br>              805                810                815 | 2448 |
| aag gca aat gag aag ttc cta gac ctc act tac cgc gta gat agc tca<br>Lys Ala Asn Glu Lys Phe Leu Asp Leu Thr Tyr Arg Val Asp Ser Ser<br>820                825                830 | 2496 |
| gtt cca gat cac gtg gtt ggt gat tca ttc cgt ctt cga caa gtt att<br>Val Pro Asp His Val Val Gly Asp Ser Phe Arg Leu Arg Gln Val Ile<br>              835                840                845 | 2544 |
| ctc aac ttg gtt gga aac gct atc aag ttc aca gag cat ggt gaa gtt<br>Leu Asn Leu Val Gly Asn Ala Ile Lys Phe Thr Glu His Gly Glu Val<br>850                855                860 | 2592 |
| tcg ttg acc atc caa aaa gcc gag caa gat cat tgt gcg ccg aac gaa<br>Ser Leu Thr Ile Gln Lys Ala Glu Gln Asp His Cys Ala Pro Asn Glu<br>865                870                875                880 | 2640 |
| tat gca gtc gag ttt tgt gtt tct gac act ggt atc ggt atc caa gct<br>Tyr Ala Val Glu Phe Cys Val Ser Asp Thr Gly Ile Gly Ile Gln Ala<br>              885                890                895 | 2688 |
| gat aag ctc aat ttg att ttc gac act ttc caa caa gct gac gga tct<br>Asp Lys Leu Asn Leu Ile Phe Asp Thr Phe Gln Gln Ala Asp Gly Ser<br>900                905                910 | 2736 |
| atg acg agg aaa ttc gga ggt act ggt cta ggt cta tca att tcg aag<br>Met Thr Arg Lys Phe Gly Gly Thr Gly Leu Gly Leu Ser Ile Ser Lys<br>              915                920                925 | 2784 |
| aga ctt gta aac ctc atg cgt gga gat gtt tgg gtt aag agt cag tac<br>Arg Leu Val Asn Leu Met Arg Gly Asp Val Trp Val Lys Ser Gln Tyr<br>930                935                940 | 2832 |
| gga aaa ggc agt tca ttc tac ttc acg tgt acc gtc cgc ctc gca acc<br>Gly Lys Gly Ser Ser Phe Tyr Phe Thr Cys Thr Val Arg Leu Ala Thr<br>945                950                955                960 | 2880 |
| tca gat atc agt ttc att cag aaa caa ctc aag cca tat caa ggt cac<br>Ser Asp Ile Ser Phe Ile Gln Lys Gln Leu Lys Pro Tyr Gln Gly His<br>              965                970                975 | 2928 |
| aat gtt ttg ttt atc gac aaa gga cag act ggc cat ggc aaa gaa ata<br>Asn Val Leu Phe Ile Asp Lys Gly Gln Thr Gly His Gly Lys Glu Ile<br>980                985                990 | 2976 |
| atc act atg ctt aca caa ctt ggt ttg gta ccc gtt gtt gtt gac tct<br>Ile Thr Met Leu Thr Gln Leu Gly Leu Val Pro Val Val Val Asp Ser<br>              995                1000                1005 | 3024 |
| gag cag cac act att ctt ctc ggc aat gga aga acc aag gag aag att<br>Glu Gln His Thr Ile Leu Leu Gly Asn Gly Arg Thr Lys Glu Lys Ile<br>1010                1015                1020 | 3072 |
| gct tca act tat gac gtg att gtt gtg gac tca att gag tcc gct cga<br>Ala Ser Thr Tyr Asp Val Ile Val Val Asp Ser Ile Glu Ser Ala Arg<br>1025                1030                1035                1040 | 3120 |
| aaa ctg cga tca atc gat gag ttc aag tat att cca att gtt ctc tta<br>Lys Leu Arg Ser Ile Asp Glu Phe Lys Tyr Ile Pro Ile Val Leu Leu<br>                1045                1050                1055 | 3168 |
| gct ccc gtt att cat gtc agc tta aag tct gct ttg gat ctt ggt atc<br>Ala Pro Val Ile His Val Ser Leu Lys Ser Ala Leu Asp Leu Gly Ile<br>                1060                1065                1070 | 3216 |
| act tct tac atg acc act cca tgt tta acg atc gat ctt ggc aat ggt<br>Thr Ser Tyr Met Thr Thr Pro Cys Leu Thr Ile Asp Leu Gly Asn Gly<br>1075                1080                1085 | 3264 |
| atg att cct gct ttg gag aat cga gct gca ccc tca ttg gcg gac aac<br>Met Ile Pro Ala Leu Glu Asn Arg Ala Ala Pro Ser Leu Ala Asp Asn<br>1090                1095                1100 | 3312 |

-continued

| | | |
|---|---|---|
| aca aaa tcc ttc gac att ctc ttg gcc gaa gat aac atc gtc aat caa<br>Thr Lys Ser Phe Asp Ile Leu Leu Ala Glu Asp Asn Ile Val Asn Gln<br>1105                  1110                  1115                  1120 | | 3360 |
| cgc tta gcg gtg aag att cta gaa aag tat cac cac gtc gtc aca gtc<br>Arg Leu Ala Val Lys Ile Leu Glu Lys Tyr His His Val Val Thr Val<br>                 1125                  1130                  1135 | | 3408 |
| gtt ggc aat ggt caa gaa gca cta gat gct atc aag gag aaa cga tac<br>Val Gly Asn Gly Gln Glu Ala Leu Asp Ala Ile Lys Glu Lys Arg Tyr<br>1140                  1145                  1150 | | 3456 |
| gat gtt att ctc atg gac gtt caa atg cca att atg gga gga ttc gaa<br>Asp Val Ile Leu Met Asp Val Gln Met Pro Ile Met Gly Gly Phe Glu<br>                 1155                  1160                  1165 | | 3504 |
| gca acc gct aag att aga gag tac gaa cgg agt ctt gga acg caa aga<br>Ala Thr Ala Lys Ile Arg Glu Tyr Glu Arg Ser Leu Gly Thr Gln Arg<br>1170                  1175                  1180 | | 3552 |
| acg cct att atc gca ctt aca gca cac gct atg ttg ggt gat cgc gaa<br>Thr Pro Ile Ile Ala Leu Thr Ala His Ala Met Leu Gly Asp Arg Glu<br>1185                    1190                  1195                  1200 | | 3600 |
| aaa tgt att caa gcc caa atg gat gaa tat ctt tct aag cct ctg aaa<br>Lys Cys Ile Gln Ala Gln Met Asp Glu Tyr Leu Ser Lys Pro Leu Lys<br>                 1205                  1210                  1215 | | 3648 |
| caa aat cat ctt att cag acg atc ttg aaa tgt gca acc ctt gga ggt<br>Gln Asn His Leu Ile Gln Thr Ile Leu Lys Cys Ala Thr Leu Gly Gly<br>1220                  1225                  1230 | | 3696 |
| gca ttg ctc gag aag ggt agg gag gtt agg caa tcc gct aat gaa gag<br>Ala Leu Leu Glu Lys Gly Arg Glu Val Arg Gln Ser Ala Asn Glu Glu<br>1235                  1240                  1245 | | 3744 |
| agc ccc aat tcg caa aat ggt cct cgc ggt aca cag cat cct gca tca<br>Ser Pro Asn Ser Gln Asn Gly Pro Arg Gly Thr Gln His Pro Ala Ser<br>                 1250                  1255                  1260 | | 3792 |
| agt ccc aca cca gcc cat atg aga ccg gct atc gaa cct cgt gca tac<br>Ser Pro Thr Pro Ala His Met Arg Pro Ala Ile Glu Pro Arg Ala Tyr<br>1265                  1270                  1275                  1280 | | 3840 |
| acg acc act ggc cct ata aat cat gga agt gca gag agt cct tca ctt<br>Thr Thr Thr Gly Pro Ile Asn His Gly Ser Ala Glu Ser Pro Ser Leu<br>                 1285                  1290                  1295 | | 3888 |
| gta acg gca gat gct gag gat cca ctt gcg agg ctt cta atg cgt gcg<br>Val Thr Ala Asp Ala Glu Asp Pro Leu Ala Arg Leu Leu Met Arg Ala<br>1300                  1305                  1310 | | 3936 |
| cat agc agc tag<br>His Ser Ser<br>       1315 | | 3948 |

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence:Designed
     oligonucleotide primer for PCR

<400> SEQUENCE: 3
tattcagaga ctagtatgga ggattctaca atagca                                36

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:Designed
     oligonucleotide primer for PCR

```
<400> SEQUENCE: 4
cagatgaatc tgcagctagc tgctatgcgc acg                                33

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 5
gatgtactca ctggtgcccc atcccgagcc                                    30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 6
ctcaaacagt tgagcatgta caccggccag                                    30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 7
acagaaggta ttctcggtgg acaagccaag                                    30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 8
gctagggagg tcggtaccga aggtagactg                                    30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 9
atcttctcca acgaagtgca aagagtcgcc                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:Designed
      oligonucleotide primer for sequencing
```

-continued

<400> SEQUENCE: 10
gaggagattc catacactct tagaggaacc                                       30

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 11
atcgacaaag gacagactgg ccatggc                                          27

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 12
atgccaatta tgggaggatt cgaagcaacc                                       30

<210> SEQ ID NO 13
<211> LENGTH: 1315
<212> TYPE: PRT
<213> ORGANISM: Botryotinia fuckeliana

<400> SEQUENCE: 13

Met Glu Asp Ser Thr Ile Ala His Thr Thr Ala Ile Leu Gln Thr Leu
 1               5                  10                  15

Ala Leu Ser Ser Ile Asp Leu Pro Leu Thr Asn Val Tyr Gly Asn Lys
                20                  25                  30

Gly Ile Arg Leu Pro Gly Ala Asp Thr Ala Glu Lys Leu Ala Leu Glu
            35                  40                  45

Arg Glu Leu Ala Ala Leu Val Ser Arg Val Gln Arg Leu Glu Ala Arg
        50                  55                  60

Ala Ile Thr Val Asn Asn Gln Thr Leu Pro Asp Thr Pro Asn Glu Leu
    65                  70                  75                  80

Gly Ala Pro Ser Ala Phe Ala Asp Val Leu Thr Gly Ala Pro Ser Arg
                85                  90                  95

Ala Ser Lys Ser Thr Thr Ser Arg Gln Gln Leu Val Asn Ser Leu Leu
            100                 105                 110

Ala Ala Arg Glu Ala Pro Thr Gly Gly Glu Arg Pro Pro Lys Phe Thr
        115                 120                 125

Lys Leu Ser Asp Glu Glu Leu Glu Ala Leu Arg Glu His Val Asp His
    130                 135                 140

Gln Ser Lys Gln Leu Asp Ser Gln Lys Ser Glu Leu Ala Gly Val His
145                 150                 155                 160

Ala Gln Leu Phe Glu Gln Lys Gln Arg Gln Glu Gln Ala Leu Asn Val
                165                 170                 175

Leu Glu Val Glu Arg Val Ala Ala Leu Glu Arg Glu Leu Lys Lys His
            180                 185                 190

Gln Gln Ala Asn Glu Ala Phe Gln Lys Ala Leu Arg Glu Ile Gly Glu
        195                 200                 205

Ile Val Thr Ala Val Ala Arg Gly Asp Leu Ser Lys Lys Val Gln Ile
    210                 215                 220

```
His Ser Val Glu Met Asp Pro Glu Ile Thr Thr Phe Lys Arg Val Ile
225                 230                 235                 240

Asn Thr Met Met Asp Gln Leu Gln Ile Phe Ser Ser Glu Val Ser Arg
            245                 250                 255

Val Ala Arg Glu Val Gly Thr Glu Gly Ile Leu Gly Gly Gln Ala Lys
        260                 265                 270

Ile Ser Gly Val Asp Gly Thr Trp Lys Glu Leu Thr Asp Asn Val Asn
    275                 280                 285

Val Met Ala Gln Asn Leu Thr Asp Gln Val Arg Glu Ile Ala Ser Val
290                 295                 300

Thr Thr Ala Val Ala His Gly Asp Leu Thr Gln Lys Ile Glu Arg Pro
305                 310                 315                 320

Ala Gln Gly Glu Ile Leu Gln Leu Gln Gln Thr Ile Asn Thr Met Val
            325                 330                 335

Asp Gln Leu Arg Thr Phe Ala Ala Glu Val Thr Arg Val Ala Arg Asp
        340                 345                 350

Val Gly Thr Glu Gly Ile Leu Gly Gly Gln Ala Glu Ser Glu Gly Val
    355                 360                 365

Gln Gly Met Trp Asn Thr Leu Ile Val Asn Val Asn Ala Met Ala Asn
370                 375                 380

Asn Leu Thr Thr Gln Val Arg Asp Ile Ala Ile Val Thr Thr Ala Val
385                 390                 395                 400

Ala Lys Gly Asp Leu Thr Gln Lys Val Gln Ala Glu Cys Lys Gly Glu
            405                 410                 415

Ile Lys Gln Leu Lys Glu Thr Ile Asn Ser Met Val Asp Gln Leu Gln
        420                 425                 430

Gln Phe Ala Arg Glu Val Thr Lys Ile Ala Arg Glu Val Gly Thr Glu
    435                 440                 445

Gly Arg Leu Gly Gly Gln Ala Thr Val His Asp Val Glu Gly Thr Trp
450                 455                 460

Arg Asp Leu Thr Glu Asn Val Asn Gly Met Ala Met Asn Leu Thr Thr
465                 470                 475                 480

Gln Val Arg Glu Ile Ala Lys Val Thr Thr Ala Val Ala Arg Gly Asp
            485                 490                 495

Leu Thr Lys Lys Ile Glu Val Glu Val Gln Gly Glu Ile Ala Ser Leu
        500                 505                 510

Lys Asp Thr Ile Asn Thr Met Val Asp Arg Leu Ser Thr Phe Ala Phe
    515                 520                 525

Glu Val Ser Lys Val Ala Arg Glu Val Gly Thr Asp Gly Thr Leu Gly
530                 535                 540

Gly Gln Ala Gln Val Asp Asn Val Glu Gly Lys Trp Lys Asp Leu Thr
545                 550                 555                 560

Glu Asn Val Asn Thr Met Ala Arg Asn Leu Thr Thr Gln Val Arg Gly
            565                 570                 575

Ile Ser Thr Val Thr Gln Ala Ile Ala Asn Gly Asp Met Ser Gln Lys
        580                 585                 590

Ile Glu Val Ala Ala Gly Glu Ile Leu Ile Leu Lys Glu Thr Ile
    595                 600                 605

Asn Asn Met Val Asp Arg Leu Ser Ile Phe Ser Asn Glu Val Gln Arg
610                 615                 620

Val Ala Lys Asp Val Gly Val Asp Gly Lys Met Gly Gly Gln Ala Asp
625                 630                 635                 640
```

-continued

```
Val Ala Gly Ile Gly Gly Arg Trp Lys Glu Ile Thr Thr Asp Val Asn
            645                 650                 655

Thr Met Ala Asn Asn Leu Thr Thr Gln Val Arg Ala Phe Gly Asp Ile
        660                 665                 670

Thr Asn Ala Ala Thr Asp Gly Asp Phe Thr Lys Leu Ile Thr Val Glu
    675                 680                 685

Ala Ser Gly Glu Met Asp Glu Leu Lys Arg Lys Ile Asn Gln Met Val
690                 695                 700

Tyr Asn Leu Arg Asp Ser Ile Gln Arg Asn Thr Leu Ala Arg Glu Ala
705                 710                 715                 720

Ala Glu Phe Ala Asn Arg Thr Lys Ser Glu Phe Leu Ala Asn Met Ser
            725                 730                 735

His Glu Ile Arg Thr Pro Met Asn Gly Ile Ile Gly Met Thr Gln Leu
        740                 745                 750

Thr Leu Asp Thr Asp Leu Thr Gln Tyr Gln Arg Glu Met Leu Asn Ile
    755                 760                 765

Val His Asn Leu Ala Asn Ser Leu Leu Thr Ile Ile Asp Asp Ile Leu
770                 775                 780

Asp Leu Ser Lys Ile Glu Ala Asn Arg Met Ile Met Glu Glu Ile Pro
785                 790                 795                 800

Tyr Thr Leu Arg Gly Thr Val Phe Asn Ala Leu Lys Thr Leu Ala Val
            805                 810                 815

Lys Ala Asn Glu Lys Phe Leu Asp Leu Thr Tyr Arg Val Asp Ser Ser
        820                 825                 830

Val Pro Asp His Val Val Gly Asp Ser Phe Arg Leu Arg Gln Val Ile
    835                 840                 845

Leu Asn Leu Val Gly Asn Ala Ile Lys Phe Thr Glu His Gly Glu Val
850                 855                 860

Ser Leu Thr Ile Gln Lys Ala Glu Gln Asp His Cys Ala Pro Asn Glu
865                 870                 875                 880

Tyr Ala Val Glu Phe Cys Val Ser Asp Thr Gly Ile Gly Ile Gln Ala
            885                 890                 895

Asp Lys Leu Asn Leu Ile Phe Asp Thr Phe Gln Gln Ala Asp Gly Ser
        900                 905                 910

Met Thr Arg Lys Phe Gly Gly Thr Gly Leu Gly Leu Ser Ile Ser Lys
    915                 920                 925

Arg Leu Val Asn Leu Met Arg Gly Asp Val Trp Val Lys Ser Gln Tyr
930                 935                 940

Gly Lys Gly Ser Ser Phe Tyr Phe Thr Cys Thr Val Arg Leu Ala Thr
945                 950                 955                 960

Ser Asp Ile Ser Phe Ile Gln Lys Gln Leu Lys Pro Tyr Gln Gly His
            965                 970                 975

Asn Val Leu Phe Ile Asp Lys Gly Gln Thr Gly His Gly Lys Glu Ile
        980                 985                 990

Ile Thr Met Leu Thr Gln Leu Gly Leu Val Pro Val Val Asp Ser
    995                 1000                1005

Glu Gln His Thr Ile Leu Leu Gly Asn Gly Arg Thr Lys Glu Lys Ile
    1010                1015                1020

Ala Ser Thr Tyr Asp Val Ile Val Asp Ser Ile Glu Ser Ala Arg
    1025                1030                1035                1040

Lys Leu Arg Ser Ile Asp Glu Phe Lys Tyr Ile Pro Ile Val Leu Leu
            1045                1050                1055
```

```
Ala Pro Val Ile His Val Ser Leu Lys Ser Ala Leu Asp Leu Gly Ile
        1060                1065                1070

Thr Ser Tyr Met Thr Thr Pro Cys Leu Thr Ile Asp Leu Gly Asn Gly
        1075                1080                1085

Met Ile Pro Ala Leu Glu Asn Arg Ala Ala Pro Ser Leu Ala Asp Asn
        1090                1095                1100

Thr Lys Ser Phe Asp Ile Leu Leu Ala Glu Asp Asn Ile Val Asn Gln
1105                1110                1115                1120

Arg Leu Ala Val Lys Ile Leu Glu Lys Tyr His His Val Val Thr Val
                1125                1130                1135

Val Gly Asn Gly Gln Glu Ala Leu Asp Ala Ile Lys Glu Lys Arg Tyr
        1140                1145                1150

Asp Val Ile Leu Met Asp Val Gln Met Pro Ile Met Gly Gly Phe Glu
        1155                1160                1165

Ala Thr Ala Lys Ile Arg Glu Tyr Glu Arg Ser Leu Gly Thr Gln Arg
        1170                1175                1180

Thr Pro Ile Ile Ala Leu Thr Ala His Ala Met Leu Gly Asp Arg Glu
1185                1190                1195                1200

Lys Cys Ile Gln Ala Gln Met Asp Glu Tyr Leu Ser Lys Pro Leu Lys
                1205                1210                1215

Gln Asn His Leu Ile Gln Thr Ile Leu Lys Cys Ala Thr Leu Gly Gly
        1220                1225                1230

Ala Leu Leu Glu Lys Gly Arg Glu Val Arg Gln Ser Ala Asn Glu Glu
        1235                1240                1245

Ser Pro Asn Ser Gln Asn Gly Pro Arg Gly Thr Gln His Pro Ala Ser
        1250                1255                1260

Ser Pro Thr Pro Ala His Met Arg Pro Ala Ile Glu Pro Arg Ala Tyr
1265                1270                1275                1280

Thr Thr Thr Gly Pro Ile Asn His Gly Ser Ala Glu Ser Pro Ser Leu
                1285                1290                1295

Val Thr Ala Asp Ala Glu Asp Pro Leu Ala Arg Leu Leu Met Arg Ala
        1300                1305                1310

His Ser Ser
       1315

<210> SEQ ID NO 14
<211> LENGTH: 3948
<212> TYPE: DNA
<213> ORGANISM: Botryotinia fuckeliana
<220> FEATURE:
<221> NAME/KEY: CDS
<222> LOCATION: (1)..(3948)

<400> SEQUENCE: 14 atg gag gat tct aca ata gct cat act act gcg atc ctg caa act ctc    48
Met Glu Asp Ser Thr Ile Ala His Thr Thr Ala Ile Leu Gln Thr Leu
 1               5                  10                  15 gca tta tcg agc atc gat ctt cca ctg acg aat gtt tac ggc aac aag    96
Ala Leu Ser Ser Ile Asp Leu Pro Leu Thr Asn Val Tyr Gly Asn Lys
            20                  25                  30 ggg att agg tta cca ggt gca gat acg gca gag aag ctt gcc ctc gaa   144
Gly Ile Arg Leu Pro Gly Ala Asp Thr Ala Glu Lys Leu Ala Leu Glu
        35                  40                  45 cga gaa ctt gcg gcc ttg gta tcc aga gtc caa aga tta gaa gca agg   192
Arg Glu Leu Ala Ala Leu Val Ser Arg Val Gln Arg Leu Glu Ala Arg
    50                  55                  60
```

| | | |
|---|---|---|
| gcg atc aca gtc aat aat caa acc ctg ccc gat acg ccg aat gaa tta<br>Ala Ile Thr Val Asn Asn Gln Thr Leu Pro Asp Thr Pro Asn Glu Leu<br>65                        70                         75                       80 | | 240 |
| gga gcg cca tct gct ttc gca gat gta ctc act ggt gcc cca tcc cga<br>Gly Ala Pro Ser Ala Phe Ala Asp Val Leu Thr Gly Ala Pro Ser Arg<br>                     85                         90                       95 | | 288 |
| gcc tca aag agt act aca tcc cga caa cag ctc gta aat tcg ttg ctt<br>Ala Ser Lys Ser Thr Thr Ser Arg Gln Gln Leu Val Asn Ser Leu Leu<br>               100                     105                     110 | | 336 |
| gcc gcc aga gaa gcg ccc acc ggc ggt gaa aga cct cct aaa ttt acg<br>Ala Ala Arg Glu Ala Pro Thr Gly Gly Glu Arg Pro Pro Lys Phe Thr<br>               115                     120                     125 | | 384 |
| aaa tta agt gac gag gaa ctc gaa gca ctc cgc gaa cat gtc gac cat<br>Lys Leu Ser Asp Glu Glu Leu Glu Ala Leu Arg Glu His Val Asp His<br>130                       135                        140 | | 432 |
| caa tcg aaa caa ctc gat agt caa aaa tct gag ctg gcc ggt gta cat<br>Gln Ser Lys Gln Leu Asp Ser Gln Lys Ser Glu Leu Ala Gly Val His<br>145                       150                     155                     160 | | 480 |
| gct caa ctg ttt gag cag aag cag aga caa gaa caa gca ctc aac gtt<br>Ala Gln Leu Phe Glu Gln Lys Gln Arg Gln Glu Gln Ala Leu Asn Val<br>               165                     170                     175 | | 528 |
| ctt gaa gtc gaa cgc gta gca gct ctc gaa aga gaa ctg aag aag cat<br>Leu Glu Val Glu Arg Val Ala Ala Leu Glu Arg Glu Leu Lys Lys His<br>               180                     185                     190 | | 576 |
| caa caa gcc aac gag gct ttc caa aaa gct cta cgg gaa ata gga gag<br>Gln Gln Ala Asn Glu Ala Phe Gln Lys Ala Leu Arg Glu Ile Gly Glu<br>               195                     200                     205 | | 624 |
| att gtc aca gct gta gct agg ggt gat ctc agt aag aag gta caa atc<br>Ile Val Thr Ala Val Ala Arg Gly Asp Leu Ser Lys Lys Val Gln Ile<br>               210                     215                     220 | | 672 |
| cac tcc gtg gag atg gac cct gag att aca act ttc aag cgt gtt att<br>His Ser Val Glu Met Asp Pro Glu Ile Thr Thr Phe Lys Arg Val Ile<br>225                       230                     235                     240 | | 720 |
| aat act atg atg gat caa ctt cag ata ttc tct agt gag gtt tct cgt<br>Asn Thr Met Met Asp Gln Leu Gln Ile Phe Ser Ser Glu Val Ser Arg<br>               245                     250                     255 | | 768 |
| gta gct aga gag gtc ggc aca gaa ggt att ctc ggt gga caa gcc aag<br>Val Ala Arg Glu Val Gly Thr Glu Gly Ile Leu Gly Gly Gln Ala Lys<br>               260                     265                     270 | | 816 |
| att tct ggt gtt gat ggt aca tgg aag gag ttg act gac aat gtc aac<br>Ile Ser Gly Val Asp Gly Thr Trp Lys Glu Leu Thr Asp Asn Val Asn<br>               275                     280                     285 | | 864 |
| gtt atg gca caa aat ctc acc gat caa gtc cga gaa att gct tcc gtc<br>Val Met Ala Gln Asn Leu Thr Asp Gln Val Arg Glu Ile Ala Ser Val<br>290                       295                     300 | | 912 |
| act act gct gta gct cat gga gat ctc aca caa aag att gag aga cca<br>Thr Thr Ala Val Ala His Gly Asp Leu Thr Gln Lys Ile Glu Arg Pro<br>305                       310                     315                     320 | | 960 |
| gcc cag ggt gag ata ctc caa ctg caa caa act atc aat acc atg gtg<br>Ala Gln Gly Glu Ile Leu Gln Leu Gln Gln Thr Ile Asn Thr Met Val<br>               325                     330                     335 | | 1008 |
| gat caa ttg aga acg ttc gcc gcc gag gtc acc cgc gta gca aga gat<br>Asp Gln Leu Arg Thr Phe Ala Ala Glu Val Thr Arg Val Ala Arg Asp<br>               340                     345                     350 | | 1056 |
| gta gga act gaa ggt att ctt ggg ggt caa gca gaa agc gaa ggc gtc<br>Val Gly Thr Glu Gly Ile Leu Gly Gly Gln Ala Glu Ser Glu Gly Val<br>               355                     360                     365 | | 1104 |
| cag ggc atg tgg aac aca ttg ata gtg aac gtc aac gct atg gcc aat<br>Gln Gly Met Trp Asn Thr Leu Ile Val Asn Val Asn Ala Met Ala Asn<br>               370                     375                     380 | | 1152 |

-continued

| | | |
|---|---|---|
| aac ctc acc aca caa gtg cgc gat ata gcc att gtc aca aca gct gtc<br>Asn Leu Thr Thr Gln Val Arg Asp Ile Ala Ile Val Thr Thr Ala Val<br>385                                        390                            395                            400 | 1200 |
| gca aag gga gac ctg act caa aag gtc caa gca gaa tgt aag ggt gaa<br>Ala Lys Gly Asp Leu Thr Gln Lys Val Gln Ala Glu Cys Lys Gly Glu<br>                          405                            410                            415 | 1248 |
| atc aag cag ttg aag gag act ata aat tcc atg gtg gac caa tta caa<br>Ile Lys Gln Leu Lys Glu Thr Ile Asn Ser Met Val Asp Gln Leu Gln<br>                     420                            425                            430 | 1296 |
| caa ttt gcg cga gaa gtc acg aag att gct agg gag gtc ggt acc gaa<br>Gln Phe Ala Arg Glu Val Thr Lys Ile Ala Arg Glu Val Gly Thr Glu<br>            435                            440                            445 | 1344 |
| ggt aga ctg ggt gga caa gca aca gtg cat gat gtt gaa ggc act tgg<br>Gly Arg Leu Gly Gly Gln Ala Thr Val His Asp Val Glu Gly Thr Trp<br>450                                        455                            460 | 1392 |
| aga gac ctc acc gaa aat gtg aat ggt atg gcc atg aat ctt acg aca<br>Arg Asp Leu Thr Glu Asn Val Asn Gly Met Ala Met Asn Leu Thr Thr<br>465                                        470                            475                            480 | 1440 |
| caa gta cga gag att gca aag gtt acc acc gct gtc gcc aga gga gat<br>Gln Val Arg Glu Ile Ala Lys Val Thr Thr Ala Val Ala Arg Gly Asp<br>                          485                            490                            495 | 1488 |
| ttg acc aag aag att gaa gtc gag gtt cag gga gaa atc gct tcg ctg<br>Leu Thr Lys Lys Ile Glu Val Glu Val Gln Gly Glu Ile Ala Ser Leu<br>            500                            505                            510 | 1536 |
| aaa gat acc atc aac acc atg gtg gac aga ctt agt aca ttc gct ttt<br>Lys Asp Thr Ile Asn Thr Met Val Asp Arg Leu Ser Thr Phe Ala Phe<br>                     515                            520                            525 | 1584 |
| gag gtt agc aaa gtc gcc agg gag gtc gga act gat ggg act ctt ggt<br>Glu Val Ser Lys Val Ala Arg Glu Val Gly Thr Asp Gly Thr Leu Gly<br>530                                        535                            540 | 1632 |
| gga caa gcg caa gtt gat aac gtc gaa gga aag tgg aaa gac ctc act<br>Gly Gln Ala Gln Val Asp Asn Val Glu Gly Lys Trp Lys Asp Leu Thr<br>545                                      550                            555                            560 | 1680 |
| gaa aat gtg aac acc atg gcc aga aac ttg act act caa gta cga ggt<br>Glu Asn Val Asn Thr Met Ala Arg Asn Leu Thr Thr Gln Val Arg Gly<br>                              565                            570                            575 | 1728 |
| atc tcg act gtt aca caa gct att gcc aat gga gac atg agt cag aag<br>Ile Ser Thr Val Thr Gln Ala Ile Ala Asn Gly Asp Met Ser Gln Lys<br>                   580                            585                            590 | 1776 |
| att gag gtt gct gct gcg ggt gaa ata ctc ata cta aag gaa acc ata<br>Ile Glu Val Ala Ala Ala Gly Glu Ile Leu Ile Leu Lys Glu Thr Ile<br>         595                            600                            605 | 1824 |
| aat aac atg gta gac aga ttg agt atc ttc tcc aac gaa gtg caa aga<br>Asn Asn Met Val Asp Arg Leu Ser Ile Phe Ser Asn Glu Val Gln Arg<br>610                                      615                            620 | 1872 |
| gtc gcc aaa gat gtg ggt gtg gat ggt aag atg ggt ggc caa gct gac<br>Val Ala Lys Asp Val Gly Val Asp Gly Lys Met Gly Gly Gln Ala Asp<br>625                                      630                            635                            640 | 1920 |
| gtt gct ggg att ggc ggc cgt tgg aaa gag atc aca acg gat gtc aat<br>Val Ala Gly Ile Gly Gly Arg Trp Lys Glu Ile Thr Thr Asp Val Asn<br>                          645                            650                            655 | 1968 |
| acc atg gct aac aac ttg aca acc caa gtg cgc gcc ttt ggt gat ata<br>Thr Met Ala Asn Asn Leu Thr Thr Gln Val Arg Ala Phe Gly Asp Ile<br>                     660                            665                            670 | 2016 |
| act aac gcc gca acc gat ggc gac ttc aca aaa ttg atc act gtc gag<br>Thr Asn Ala Ala Thr Asp Gly Asp Phe Thr Lys Leu Ile Thr Val Glu<br>                          675                            680                            685 | 2064 |
| gca tct gga gag atg gat gag ctg aag cga aag atc aac cag atg gtg<br>Ala Ser Gly Glu Met Asp Glu Leu Lys Arg Lys Ile Asn Gln Met Val<br>690                                        695                            700 | 2112 |

```
tac aat ctg agg gac agt att caa aga aac acc ttg gct agg gag gct        2160
Tyr Asn Leu Arg Asp Ser Ile Gln Arg Asn Thr Leu Ala Arg Glu Ala
705                 710                 715                 720 gcc gaa ttc gcc aat agg acg aag tct gaa ttc ttg gct aac atg tct        2208
Ala Glu Phe Ala Asn Arg Thr Lys Ser Glu Phe Leu Ala Asn Met Ser
                725                 730                 735 cac gag att cga aca cct atg aac ggt atc att ggt atg act cag ttg        2256
His Glu Ile Arg Thr Pro Met Asn Gly Ile Ile Gly Met Thr Gln Leu
            740                 745                 750 aca ctc gac acc gat ctt act caa tat caa cga gaa atg ctc aac att        2304
Thr Leu Asp Thr Asp Leu Thr Gln Tyr Gln Arg Glu Met Leu Asn Ile
        755                 760                 765 gtt cac aac ttg gcc aac agt tta ttg acc atc att gat gat att ctc        2352
Val His Asn Leu Ala Asn Ser Leu Leu Thr Ile Ile Asp Asp Ile Leu
    770                 775                 780 gat tta tca aag atc gaa gca aac cgt atg atc atg gag gag att cca        2400
Asp Leu Ser Lys Ile Glu Ala Asn Arg Met Ile Met Glu Glu Ile Pro
785                 790                 795                 800 tac act ctt aga gga acc gtc ttc aac gcc ctc aag act ctc gct gtc        2448
Tyr Thr Leu Arg Gly Thr Val Phe Asn Ala Leu Lys Thr Leu Ala Val
                805                 810                 815 aag gca aat gag aag ttc cta gac ctc act tac cgc gta gat agc tca        2496
Lys Ala Asn Glu Lys Phe Leu Asp Leu Thr Tyr Arg Val Asp Ser Ser
            820                 825                 830 gtt cca gat cac gtg gtt ggt gat tca ttc cgt ctt cga caa gtt att        2544
Val Pro Asp His Val Val Gly Asp Ser Phe Arg Leu Arg Gln Val Ile
        835                 840                 845 ctc aac ttg gtt gga aac gct atc aag ttc aca gag cat ggt gaa gtt        2592
Leu Asn Leu Val Gly Asn Ala Ile Lys Phe Thr Glu His Gly Glu Val
    850                 855                 860 tcg ttg acc atc caa aaa gcc gag caa gat cat tgt gcg ccg aac gaa        2640
Ser Leu Thr Ile Gln Lys Ala Glu Gln Asp His Cys Ala Pro Asn Glu
865                 870                 875                 880 tat gca gtc gag ttt tgt gtt tct gac act ggt atc ggt atc caa gct        2688
Tyr Ala Val Glu Phe Cys Val Ser Asp Thr Gly Ile Gly Ile Gln Ala
                885                 890                 895 gat aag ctc aat ttg att ttc gac act ttc caa caa gct gac gga tct        2736
Asp Lys Leu Asn Leu Ile Phe Asp Thr Phe Gln Gln Ala Asp Gly Ser
            900                 905                 910 atg acg agg aaa ttc gga ggt act ggt cta ggt cta tca att tcg aag        2784
Met Thr Arg Lys Phe Gly Gly Thr Gly Leu Gly Leu Ser Ile Ser Lys
        915                 920                 925 aga ctt gta aac ctc atg cgt gga gat gtt tgg gtt aag agt cag tac        2832
Arg Leu Val Asn Leu Met Arg Gly Asp Val Trp Val Lys Ser Gln Tyr
    930                 935                 940 gga aaa ggc agt tca ttc tac ttc acg tgt acc gtc cgc ctc gca acc        2880
Gly Lys Gly Ser Ser Phe Tyr Phe Thr Cys Thr Val Arg Leu Ala Thr
945                 950                 955                 960 tca gat atc agt ttc att cag aaa caa ctc aag cca tat caa ggt cac        2928
Ser Asp Ile Ser Phe Ile Gln Lys Gln Leu Lys Pro Tyr Gln Gly His
                965                 970                 975 aat gtt ttg ttt atc gac aaa gga cag act ggc cat ggc aaa gaa ata        2976
Asn Val Leu Phe Ile Asp Lys Gly Gln Thr Gly His Gly Lys Glu Ile
            980                 985                 990 atc act atg ctt aca caa ctt ggt ttg gta ccc gtt gtt gtt gac tct        3024
Ile Thr Met Leu Thr Gln Leu Gly Leu Val Pro Val Val Val Asp Ser
        995                 1000                1005 gag cag cac act att ctt ctc ggc aat gga aga acc aag gag aag att        3072
Glu Gln His Thr Ile Leu Leu Gly Asn Gly Arg Thr Lys Glu Lys Ile
    1010                1015                1020
```

```
gct tca act tat gac gtg att gtt gtg gac tca att gag tcc gct cga      3120
Ala Ser Thr Tyr Asp Val Ile Val Val Asp Ser Ile Glu Ser Ala Arg
1025                1030                1035                1040 aaa ctg cga tca atc gat gag ttc aag tat att cca att gtt ctc tta      3168
Lys Leu Arg Ser Ile Asp Glu Phe Lys Tyr Ile Pro Ile Val Leu Leu
            1045                1050                1055 gct ccc gtt att cat gtc agc tta aag tct gct ttg gat ctt ggt atc      3216
Ala Pro Val Ile His Val Ser Leu Lys Ser Ala Leu Asp Leu Gly Ile
        1060                1065                1070 act tct tac atg acc act cca tgt tta acg atc gat ctt ggc aat ggt      3264
Thr Ser Tyr Met Thr Thr Pro Cys Leu Thr Ile Asp Leu Gly Asn Gly
    1075                1080                1085 atg att cct gct ttg gag aat cga gct gca ccc tca ttg gcg gac aac      3312
Met Ile Pro Ala Leu Glu Asn Arg Ala Ala Pro Ser Leu Ala Asp Asn
1090                1095                1100 aca aaa tcc ttc gac att ctc ttg gcc gaa gat aac atc gtc aat caa      3360
Thr Lys Ser Phe Asp Ile Leu Leu Ala Glu Asp Asn Ile Val Asn Gln
1105                1110                1115                1120 cgc tta gcg gtg aag att cta gaa aag tat cac cac gtc gtc aca gtc      3408
Arg Leu Ala Val Lys Ile Leu Glu Lys Tyr His His Val Val Thr Val
            1125                1130                1135 gtt ggc aat ggt caa gaa gca cta gat gct atc aag gag aaa cga tac      3456
Val Gly Asn Gly Gln Glu Ala Leu Asp Ala Ile Lys Glu Lys Arg Tyr
        1140                1145                1150 gat gtt att ctc atg gac gtt caa atg cca att atg gga gga ttc gaa      3504
Asp Val Ile Leu Met Asp Val Gln Met Pro Ile Met Gly Gly Phe Glu
    1155                1160                1165 gca acc gct aag att aga gag tac gaa cgg agt ctt gga acg caa aga      3552
Ala Thr Ala Lys Ile Arg Glu Tyr Glu Arg Ser Leu Gly Thr Gln Arg
1170                1175                1180 acg cct att atc gca ctt aca gca cac gct atg ttg ggt gat cgc gaa      3600
Thr Pro Ile Ile Ala Leu Thr Ala His Ala Met Leu Gly Asp Arg Glu
1185                1190                1195                1200 aaa tgt att caa gcc caa atg gat gaa tat ctt tct aag cct ctg aaa      3648
Lys Cys Ile Gln Ala Gln Met Asp Glu Tyr Leu Ser Lys Pro Leu Lys
            1205                1210                1215 caa aat cat ctt att cag acg atc ttg aaa tgt gca acc ctt gga ggt      3696
Gln Asn His Leu Ile Gln Thr Ile Leu Lys Cys Ala Thr Leu Gly Gly
        1220                1225                1230 gca ttg ctc gag aag ggt agg gag gtt agg caa tcc gct aat gaa gag      3744
Ala Leu Leu Glu Lys Gly Arg Glu Val Arg Gln Ser Ala Asn Glu Glu
    1235                1240                1245 agc ccc aat tcg caa aat ggt cct cgc ggt aca cag cat cct gca tca      3792
Ser Pro Asn Ser Gln Asn Gly Pro Arg Gly Thr Gln His Pro Ala Ser
1250                1255                1260 agt ccc aca cca gcc cat atg aga ccg gct atc gaa cct cgt gca tac      3840
Ser Pro Thr Pro Ala His Met Arg Pro Ala Ile Glu Pro Arg Ala Tyr
1265                1270                1275                1280 acg acc act ggc cct ata aat cat gga agt gca gag agt cct tca ctt      3888
Thr Thr Thr Gly Pro Ile Asn His Gly Ser Ala Glu Ser Pro Ser Leu
            1285                1290                1295 gta acg gca gat gct gag gat cca ctt gcg agg ctt cta atg cgt gcg      3936
Val Thr Ala Asp Ala Glu Asp Pro Leu Ala Arg Leu Leu Met Arg Ala
        1300                1305                1310 cat agc agc tag                                                      3948
His Ser Ser
    1315
```

-continued

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:Designed oligonucleotide primer for PCR

<400> SEQUENCE: 15
ggtcaagcag aaagcgaagg cgtccagggc 30

<210> SEQ ID NO 16
<211> LENGTH: 1307
<212> TYPE: PRT
<213> ORGANISM: Magnapotrthe grisea

<400> SEQUENCE: 16

```
Met Ala Asp Ala Ala Thr Leu Ala Ala Val Ala Ala Ile Val Glu Asn
  1               5                  10                  15

Ile Ala Thr Asn Ser Gly Ala Pro Gly Lys Asn Ala Ser Phe Arg Ser
             20                  25                  30

Ser Thr Tyr Val Gln Leu Pro Gly Pro Glu Ser Asp Glu Lys Lys Gln
         35                  40                  45

Leu Glu Arg Glu Leu Ala Ala Leu Val Ile Arg Val Gln Gln Leu Glu
     50                  55                  60

Thr Arg Ala Asn Ala Ala Pro Ala Thr Ile Phe Pro Asp Thr Pro Asn
 65                  70                  75                  80

Glu Thr Ala His Ser Leu Phe Gly Asp Asp Ser Ser Ser Pro Thr Ser
                 85                  90                  95

Ser Ser Ser Gly Arg Glu Pro Lys Arg Leu Lys Ser Ala Ser Ser Thr
            100                 105                 110

Thr Arg Asn Gly Phe Thr Thr Asp Gly Arg Pro Ser Lys Leu Asn Ala
        115                 120                 125

Ile Thr Asp Glu Glu Leu Glu Gly Leu Arg Glu His Val Asp Gly Gln
    130                 135                 140

Ser Arg Leu Leu Asp Ser Gln Arg Ala Glu Leu Asp Gly Val Asn Ala
145                 150                 155                 160

Gln Leu Leu Glu Gln Lys Gln Leu Gln Glu Arg Ala Leu Ala Ile Ile
                165                 170                 175

Glu Gln Glu Arg Val Ala Thr Leu Glu Arg Glu Leu Trp Lys His Gln
            180                 185                 190

Lys Ala Asn Glu Ala Phe Gln Lys Ala Leu Arg Glu Ile Gly Ser Ile
        195                 200                 205

Val Thr Ala Ala Ala Arg Gly Asp Leu Ser Lys Arg Val Lys Ile Asn
    210                 215                 220

Pro Ile Glu Met Asp Pro Glu Ile Thr Thr Phe Lys Arg Thr Met Asn
225                 230                 235                 240

Ala Met Met Asp Gln Leu Gly Val Phe Ser Ser Glu Val Ser Arg Val
                245                 250                 255

Ala Arg Glu Val Gly Thr Glu Gly Ile Leu Gly Gly Gln Ala Gln Ile
            260                 265                 270

Glu Gly Val Asp Gly Thr Trp Lys Glu Leu Thr Asp Asn Val Asn Val
        275                 280                 285

Met Ala Gln Asn Leu Thr Asp Gln Val Arg Glu Ile Ala Ser Val Thr
    290                 295                 300

Thr Ala Val Ala His Gly Asp Leu Thr Gln Lys Ile Glu Ser Ala Ala
305                 310                 315                 320
```

```
Lys Gly Glu Ile Leu Gln Leu Gln Gln Thr Ile Asn Thr Met Val Asp
            325                 330                 335

Gln Leu Arg Thr Phe Ala Ser Glu Val Thr Arg Val Ala Arg Asp Val
        340                 345                 350

Gly Thr Glu Gly Met Leu Gly Gly Gln Ala Asp Val Glu Gly Val Lys
            355                 360                 365

Gly Met Trp Asn Glu Leu Thr Val Asn Val Asn Ala Met Ala Asn Asn
370                 375                 380

Leu Thr Thr Gln Val Arg Asp Ile Ile Asn Val Thr Thr Ala Val Ala
385                 390                 395                 400

Lys Gly Asp Leu Thr Gln Lys Val Gln Ala Glu Cys Arg Gly Glu Ile
                405                 410                 415

Phe Glu Leu Lys Asn Thr Ile Asn Ser Met Val Asp Gln Leu Gln Gln
            420                 425                 430

Phe Ala Arg Glu Val Thr Lys Ile Ala Arg Glu Val Gly Thr Glu Gly
        435                 440                 445

Arg Leu Gly Gly Gln Ala Thr Val His Asp Val Gln Gly Thr Trp Arg
    450                 455                 460

Asp Leu Thr Glu Asn Val Asn Gly Met Ala Met Asn Leu Thr Thr Gln
465                 470                 475                 480

Val Arg Glu Ile Ala Asn Val Thr Ser Ala Val Ala Ala Gly Asp Leu
                485                 490                 495

Ser Lys Lys Ile Arg Val Glu Val Lys Gly Glu Ile Leu Asp Leu Lys
            500                 505                 510

Asn Thr Ile Asn Thr Met Val Asp Arg Leu Gly Thr Phe Ala Phe Glu
        515                 520                 525

Val Ser Lys Val Ala Arg Ala Val Gly Thr Asp Gly Thr Leu Gly Gly
    530                 535                 540

Gln Ala Gln Val Glu Asn Val Glu Gly Lys Trp Lys Asp Leu Thr Glu
545                 550                 555                 560

Asn Val Asn Thr Met Ala Ser Asn Leu Thr Ser Gln Val Arg Gly Ile
                565                 570                 575

Ser Thr Val Thr Gln Ala Ile Ala Asn Gly Asp Met Ser Arg Lys Ile
            580                 585                 590

Asp Val Glu Ala Lys Gly Glu Ile Leu Ile Leu Lys Glu Thr Ile Asn
        595                 600                 605

Asn Met Val Asp Arg Leu Ser Ile Phe Cys Asn Glu Val Gln Arg Val
    610                 615                 620

Ala Lys Asp Val Gly Val Asp Gly Ile Met Gly Gly Gln Ala Asp Val
625                 630                 635                 640

Ala Gly Leu Lys Gly Arg Trp Lys Glu Ile Thr Thr Asp Val Asn Thr
                645                 650                 655

Met Ala Asn Asn Leu Thr Ala Gln Val Arg Ala Phe Gly Asp Ile Thr
            660                 665                 670

Asn Ala Ala Thr Asp Gly Asp Phe Thr Lys Leu Val Glu Val Glu Ala
        675                 680                 685

Ser Gly Glu Met Asp Glu Leu Lys Arg Lys Ile Asn Gln Met Val Tyr
    690                 695                 700

Asn Leu Arg Asp Ser Ile Gln Arg Asn Thr Gln Ala Arg Glu Ala Ala
705                 710                 715                 720

Glu Leu Ala Asn Lys Thr Lys Ser Glu Phe Leu Ala Asn Met Ser His
                725                 730                 735
```

-continued

```
Glu Ile Arg Thr Pro Met Asn Gly Ile Ile Gly Met Thr Gln Leu Thr
            740                 745                 750

Leu Asp Thr Asp Leu Thr Gln Tyr Gln Arg Glu Met Leu Asn Ile Val
        755                 760                 765

Asn Asn Leu Ala Met Ser Leu Leu Thr Ile Ile Asp Asp Ile Leu Asp
    770                 775                 780

Leu Ser Lys Ile Glu Ala Lys Arg Met Val Ile Glu Glu Ile Pro Tyr
785                 790                 795                 800

Thr Leu Arg Gly Thr Val Phe Asn Ala Leu Lys Thr Leu Ala Val Lys
            805                 810                 815

Ala Asn Asp Lys Phe Leu Asp Leu Thr Tyr Arg Val Asp Ser Ser Val
        820                 825                 830

Pro Asp His Val Ile Gly Asp Ser Phe Arg Leu Arg Gln Ile Ile Leu
    835                 840                 845

Asn Leu Val Gly Asn Ala Ile Lys Phe Thr Glu His Gly Glu Val Ser
    850                 855                 860

Leu Thr Ile Gln Lys Gly Asn Asp Val Thr Cys Leu Pro Asn Glu Tyr
865                 870                 875                 880

Met Ile Glu Phe Val Val Ser Asp Thr Gly Ile Gly Ile Pro Thr Asp
            885                 890                 895

Lys Leu Gly Leu Ile Phe Asp Thr Phe Gln Gln Ala Asp Gly Ser Met
        900                 905                 910

Thr Arg Lys Phe Gly Gly Thr Gly Leu Gly Leu Ser Ile Ser Lys Arg
    915                 920                 925

Leu Val Asn Leu Met Gly Gly Asp Val Trp Val Lys Ser Gln Tyr Gly
    930                 935                 940

Lys Gly Ser Ser Phe Tyr Phe Thr Cys Arg Val Arg Leu Ala Asp Val
945                 950                 955                 960

Asp Ile Ser Leu Ile Arg Lys Gln Leu Lys Pro Tyr Lys Gly His Gln
            965                 970                 975

Val Leu Phe Ile Asp Lys Gly Lys Thr Gly His Gly Pro Glu Val Gly
        980                 985                 990

Gln Met Leu Gly Gln Leu Gly Leu Val Pro Ile Val Leu Glu Ser Glu
    995                 1000                1005

Gln Asn His Thr Leu Thr Arg Val Arg Gly Lys Glu Cys Pro Tyr Asp
    1010                1015                1020

Val Ile Val Val Asp Ser Ile Asp Thr Ala Arg Arg Leu Arg Gly Ile
1025                1030                1035                1040

Asp Asp Phe Lys Tyr Leu Pro Ile Val Leu Leu Ala Pro Thr Val His
            1045                1050                1055

Val Ser Leu Lys Ser Cys Leu Asp Leu Gly Ile Thr Ser Tyr Met Thr
        1060                1065                1070

Met Pro Cys Lys Leu Ile Asp Leu Gly Asn Gly Met Val Pro Ala Leu
    1075                1080                1085

Glu Asn Arg Ala Thr Pro Ser Leu Ser Asp Asn Thr Lys Ser Phe Glu
    1090                1095                1100

Ile Leu Leu Ala Glu Asp Asn Thr Val Asn Gln Arg Leu Ala Val Lys
1105                1110                1115                1120

Ile Leu Glu Lys Tyr Asn His Val Val Thr Val Val Ser Asn Gly Ala
            1125                1130                1135

Glu Ala Leu Glu Ala Val Lys Asp Asn Lys Tyr Asp Val Ile Leu Met
        1140                1145                1150
```

```
Asp Val Gln Met Pro Val Met Gly Gly Phe Glu Ala Thr Ala Lys Ile
        1155                1160                1165

Arg Glu Tyr Glu Arg Ser Leu Gly Thr Gln Arg Thr Pro Ile Ile Ala
    1170                1175                1180

Leu Thr Ala His Ala Met Met Gly Asp Arg Glu Lys Cys Ile Glu Ala
1185                1190                1195                1200

Gln Met Asp Glu Tyr Leu Ser Lys Pro Leu Gln Gln Asn His Leu Ile
        1205                1210                1215

Gln Thr Ile Leu Lys Cys Ala Thr Leu Gly Gly Ala Leu Leu Glu Gln
        1220                1225                1230

Asn Arg Glu Arg Glu Leu Glu Leu Ala Arg His Ala Glu His Lys Gly
        1235                1240                1245

Gly Leu Ser Thr Asp Pro Ala Arg Ala Ser Ser Val Met Arg Pro Pro
    1250                1255                1260

Leu His His Arg Pro Val Thr Thr Ala Glu Ser Leu Ser Gly Gly Ala
1265                1270                1275                1280

Glu Ser Pro Ser Leu Met Ala Asn Asp Gly Glu Asp Pro Ile Gln Arg
        1285                1290                1295

Ala Arg Ser Ser Leu Ser Glu Pro Gly Cys Leu
        1300                1305

<210> SEQ ID NO 17
<211> LENGTH: 3924
<212> TYPE: DNA
<213> ORGANISM: Magnapotrthe grisea
<220> FEATURE:
<221> NAME/KEY: CDS
<222> LOCATION: (1)..(3924)

<400> SEQUENCE: 17 atg gcg gac gcg gcg act ctg gca gct gtc gct gcg att gtg gag aat      48
Met Ala Asp Ala Ala Thr Leu Ala Ala Val Ala Ala Ile Val Glu Asn
 1               5                  10                  15 atc gct acc aac tcg ggg gcc cct gga aaa aat gct tca ttt cgc tcc      96
Ile Ala Thr Asn Ser Gly Ala Pro Gly Lys Asn Ala Ser Phe Arg Ser
            20                  25                  30 agt acc tat gtc cag ctt ccc ggt ccg gaa tcc gac gag aag aaa cag     144
Ser Thr Tyr Val Gln Leu Pro Gly Pro Glu Ser Asp Glu Lys Lys Gln
        35                  40                  45 ctc gag cgc gag ctt gcc gcc ctg gtg ata agg gta cag cag ctc gaa     192
Leu Glu Arg Glu Leu Ala Ala Leu Val Ile Arg Val Gln Gln Leu Glu
    50                  55                  60 acc cgt gcc aac gcg gct cct gct aca ata ttc ccc gac aca ccc aac     240
Thr Arg Ala Asn Ala Ala Pro Ala Thr Ile Phe Pro Asp Thr Pro Asn
65                  70                  75                  80 gaa act gca cat tca ctc ttt ggc gat gat agc tcg tcc cct acc agt     288
Glu Thr Ala His Ser Leu Phe Gly Asp Asp Ser Ser Ser Pro Thr Ser
                85                  90                  95 tcg agc tca ggc cgg gag cct aaa cga ctg aag tcg gca tcc agc aca     336
Ser Ser Ser Gly Arg Glu Pro Lys Arg Leu Lys Ser Ala Ser Ser Thr
            100                 105                 110 acg agg aat ggt ttc act acg gac ggt cgt cca tca aag ctc aac gca     384
Thr Arg Asn Gly Phe Thr Thr Asp Gly Arg Pro Ser Lys Leu Asn Ala
        115                 120                 125 atc acc gat gag gag ctc gaa ggc ttg cgc gaa cat gtt gac ggc cag     432
Ile Thr Asp Glu Glu Leu Glu Gly Leu Arg Glu His Val Asp Gly Gln
    130                 135                 140
```

-continued

| | |
|---|---|
| tcc cgg ctg ctc gac agc caa agg gcc gag ctg gac ggc gtc aat gcc<br>Ser Arg Leu Leu Asp Ser Gln Arg Ala Glu Leu Asp Gly Val Asn Ala<br>145                    150                    155                    160 | 480 |
| caa ctc ttg gag cag aag cag ctg caa gag cgc gcc ctt gcc ata atc<br>Gln Leu Leu Glu Gln Lys Gln Leu Gln Glu Arg Ala Leu Ala Ile Ile<br>                    165                    170                    175 | 528 |
| gag cag gaa cgt gta gcc act ttg gag aga gag cta tgg aaa cat caa<br>Glu Gln Glu Arg Val Ala Thr Leu Glu Arg Glu Leu Trp Lys His Gln<br>            180                    185                    190 | 576 |
| aag gcc aac gag gcc ttc cag aag gct ctc cgg gag att gga tcg ata<br>Lys Ala Asn Glu Ala Phe Gln Lys Ala Leu Arg Glu Ile Gly Ser Ile<br>                    195                    200                    205 | 624 |
| gtg acc gct gca gcc cgg ggt gac ctc tct aag agg gtc aag ata aac<br>Val Thr Ala Ala Ala Arg Gly Asp Leu Ser Lys Arg Val Lys Ile Asn<br>      210                    215                    220 | 672 |
| ccg att gag atg gac cct gaa atc acc aca ttc aag agg acc atg aac<br>Pro Ile Glu Met Asp Pro Glu Ile Thr Thr Phe Lys Arg Thr Met Asn<br>225                      230                    235                    240 | 720 |
| gcc atg atg gat caa ctt ggc gtc ttc tct agt gaa gtc tcg cga gtg<br>Ala Met Met Asp Gln Leu Gly Val Phe Ser Ser Glu Val Ser Arg Val<br>                    245                    250                    255 | 768 |
| gca aga gag gtc gga acc gag ggc ata tta ggt gga cag gcc cag atc<br>Ala Arg Glu Val Gly Thr Glu Gly Ile Leu Gly Gly Gln Ala Gln Ile<br>            260                    265                    270 | 816 |
| gag gga gtg gac ggc acg tgg aaa gaa ctg acg gac aat gtc aac gtc<br>Glu Gly Val Asp Gly Thr Trp Lys Glu Leu Thr Asp Asn Val Asn Val<br>                    275                    280                    285 | 864 |
| atg gcg cag aac ctg acc gac caa gtc cgc gaa atc gcc tca gtc act<br>Met Ala Gln Asn Leu Thr Asp Gln Val Arg Glu Ile Ala Ser Val Thr<br>        290                    295                    300 | 912 |
| aca gct gtg gcc cac gga gat ttg acc caa aag att gag agt gcg gcc<br>Thr Ala Val Ala His Gly Asp Leu Thr Gln Lys Ile Glu Ser Ala Ala<br>305                      310                    315                    320 | 960 |
| aag gga gaa atc cta cag ctt caa caa act ata aat acc atg gtg gac<br>Lys Gly Glu Ile Leu Gln Leu Gln Gln Thr Ile Asn Thr Met Val Asp<br>                    325                    330                    335 | 1008 |
| caa cta cgc aca ttt gct tca gag gtt acc cgt gtc gcc cgt gac gtc<br>Gln Leu Arg Thr Phe Ala Ser Glu Val Thr Arg Val Ala Arg Asp Val<br>            340                    345                    350 | 1056 |
| gga acc gag gga atg ctc ggc ggg cag gct gac gtt gaa ggg gtc aag<br>Gly Thr Glu Gly Met Leu Gly Gly Gln Ala Asp Val Glu Gly Val Lys<br>                355                    360                    365 | 1104 |
| ggc atg tgg aat gag ctg acg gtc aac gtc aac gcc atg gcc aac aat<br>Gly Met Trp Asn Glu Leu Thr Val Asn Val Asn Ala Met Ala Asn Asn<br>370                      375                    380 | 1152 |
| tta aca acc caa gtg cgc gac atc atc aac gtt acc aca gcc gtc gca<br>Leu Thr Thr Gln Val Arg Asp Ile Ile Asn Val Thr Thr Ala Val Ala<br>385                      390                    395                    400 | 1200 |
| aag gga gat ctt aca caa aag gtg cag gcg gaa tgt cgc ggc gag att<br>Lys Gly Asp Leu Thr Gln Lys Val Gln Ala Glu Cys Arg Gly Glu Ile<br>                    405                    410                    415 | 1248 |
| ttt gag ctc aag aac acg atc aat tcc atg gtg gac cag ctg cag caa<br>Phe Glu Leu Lys Asn Thr Ile Asn Ser Met Val Asp Gln Leu Gln Gln<br>                    420                    425                    430 | 1296 |
| ttt gct cgc gag gtt acc aag atc gcc aga gag gtt ggt acc gaa gga<br>Phe Ala Arg Glu Val Thr Lys Ile Ala Arg Glu Val Gly Thr Glu Gly<br>                435                    440                    445 | 1344 |
| cgg ctg ggc ggc caa gca act gtt cac gat gta cag gga act tgg cga<br>Arg Leu Gly Gly Gln Ala Thr Val His Asp Val Gln Gly Thr Trp Arg<br>450                      455                    460 | 1392 |

```
gat ctc aca gaa aac gtg aac gga atg gct atg aat ctc acc aca caa      1440
Asp Leu Thr Glu Asn Val Asn Gly Met Ala Met Asn Leu Thr Thr Gln
465                 470                 475                 480 gta cga gag ata gcc aat gtt acc agt gcc gtc gct gca ggc gac cta      1488
Val Arg Glu Ile Ala Asn Val Thr Ser Ala Val Ala Ala Gly Asp Leu
                485                 490                 495 tcc aag aag atc agg gta gag gtc aag ggc gag att ctg gac ctc aaa      1536
Ser Lys Lys Ile Arg Val Glu Val Lys Gly Glu Ile Leu Asp Leu Lys
    500                 505                 510 aat acc atc aac acc atg gtt gac cgc ctc gga act ttc gcc ttc gaa      1584
Asn Thr Ile Asn Thr Met Val Asp Arg Leu Gly Thr Phe Ala Phe Glu
515                 520                 525 gtc agc aaa gta gcc cga gcc gtc ggc aca gat ggc act ctt ggt ggt      1632
Val Ser Lys Val Ala Arg Ala Val Gly Thr Asp Gly Thr Leu Gly Gly
530                 535                 540 cag gct caa gtt gag aat gtg gag ggc aaa tgg aaa gac ctc acc gaa      1680
Gln Ala Gln Val Glu Asn Val Glu Gly Lys Trp Lys Asp Leu Thr Glu
545                 550                 555                 560 aac gtc aac acc atg gcg tca aac ctc act tct cag gtc agg gga ata      1728
Asn Val Asn Thr Met Ala Ser Asn Leu Thr Ser Gln Val Arg Gly Ile
                565                 570                 575 tca acc gtg aca caa gcc atc gcg aac ggt gac atg agc cga aag atc      1776
Ser Thr Val Thr Gln Ala Ile Ala Asn Gly Asp Met Ser Arg Lys Ile
            580                 585                 590 gac gtg gaa gcc aag ggc gag ata cta atc ctc aag gaa act atc aac      1824
Asp Val Glu Ala Lys Gly Glu Ile Leu Ile Leu Lys Glu Thr Ile Asn
        595                 600                 605 aac atg gtt gat cgt ctg tcg ata ttc tgc aat gaa gta caa cga gtc      1872
Asn Met Val Asp Arg Leu Ser Ile Phe Cys Asn Glu Val Gln Arg Val
    610                 615                 620 gca aaa gat gta ggc gtt gat ggc att atg ggg gga caa gcc gac gtt      1920
Ala Lys Asp Val Gly Val Asp Gly Ile Met Gly Gly Gln Ala Asp Val
625                 630                 635                 640 gca ggt ctc aag ggg cga tgg aag gag att acc acc gat gtc aac acc      1968
Ala Gly Leu Lys Gly Arg Trp Lys Glu Ile Thr Thr Asp Val Asn Thr
                645                 650                 655 atg gcc aac aat ctt acg gcg caa gta cgc gct ttc gga gat ata acc      2016
Met Ala Asn Asn Leu Thr Ala Gln Val Arg Ala Phe Gly Asp Ile Thr
            660                 665                 670 aat gcc gct acc gac gga gac ttc acc aag ctg gtc gag gtt gag gcg      2064
Asn Ala Ala Thr Asp Gly Asp Phe Thr Lys Leu Val Glu Val Glu Ala
        675                 680                 685 tcg ggc gaa atg gac gaa ctg aag cgc aag atc aat caa atg gtc tac      2112
Ser Gly Glu Met Asp Glu Leu Lys Arg Lys Ile Asn Gln Met Val Tyr
    690                 695                 700 aat ctc cga gac agt atc caa aga aac acg caa gca aga gaa gcc gca      2160
Asn Leu Arg Asp Ser Ile Gln Arg Asn Thr Gln Ala Arg Glu Ala Ala
705                 710                 715                 720 gaa ttg gcc aac aag acg aag tcg gag ttc ctc gct aac atg tcc cac      2208
Glu Leu Ala Asn Lys Thr Lys Ser Glu Phe Leu Ala Asn Met Ser His
                725                 730                 735 gaa atc cgc aca ccc atg aac ggt atc atc ggc atg aca caa ctt act      2256
Glu Ile Arg Thr Pro Met Asn Gly Ile Ile Gly Met Thr Gln Leu Thr
            740                 745                 750 ctt gat aca gat ttg acg caa tac caa cgc gaa atg ctc aac att gtc      2304
Leu Asp Thr Asp Leu Thr Gln Tyr Gln Arg Glu Met Leu Asn Ile Val
        755                 760                 765 aac aat ctc gcc atg agt ctg ctc acc att atc gac gac atc ctc gat      2352
Asn Asn Leu Ala Met Ser Leu Leu Thr Ile Ile Asp Asp Ile Leu Asp
    770                 775                 780
```

```
ctg tca aag att gag gct aag cgg atg gtt atc gag gag att cca tac    2400
Leu Ser Lys Ile Glu Ala Lys Arg Met Val Ile Glu Glu Ile Pro Tyr
785                 790                 795                 800 acg tta cga gga acg gtc ttc aac gca ctg aag act ttg gcg gtc aag    2448
Thr Leu Arg Gly Thr Val Phe Asn Ala Leu Lys Thr Leu Ala Val Lys
                805                 810                 815 gcg aac gac aag ttt ttg gat ctc acg tac cgt gtg gac agc tca gtt    2496
Ala Asn Asp Lys Phe Leu Asp Leu Thr Tyr Arg Val Asp Ser Ser Val
            820                 825                 830 cct gac cac gtc atc ggt gac tcg ttc cgt ctg cgc cag att atc ctg    2544
Pro Asp His Val Ile Gly Asp Ser Phe Arg Leu Arg Gln Ile Ile Leu
        835                 840                 845 aac ctg gtt ggc aat gcc atc aaa ttc acc gag cat gga gag gtc agc    2592
Asn Leu Val Gly Asn Ala Ile Lys Phe Thr Glu His Gly Glu Val Ser
850                 855                 860 ctt act atc cag aag ggc aac gac gtg acg tgc ctg cca aac gag tac    2640
Leu Thr Ile Gln Lys Gly Asn Asp Val Thr Cys Leu Pro Asn Glu Tyr
865                 870                 875                 880 atg atc gaa ttt gtc gtg tcg gac acg ggc ata gga att cca acg gac    2688
Met Ile Glu Phe Val Val Ser Asp Thr Gly Ile Gly Ile Pro Thr Asp
                885                 890                 895 aaa ctg ggt ctc atc ttc gac aca ttc cag cag gct gat gga tcc atg    2736
Lys Leu Gly Leu Ile Phe Asp Thr Phe Gln Gln Ala Asp Gly Ser Met
            900                 905                 910 aca cgc aag ttt ggc gga acc ggg ctt ggt ctg tct att tcc aag agg    2784
Thr Arg Lys Phe Gly Gly Thr Gly Leu Gly Leu Ser Ile Ser Lys Arg
        915                 920                 925 ctc gtc aac ctc atg ggc ggt gac gtg tgg gtc aag tca caa tac ggc    2832
Leu Val Asn Leu Met Gly Gly Asp Val Trp Val Lys Ser Gln Tyr Gly
930                 935                 940 aag ggc agc tcg ttc tac ttc act tgt cgt gtc cgc ctc gcc gac gtg    2880
Lys Gly Ser Ser Phe Tyr Phe Thr Cys Arg Val Arg Leu Ala Asp Val
945                 950                 955                 960 gat atc tca ctc atc agg aag cag ctg aag cct tac aag gga cac cag    2928
Asp Ile Ser Leu Ile Arg Lys Gln Leu Lys Pro Tyr Lys Gly His Gln
                965                 970                 975 gtc ctg ttc atc gat aag ggc aag act gga cac ggg ccc gag gtg ggg    2976
Val Leu Phe Ile Asp Lys Gly Lys Thr Gly His Gly Pro Glu Val Gly
            980                 985                 990 cag atg ctc ggc cag ctg ggt ttg gtg ccc atc gtg ctg gaa tcc gag    3024
Gln Met Leu Gly Gln Leu Gly Leu Val Pro Ile Val Leu Glu Ser Glu
        995                 1000                1005 caa aat cac acc ctg acg cgg gtg cgc ggc aag gaa tgt ccc tac gac    3072
Gln Asn His Thr Leu Thr Arg Val Arg Gly Lys Glu Cys Pro Tyr Asp
    1010                1015                1020 gtg ata gtt gtc gac tca atc gac aca gcc cgg cgc ctg aga gga att    3120
Val Ile Val Val Asp Ser Ile Asp Thr Ala Arg Arg Leu Arg Gly Ile
1025                1030                1035                1040 gac gac ttc aag tat ctg ccc atc gtt ctc ctg gcg cca act gtc cac    3168
Asp Asp Phe Lys Tyr Leu Pro Ile Val Leu Leu Ala Pro Thr Val His
                1045                1050                1055 gtc agc ctg aaa tcc tgc ttg gac ttg ggt att acc tcg tat atg acg    3216
Val Ser Leu Lys Ser Cys Leu Asp Leu Gly Ile Thr Ser Tyr Met Thr
            1060                1065                1070 atg ccc tgc aag ctc atc gac ctc ggc aat ggt atg gtt ccc gct ctt    3264
Met Pro Cys Lys Leu Ile Asp Leu Gly Asn Gly Met Val Pro Ala Leu
        1075                1080                1085 gag aac cgt gcc aca cca tca cta tca gac aac act aag tcg ttc gaa    3312
Glu Asn Arg Ala Thr Pro Ser Leu Ser Asp Asn Thr Lys Ser Phe Glu
    1090                1095                1100
```

```
att ctg ctg gcc gag gac aac acc gtc aac cag cgc ctg gcc gtt aag      3360
Ile Leu Leu Ala Glu Asp Asn Thr Val Asn Gln Arg Leu Ala Val Lys
1105                1110                1115                1120 att ctt gaa aag tac aac cac gtt gtg acg gta gtc agc aac ggt gct      3408
Ile Leu Glu Lys Tyr Asn His Val Val Thr Val Val Ser Asn Gly Ala
            1125                1130                1135 gaa gct ctt gaa gct gtc aag gat aac aaa tac gat gtg atc ctg atg      3456
Glu Ala Leu Glu Ala Val Lys Asp Asn Lys Tyr Asp Val Ile Leu Met
1140                1145                1150 gat gtt caa atg cct gtc atg ggt gga ttt gag gcg acg gca aag att      3504
Asp Val Gln Met Pro Val Met Gly Gly Phe Glu Ala Thr Ala Lys Ile
            1155                1160                1165 cgt gaa tac gag cgc agc ctg ggc aca cag agg aca cca atc atc gcg      3552
Arg Glu Tyr Glu Arg Ser Leu Gly Thr Gln Arg Thr Pro Ile Ile Ala
    1170                1175                1180 ctt acc gct cac gca atg atg ggc gac cgt gag aag tgt atc gag gcc      3600
Leu Thr Ala His Ala Met Met Gly Asp Arg Glu Lys Cys Ile Glu Ala
1185                1190                1195                1200 cag atg gac gag tac ctg tcg aag cct ctg cag cag aac cac ttg ata      3648
Gln Met Asp Glu Tyr Leu Ser Lys Pro Leu Gln Gln Asn His Leu Ile
            1205                1210                1215 caa aca att ctc aag tgt gca acg ctg ggt ggc gcc ttg ttg gaa caa      3696
Gln Thr Ile Leu Lys Cys Ala Thr Leu Gly Gly Ala Leu Leu Glu Gln
        1220                1225                1230 aat cgt gag cgc gag ctt gaa cta gca agg cat gcc gaa cac aaa gga      3744
Asn Arg Glu Arg Glu Leu Glu Leu Ala Arg His Ala Glu His Lys Gly
            1235                1240                1245 gga ctg tct acg gac ccg gcg agg gca tcg tcg gta atg cgt ccg cca      3792
Gly Leu Ser Thr Asp Pro Ala Arg Ala Ser Ser Val Met Arg Pro Pro
    1250                1255                1260 cta cac cac cga ccg gtg act aca gcc gag tcg ctt tct ggt ggc gcc      3840
Leu His His Arg Pro Val Thr Thr Ala Glu Ser Leu Ser Gly Gly Ala
1265                1270                1275                1280 gaa agc ccc tcg ttg atg gca aat gac ggc gaa gat cca ata caa agg      3888
Glu Ser Pro Ser Leu Met Ala Asn Asp Gly Glu Asp Pro Ile Gln Arg
            1285                1290                1295 gca cgt agc agt ctc tct gaa cca gga tgc cta taa                      3924
Ala Arg Ser Ser Leu Ser Glu Pro Gly Cys Leu
        1300                1305

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 18
acgactagta tggcggacgc cgcgactctg gcag                                34

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 19
ctgaagcttt tataggcatc ctgtttcaga gaga                                34
```

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for Sequencing

<400> SEQUENCE: 20
ttcactacgg acggtcgtcc atcaa                                         25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 21
ttaggtggac aggcccagat cgagg                                         25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 22
tcaagaacac gatcaattcc atggt                                         25

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 23
gtcaaacctc agcttctcag gtcag                                         25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 24
ccaacaagac gaagtcggag ttcct                                         25

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 25
cgtgacgtgc ctgccaaacg agtac                                         25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 26
atagttgtcg actcaatcga cacag                                          25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 27
acagaggaca ccaatcatcg cgctt                                          25

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 28
gttttcccag tcacgac                                                   17

<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence:Designed
      oligonucleotide primer for sequencing

<400> SEQUENCE: 29
caggaaacag ctatgac                                                   17

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 30
aacatgtccc acgarattcg macacc                                         26

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 31
cacgagattc gvacacccat gaaygg                                         26

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 32
aggccttcca aaaggctctv cggga                                          25

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 33
gagatggacc ctgaaatcac mac                                            23

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 34
cagatattct cyagygaagt ytckcg                                         26

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 35
atagcrttgc caacmaggtt magaataa                                       28

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 36
aacttgatgg crttkccaac maggtt                                         26

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 37
ctctgtgaac ttgatrgcrt tkccaac                                        27

```
<210> SEQ ID NO 38
<211> LENGTH: 26
<212> TYPE: DNA
<213> ORGANISM: Artificial Sequence
<220> FEATURE:
<221> NAME/KEY: misc_feature
<222> LOCATION: (12)...(12)
<223> OTHER INFORMATION: n is a, c, g, or t

<400> SEQUENCE: 38
atacactttt cncggtcacc catcat                                              26

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 39
tccatctgbg cctggataca cttttc                                              26

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 40
ggcttvgava gatactcgtc catctg                                              26

<210> SEQ ID NO 41
<211> LENGTH: 1293
<212> TYPE: PRT
<213> ORGANISM: Fusarium oxysporum

<400> SEQUENCE: 41

Met Val Asp Asp Ala Ala Leu Ala Ala Ala Ser Ile Val Ala Ser
 1               5                  10                  15

Ile Ala Pro Asp Pro Arg Leu Pro Asn Ser Ile Pro Val Gly Val Ala
                20                  25                  30

Ser Gln Val Gln Leu Pro Gly Pro Asp Thr Pro Ala Lys Arg Lys Leu
            35                  40                  45

Glu Leu Glu Leu Gln Asn Leu Ala Leu Arg Val Gly Lys Leu Glu Ser
50                  55                  60

Gln Ala Ser Ala Thr Ser Pro Phe Pro Glu Thr Pro Asn Glu Val Ile
65                  70                  75                  80

Asp Thr Leu Phe Gly Glu Glu Ala Gln Ala Val Ala Val Arg Pro Lys
                85                  90                  95

Pro Lys Val Phe His Ala Gln Gly Ser Leu His Ser Pro His Leu Pro
            100                 105                 110

Ser Tyr Gln Leu Thr Glu Glu Ala Leu Glu Gly Leu Arg Glu His Val
        115                 120                 125

Asp Asp Gln Ser Lys Leu Leu Asp Ser Gln Arg Gln Glu Leu Ala Gly
    130                 135                 140

Val Asn Ala Gln Leu Leu Glu Gln Lys Gln Leu Gln Glu Arg Ala Leu
145                 150                 155                 160

Glu Ile Leu Glu Gln Glu Arg Ile Ala Thr Leu Glu Arg Glu Leu Trp
                165                 170                 175
```

```
Lys His Gln Lys Ala Asn Glu Ala Phe Gln Lys Ala Leu Arg Glu Ile
            180                 185                 190
Gly Glu Ile Val Thr Ala Val Ala Arg Gly Asp Leu Thr Met Lys Val
            195                 200                 205
Arg Met Asn Thr Val Glu Met Asp Pro Glu Ile Thr Thr Phe Lys Arg
            210                 215                 220
Thr Ile Asn Ala Met Met Asp Gln Leu Gln Ile Phe Ala Ser Glu Val
225                 230                 235                 240
Ser Arg Val Ala Arg Glu Val Gly Thr Glu Gly Leu Leu Gly Gly Gln
                245                 250                 255
Ala Arg Ile Gly Gly Val Asp Gly Thr Trp Lys Glu Leu Thr Asp Asn
                260                 265                 270
Val Asn Val Met Ala Gln Asn Leu Thr Asp Gln Val Arg Glu Ile Ala
                275                 280                 285
Ser Val Thr Thr Ala Val Ala His Gly Asp Leu Thr Lys Lys Ile Glu
                290                 295                 300
Arg Pro Ala Arg Gly Glu Ile Leu Gln Leu Gln Gln Thr Ile Asn Thr
305                 310                 315                 320
Met Val Asp Gln Leu Arg Thr Phe Ala Ser Glu Val Thr Arg Val Ala
                325                 330                 335
Arg Asp Val Gly Thr Glu Gly Met Leu Gly Gly Gln Ala Asp Val Gly
                340                 345                 350
Gly Val Gln Gly Met Trp Asn Asp Leu Thr Val Asn Val Asn Ala Met
                355                 360                 365
Ala Asn Asn Leu Thr Thr Gln Val Arg Asp Ile Ile Lys Val Thr Thr
                370                 375                 380
Ala Val Ala Lys Gly Asp Leu Thr Gln Lys Val Gln Ala Asp Cys Arg
385                 390                 395                 400
Gly Glu Ile Phe Glu Leu Lys Ser Thr Ile Asn Ser Met Val Asp Gln
                405                 410                 415
Leu Gln Gln Phe Ala Arg Glu Val Thr Lys Ile Ala Arg Glu Val Gly
                420                 425                 430
Thr Glu Gly Arg Leu Gly Gly Gln Ala Thr Val His Asp Val Glu Gly
                435                 440                 445
Thr Trp Arg Asp Leu Thr Glu Asn Val Asn Gly Met Ala Met Asn Leu
                450                 455                 460
Thr Thr Gln Val Arg Glu Ile Ala Lys Val Thr Thr Ala Val Ala Lys
465                 470                 475                 480
Gly Asp Leu Thr Lys Lys Ile Gly Val Glu Val Lys Gly Glu Ile Ala
                485                 490                 495
Glu Leu Lys Asn Thr Ile Asn Gln Met Val Asp Arg Leu Gly Thr Phe
                500                 505                 510
Ala Val Glu Val Ser Lys Val Ala Arg Glu Val Gly Thr Asp Gly Thr
                515                 520                 525
Leu Gly Gly Gln Ala Gln Val Ala Asn Val Glu Gly Lys Trp Lys Asp
                530                 535                 540
Leu Thr Glu Asn Val Asn Thr Met Ala Ser Asn Leu Thr Val Gln Val
545                 550                 555                 560
Arg Ser Ile Ser Thr Val Thr Gln Ala Ile Ala Asn Gly Asp Met Ser
                565                 570                 575
Gln Lys Ile Lys Val Glu Ala Asn Gly Glu Ile Gln Val Leu Lys Glu
                580                 585                 590
```

-continued

```
Thr Ile Asn Asn Met Val Asp Arg Leu Ser Ser Phe Cys Tyr Glu Val
        595                 600                 605

Gln Arg Val Ala Lys Asp Val Gly Val Asp Gly Lys Met Gly Ala Gln
        610                 615                 620

Ala Asp Val Gly Gly Leu Asp Gly Arg Trp Lys Glu Ile Thr Thr Asp
625                 630                 635                 640

Val Asn Thr Met Ala Ser Asn Leu Thr Thr Gln Val Arg Ala Phe Ser
                645                 650                 655

Asp Ile Thr Asn Leu Ala Thr Asp Gly Asp Phe Thr Lys Leu Val Asp
            660                 665                 670

Val Glu Ala Ser Gly Glu Met Asp Glu Leu Lys Arg Lys Ile Asn Gln
        675                 680                 685

Met Ile Ser Asn Leu Arg Asp Ser Ile Gln Arg Asn Thr Gln Ala Arg
        690                 695                 700

Glu Ala Ala Glu Leu Ala Asn Lys Thr Lys Ser Glu Phe Leu Ala Asn
705                 710                 715                 720

Met Ser His Glu Ile Arg Thr Pro Met Asn Gly Ile Ile Gly Met Thr
                725                 730                 735

Gln Leu Thr Leu Asp Thr Asp Leu Thr Gln Tyr Gln Arg Glu Met Leu
            740                 745                 750

Asn Ile Val Asn Asn Leu Ala Asn Ser Leu Leu Thr Ile Ile Asp Asp
        755                 760                 765

Ile Leu Asp Leu Ser Lys Ile Glu Ala Arg Arg Met Val Ile Glu Glu
        770                 775                 780

Ile Pro Tyr Thr Leu Arg Gly Thr Val Phe Asn Ala Leu Lys Thr Leu
785                 790                 795                 800

Ala Val Lys Ala Asn Glu Lys Phe Leu Asp Leu Thr Tyr Lys Val Asp
                805                 810                 815

Ser Ser Val Pro Asp Tyr Val Ile Gly Asp Ser Phe Arg Leu Arg Gln
            820                 825                 830

Ile Ile Leu Asn Leu Val Gly Asn Ala Ile Lys Phe Thr Glu His Gly
        835                 840                 845

Glu Val Ser Leu Thr Ile Lys Glu Ser Met Gly Gln Asn Asn Val Arg
        850                 855                 860

Pro Gly Glu Tyr Ala Val Glu Phe Val Val Glu Asp Thr Gly Ile Gly
865                 870                 875                 880

Ile Ala Gln Asp Lys Leu Asp Leu Ile Phe Asp Thr Phe Gln Gln Ala
                885                 890                 895

Asp Gly Ser Met Thr Arg Lys Phe Gly Gly Thr Gly Leu Gly Leu Ser
            900                 905                 910

Ile Ser Lys Arg Leu Val Asn Leu Met Gly Gly Asp Leu Trp Val Asn
        915                 920                 925

Ser Glu His Gly Lys Gly Ser Glu Phe His Phe Thr Cys Leu Val Lys
        930                 935                 940

Leu Ala Pro Asp Asp Ala Ala Leu Ile Glu Gln Gln Ile Arg Pro Tyr
945                 950                 955                 960

Arg Gly His Gln Val Leu Phe Val Asp Lys Ala Gln Ser Gln Asn Ala
                965                 970                 975

Thr Ser Ile Lys Pro Met Leu Glu Lys Ile Gly Leu Lys Pro Val Val
            980                 985                 990

Val Asp Ser Glu Lys Ser Pro Ala Leu Thr Arg Leu Gln Ser Gly Gly
        995                 1000                1005
```

Ser Leu Pro Tyr Asp Ala Ile Leu Val Asp Ser Ile Asp Thr Ala Arg
    1010                1015                1020

Arg Leu Arg Ala Val Asp Asp Phe Lys Tyr Leu Pro Ile Val Leu Leu
1025                1030                1035                1040

Ala Pro Val Val His Val Ser Leu Lys Ser Cys Leu Asp Leu Gly Ile
                1045                1050                1055

Thr Ser Tyr Met Thr Thr Pro Cys Lys Leu Ile Asp Leu Gly Asn Gly
            1060                1065                1070

Met Ile Pro Ala Leu Glu Asn Arg Ala Thr Pro Ser Leu Ala Asp Asn
        1075                1080                1085

Thr Lys Ser Phe Glu Ile Leu Leu Ala Glu Asp Asn Thr Val Asn Gln
    1090                1095                1100

Arg Leu Ala Val Lys Ile Leu Glu Lys Tyr His His Val Val Thr Val
1105                1110                1115                1120

Val Gly Asn Gly Trp Glu Ala Val Lys Ala Val Gln Ser Lys Lys Phe
                1125                1130                1135

Asp Val Ile Leu Met Asp Val Gln Met Pro Ile Met Gly Gly Phe Glu
            1140                1145                1150

Ala Thr Gly Lys Ile Arg Glu Tyr Glu Arg Gly Ile Gly Ser His Arg
        1155                1160                1165

Thr Pro Ile Ile Ala Leu Thr Ala His Ala Met Met Gly Asp Arg Glu
    1170                1175                1180

Lys Cys Ile Gln Ala Gln Met Asp Glu Tyr Leu Ser Lys Pro Leu Gln
1185                1190                1195                1200

Gln Asn His Leu Ile Gln Thr Ile Leu Lys Cys Ala Thr Leu Gly Gly
                1205                1210                1215

Pro Leu Leu Glu Lys Asn Arg Glu Arg Glu Leu Ala Leu His Ala Glu
            1220                1225                1230

Thr Lys Ser Lys His Lys Glu Gly Gly Gln Gly Leu Leu Arg Pro Thr
        1235                1240                1245

Leu Glu Ser Arg Ser Phe Thr Ser Arg Glu Pro Leu Leu Gly Asn Gly
    1250                1255                1260

Lys Glu Ser Pro Ala Ile Leu Ala Thr Asp Glu Asp Pro Leu Ala Arg
1265                1270                1275                1280

Ala Arg Leu Asp Leu Ser Asp Met Arg Ser Leu Thr Asn
                1285                1290

<210> SEQ ID NO 42
<211> LENGTH: 3882
<212> TYPE: DNA
<213> ORGANISM: Fusarium oxysporum
<220> FEATURE:
<221> NAME/KEY: CDS
<222> LOCATION: (1)..(3882)

<400> SEQUENCE: 42 atg gtt g

-continued

```
gaa ctc gag ctt cag aac ctt gct cta cgt gtt gga aag ctc gag agc      192
Glu Leu Glu Leu Gln Asn Leu Ala Leu Arg Val Gly Lys Leu Glu Ser
 50                  55                  60 cag gcc tca gct acc tct cca ttc cca gaa acg ccc aac gag gtt att      240
Gln Ala Ser Ala Thr Ser Pro Phe Pro Glu Thr Pro Asn Glu Val Ile
 65                  70                  75                  80 gac act ctt ttt ggc gaa gag gct cag gct gtg gcg gtc cgt ccc aag      288
Asp Thr Leu Phe Gly Glu Glu Ala Gln Ala Val Ala Val Arg Pro Lys
                 85                  90                  95 cct aaa gtc ttt cac gcc caa ggt agc ctg cac tct ccg cat ctg cca      336
Pro Lys Val Phe His Ala Gln Gly Ser Leu His Ser Pro His Leu Pro
            100                 105                 110 tct tat cag ctg acc gaa gaa gcc ctt gaa gga ctt cga gaa cat gtg      384
Ser Tyr Gln Leu Thr Glu Glu Ala Leu Glu Gly Leu Arg Glu His Val
        115                 120                 125 gac gac caa tcc aag tta ctc gat agt cag cgc cag gag ctc gct ggt      432
Asp Asp Gln Ser Lys Leu Leu Asp Ser Gln Arg Gln Glu Leu Ala Gly
130                 135                 140 gta aat gct cag ctc ttg gag cag aag cag cta caa gag cga gcc ctc      480
Val Asn Ala Gln Leu Leu Glu Gln Lys Gln Leu Gln Glu Arg Ala Leu
145                 150                 155                 160 gag atc ctc gag cag gaa cgt att gct act ctg gag cgc gag ctt tgg      528
Glu Ile Leu Glu Gln Glu Arg Ile Ala Thr Leu Glu Arg Glu Leu Trp
                165                 170                 175 aag cat cag aaa gcc aac gag gct ttc caa aag gct cta cga gaa att      576
Lys His Gln Lys Ala Asn Glu Ala Phe Gln Lys Ala Leu Arg Glu Ile
            180                 185                 190 gga gag att gtt aca gcc gtt gct cgc ggt gat ttg acc atg aag gtt      624
Gly Glu Ile Val Thr Ala Val Ala Arg Gly Asp Leu Thr Met Lys Val
        195                 200                 205 cgc atg aac act gtt gaa atg gac cct gaa atc aca aca ttc aag cgc      672
Arg Met Asn Thr Val Glu Met Asp Pro Glu Ile Thr Thr Phe Lys Arg
210                 215                 220 act atc aac gct atg atg gac cag ctg caa ata ttt gct agc gaa gtc      720
Thr Ile Asn Ala Met Met Asp Gln Leu Gln Ile Phe Ala Ser Glu Val
225                 230                 235                 240 tcg cga gtc gct cgt gaa gtc ggt acc gaa gga ttg ctt ggt ggc caa      768
Ser Arg Val Ala Arg Glu Val Gly Thr Glu Gly Leu Leu Gly Gly Gln
                245                 250                 255 gcc cgt atc ggc ggc gtc gac gga aca tgg aag gaa ttg act gac aac      816
Ala Arg Ile Gly Gly Val Asp Gly Thr Trp Lys Glu Leu Thr Asp Asn
            260                 265                 270 gta aac gtt atg gcc cag aat ctt act gat caa gtg agg gag ata gca      864
Val Asn Val Met Ala Gln Asn Leu Thr Asp Gln Val Arg Glu Ile Ala
        275                 280                 285 tcg gtt acc acc gcc gtg gcc cac ggc gat ctg act aaa aag atc gaa      912
Ser Val Thr Thr Ala Val Ala His Gly Asp Leu Thr Lys Lys Ile Glu
290                 295                 300 cga cct gcc aga ggc gag ata ttg caa tta caa caa acg att aac acc      960
Arg Pro Ala Arg Gly Glu Ile Leu Gln Leu Gln Gln Thr Ile Asn Thr
305                 310                 315                 320 atg gtg gac caa tta cga aca ttt gct tct gaa gtc aca cgt gta gcg     1008
Met Val Asp Gln Leu Arg Thr Phe Ala Ser Glu Val Thr Arg Val Ala
                325                 330                 335 aga gat gtc ggg acc gaa ggc atg tta ggc ggg caa gcc gat gtt ggg     1056
Arg Asp Val Gly Thr Glu Gly Met Leu Gly Gly Gln Ala Asp Val Gly
            340                 345                 350 gga gtg cag ggc atg tgg aac gat ctc acc gtc aat gtc aat gcc atg     1104
Gly Val Gln Gly Met Trp Asn Asp Leu Thr Val Asn Val Asn Ala Met
        355                 360                 365
```

```
                                                      -continued
gcc aac aac ttg acg act caa gtg cgc gac att atc aag gtt acc aca       1152
Ala Asn Asn Leu Thr Thr Gln Val Arg Asp Ile Ile Lys Val Thr Thr
    370                 375                 380 gct gtc gcc aag gga gat ctt aca caa aag gtc caa gcc gat tgc agg       1200
Ala Val Ala Lys Gly Asp Leu Thr Gln Lys Val Gln Ala Asp Cys Arg
385                 390                 395                 400 gga gag ata ttc gag ctc aag tca acc atc aac tcc atg gtt gac cag       1248
Gly Glu Ile Phe Glu Leu Lys Ser Thr Ile Asn Ser Met Val Asp Gln
                405                 410                 415 ctg caa cag ttc gcc cgc gag gtt acc aag att gcc cgt gaa gtc gga       1296
Leu Gln Gln Phe Ala Arg Glu Val Thr Lys Ile Ala Arg Glu Val Gly
            420                 425                 430 acc gaa gga cgc ctg gga ggg cag gcc act gtg cat gat gtt gaa ggc       1344
Thr Glu Gly Arg Leu Gly Gly Gln Ala Thr Val His Asp Val Glu Gly
        435                 440                 445 acc tgg agg gat ctg acg gag aac gtc aac ggc atg gcc atg aac ttg       1392
Thr Trp Arg Asp Leu Thr Glu Asn Val Asn Gly Met Ala Met Asn Leu
450                 455                 460 acc act caa gtg cga gaa att gcc aag gtt aca aca gct gtc gcc aaa       1440
Thr Thr Gln Val Arg Glu Ile Ala Lys Val Thr Thr Ala Val Ala Lys
465                 470                 475                 480 ggt gac ttg aca aag aag att ggg gtt gag gtc aag ggt gaa att gca       1488
Gly Asp Leu Thr Lys Lys Ile Gly Val Glu Val Lys Gly Glu Ile Ala
                485                 490                 495 gaa ctg aag aac acc att aac cag atg gtg gat cgt ctt ggt acg ttt       1536
Glu Leu Lys Asn Thr Ile Asn Gln Met Val Asp Arg Leu Gly Thr Phe
            500                 505                 510 gcc gtt gag gtg agc aag gta gcc agg gaa gta ggc aca gat gga aca       1584
Ala Val Glu Val Ser Lys Val Ala Arg Glu Val Gly Thr Asp Gly Thr
        515                 520                 525 ttg ggt gga cag gct caa gtt gcc aat gtt gaa ggt aaa tgg aag gat       1632
Leu Gly Gly Gln Ala Gln Val Ala Asn Val Glu Gly Lys Trp Lys Asp
530                 535                 540 ctc aca gaa aac gtc aac aca atg gcg tca aat ctc aca gtc cag gtc       1680
Leu Thr Glu Asn Val Asn Thr Met Ala Ser Asn Leu Thr Val Gln Val
545                 550                 555                 560 cga agt atc tca aca gtt act caa gcc att gcg aac ggc gac atg agc       1728
Arg Ser Ile Ser Thr Val Thr Gln Ala Ile Ala Asn Gly Asp Met Ser
                565                 570                 575 cag aag atc aag gtc gaa gca aat gga gag ata caa gtg ctg aaa gaa       1776
Gln Lys Ile Lys Val Glu Ala Asn Gly Glu Ile Gln Val Leu Lys Glu
            580                 585                 590 acc atc aat aac atg gtt gac cgt ttg tct agc ttc tgt tac gaa gtg       1824
Thr Ile Asn Asn Met Val Asp Arg Leu Ser Ser Phe Cys Tyr Glu Val
        595                 600                 605 cag cga gtt gcc aag gat gtg ggt gtt gat gga aag atg ggt gct caa       1872
Gln Arg Val Ala Lys Asp Val Gly Val Asp Gly Lys Met Gly Ala Gln
610                 615                 620 gcc gac gta ggt ggt cta gac ggc cgc tgg aaa gag atc acc aca gat       1920
Ala Asp Val Gly Gly Leu Asp Gly Arg Trp Lys Glu Ile Thr Thr Asp
625                 630                 635                 640 gtc aac aca atg gct agt aac ctg act aca caa gtg cgc gcc ttc tca       1968
Val Asn Thr Met Ala Ser Asn Leu Thr Thr Gln Val Arg Ala Phe Ser
                645                 650                 655 gat ata acc aac ttg gcc acc gac ggg gat ttc acc aag cta gtc gac       2016
Asp Ile Thr Asn Leu Ala Thr Asp Gly Asp Phe Thr Lys Leu Val Asp
            660                 665                 670 gtc gaa gca tcg ggt gag atg gac gag ctc aag cgc aag atc aac cag       2064
Val Glu Ala Ser Gly Glu Met Asp Glu Leu Lys Arg Lys Ile Asn Gln
        675                 680                 685
```

```
atg att tca aat ctg cgc gat tct att cag cgt aat act cag gcc agg      2112
Met Ile Ser Asn Leu Arg Asp Ser Ile Gln Arg Asn Thr Gln Ala Arg
690             695                 700 gaa gct gcc gaa ctt gcc aac aag acc aag tca gag ttc ctc gcc aac      2160
Glu Ala Ala Glu Leu Ala Asn Lys Thr Lys Ser Glu Phe Leu Ala Asn
705             710                 715                 720 atg tcc cat gaa att cga acg ccg atg aac ggt atc atc gga atg act      2208
Met Ser His Glu Ile Arg Thr Pro Met Asn Gly Ile Ile Gly Met Thr
                725                 730                 735 caa ctg aca ttg gac acc gat ctg act caa tat cag agg gag atg ctt      2256
Gln Leu Thr Leu Asp Thr Asp Leu Thr Gln Tyr Gln Arg Glu Met Leu
        740                 745                 750 aac att gtc aat aat ctt gcc aat agc ctc ttg acg ata att gac gat      2304
Asn Ile Val Asn Asn Leu Ala Asn Ser Leu Leu Thr Ile Ile Asp Asp
    755                 760                 765 atc ttg gat ctt tcc aag att gaa gct cgg aga atg gtc att gag gag      2352
Ile Leu Asp Leu Ser Lys Ile Glu Ala Arg Arg Met Val Ile Glu Glu
770             775                 780 att cct tac aca ctg cgt gga acc gtc ttc aat gcc ctc aag act ctc      2400
Ile Pro Tyr Thr Leu Arg Gly Thr Val Phe Asn Ala Leu Lys Thr Leu
785             790                 795                 800 gct gtc aag gca aat gag aag ttc ttg gat ctc acc tac aag gtc gat      2448
Ala Val Lys Ala Asn Glu Lys Phe Leu Asp Leu Thr Tyr Lys Val Asp
                805                 810                 815 agc tcc gtg cct gac tac gtt att ggc gac tcc ttc cgt ctc aga caa      2496
Ser Ser Val Pro Asp Tyr Val Ile Gly Asp Ser Phe Arg Leu Arg Gln
        820                 825                 830 att atc ctc aac ctt gtt ggc aat gct atc aag ttc aca gag cat ggt      2544
Ile Ile Leu Asn Leu Val Gly Asn Ala Ile Lys Phe Thr Glu His Gly
    835                 840                 845 gag gtc agc cta acg atc aag gag agc atg ggg caa aac aat gtc cga      2592
Glu Val Ser Leu Thr Ile Lys Glu Ser Met Gly Gln Asn Asn Val Arg
850             855                 860 cct gga gag tat gcg gtt gag ttt gtc gtg gag gac acg ggc ata gga      2640
Pro Gly Glu Tyr Ala Val Glu Phe Val Val Glu Asp Thr Gly Ile Gly
865             870                 875                 880 atc gcc caa gat aaa ctg gat ttg atc ttc gac acg ttc caa caa gcg      2688
Ile Ala Gln Asp Lys Leu Asp Leu Ile Phe Asp Thr Phe Gln Gln Ala
                885                 890                 895 gat ggt tcc atg acg cgc aag ttt ggc gga aca ggt cta ggt cta tct      2736
Asp Gly Ser Met Thr Arg Lys Phe Gly Gly Thr Gly Leu Gly Leu Ser
        900                 905                 910 att tcg aaa cga ctc gtc aat ctc atg ggt ggt gat ctc tgg gta aac      2784
Ile Ser Lys Arg Leu Val Asn Leu Met Gly Gly Asp Leu Trp Val Asn
    915                 920                 925 agt gaa cat ggc aag ggc agt gaa ttt cac ttc aca tgc tta gtc aag      2832
Ser Glu His Gly Lys Gly Ser Glu Phe His Phe Thr Cys Leu Val Lys
930             935                 940 ctt gct cct gac gat gct gct ctg atc gag caa cag atc cgc ccc tac      2880
Leu Ala Pro Asp Asp Ala Ala Leu Ile Glu Gln Gln Ile Arg Pro Tyr
945             950                 955                 960 cga ggt cat caa gtg cta ttc gtc gac aag gcc cag tcg cag aac gcc      2928
Arg Gly His Gln Val Leu Phe Val Asp Lys Ala Gln Ser Gln Asn Ala
                965                 970                 975 acc tca atc aag cct atg ctt gag aag atc ggg ctg aag cct gtc gtt      2976
Thr Ser Ile Lys Pro Met Leu Glu Lys Ile Gly Leu Lys Pro Val Val
        980                 985                 990 gtg gat tcg gag aag agt cct gcg ctg act cgt ctt caa agc ggt ggc      3024
Val Asp Ser Glu Lys Ser Pro Ala Leu Thr Arg Leu Gln Ser Gly Gly
    995                 1000                1005
```

```
tcc ctt ccc tat gat gct atc ctc gtc gat tcc atc gac act gcg aga      3072
Ser Leu Pro Tyr Asp Ala Ile Leu Val Asp Ser Ile Asp Thr Ala Arg
    1010                1015                1020 agg tta aga gcc gtg gac gat ttc aag tac ctt cct atc gtc ttg ctg      3120
Arg Leu Arg Ala Val Asp Asp Phe Lys Tyr Leu Pro Ile Val Leu Leu
1025                1030                1035                1040 gca cca gtt gtt cac gtt agt ctg aag tcg tgc ttg gat ctg gga att      3168
Ala Pro Val Val His Val Ser Leu Lys Ser Cys Leu Asp Leu Gly Ile
                1045                1050                1055 acg tcg tat atg acc acg cca tgc aag ctc att gat cta gga aat ggc      3216
Thr Ser Tyr Met Thr Thr Pro Cys Lys Leu Ile Asp Leu Gly Asn Gly
    1060                1065                1070 atg att ccg gct ctc gag aac cgg gcg aca cct tca ctc gct gac aac      3264
Met Ile Pro Ala Leu Glu Asn Arg Ala Thr Pro Ser Leu Ala Asp Asn
1075                1080                1085 acg aaa tct ttc gaa att ctg ctc gcc gaa gac aac acc gtc aac caa      3312
Thr Lys Ser Phe Glu Ile Leu Leu Ala Glu Asp Asn Thr Val Asn Gln
                1090                1095                1100 cga tta gca gtg aaa att ctc gag aag tat cac cat gtg gta aca gtg      3360
Arg Leu Ala Val Lys Ile Leu Glu Lys Tyr His His Val Val Thr Val
1105                1110                1115                1120 gtt ggt aac ggc tgg gaa gct gtc aaa gcc gtc caa agc aag aaa ttc      3408
Val Gly Asn Gly Trp Glu Ala Val Lys Ala Val Gln Ser Lys Lys Phe
                1125                1130                1135 gat gtc att ctt atg gat gta caa atg ccg atc atg gga ggc ttc gaa      3456
Asp Val Ile Leu Met Asp Val Gln Met Pro Ile Met Gly Gly Phe Glu
    1140                1145                1150 gcc acg ggc aag att cga gaa tac gaa cgt ggc ata ggg agc cac cgc      3504
Ala Thr Gly Lys Ile Arg Glu Tyr Glu Arg Gly Ile Gly Ser His Arg
1155                1160                1165 aca ccc atc att gct cta acg gcc cac gcc atg atg ggt gac cga gag      3552
Thr Pro Ile Ile Ala Leu Thr Ala His Ala Met Met Gly Asp Arg Glu
    1170                1175                1180 aag tgt atc caa gct cag atg gac gag tat ttg tcc aaa ccc ttg cag      3600
Lys Cys Ile Gln Ala Gln Met Asp Glu Tyr Leu Ser Lys Pro Leu Gln
1185                1190                1195                1200 caa aac cat ctc atc cag acg atc ctc aaa tgc gcg acg ctc ggc ggc      3648
Gln Asn His Leu Ile Gln Thr Ile Leu Lys Cys Ala Thr Leu Gly Gly
                1205                1210                1215 cct ttg ctt gaa aag aat cgt gaa cgg gaa ctg gca ctt cat gcc gag      3696
Pro Leu Leu Glu Lys Asn Arg Glu Arg Glu Leu Ala Leu His Ala Glu
    1220                1225                1230 acg aaa tcg aag cac aag gag ggg gga cag ggt ctg cta cga ccc aca      3744
Thr Lys Ser Lys His Lys Glu Gly Gly Gln Gly Leu Leu Arg Pro Thr
1235                1240                1245 ctc gag agc cgc tca ttc aca agt cga gaa cct ctg ttg gga aat ggc      3792
Leu Glu Ser Arg Ser Phe Thr Ser Arg Glu Pro Leu Leu Gly Asn Gly
    1250                1255                1260 aag gag agc cct gcc att ctg gct act gat gag gat ccc ctg gca aga      3840
Lys Glu Ser Pro Ala Ile Leu Ala Thr Asp Glu Asp Pro Leu Ala Arg
1265                1270                1275                1280 gca cgt ctt gac ctc tct gat atg cga agt ctt acc aac taa              3882
Ala Arg Leu Asp Leu Ser Asp Met Arg Ser Leu Thr Asn
                1285                1290

<210> SEQ ID NO 43
<211> LENGTH: 29
<212> TYPE: DNA
<213> ORGANISM: Artificial Sequence
```

```
<220> FEATURE:
<223> OTHER INFORMATION: Description of Artificial Sequence : Designed
      oligonucleotide primer for PCR

<400> SEQUENCE: 43
tcagatcgcc gtgggccacg gcggtggta                                          29

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 44
cgacaaggcc cagtcgcaga acgccacc                                           28

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 45
aagtttggcg gaacaggtct aggtctatc                                          29

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 46
tgccagcaag acgataggaa ggtacttga                                          29

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 47
cctcaccatg ctctgtgaac ttgatagc                                           28

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 48
gccattgtgt tgacatctgt ggtgatctc                                          29

<210> SEQ ID NO 49
<211> LENGTH: 30
<212> TYPE: DNA
<213> ORGANISM: Artificial Sequence
```

```
<220> FEATURE:
<223> OTHER INFORMATION: Description of Artificial Sequence : Designed
      oligonucleotide primer for DNA sequencing

<400> SEQUENCE: 49
gatgcttcca aagctcgcgc tccagagtag                                          30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 50
ccgaagacaa caccgtcaac caacgattag                                          30

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 51
ggaccctgaa atcacaacat tcaagcgc                                            28

<210> SEQ ID NO 52
<211> LENGTH: 32
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 52
tgcactagta tggttgacga cgcggccctc gc                                       32

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 53
gagctgcagt tagttggtaa gacttcgcat atc                                      33

<210> SEQ ID NO 54
<211> LENGTH: 16
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 54
gtaaaacgac ggccag                                                         16

<210> SEQ ID NO 55
<211> LENGTH: 1307
<212> TYPE: PRT
<213> ORGANISM: Mycospharella tritici
```

```
<220> FEATURE:
<221> NAME/KEY: misc_feature
<222> LOCATION: (956)..(956)
<223> OTHER INFORMATION: Xaa is any amino acid
<220> FEATURE:
<221> NAME/KEY: misc_feature
<222> LOCATION: (1213)..(1213)
<223> OTHER INFORMATION: Xaa is any amino acid

<400> SEQUENCE: 55
```

Met Leu Gln Glu Glu Thr Ser Ala Ala Val Ala Ser Ile Leu Ser Asn
1               5                   10                  15

Phe Ala Lys Gln Tyr Ala Pro Leu Glu Ala Asp Ser Phe Pro Ala Lys
            20                  25                  30

Ala Ile Ala Asn Gly Ile Lys Asn Thr Lys Ile Ala Leu Pro Gly Asp
        35                  40                  45

Asp Ser Val Glu Lys Arg Thr Leu Glu Arg Glu Leu Thr Ser Leu Ala
    50                  55                  60

Thr Arg Ile Gln Phe Leu Glu Ala Arg Ala Thr Ser Gly Thr Ser Ser
65                  70                  75                  80

Leu Pro Ile Thr Pro Asn Glu Pro Leu Ser Ser Ala Phe Ser Glu Asp
                85                  90                  95

Thr Ser Ser Pro Arg Ser Ala Ala Asn Gln His Arg Gln Arg Ser Ser
            100                 105                 110

Ser Trp Val Asn Asn Leu Leu Ala Lys Ser Glu Gly Glu Pro His Pro
        115                 120                 125

Arg Gln Leu Thr Glu Glu Gln Phe Ser Phe Leu Arg Glu His Ile Asp
    130                 135                 140

Gln Gln Ala Gln Glu Ile Arg Thr Gln Lys Glu Phe Ile Asp Gly Ile
145                 150                 155                 160

Lys Ser Gln Leu Thr His Gln Thr Ala Thr Lys Ala Ala Leu Asp
                165                 170                 175

Thr Leu Gly Asn Ser Gln Ser Ile Glu Gln Leu Lys Arg Glu Ile Glu
                180                 185                 190

Lys Asn Ala Gln Ile Asn Ala Thr Tyr Gln Lys Val Leu Arg Glu Ile
            195                 200                 205

Gly Thr Ile Ile Thr Ala Val Ala Asn Gly Asp Leu Ser Lys Lys Val
    210                 215                 220

Leu Ile His Ala Thr Glu Lys Asp Pro Glu Ile Ala Arg Phe Lys His
225                 230                 235                 240

Thr Ile Asn Lys Met Val Asp Gln Leu Gln Glu Phe Ala Ser Gln Val
                245                 250                 255

Thr His Leu Ala Lys Glu Val Gly Thr Glu Gly Arg Leu Gly Gly Gln
            260                 265                 270

Ala Val Val Pro Gly Val Asp Gly Ile Trp Ala Glu Leu Thr Gln Asn
        275                 280                 285

Val Asn Val Met Ala Gln Asn Leu Thr Asp Gln Val Arg Glu Ile Ala
    290                 295                 300

Val Val Thr Thr Ala Val Ala Gln Gly Asp Leu Ser Arg Lys Ile Gln
305                 310                 315                 320

Arg Pro Ala Arg Gly Glu Ile Leu Gln Leu Gln Gln Thr Ile Asn Ser
                325                 330                 335

Met Val Gly Gln Leu Arg Thr Phe Ala Thr Glu Val Thr Arg Val Ser
            340                 345                 350

Arg Asp Val Gly Thr Glu Gly Val Leu Gly Gly Gln Ala Gln Ile Glu
        355                 360                 365

-continued

```
Gly Val Gln Gly Met Trp Ser Asp Leu Thr Val Asn Ala Met
    370                 375                 380
Ala Asn Asn Leu Thr Ala Gln Val Arg Asp Ile Ala Glu Val Thr Thr
385                 390                 395                 400
Ala Val Ala Arg Gly Asp Leu Thr Gln Gln Val Lys Ala Gln Cys Lys
                405                 410                 415
Gly Glu Ile Leu Ala Leu Lys Thr Thr Ile Asn Ser Met Val His Gln
            420                 425                 430
Leu Arg Gln Phe Ala His Glu Val Thr Lys Ile Ala Arg Glu Val Gly
        435                 440                 445
Thr Glu Gly Arg Leu Gly Gln Ala Thr Val His Gly Val Glu Gly
    450                 455                 460
Thr Trp Lys Asp Leu Thr Glu Asn Val Asn Gly Met Ala Met Asn Leu
465                 470                 475                 480
Thr Thr Gln Val Arg Glu Ile Ala Glu Val Thr Thr Ala Val Ala Gln
                485                 490                 495
Gly Asp Leu Ser Lys Lys Val Glu Ala Glu Val Lys Gly Glu Ile Leu
            500                 505                 510
Ala Leu Lys Ser Thr Ile Asn Ser Met Val Asp Arg Leu Gly Thr Phe
        515                 520                 525
Ala Phe Glu Val Ser Lys Val Ala Arg Glu Val Gly Thr Glu Gly Val
    530                 535                 540
Leu Gly Gly Gln Ala Glu Val Ala Asn Val Glu Gly Lys Trp Lys Asp
545                 550                 555                 560
Leu Thr Asp Asn Val Asn Thr Met Ala Asn Asn Leu Thr Gly Gln Val
                565                 570                 575
Arg Ser Ile Ser Asp Val Thr Gln Ala Ile Ala Arg Gly Asp Met Ser
            580                 585                 590
Gln Arg Ile Lys Val His Ala Gln Gly Glu Ile Gln Thr Leu Lys Asp
        595                 600                 605
Thr Ile Asn Asp Met Val Thr Arg Leu Asp Ala Trp Ser Leu Ala Val
    610                 615                 620
Lys Arg Val Ala Arg Asp Val Gly Val Asp Gly Lys Met Gly Gly Gln
625                 630                 635                 640
Ala Glu Val Glu Gly Ile Thr Gly Arg Trp Lys Glu Ile Thr Thr Asp
                645                 650                 655
Val Asn Ile Met Ala Gln Asn Leu Thr Ser Gln Val Arg Ala Phe Ala
            660                 665                 670
Asp Ile Thr His Ala Ala Met Lys Gly Asp Phe Thr Lys Met Ile Asn
        675                 680                 685
Val Glu Ala Ser Gly Glu Met Asn Glu Leu Lys Asn Lys Ile Asn Lys
    690                 695                 700
Met Val Leu Asn Leu Arg Glu Ser Ile Gln Lys Asn Asn Gln Ala Arg
705                 710                 715                 720
Glu Ala Ala Glu Leu Ala Asn Lys Thr Lys Ser Glu Phe Leu Ala Asn
                725                 730                 735
Met Ser His Glu Ile Arg Thr Pro Met Asn Gly Ile Ile Gly Met Thr
            740                 745                 750
Gln Leu Thr Leu Asp Thr Glu Leu Glu Gln Asn Gln Arg Asp Met Leu
        755                 760                 765
Asn Ile Val Phe Ser Leu Ala Asn Ser Leu Leu Thr Ile Ile Asp Asp
    770                 775                 780
```

-continued

```
Ile Leu Asp Ile Ser Lys Ile Glu Ala Asn Arg Met Ile Leu Glu Glu
785                 790                 795                 800

Glu Pro Phe Ser Leu Arg Gly Leu Val Phe Asn Ser Leu Lys Ser Leu
            805                 810                 815

Ala Val Arg Ala Asn Glu Lys Asp Ile Ser Leu Val Tyr Asp Thr Asp
        820                 825                 830

Ser Ser Val Pro Asp Tyr Ile Val Gly Asp Ser Phe Arg Leu Arg Gln
    835                 840                 845

Ile Ile Leu Asn Leu Ala Gly Asn Ala Ile Lys Phe Thr Glu His Gly
850                 855                 860

Glu Val Arg Val Lys Ile Phe Ser Asp His Ser Thr Arg Cys Thr Asp
865                 870                 875                 880

Ser Glu Val Val Lys Phe Ala Val Ser Asp Thr Gly Ile Gly Ile
            885                 890                 895

His Ser Asn Lys Leu Asp Leu Ile Phe Asp Thr Phe Gln Gln Ala Asp
        900                 905                 910

Gly Ser Thr Thr Arg Lys Phe Gly Gly Thr Gly Leu Gly Leu Ser Ile
    915                 920                 925

Ser Arg Arg Leu Val Thr Leu Met Arg Gly Lys Met Trp Val Glu Ser
930                 935                 940

Asn Tyr Gly Ser Gly Ser Thr Phe Phe Phe Thr Xaa Val Val Arg Leu
945                 950                 955                 960

Gly Asn Pro Asp Val Ala Lys Ile Met Pro Gln Leu Gln Gln Tyr Arg
            965                 970                 975

Lys His Asn Val Leu Phe Val Asp Asn Gly Asn Thr Asp Ser Ser Glu
        980                 985                 990

Glu Ile Ala Ala Gly Ile Arg Ala Leu Asp Leu Val Pro Cys Val Val
    995                 1000                1005

Gly Lys Gly Lys Val Pro His Ser Glu Ile Ser Pro Asp Asp Gln Tyr
1010                1015                1020

Asp Cys Val Ile Ile Asp Asn Ser Glu Thr Ala Gln Lys Leu Arg Ser
1025                1030                1035                1040

Leu Glu Arg Phe Lys Tyr Ile Pro Ile Val Met Val Ala Pro Ala Ile
            1045                1050                1055

Ser Val Asn Phe Lys Thr Ala Leu Glu Asn Gly Ile Ser Ser Tyr Met
        1060                1065                1070

Thr Thr Pro Cys Leu Pro Ile Asp Leu Gly Asn Ala Leu Val Pro Ala
    1075                1080                1085

Leu Glu Gly Arg Ala Ala Pro Met Ser Ala Asp His Ser Arg Thr Phe
1090                1095                1100

Asp Ile Leu Leu Ala Glu Asp Asn Ala Val Asn Gln Lys Leu Ala Val
1105                1110                1115                1120

Lys Ile Leu Thr Lys His Asn His Thr Val Thr Val Ala Asn Asn Gly
            1125                1130                1135

Leu Glu Ala Phe Glu Ala Ile Arg Lys Lys Arg Phe Asp Val Val Leu
        1140                1145                1150

Met Asp Val Gln Met Pro Val Met Gly Gly Phe Glu Ala Thr Ala Lys
    1155                1160                1165

Ile Arg Glu Tyr Glu Arg Thr His Glu Leu Ala Arg Ser Pro Ile Ile
1170                1175                1180

Ala Leu Thr Ala His Ala Met Leu Gly Asp Arg Glu Lys Cys Ile Gln
1185                1190                1195                1200
```

```
Ala Gln Met Asp Glu Tyr Leu Ser Lys Pro Leu Lys Xaa Asn Gln Leu
            1205                1210                1215

Ile Gln Thr Ile Leu Lys Cys Ala Thr Leu Gly Gly Ala Leu Leu Asp
        1220                1225                1230

Arg Arg Asn Asp Gly Arg Gly Leu Leu Met Glu Glu Asp Lys Pro Val
    1235                1240                1245

Ser Asp Asn Ser Ser Leu Pro Ala Asp His Asn Arg Leu Leu Thr Pro
1250                1255                1260

Pro Lys Arg Pro Gly Val Asp Arg Gly Tyr Thr Glu Asn Gly Pro Pro
1265                1270                1275                1280

Gly Leu Glu Ser Pro Ala Ile Val Thr Asp Gln Asp Asp Pro Met
            1285                1290                1295

Ile Arg Glu Ser Leu Val Arg Ala His Ser Ser
        1300                1305

<210> SEQ ID NO 56
<211> LENGTH: 3924
<212> TYPE: DNA
<213> ORGANISM: Mycospharella tritici
<220> FEATURE:
<221> NAME/KEY: CDS
<222> LOCATION: (1)..(3924)
<220> FEATURE:
<221> NAME/KEY: misc_feature
<222> LOCATION: (956)..(956)
<223> OTHER INFORMATION: Xaa is any amino acid
<220> FEATURE:
<221> NAME/KEY: misc_feature
<222> LOCATION: (1213)..(1213)
<223> OTHER INFORMATION: Xaa is any amino acid

<400> SEQUENCE: 56 atg ctg caa gaa gag act tcg gca gct gtg gcc agc atc ctc tcc aac      48
Met Leu Gln Glu Glu Thr Ser Ala Ala Val Ala Ser Ile Leu Ser Asn
 1               5                  10                  15 ttc gcc aag cag tat gct cct ctg gaa gcg gat tca ttc cct gca aag      96
Phe Ala Lys Gln Tyr Ala Pro Leu Glu Ala Asp Ser Phe Pro Ala Lys
             20                  25                  30 gcc atc gcg aat gga att aag aac acc aaa att gct cta ccg ggc gat     144
Ala Ile Ala Asn Gly Ile Lys Asn Thr Lys Ile Ala Leu Pro Gly Asp
         35                  40                  45 gat tca gtg gag aag cgt act cta gag cgc gag ctg act agc ctt gcg     192
Asp Ser Val Glu Lys Arg Thr Leu Glu Arg Glu Leu Thr Ser Leu Ala
     50                  55                  60 acg cgg atc cag ttt ctc gag gct cgc gct aca agc gga acc agt tcg     240
Thr Arg Ile Gln Phe Leu Glu Ala Arg Ala Thr Ser Gly Thr Ser Ser
 65                  70                  75                  80 tta ccc atc act ccc aac gag cca ctt tct tcg gca ttc tcg gag gac     288
Leu Pro Ile Thr Pro Asn Glu Pro Leu Ser Ser Ala Phe Ser Glu Asp
                 85                  90                  95 acc tcg tcg cca agg tcc gca gcg aac cag cac cgc cag cgc tca tcg     336
Thr Ser Ser Pro Arg Ser Ala Ala Asn Gln His Arg Gln Arg Ser Ser
            100                 105                 110 tca tgg gtc aac aac ctc ctg gct aag agc gag ggc gag cct cat cct     384
Ser Trp Val Asn Asn Leu Leu Ala Lys Ser Glu Gly Glu Pro His Pro
        115                 120                 125 cga caa ctc act gaa gaa caa ttt tca ttt cta cgt gag cac atc gac     432
Arg Gln Leu Thr Glu Glu Gln Phe Ser Phe Leu Arg Glu His Ile Asp
    130                 135                 140 caa caa gcg caa gag att cgg act cag aag gaa ttt atc gac ggt atc     480
Gln Gln Ala Gln Glu Ile Arg Thr Gln Lys Glu Phe Ile Asp Gly Ile
145                 150                 155                 160
```

-continued

| | |
|---|---|
| aaa tcg cag ctg acg cac cag caa acc gct aca aaa gct gca ctc gat<br>Lys Ser Gln Leu Thr His Gln Gln Thr Ala Thr Lys Ala Ala Leu Asp<br>165                    170                    175 | 528 |
| acc ttg ggc aac tcg cag tca atc gag cag ctg aag cgg gag att gag<br>Thr Leu Gly Asn Ser Gln Ser Ile Glu Gln Leu Lys Arg Glu Ile Glu<br>          180                    185                    190 | 576 |
| aaa aat gcg caa atc aat gct aca tac caa aaa gtg ctg cga gag atc<br>Lys Asn Ala Gln Ile Asn Ala Thr Tyr Gln Lys Val Leu Arg Glu Ile<br>               195                    200                    205 | 624 |
| ggc acc atc att aca gct gtc gcc aat gga gat ctc agc aag aaa gtg<br>Gly Thr Ile Ile Thr Ala Val Ala Asn Gly Asp Leu Ser Lys Lys Val<br>210                    215                    220 | 672 |
| ctc att cat gcc acg gag aaa gat ccg gag att gcg agg ttc aag cac<br>Leu Ile His Ala Thr Glu Lys Asp Pro Glu Ile Ala Arg Phe Lys His<br>225                    230                    235                    240 | 720 |
| acg atc aac aag atg gtg gac cag ttg caa gag ttt gct agt caa gta<br>Thr Ile Asn Lys Met Val Asp Gln Leu Gln Glu Phe Ala Ser Gln Val<br>               245                    250                    255 | 768 |
| aca cat ttg gcg aaa gag gtg gga aca gaa gga cgc ctc gga gga caa<br>Thr His Leu Ala Lys Glu Val Gly Thr Glu Gly Arg Leu Gly Gly Gln<br>          260                    265                    270 | 816 |
| gcc gtc gtg cct ggc gtc gac ggt att tgg gcg gag ctt acg caa aac<br>Ala Val Val Pro Gly Val Asp Gly Ile Trp Ala Glu Leu Thr Gln Asn<br>               275                    280                    285 | 864 |
| gtg aac gtc atg gcc caa aat ttg acc gac cag gtg cga gaa atc gca<br>Val Asn Val Met Ala Gln Asn Leu Thr Asp Gln Val Arg Glu Ile Ala<br>290                    295                    300 | 912 |
| gtt gta acc acc gcc gtt gca caa ggt gat ctg agc cgc aag att caa<br>Val Val Thr Thr Ala Val Ala Gln Gly Asp Leu Ser Arg Lys Ile Gln<br>305                    310                    315                    320 | 960 |
| cga cca gcc aga ggc gag att ctc caa ctt caa cag act atc aac tcc<br>Arg Pro Ala Arg Gly Glu Ile Leu Gln Leu Gln Gln Thr Ile Asn Ser<br>               325                    330                    335 | 1008 |
| atg gtg gga cag ctc cgg acc ttc gca acg gaa gtt acg aga gtg tcg<br>Met Val Gly Gln Leu Arg Thr Phe Ala Thr Glu Val Thr Arg Val Ser<br>          340                    345                    350 | 1056 |
| cgc gat gtc ggc acg gag ggt gtt ctt gga ggt caa gct caa atc gaa<br>Arg Asp Val Gly Thr Glu Gly Val Leu Gly Gly Gln Ala Gln Ile Glu<br>               355                    360                    365 | 1104 |
| ggc gta cag ggc atg tgg agc gac ctt act gtg aac gtg aat gct atg<br>Gly Val Gln Gly Met Trp Ser Asp Leu Thr Val Asn Val Asn Ala Met<br>          370                    375                    380 | 1152 |
| gca aac aat ctc act gcc cag gtg cga gat att gcg gag gtg aca aca<br>Ala Asn Asn Leu Thr Ala Gln Val Arg Asp Ile Ala Glu Val Thr Thr<br>385                    390                    395                    400 | 1200 |
| gcc gtg gcc cga ggc gac ctc acg cag cag gtt aaa gcg caa tgt aag<br>Ala Val Ala Arg Gly Asp Leu Thr Gln Gln Val Lys Ala Gln Cys Lys<br>               405                    410                    415 | 1248 |
| ggg gag atc ctg gcc ttg aaa acc acc atc aac tcc atg gtg cac cag<br>Gly Glu Ile Leu Ala Leu Lys Thr Thr Ile Asn Ser Met Val His Gln<br>          420                    425                    430 | 1296 |
| cta cgg caa ttc gcg cat gaa gtc acc aag atc gcg cgt gag gtc ggg<br>Leu Arg Gln Phe Ala His Glu Val Thr Lys Ile Ala Arg Glu Val Gly<br>               435                    440                    445 | 1344 |
| aca gaa ggt cgc cta ggt gga caa gca aca gtt cac gga gtc gag ggc<br>Thr Glu Gly Arg Leu Gly Gly Gln Ala Thr Val His Gly Val Glu Gly<br>          450                    455                    460 | 1392 |
| aca tgg aaa gac ttg acg gag aac gta aat ggc atg gcc atg aat ctg<br>Thr Trp Lys Asp Leu Thr Glu Asn Val Asn Gly Met Ala Met Asn Leu<br>465                    470                    475                    480 | 1440 |

```
acc acc caa gtg cgc gag atc gca gaa gtc aca acc gcc gtc gcg caa    1488
Thr Thr Gln Val Arg Glu Ile Ala Glu Val Thr Thr Ala Val Ala Gln
            485                 490                 495 gga gat ctc agc aaa aag gtc gag gcc gaa gtc aag ggt gaa att ttg    1536
Gly Asp Leu Ser Lys Lys Val Glu Ala Glu Val Lys Gly Glu Ile Leu
        500                 505                 510 gcc ttg aag agc acc atc aat tcc atg gtt gac cgt ctg ggt acg ttt    1584
Ala Leu Lys Ser Thr Ile Asn Ser Met Val Asp Arg Leu Gly Thr Phe
    515                 520                 525 gct ttc gag gtt agc aag gtc gcg aga gaa gtc gga acc gaa gga gtt    1632
Ala Phe Glu Val Ser Lys Val Ala Arg Glu Val Gly Thr Glu Gly Val
530                 535                 540 ttg ggc gga caa gca gag gtt gcc aat gtc gaa gga aaa tgg aaa gat    1680
Leu Gly Gly Gln Ala Glu Val Ala Asn Val Glu Gly Lys Trp Lys Asp
545                 550                 555                 560 ctt acc gac aat gtc aac acc atg gcc aac aac ttg act ggt cag gtg    1728
Leu Thr Asp Asn Val Asn Thr Met Ala Asn Asn Leu Thr Gly Gln Val
            565                 570                 575 cgg agc att tca gac gtc aca cag gcc att gca cgc ggt gac atg agc    1776
Arg Ser Ile Ser Asp Val Thr Gln Ala Ile Ala Arg Gly Asp Met Ser
        580                 585                 590 cag cga atc aag gtg cac gct cag gga gag att cag aca ttg aag gac    1824
Gln Arg Ile Lys Val His Ala Gln Gly Glu Ile Gln Thr Leu Lys Asp
    595                 600                 605 acg atc aac gac atg gtg acg cga ctg gac gct tgg tca ctc gcg gtg    1872
Thr Ile Asn Asp Met Val Thr Arg Leu Asp Ala Trp Ser Leu Ala Val
610                 615                 620 aag cgg gtg gct cgt gac gtc ggt gtc gac ggc aag atg ggt gga cag    1920
Lys Arg Val Ala Arg Asp Val Gly Val Asp Gly Lys Met Gly Gly Gln
625                 630                 635                 640 gca gaa gtc gaa ggc atc act ggt cgc tgg aag gag atc acg acc gat    1968
Ala Glu Val Glu Gly Ile Thr Gly Arg Trp Lys Glu Ile Thr Thr Asp
            645                 650                 655 gtg aac att atg gct caa aat ttg acc tcg caa gtg aga gct ttt gcc    2016
Val Asn Ile Met Ala Gln Asn Leu Thr Ser Gln Val Arg Ala Phe Ala
        660                 665                 670 gac att acc cac gcg gcc atg aaa gga gat ttc acc aag atg atc aat    2064
Asp Ile Thr His Ala Ala Met Lys Gly Asp Phe Thr Lys Met Ile Asn
    675                 680                 685 gtc gaa gcg tct ggc gaa atg aac gag ctg aag aac aag atc aac aag    2112
Val Glu Ala Ser Gly Glu Met Asn Glu Leu Lys Asn Lys Ile Asn Lys
690                 695                 700 atg gtc ctc aac ttg cgc gaa agt atc cag aag aac aat caa gca aga    2160
Met Val Leu Asn Leu Arg Glu Ser Ile Gln Lys Asn Asn Gln Ala Arg
705                 710                 715                 720 gag gcc gcc gag ttg gcc aac aag acg aaa tcg gag ttc ctg gca aac    2208
Glu Ala Ala Glu Leu Ala Asn Lys Thr Lys Ser Glu Phe Leu Ala Asn
            725                 730                 735 atg tcc cac gag att cga aca cct atg aac gga atc atc gga atg aca    2256
Met Ser His Glu Ile Arg Thr Pro Met Asn Gly Ile Ile Gly Met Thr
        740                 745                 750 cag ctt acc ttg gac acc gag ctt gag cag aac caa cgg gac atg ctc    2304
Gln Leu Thr Leu Asp Thr Glu Leu Glu Gln Asn Gln Arg Asp Met Leu
    755                 760                 765 aac atc gtc ttc tcg ctc gcc aac agc tta ctg acg att att gat gac    2352
Asn Ile Val Phe Ser Leu Ala Asn Ser Leu Leu Thr Ile Ile Asp Asp
770                 775                 780 atc ttg gac att tcc aag att gaa gca aat cgc atg atc cta gag gaa    2400
Ile Leu Asp Ile Ser Lys Ile Glu Ala Asn Arg Met Ile Leu Glu Glu
785                 790                 795                 800
```

```
gag ccg ttc tca ctg cga ggt ctc gtc ttc aac agc tta aag tca ctt    2448
Glu Pro Phe Ser Leu Arg Gly Leu Val Phe Asn Ser Leu Lys Ser Leu
            805                 810                 815 gca gtc cga gcc aac gag aag gac atc agc ttg gtg tat gat acc gac    2496
Ala Val Arg Ala Asn Glu Lys Asp Ile Ser Leu Val Tyr Asp Thr Asp
        820                 825                 830 agc tca gtg ccc gac tac atc gtg ggc gac tcc ttc cga ctt cga cag    2544
Ser Ser Val Pro Asp Tyr Ile Val Gly Asp Ser Phe Arg Leu Arg Gln
    835                 840                 845 atc att ctc aat ctc gcc ggc aac gcc atc aaa ttc acc gag cac ggg    2592
Ile Ile Leu Asn Leu Ala Gly Asn Ala Ile Lys Phe Thr Glu His Gly
850                 855                 860 gaa gtg cgt gtt aag ata ttc tct gac cac agt aca cga tgc acc gat    2640
Glu Val Arg Val Lys Ile Phe Ser Asp His Ser Thr Arg Cys Thr Asp
865                 870                 875                 880 agt gag gtt gtc gtc aaa ttc gcc gtc tcc gat act ggt att ggc atc    2688
Ser Glu Val Val Val Lys Phe Ala Val Ser Asp Thr Gly Ile Gly Ile
                885                 890                 895 cac tcc aac aag ttg gat ttg atc ttc gac acg ttt cag cag gct gac    2736
His Ser Asn Lys Leu Asp Leu Ile Phe Asp Thr Phe Gln Gln Ala Asp
            900                 905                 910 ggg tcg acc aca cgg aag ttc gga ggt act gga ttg ggc ctg tcg atc    2784
Gly Ser Thr Thr Arg Lys Phe Gly Gly Thr Gly Leu Gly Leu Ser Ile
        915                 920                 925 tct cgg aga ctg gtg act ttg atg cgt ggc aag atg tgg gtc gaa tca    2832
Ser Arg Arg Leu Val Thr Leu Met Arg Gly Lys Met Trp Val Glu Ser
    930                 935                 940 aat tat ggc tca ggc agc aca ttc ttc ttc acc tgk gtt gta cgg ctg    2880
Asn Tyr Gly Ser Gly Ser Thr Phe Phe Phe Thr Xaa Val Val Arg Leu
945                 950                 955                 960 ggc aat ccg gat gtt gca aaa atc atg cca caa cta cag cag tat cga    2928
Gly Asn Pro Asp Val Ala Lys Ile Met Pro Gln Leu Gln Gln Tyr Arg
                965                 970                 975 aag cac aac gtg ctc ttt gtc gac aac ggt aat acg gac agt tcg gag    2976
Lys His Asn Val Leu Phe Val Asp Asn Gly Asn Thr Asp Ser Ser Glu
            980                 985                 990 gag atc gcg gct ggc atc cga gct ttg gat ctg gtc cct tgt gtg gtg    3024
Glu Ile Ala Ala Gly Ile Arg Ala Leu Asp Leu Val Pro Cys Val Val
        995                 1000                1005 ggc aag gga aag gtt cct cac tcc gaa atc agc cca gac gac cag tac    3072
Gly Lys Gly Lys Val Pro His Ser Glu Ile Ser Pro Asp Asp Gln Tyr
    1010                1015                1020 gac tgc gtg atc atc gat aac agc gag acg gct cag aag ttg cgc agc    3120
Asp Cys Val Ile Ile Asp Asn Ser Glu Thr Ala Gln Lys Leu Arg Ser
1025                1030                1035                1040 ttg gaa cgt ttc aag tac att ccc atc gtc atg gtg gcg ccg gcc atc    3168
Leu Glu Arg Phe Lys Tyr Ile Pro Ile Val Met Val Ala Pro Ala Ile
                1045                1050                1055 tcg gtg aac ttc aag acc gcg ttg gag aac gga atc tca agc tac atg    3216
Ser Val Asn Phe Lys Thr Ala Leu Glu Asn Gly Ile Ser Ser Tyr Met
            1060                1065                1070 act acg cca tgc ctt cca atc gac ctg ggc aat gct ctg gtg ccc gca    3264
Thr Thr Pro Cys Leu Pro Ile Asp Leu Gly Asn Ala Leu Val Pro Ala
        1075                1080                1085 ctc gag ggc cgc gca gca ccc atg tca gcc gac cac agt cgg aca ttc    3312
Leu Glu Gly Arg Ala Ala Pro Met Ser Ala Asp His Ser Arg Thr Phe
    1090                1095                1100 gat atc ctc ctc gca gaa gac aac gcg gtg aat caa aaa ctc gcc gtc    3360
Asp Ile Leu Leu Ala Glu Asp Asn Ala Val Asn Gln Lys Leu Ala Val
1105                1110                1115                1120
```

```
aag atc ctg acc aag cac aac cac aca gtg aca gtc gcc aac aac ggc    3408
Lys Ile Leu Thr Lys His Asn His Thr Val Thr Val Ala Asn Asn Gly
            1125                1130                1135 ctt gaa gcc ttt gaa gcg att cgc aag aag cgc ttc gat gtc gtt ctc    3456
Leu Glu Ala Phe Glu Ala Ile Arg Lys Lys Arg Phe Asp Val Val Leu
        1140                1145                1150 atg gac gtg caa atg ccc gtc atg gga ggg ttc gaa gcg acg gcc aag    3504
Met Asp Val Gln Met Pro Val Met Gly Gly Phe Glu Ala Thr Ala Lys
    1155                1160                1165 att cgc gaa tac gaa cga act cac gag cta gca cgt tcg ccc att atc    3552
Ile Arg Glu Tyr Glu Arg Thr His Glu Leu Ala Arg Ser Pro Ile Ile
1170                1175                1180 gcc ctc acc gca cac gcc atg ctt ggc gac cgc gag aag tgt atc caa    3600
Ala Leu Thr Ala His Ala Met Leu Gly Asp Arg Glu Lys Cys Ile Gln
1185                1190                1195                1200 gcg caa atg gac gag tat ctc tcc aaa ccc ctc aag ycc aat cag ctc    3648
Ala Gln Met Asp Glu Tyr Leu Ser Lys Pro Leu Lys Xaa Asn Gln Leu
            1205                1210                1215 att cag acg atc ctg aaa tgt gcg acc cta ggc ggt gcg tta ctt gac    3696
Ile Gln Thr Ile Leu Lys Cys Ala Thr Leu Gly Gly Ala Leu Leu Asp
        1220                1225                1230 cgg agg aac gat ggg cgc ggt ttg ctc atg gaa gag gac aaa ccc gtt    3744
Arg Arg Asn Asp Gly Arg Gly Leu Leu Met Glu Glu Asp Lys Pro Val
    1235                1240                1245 tct gat aat tcg agt ctt cct gca gat cac aat cgg ttg ctc acg ccc    3792
Ser Asp Asn Ser Ser Leu Pro Ala Asp His Asn Arg Leu Leu Thr Pro
1250                1255                1260 ccg aaa cga ccg ggt gtc gat cgt ggg tac acg gag aat gga ccg ccc    3840
Pro Lys Arg Pro Gly Val Asp Arg Gly Tyr Thr Glu Asn Gly Pro Pro
1265                1270                1275                1280 ggt ttg gaa agt ccg gcg ata gta acc gac gac cag gat gat ccg atg    3888
Gly Leu Glu Ser Pro Ala Ile Val Thr Asp Asp Gln Asp Asp Pro Met
            1285                1290                1295 atc aga gag agt ctt gtt cgt gcc cat agc agc tga                    3924
Ile Arg Glu Ser Leu Val Arg Ala His Ser Ser
        1300                1305

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 57
cggaaggagt cgcccacgat gtagtcgg                                       28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 58
catggtggcg ccggccatct cggtgaac                                       28

<210> SEQ ID NO 59
<211> LENGTH: 30
<212> TYPE: DNA
<213> ORGANISM: Artificial Sequence
```

-continued

```
<220> FEATURE:
<223> OTHER INFORMATION: Description of Artificial Sequence : Designed
      oligonucleotide primer for DNA sequencing

<400> SEQUENCE: 59
tcgccagacg cttcgacatt gatcatcttg                                    30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 60
ttcatggcca tgccatttac gttctccgtc                                    30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 61
tacaagcgga accagttcgt tacccatcac                                    30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 62
gactccttcc gacttcgaca gatcattctc                                    30

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 63
tccgtgtggt cgacccgtca gcctgctg                                      28

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence : Designed
      oligonucleotide primer for PCR

<400> SEQUENCE: 64
cccactagta tgctgcaaga agagacttcg                                    30

<210> SEQ ID NO 65
<211> LENGTH: 30
<212> TYPE: DNA
<213> ORGANISM: Artificial Sequence
```

-continued

```
<220> FEATURE:
<223> OTHER INFORMATION: Description of Artificial Sequence : Designed
      oligonucleotide primer for PCR

<400> SEQUENCE: 65
cctaagcttc tcagctgcta tgggcacgaa                                        30

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 66
caggaaacag ctatgaccat gattacgcca                                        30

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence : Designed
      oligonucleotide primer for DNA sequencing

<400> SEQUENCE: 67
tgtaaaacga cggccagtga attgtaatac                                        30

<210> SEQ ID NO 68
<211> LENGTH: 1438
<212> TYPE: PRT
<213> ORGANISM: Thanatephorus cucumeris

<400> SEQUENCE: 68
```

Met Ala Gly Thr Thr Gly Gly His Pro Phe Thr Ala His Leu Val Ala
 1               5                  10                  15

Val Leu Ser Ile Tyr Glu Leu Gly Pro Gly Arg Pro Val Arg Ala Leu
            20                  25                  30

Pro Thr Arg Ser Ser His Ser His Ser Ser Gly Ser Arg His Ala
        35                  40                  45

Arg Ala Leu Ser Val Pro Pro Phe Pro Pro Pro Pro Met Ser Pro
    50                  55                  60

Pro Asn Ala Pro Ile Asp Tyr Val Gly Ala Ala Pro Leu Pro Arg Tyr
 65                  70                  75                  80

Asp Gly Pro Arg Asp Trp Gln Thr Asp Ala Val Glu Arg Ala Leu Gly
                85                  90                  95

Arg Val Ala Ala Arg Met Tyr Ala Ala Glu Ala Gln Leu Gln Asp Leu
            100                 105                 110

Leu Ser Arg Glu Ser Ser Thr Ser Thr Pro Asp Pro Ala Leu Ser Pro
        115                 120                 125

Arg Ser Asn Gly Leu Lys Lys Arg Glu Asn Pro Gly Thr Pro Asp
    130                 135                 140

Glu Arg Asp Pro Trp Gln Thr Val Arg Phe Gln Glu Val Gly Asp Gln
145                 150                 155                 160

Asp Met Asp Pro Glu Pro Asp Thr Pro Val Ala Arg Pro Lys Asp Lys
                165                 170                 175

Val Lys Pro Gly Thr Ile Asp Leu Ser Thr Leu Ser Gln Pro Thr Pro
            180                 185                 190

-continued

```
Leu Ser Lys Val Ala Thr Asp Asn Pro Val Leu Pro Lys Pro Gly Pro
        195                 200                 205

Arg Ser Ala Pro Thr Ser Ser Val Gly Ser Ile Met Pro Pro Phe Thr
    210                 215                 220

Cys His Ser Cys Gly Arg Pro Met Gln Gly Pro Ala Ala Pro Asp Val
225                 230                 235                 240

Ile His Ala Pro Gly Pro Leu Asp Val Val Thr Pro Ala Leu Gly Met
                245                 250                 255

Gly Leu Gly Leu Ser Asp His Gly Ala Ala Glu Leu Arg Gln Lys Leu
                260                 265                 270

Gly Phe Gly Asp His Glu Asp Thr Gly Ser Pro Leu Val Leu Pro
        275                 280                 285

Pro Gly Pro Leu Ser Ala Ala Ala Phe Glu Ser Ala Pro Gly Met Ser
    290                 295                 300

Ala Val Glu Glu Leu Lys Leu Leu Lys Ala Gln Val Gln Asp Val Ala
305                 310                 315                 320

Arg Val Cys Lys Ala Val Ala Glu Gly Asp Leu Ser Gln Lys Ile Thr
                325                 330                 335

Val Pro Val Gln Gly Pro Val Met Val Gln Leu Lys Asp Val Ile Asn
                340                 345                 350

Thr Met Val Asp Lys Leu Gly Arg Phe Ala Gln Glu Val Thr Arg Val
        355                 360                 365

Ser Leu Glu Val Gly Thr Glu Gly Arg Leu Gly Gly Gln Ala Ile Val
    370                 375                 380

Arg Asp Val Arg Gly Thr Trp Ser Glu Leu Thr Thr Val Val Asn Arg
385                 390                 395                 400

Leu Ala Ala Asn Leu Thr Ser Gln Val Arg Gly Ile Ala Glu Val Thr
                405                 410                 415

Lys Ala Val Ala Lys Gly Asp Leu Ser Lys Gln Ile Gly Val Asp Ala
                420                 425                 430

Lys Gly Glu Ile Leu Glu Leu Lys Asn Thr Val Asn Thr Met Val Val
        435                 440                 445

Arg Leu Arg Met Phe Ala Gly Glu Val Thr Arg Val Ala Leu Asp Val
    450                 455                 460

Gly Ser Arg Gly Ile Leu Gly Gly Gln Ala Tyr Val Pro Asp Val Glu
465                 470                 475                 480

Gly Val Trp Gln Glu Leu Thr Asp Asn Val Asn Arg Met Cys Ser Asn
                485                 490                 495

Leu Thr Asn Gln Val Arg Ser Ile Ala Leu Val Thr Thr Ala Val Ala
                500                 505                 510

Glu Gly Asp Leu Thr Arg Lys Ile Glu Ile Glu Val Glu Gly Glu Met
        515                 520                 525

Leu Thr Leu Lys Asn Thr Val Asn Ser Met Val Asp Gln Leu Ser Thr
    530                 535                 540

Phe Ala Ser Glu Val Thr Arg Val Ala Leu Glu Val Gly Ser Met Gly
545                 550                 555                 560

Ile Leu Gly Gly Gln Ala Gln Val Glu Gly Val Lys Gly Thr Trp Ala
                565                 570                 575

Asp Leu Thr Arg Asn Val Asn Asn Met Ala Ser Asn Leu Thr Asn Gln
                580                 585                 590

Val Arg Ser Ile Ala Lys Val Thr Thr Ala Val Ala His Gly Asp Leu
        595                 600                 605
```

```
Arg Gln Phe Val Glu Val Asp Val Gln Gly Glu Met Leu Met Leu Lys
    610                 615                 620

Asn Thr Val Asn Ser Met Val Ala Gln Leu Asp Thr Leu Ala Ser Glu
625                 630                 635                 640

Val Ser Arg Val Ala Leu Glu Val Gly Ile Glu Gly Arg Leu Gly Gly
                645                 650                 655

Gln Ala Val Val Gln Gly Val Glu Gly Val Trp Lys Val Leu Thr Asp
                660                 665                 670

Asn Val Asn Leu Met Ala Leu Asn Leu Thr Thr Gln Val Arg Ser Ile
            675                 680                 685

Ala Ala Val Thr Thr Ala Val Ala Arg Gly Asp Leu Ser Lys Asn Ile
    690                 695                 700

Asp Val Asp Val Lys Gly Glu Ile Leu Asp Leu Lys Ile Thr Val Asn
705                 710                 715                 720

Arg Met Thr Asp Ser Leu Arg Ile Phe Ala Ala Glu Val Thr Arg Val
                725                 730                 735

Ala Arg Glu Val Gly Thr Leu Gly Arg Leu Gly Gly Gln Ala Phe Val
                740                 745                 750

Pro Gly Val Ala Gly Val Trp Lys Asp Leu Thr Asp Asn Val Asn Val
            755                 760                 765

Met Ala Ala Asn Leu Thr Leu Gln Val Arg Ala Ile Ala Arg Val Thr
    770                 775                 780

Thr Ala Val Ser Val Gly Asp Leu Thr Thr Lys Val Glu Gly Ile Asp
785                 790                 795                 800

Val Ala Gly Glu Ile Leu Asp Leu Val Asn Thr Ile Asn Gly Met Val
                805                 810                 815

Asp Gln Leu Ala Val Phe Ala Ala Glu Val Thr Arg Val Ala Arg Glu
                820                 825                 830

Val Gly Thr Glu Gly Arg Leu Gly Val Gln Ala Arg Val Glu Gly Met
            835                 840                 845

Gln Gly Ser Trp Gln Ala Ile Thr Val Ser Val Asn Thr Met Ala Ala
    850                 855                 860

Asn Leu Thr Ser Gln Val Arg Gly Phe Ala Gln Ile Ser Ala Ala Ala
865                 870                 875                 880

Thr Asp Gly Asp Phe Thr Arg Phe Ile Thr Val Glu Ala Ser Gly Glu
                885                 890                 895

Met Asp Ser Leu Lys Thr Gln Ile Asn Gln Met Val Tyr Asn Leu Arg
                900                 905                 910

Glu Ser Ile Gln Arg Asn Thr Ala Ala Arg Glu Ala Ala Glu Leu Ala
            915                 920                 925

Asn Arg Ser Lys Ser Glu Phe Leu Ala Asn Met Ser His Glu Ile Arg
    930                 935                 940

Thr Pro Met Asn Gly Ile Ile Gly Met Thr Asp Leu Thr Leu Asp Thr
945                 950                 955                 960

Glu Leu Thr Arg Thr Gln Lys Glu Asn Leu Leu Val His Gln Leu
                965                 970                 975

Ala Lys Ser Leu Leu Leu Ile Ile Asp Asp Ile Leu Asp Ile Ser Lys
                980                 985                 990

Ile Glu Ala Gly Arg Met Thr Met Glu Gln Val Thr Tyr Ser Leu Arg
            995                 1000                1005

Gly Thr Ala Phe Gly Ile Leu Lys Thr Leu Val Val Arg Ala His Gln
    1010                1015                1020
```

```
Gln Asn Leu Asn Leu Phe Tyr Glu Val Asp Pro Glu Ile Pro Asp Gln
1025                1030                1035                1040

Val Ile Gly Asp Ser Leu Arg Leu Arg Gln Val Ile Thr Asn Leu Val
            1045                1050                1055

Gly Asn Ala Ile Lys Phe Thr Pro Ser Lys Pro Asn Lys Lys Gly Met
            1060                1065                1070

Val Cys Leu Ser Cys Lys Leu Ile Ser Met Asp Glu Gln Asn Val Thr
    1075                1080                1085

Val Arg Phe Cys Val Glu Asp Thr Gly Ile Gly Ile Lys Gln Asp Lys
    1090                1095                1100

Leu Ala Ile Ile Phe Asp Thr Phe Cys Gln Ala Asp Gly Ser Thr Thr
1105                1110                1115                1120

Arg Glu Tyr Gly Gly Thr Gly Leu Gly Leu Ser Ile Ser Lys Arg Leu
            1125                1130                1135

Val Ser Leu Met Asn Gly Gln Met Trp Val Glu Ser Glu Val Gly Val
            1140                1145                1150

Gly Ser Arg Phe Tyr Phe Thr Ile Thr Ala Glu Ile Ser Arg Pro Asn
            1155                1160                1165

Met Ala Gln Ser Leu Gln Lys Val Ala Ile Tyr Lys Glu Arg Thr Ile
    1170                1175                1180

Leu Phe Val Asp Thr Leu Gly Asp Arg Ser Gly Val Ala Glu Arg Ile
1185                1190                1195                1200

Glu Glu Leu Gln Leu Arg Pro Phe Val Val Arg Asp Ile Ser Gln Val
            1205                1210                1215

Ala Asp Lys Ala Lys Ile Pro Phe Ile Asp Thr Val Ile Val Asp Ser
            1220                1225                1230

Leu Glu Val Thr Glu Lys Leu Arg Glu Leu Asp His Leu Arg Tyr Thr
    1235                1240                1245

Pro Ala Val Leu Leu Thr Pro Val Met Pro Arg Leu Asn Leu Thr Trp
1250                1255                1260

Cys Leu Glu Asn Phe Ile Ser Gly His Val Ala Thr Pro Ser Ser Leu
1265                1270                1275                1280

Asp Asp Leu Ala Glu Ala Leu Ala Lys Gly Leu Glu Ala Asn Ala Ser
            1285                1290                1295

Gln Pro Glu Val Thr Pro Ser Asp Val Ala Tyr Asp Ile Leu Leu Ala
            1300                1305                1310

Glu Asp Asn Val Val Asn Gln Arg Val Ala Val Lys Ile Leu Glu Lys
            1315                1320                1325

Phe Gly His Thr Val Gln Ile Ala Glu Asn Gly Gln Phe Ala Val Asp
    1330                1335                1340

Ala Val Lys Ala Arg Tyr Glu Gln Glu Lys Met Phe Asp Val Ile Leu
1345                1350                1355                1360

Met Asp Val Ser Met Pro Phe Met Gly Gly Met Glu Ala Thr Glu Ile
            1365                1370                1375

Ile Arg Ala Phe Glu Lys Glu Lys Gly Ile Arg Arg Thr Pro Ile Ile
            1380                1385                1390

Ala Leu Thr Ala His Ala Met Ile Gly Asp Arg Glu Arg Cys Ile Gln
    1395                1400                1405

Ala Gly Met Asp Glu His Val Thr Lys Pro Leu Arg Arg Thr Asp Leu
    1410                1415                1420

Val Ser Ala Ile Lys Arg Leu Val Thr Pro His Gly Ala His
1425                1430                1435
```

```
<210> SEQ ID NO 69
<211> LENGTH: 4317
<212> TYPE: DNA
<213> ORGANISM: Thanatephorus cucumeris
<220> FEATURE:
<221> NAME/KEY: CDS
<222> LOCATION: (1)..(4317)

<400> SEQUENCE: 69 atg gca ggt aca acg ggg gga cac ccg ttt acg gcg cac cta gtt gcg        48
Met Ala Gly Thr Thr Gly Gly His Pro Phe Thr Ala His Leu Val Ala
  1               5                  10                  15 gtg ctg agt atc tat gag tta gga ccg gga cga cca gtg cgc gca ctg        96
Val Leu Ser Ile Tyr Glu Leu Gly Pro Gly Arg Pro Val Arg Ala Leu
             20                  25                  30 ccg acc cgg agc tca cat tcc cat tcc tct tcc ggt tcc cgc cat gcg       144
Pro Thr Arg Ser Ser His Ser His Ser Ser Ser Gly Ser Arg His Ala
         35                  40                  45 cgt gcg ctg tct gtg ccg ccg ttc cca cca ccg cca ccg atg tct ccg       192
Arg Ala Leu Ser Val Pro Pro Phe Pro Pro Pro Pro Pro Met Ser Pro
     50                  55                  60 ccg aac gca ccg atc gac tac gta ggc gct gct ccg ctg ccc cga tac       240
Pro Asn Ala Pro Ile Asp Tyr Val Gly Ala Ala Pro Leu Pro Arg Tyr
 65                  70                  75                  80 gat gga ccg cgt gac tgg cag acg gat gcg gtc gag cga gca ctg ggc       288
Asp Gly Pro Arg Asp Trp Gln Thr Asp Ala Val Glu Arg Ala Leu Gly
                 85                  90                  95 cgt gtt gcc gcg cgg atg tac gcg gcc gag gcc cag ctg cag gac ctg       336
Arg Val Ala Ala Arg Met Tyr Ala Ala Glu Ala Gln Leu Gln Asp Leu
            100                 105                 110 ctg agc cgc gag tcg agc aca tcc acc ccc gat ccc gct ctc tcg ccc       384
Leu Ser Arg Glu Ser Ser Thr Ser Thr Pro Asp Pro Ala Leu Ser Pro
        115                 120                 125 cgc tcc aac ggc ctc aaa aaa cgc aga gag aac ccg gga aca ccc gat       432
Arg Ser Asn Gly Leu Lys Lys Arg Arg Glu Asn Pro Gly Thr Pro Asp
    130                 135                 140 gag cgc gat ccg tgg cag act gtg cgc ttt caa gag gtc ggt gac cag       480
Glu Arg Asp Pro Trp Gln Thr Val Arg Phe Gln Glu Val Gly Asp Gln
145                 150                 155                 160 gac atg gat ccc gag cca gac acc cct gtt gcc cgc ccc aag gac aag       528
Asp Met Asp Pro Glu Pro Asp Thr Pro Val Ala Arg Pro Lys Asp Lys
                165                 170                 175 gtc aag cct ggt acc att gac ctg agt aca ctc tcc cag ccc act ccg       576
Val Lys Pro Gly Thr Ile Asp Leu Ser Thr Leu Ser Gln Pro Thr Pro
            180                 185                 190 ctc tcc aag gtg gcc acg gac aat ccg gtg ctg ccc aag cct ggt ccc       624
Leu Ser Lys Val Ala Thr Asp Asn Pro Val Leu Pro Lys Pro Gly Pro
        195                 200                 205 cgc agc gca ccc acc agc agc gtc gga tcc atc atg cct ccc ttc acg       672
Arg Ser Ala Pro Thr Ser Ser Val Gly Ser Ile Met Pro Pro Phe Thr
    210                 215                 220 tgc cac tcg tgc gga cgc ccc atg cag ggc ccc gct gcc ccc gat gtc       720
Cys His Ser Cys Gly Arg Pro Met Gln Gly Pro Ala Ala Pro Asp Val
225                 230                 235                 240 ata cac gca ccc ggt ccc ctc gac gtt gtc acc cct gca ctt ggc atg       768
Ile His Ala Pro Gly Pro Leu Asp Val Val Thr Pro Ala Leu Gly Met
                245                 250                 255 ggc ctc ggt ctc tct gac cat ggc gct gcc gag ctc aga cag aaa ctt       816
Gly Leu Gly Leu Ser Asp His Gly Ala Ala Glu Leu Arg Gln Lys Leu
            260                 265                 270
```

```
                                              -continued ggc ttt ggc gat cac gaa gac gac acc ggt agt ccc ctt gtt ctc ccc        864
Gly Phe Gly Asp His Glu Asp Asp Thr Gly Ser Pro Leu Val Leu Pro
            275                 280                 285 cct ggc cct ctc agt gct gct gcc ttt gag agc gct cca ggc atg tcc        912
Pro Gly Pro Leu Ser Ala Ala Ala Phe Glu Ser Ala Pro Gly Met Ser
290                 295                 300 gcc gtc gaa gaa ctc aag ctg ctc aag gcc cag gtc cag gat gtc gct        960
Ala Val Glu Glu Leu Lys Leu Leu Lys Ala Gln Val Gln Asp Val Ala
305                 310                 315                 320 cgt gta tgc aag gcc gtc gcc gag ggt gat ttg tct caa aag att acc       1008
Arg Val Cys Lys Ala Val Ala Glu Gly Asp Leu Ser Gln Lys Ile Thr
            325                 330                 335 gtc ccc gtt caa ggt ccc gtc atg gtc cag ctc aag gat gtc atc aac       1056
Val Pro Val Gln Gly Pro Val Met Val Gln Leu Lys Asp Val Ile Asn
            340                 345                 350 acc atg gtc gat aaa cta ggc agg ttt gcg cag gag gtc act cgt gtc       1104
Thr Met Val Asp Lys Leu Gly Arg Phe Ala Gln Glu Val Thr Arg Val
            355                 360                 365 tcg ctc gaa gtc gga act gaa ggc cgg ctc ggt ggt cag gcc att gtt       1152
Ser Leu Glu Val Gly Thr Glu Gly Arg Leu Gly Gly Gln Ala Ile Val
370                 375                 380 cgc gat gtc cgc gga aca tgg agc gaa ctc aca acc gtc gtc aat cgt       1200
Arg Asp Val Arg Gly Thr Trp Ser Glu Leu Thr Thr Val Val Asn Arg
385                 390                 395                 400 ctc gcc gct aat ctc aca agc cag gtc cgg gga atc gca gaa gtc acc       1248
Leu Ala Ala Asn Leu Thr Ser Gln Val Arg Gly Ile Ala Glu Val Thr
            405                 410                 415 aag gca gtc gcc aag ggc gat ctc tcc aaa caa atc ggc gtc gat gca       1296
Lys Ala Val Ala Lys Gly Asp Leu Ser Lys Gln Ile Gly Val Asp Ala
            420                 425                 430 aaa ggt gaa ata ttg gaa ttg aag aat acg gtt aat acc atg gtc gtc       1344
Lys Gly Glu Ile Leu Glu Leu Lys Asn Thr Val Asn Thr Met Val Val
            435                 440                 445 cgg ttg cgt atg ttt gca ggc gaa gtc acc cga gtc gcg ctc gat gtc       1392
Arg Leu Arg Met Phe Ala Gly Glu Val Thr Arg Val Ala Leu Asp Val
450                 455                 460 ggc agt cgt ggt att cta ggc ggt cag gct tat gtc ccg gat gtc gag       1440
Gly Ser Arg Gly Ile Leu Gly Gly Gln Ala Tyr Val Pro Asp Val Glu
465                 470                 475                 480 ggt gtt tgg caa gag ttg acg gat aat gta aat cgc atg tgc tcc aat       1488
Gly Val Trp Gln Glu Leu Thr Asp Asn Val Asn Arg Met Cys Ser Asn
            485                 490                 495 ttg acc aac caa gtc cgt tcg att gcg ctc gtt act acc gcc gtc gcc       1536
Leu Thr Asn Gln Val Arg Ser Ile Ala Leu Val Thr Thr Ala Val Ala
            500                 505                 510 gag ggt gac ctc aca cgt aaa atc gaa att gaa gtc gag ggc gaa atg       1584
Glu Gly Asp Leu Thr Arg Lys Ile Glu Ile Glu Val Glu Gly Glu Met
            515                 520                 525 ttg acg ctc aag aat acg gta aac agc atg gtg gac cag ctt tcg acg       1632
Leu Thr Leu Lys Asn Thr Val Asn Ser Met Val Asp Gln Leu Ser Thr
530                 535                 540 ttt gcg agc gaa gtc acg cgg gtc gcg ctc gag gtt ggc tcg atg ggt       1680
Phe Ala Ser Glu Val Thr Arg Val Ala Leu Glu Val Gly Ser Met Gly
545                 550                 555                 560 ata ctc ggt ggt cag gcg cag gtc gag ggt gta aaa gga act tgg gcc       1728
Ile Leu Gly Gly Gln Ala Gln Val Glu Gly Val Lys Gly Thr Trp Ala
            565                 570                 575 gac ttg acg agg aat gtg aat aat atg gcg tcc aat cta acc aat caa       1776
Asp Leu Thr Arg Asn Val Asn Asn Met Ala Ser Asn Leu Thr Asn Gln
            580                 585                 590
```

```
gtc cgt tcg atc gcc aag gtc acg acg gcc gtc gcg cac ggt gac ctg    1824
Val Arg Ser Ile Ala Lys Val Thr Thr Ala Val Ala His Gly Asp Leu
        595                 600                 605 cgg cag ttt gtc gaa gtc gat gtc cag gga gag atg ctc atg ttg aag    1872
Arg Gln Phe Val Glu Val Asp Val Gln Gly Glu Met Leu Met Leu Lys
    610                 615                 620 aac acg gtg aat agc atg gtg gct cag ctc gat acg ctc gcg agc gag    1920
Asn Thr Val Asn Ser Met Val Ala Gln Leu Asp Thr Leu Ala Ser Glu
625                 630                 635                 640 gtg tcg cgt gtc gcg ctc gag gtc ggt atc gag ggt cga ctc ggt gga    1968
Val Ser Arg Val Ala Leu Glu Val Gly Ile Glu Gly Arg Leu Gly Gly
                645                 650                 655 cag gct gtg gtt cag ggt gtg gag ggt gtg tgg aag gtt tta acg gac    2016
Gln Ala Val Val Gln Gly Val Glu Gly Val Trp Lys Val Leu Thr Asp
            660                 665                 670 aat gtc aac ttg atg gct ctg aat ctg acg acc caa gtg cgg tct att    2064
Asn Val Asn Leu Met Ala Leu Asn Leu Thr Thr Gln Val Arg Ser Ile
        675                 680                 685 gcg gct gtg acg act gcc gtg gcg cgt ggt gac ctt agc aag aat atc    2112
Ala Ala Val Thr Thr Ala Val Ala Arg Gly Asp Leu Ser Lys Asn Ile
    690                 695                 700 gat gtc gat gtc aag ggc gag att ttg gat ttg aag att acg gtc aat    2160
Asp Val Asp Val Lys Gly Glu Ile Leu Asp Leu Lys Ile Thr Val Asn
705                 710                 715                 720 cgc atg acg gat agt ttg cgg ata ttc gct gct gaa gtg act cgt gtc    2208
Arg Met Thr Asp Ser Leu Arg Ile Phe Ala Ala Glu Val Thr Arg Val
                725                 730                 735 gcg cgc gag gtc ggt acg ctc gga cga ctc ggc gga cag gcg ttt gtt    2256
Ala Arg Glu Val Gly Thr Leu Gly Arg Leu Gly Gly Gln Ala Phe Val
            740                 745                 750 cct ggt gtg gct ggc gtg tgg aag gat ttg acg gat aat gtg aat gtt    2304
Pro Gly Val Ala Gly Val Trp Lys Asp Leu Thr Asp Asn Val Asn Val
        755                 760                 765 atg gct gcc aat ttg acg ttg caa gta cga gct att gcc cga gtc aca    2352
Met Ala Ala Asn Leu Thr Leu Gln Val Arg Ala Ile Ala Arg Val Thr
    770                 775                 780 acg gcc gtg tcg gtc gga gac ttg acg acc aag gtc gaa ggc atc gat    2400
Thr Ala Val Ser Val Gly Asp Leu Thr Thr Lys Val Glu Gly Ile Asp
785                 790                 795                 800 gtc gcg ggt gaa atc ttg gat ctc gtc aac acg atc aac gga atg gtg    2448
Val Ala Gly Glu Ile Leu Asp Leu Val Asn Thr Ile Asn Gly Met Val
                805                 810                 815 gac cag ctc gcc gtg ttt gcg gcc gag gtc acg agg gtc gca cgc gaa    2496
Asp Gln Leu Ala Val Phe Ala Ala Glu Val Thr Arg Val Ala Arg Glu
            820                 825                 830 gtc gga acc gag ggt cgg ttg ggt gtt cag gct cgc gtc gaa ggt atg    2544
Val Gly Thr Glu Gly Arg Leu Gly Val Gln Ala Arg Val Glu Gly Met
        835                 840                 845 caa ggc agc tgg cag gcg att acc gta tct gta aac acg atg gct gcc    2592
Gln Gly Ser Trp Gln Ala Ile Thr Val Ser Val Asn Thr Met Ala Ala
    850                 855                 860 aac ttg acg tcc caa gtg cgt ggg ttt gcg caa atc tcg gca gcg gcg    2640
Asn Leu Thr Ser Gln Val Arg Gly Phe Ala Gln Ile Ser Ala Ala Ala
865                 870                 875                 880 acc gac gga gac ttt acg cgc ttc atc acg gtc gaa gcg agc gga gag    2688
Thr Asp Gly Asp Phe Thr Arg Phe Ile Thr Val Glu Ala Ser Gly Glu
                885                 890                 895 atg gac tcg ctc aag acg cag atc aat cag atg gtg tac aac ctc cgg    2736
Met Asp Ser Leu Lys Thr Gln Ile Asn Gln Met Val Tyr Asn Leu Arg
            900                 905                 910
```

| | |
|---|---|
| gag agt att cag agg aac acg gct gcg cgt gag gct gct gag ctt gcg<br>Glu Ser Ile Gln Arg Asn Thr Ala Ala Arg Glu Ala Ala Glu Leu Ala<br>       915                 920              925 | 2784 |
| aat cgg tcc aag tcc gag ttc ctt gcc aac atg tcg cac gag att cga<br>Asn Arg Ser Lys Ser Glu Phe Leu Ala Asn Met Ser His Glu Ile Arg<br>930               935                 940 | 2832 |
| acg ccg atg aac ggg att att ggc atg acg gat ctc acg ctt gat acc<br>Thr Pro Met Asn Gly Ile Ile Gly Met Thr Asp Leu Thr Leu Asp Thr<br>945               950                955           960 | 2880 |
| gaa ctt aca cgg acg caa aaa gaa aac ttg ttg ctc gtt cac cag ctc<br>Glu Leu Thr Arg Thr Gln Lys Glu Asn Leu Leu Leu Val His Gln Leu<br>       965                 970              975 | 2928 |
| gcc aag tct cta ttg ctt att atc gat gat att ctt gat att tcc aag<br>Ala Lys Ser Leu Leu Leu Ile Ile Asp Asp Ile Leu Asp Ile Ser Lys<br>       980                 985              990 | 2976 |
| atc gag gct ggc agg atg acc atg gaa caa gtc acg tat tct ctc cgc<br>Ile Glu Ala Gly Arg Met Thr Met Glu Gln Val Thr Tyr Ser Leu Arg<br>       995               1000            1005 | 3024 |
| ggt act gca ttc ggt atc ctc aag acc ctt gtc gtc cgg gct cac caa<br>Gly Thr Ala Phe Gly Ile Leu Lys Thr Leu Val Val Arg Ala His Gln<br>   1010                 1015            1020 | 3072 |
| caa aat ctc aac ctg ttc tac gaa gtc gat ccc gag att ccg gac caa<br>Gln Asn Leu Asn Leu Phe Tyr Glu Val Asp Pro Glu Ile Pro Asp Gln<br>1025                 1030            1035            1040 | 3120 |
| gtc att ggc gat tcg ctc cgt ctg cga caa gtc att acc aac ctc gtc<br>Val Ile Gly Asp Ser Leu Arg Leu Arg Gln Val Ile Thr Asn Leu Val<br>             1045            1050            1055 | 3168 |
| gga aac gct atc aag ttc act ccc agc aag ccc aac aaa aag ggc atg<br>Gly Asn Ala Ile Lys Phe Thr Pro Ser Lys Pro Asn Lys Lys Gly Met<br>   1060                 1065            1070 | 3216 |
| gtc tgc ctc tcg tgc aag ctc atc tcg atg gac gag cag aat gtg acg<br>Val Cys Leu Ser Cys Lys Leu Ile Ser Met Asp Glu Gln Asn Val Thr<br>             1075            1080            1085 | 3264 |
| gtt cgg ttc tgt gtc gag gac acg ggt atc ggt atc aag cag gat aaa<br>Val Arg Phe Cys Val Glu Asp Thr Gly Ile Gly Ile Lys Gln Asp Lys<br>   1090                 1095            1100 | 3312 |
| ctc gcg atc atc ttt gat acg ttc tgt caa gcc gat ggg tcc acg act<br>Leu Ala Ile Ile Phe Asp Thr Phe Cys Gln Ala Asp Gly Ser Thr Thr<br>1105                 1110            1115            1120 | 3360 |
| cgt gaa tac ggt ggt acc ggt ctc ggc ttg tcc atc tcg aaa cga ctc<br>Arg Glu Tyr Gly Gly Thr Gly Leu Gly Leu Ser Ile Ser Lys Arg Leu<br>             1125            1130            1135 | 3408 |
| gtg tct ctg atg aat ggc caa atg tgg gtc gag tcc gag gtc gga gtc<br>Val Ser Leu Met Asn Gly Gln Met Trp Val Glu Ser Glu Val Gly Val<br>   1140                 1145            1150 | 3456 |
| ggg tcc cgc ttc tac ttt acg atc acc gcc gaa atc tcc cgg ccg aac<br>Gly Ser Arg Phe Tyr Phe Thr Ile Thr Ala Glu Ile Ser Arg Pro Asn<br>             1155            1160            1165 | 3504 |
| atg gcg caa agt ctg caa aag gtc gcg atc tac aag gag cgc acg atc<br>Met Ala Gln Ser Leu Gln Lys Val Ala Ile Tyr Lys Glu Arg Thr Ile<br>   1170                 1175            1180 | 3552 |
| ttg ttt gtc gat act ctg ggc gac cgg tcg ggt gtg gcg gag cgt atc<br>Leu Phe Val Asp Thr Leu Gly Asp Arg Ser Gly Val Ala Glu Arg Ile<br>1185                 1190            1195            1200 | 3600 |
| gaa gag ctg cag ctg cgt ccg ttt gtc gtg cgg gat atc agc cag gtg<br>Glu Glu Leu Gln Leu Arg Pro Phe Val Val Arg Asp Ile Ser Gln Val<br>             1205            1210            1215 | 3648 |
| gcg gac aag gcc aag att ccg ttt atc gat acg gtg att gtg gat tcg<br>Ala Asp Lys Ala Lys Ile Pro Phe Ile Asp Thr Val Ile Val Asp Ser<br>   1220                 1225            1230 | 3696 |

```
ctc gag gtg act gag aaa ttg cgc gag ttg gat cat ttg agg tat acc     3744
Leu Glu Val Thr Glu Lys Leu Arg Glu Leu Asp His Leu Arg Tyr Thr
        1235                1240                1245 ccg gcc gtg ctc ttg acg cca gtt atg ccc cga ctg aat ctg acg tgg     3792
Pro Ala Val Leu Leu Thr Pro Val Met Pro Arg Leu Asn Leu Thr Trp
    1250                1255                1260 tgt ctt gag aac ttt atc tcg ggt cat gtc gcg acc ccg tct tcg ctc     3840
Cys Leu Glu Asn Phe Ile Ser Gly His Val Ala Thr Pro Ser Ser Leu
1265                1270                1275                1280 gac gat ctt gcc gag gcg ctc gca aag gga ctg gaa gcc aac gca tct     3888
Asp Asp Leu Ala Glu Ala Leu Ala Lys Gly Leu Glu Ala Asn Ala Ser
                1285                1290                1295 cag ccc gag gtt acg ccc agc gac gtt gcg tac gac att cta ctg gcc     3936
Gln Pro Glu Val Thr Pro Ser Asp Val Ala Tyr Asp Ile Leu Leu Ala
            1300                1305                1310 gaa gac aat gtt gtc aac caa cgt gtg gcc gtc aag att ctc gaa aag     3984
Glu Asp Asn Val Val Asn Gln Arg Val Ala Val Lys Ile Leu Glu Lys
        1315                1320                1325 ttt ggt cac acg gtt cag att gcc gag aat gga cag ttt gcg gtc gac     4032
Phe Gly His Thr Val Gln Ile Ala Glu Asn Gly Gln Phe Ala Val Asp
    1330                1335                1340 gct gtc aag gct cga tac gaa caa gag aag atg ttt gat gtc att ctt     4080
Ala Val Lys Ala Arg Tyr Glu Gln Glu Lys Met Phe Asp Val Ile Leu
1345                1350                1355                1360 atg gac gtg tct atg ccg ttc atg ggt gga atg gag gca aca gaa att     4128
Met Asp Val Ser Met Pro Phe Met Gly Gly Met Glu Ala Thr Glu Ile
                1365                1370                1375 att cgc gcg ttt gag aag gaa aag ggc atc cgc cgc acg cct att atc     4176
Ile Arg Ala Phe Glu Lys Glu Lys Gly Ile Arg Arg Thr Pro Ile Ile
            1380                1385                1390 gct ctc aca gcg cac gcg atg att ggt gat cgt gag cgc tgt atc cag     4224
Ala Leu Thr Ala His Ala Met Ile Gly Asp Arg Glu Arg Cys Ile Gln
        1395                1400                1405 gct ggc atg gat gaa cac gtt acg aaa ccg ttg agg aga acc gat ctc     4272
Ala Gly Met Asp Glu His Val Thr Lys Pro Leu Arg Arg Thr Asp Leu
    1410                1415                1420 gtg agc gcg atc aaa cgc ctc gta aca ccc cac ggt gcc cac taa         4317
Val Ser Ala Ile Lys Arg Leu Val Thr Pro His Gly Ala His
1425                1430                1435

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 70
cgaagtcgat cccgagattc cggacc                                        26

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 71
cccgactccg acctcggact cgacccac                                      28
```

```
<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 72
ggtgagcccg gacgacaagg gtcttgag                                        28

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 73
attcgctcga ggtgactgag aa                                              22

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 74
ttacctcatc gctatctctt                                                 20

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 75
aaggtcgcga tctacaagga gc                                              22

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 76
atggacgtgt ctatgccgtt ca                                              22

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 77
cttcgaccgt gatgaagcgc gta                                             23
```

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence:Designed
oligonucleotide primer for PCR

<400> SEQUENCE: 78
acgaagacga caccggtagt cc                                            22

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence:Designed
oligonucleotide primer for PCR

<400> SEQUENCE: 79
atcgcagaag tcaccaaggc agt                                           23

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence:Designed
oligonucleotide primer for PCR

<400> SEQUENCE: 80
gccaccgatg tctccgccga ac                                            22

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence:Designed
oligonucleotide primer for PCR

<400> SEQUENCE: 81
cttgctaagg tcaccacgcg cca                                           23

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence:Designed
oligonucleotide primer for PCR

<400> SEQUENCE: 82
ttctaggtgg tcaggcttat gtcc                                          24

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence:Designed
oligonucleotide primer for PCR

<400> SEQUENCE: 83
ccagctgcag gacctgctga gc                                            22

<210> SEQ ID NO 84
<211> LENGTH: 28
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 84
ctcaagaccc ttgtcgtccg ggctcacc                                      28

<210> SEQ ID NO 85
<211> LENGTH: 34
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 85
ggaactagta tggcaggtac aacgggggga cacc                               34

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 86
tgcaagcttt tagtgggcac cgtggggtgt tacg                               34

<210> SEQ ID NO 87
<211> LENGTH: 27
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 87
tttctgcaca atatttcaag ctatacc                                       27

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence:Designed
      oligonucleotide primer for PCR

<400> SEQUENCE: 88
gacctagact tcaggttgtc taactcc                                       27

<210> SEQ ID NO 89
<211> LENGTH: 372
<212> TYPE: DNA
<213> ORGANISM: Phytophthora infestans
<220> FEATURE:
<221> NAME/KEY: CDS
<222> LOCATION: (1)..(372)

<400> SEQUENCE: 89

```
cac gag att cgc aca ccc atg aat ggg att att ggc atg acg gat ctc       48
His Glu Ile Arg Thr Pro Met Asn Gly Ile Ile Gly Met Thr Asp Leu
  1               5                  10                  15
```

```
acg ctt gat acc gaa ctt aca cgg acg caa aaa gaa aac ttg ttg ctc    96
Thr Leu Asp Thr Glu Leu Thr Arg Thr Gln Lys Glu Asn Leu Leu Leu
         20                  25                  30 gtt cac cag ctc gcc aag tct cta ttg ctc att atc gat gat att ctt   144
Val His Gln Leu Ala Lys Ser Leu Leu Leu Ile Ile Asp Asp Ile Leu
     35                  40                  45 gat att tcc aag atc gag gct ggc agg atg acc atg gaa caa gtc acg   192
Asp Ile Ser Lys Ile Glu Ala Gly Arg Met Thr Met Glu Gln Val Thr
 50                  55                  60 tat tct ctc cgc ggc acc gca ttc ggt atc ctc aag acc ctt gtc gtc   240
Tyr Ser Leu Arg Gly Thr Ala Phe Gly Ile Leu Lys Thr Leu Val Val
 65                  70                  75                  80 cgg gct cac caa caa aat ctc aac ctg ttc tac gaa gtc gat ccc gag   288
Arg Ala His Gln Gln Asn Leu Asn Leu Phe Tyr Glu Val Asp Pro Glu
                 85                  90                  95 att ccg gac caa gtc att ggt gat tcg ctc cgt ctg cga caa gtc att   336
Ile Pro Asp Gln Val Ile Gly Asp Ser Leu Arg Leu Arg Gln Val Ile
             100                 105                 110 acc aac ctc gtt gga aac gcc atc aag ttc aca gag                   372
Thr Asn Leu Val Gly Asn Ala Ile Lys Phe Thr Glu
         115                 120

<210> SEQ ID NO 90
<211> LENGTH: 124
<212> TYPE: PRT
<213> ORGANISM: Phytophthora infestans

<400> SEQUENCE: 90

His Glu Ile Arg Thr Pro Met Asn Gly Ile Ile Gly Met Thr Asp Leu
 1               5                  10                  15

Thr Leu Asp Thr Glu Leu Thr Arg Thr Gln Lys Glu Asn Leu Leu Leu
             20                  25                  30

Val His Gln Leu Ala Lys Ser Leu Leu Leu Ile Ile Asp Asp Ile Leu
         35                  40                  45

Asp Ile Ser Lys Ile Glu Ala Gly Arg Met Thr Met Glu Gln Val Thr
     50                  55                  60

Tyr Ser Leu Arg Gly Thr Ala Phe Gly Ile Leu Lys Thr Leu Val Val
 65                  70                  75                  80

Arg Ala His Gln Gln Asn Leu Asn Leu Phe Tyr Glu Val Asp Pro Glu
                 85                  90                  95

Ile Pro Asp Gln Val Ile Gly Asp Ser Leu Arg Leu Arg Gln Val Ile
            100                 105                 110

Thr Asn Leu Val Gly Asn Ala Ile Lys Phe Thr Glu
        115                 120
```

TRANSFORMED CELL WITH ENHANCED SENSITIVITY TO ANTIFUNGAL COMPOUND AND USE THEREOF

CROSS-REFERENCED INFORMATION

This application is a Divisional of U.S. application Ser. No. 12/272,705, filed Nov. 17, 2008 now U.S. Pat. No. 7,759,084; which is a Divisional of U.S. application Ser. No. 10/697,036 filed Oct. 31, 2003 (now U.S. Pat. No. 7,452,688), which claims priority of Japanese Application No. 2002-317736 filed Oct. 31, 2002. The entire disclosures are hereby incorporated by reference of its entirety.

BACKGROUND OF THE INVENTION

1. Field of the Invention

The present invention relates to a transformed cell with enhanced sensitivity to an antifungal compound and use thereof.

2. Description of the Related Art

It is known that, when a fungicide containing a dicarboxyimide antifungal compound, an "aromatic hydrocarbon antifungal compound" or a phenylpyrrole antifungal compound as an active ingredient is acted on a certain plant-pathogenic filamentous fungus, glycerol synthesis in a cell is stimulated in the fungus like as when undergoes high osmotic stress, and the fungus can not control an intracellular osmolarity, leading to death. From such the activity to the plant-pathogenic filamentous fungus, a protein in a signal transduction system which is involved in osmolarity response was predicted as a target protein of an antifungal compound contained in these fungicides as an active ingredient.

In *Neurospora crassa* exhibiting sensitivity to the aforementioned antifungal compound, an osmosensitive mutant os-1 was reported. This mutant os-1 exhibited resistance to the aforementioned antifungal compound and, by analysis of the mutant, an os-1 gene which is an osmosensing histidine kinase gene was isolated as a causative gene. A protein having an amino acid sequence encoded by a nucleotide sequence of this os-1 gene was a protein which has a structure of histidine kinase of a two-component regulatory system and, at the same time, has a characteristic region (hereinafter, referred to repeat sequence region in some cases) in which amino acid sequences composed of about 90 amino acids and having homology to each other are present repetitively about 6 times (see, for example, U.S. Pat. No. 5,939,306; Genebank accession U50263, U53189, AAB03698, AAB01979; Alex, A. L. et al., Proc. Natl. Acd. Sci. USA 93:3416-3421; Schumacher, M. M. et al., Current Microbiology 34:340-347; Oshima, M. et al., Phytopathology 92 (1):75-80; Fijimura, M. et al., J. Pesticide Sci. 25:31-36). A gene having homology to the os-1 gene was also isolated from plant-pathogenic filamentous fungus such as *Botryotinia fuckeliana, Magnaporthe grisea, Fusarium solani* and the like, and its nucleotide sequence and an amino acid sequence encoded by the gene are published. It is known that genes having homology with the os-1 gene are specifically present in filamentous fungus among eukaryotic organisms (see, for example, GeneBank accession AF396827, AF435964, AAL37947, AAL30826; Fujimura, M. et al., Pesticide Biochem. Physiol. 67:125-133; GeneBank accession AB041647, BAB40497).

SUMMARY OF THE INVENTION

An object of the present invention is to provide a method of detecting the antifungal activity and a method of selecting an antifungal compound using the os-1 gene and a gene having homology with the gene.

Under such the circumstances, the present inventor intensively studied and, as a result, found a transformed cell with enhanced sensitivity to an antifungal compound, and found a method of detecting the antifungal activity using this transformed cell and a method of selecting an antifungal compound using this transformed cell, which resulted in completion of the present invention.

Thus, the present invention provides:

A transformed cell in which a polynucleotide encoding an osmosensing histidine kinase having no transmembrane region is introduced in a functional form into a cell that is deficient in at least one hybrid-sensor kinase, wherein the osmosensing histidine kinase having no transmembrane region has been obtained from *Fusarium oxysporum, Mycospharella tritici* or *Thanatephorus cucumeris*.

The transformed cell according to claim 1, wherein the polynucleotide complements the hybrid-sensor kinase deficiency.

The transformed cell according to claim 1, wherein the cell is a microorganism cell.

The transformed cell according to claim 1, wherein the cell is a budding yeast cell.

The transformed cell according to claim 1, wherein the osmosensing histidine kinase having no transmembrane region has an amino acid sequence selected from the group consisting of:

(a) an amino acid sequence of an osmosensing histidine kinase having no transmembrane region, which has amino acid sequence homology of 95% or more to the amino acid sequence of any of SEQ ID NOs: 41, 55 and 68;

(b) an amino acid sequence of an osmosensing histidine kinase having no transmembrane region, which is encoded by a DNA amplified by a polymerase chain reaction using a cDNA obtained from *Fusarium oxysporum* as a template and using as primers an oligonucleotide comprising the nucleotide sequence of SEQ ID NO: 52 and an oligonucleotide comprising the nucleotide sequence of SEQ ID NO: 53;

(c) an amino acid sequence of an osmosensing histidine kinase having no transmembrane region, which is encoded by a DNA amplified by a polymerase chain reaction using a cDNA obtained from *Mycospharella tritici* as a template and using as primers an oligonucleotide comprising the nucleotide sequence of SEQ ID NO: 64 and an oligonucleotide comprising the nucleotide sequence of SEQ ID NO: 65;

(d) an amino acid sequence of an osmosensing histidine kinase having no transmembrane region, which is encoded by a DNA amplified by a polymerase chain reaction using a cDNA obtained from *Thanatephorus cucumeris* as a template and using as primers an oligonucleotide comprising the nucleotide sequence of SEQ ID NO: 85 and an oligonucleotide comprising the nucleotide sequence of SEQ ID NO: 86;

(e) the amino acid sequence of SEQ ID NO: 41;

(f) the amino acid sequence of SEQ ID NO: 55; and (g) the amino acid sequence of SEQ ID NO: 68.

The transformed cell according to claim 1, wherein the osmosensing histidine kinase having no transmembrane region has the amino acid sequence of any of SEQ ID NOs: 41, 55 and 68.

The transformed cell according to claim 1, wherein the polynucleotide has the nucleotide sequence of any of SEQ ID NOs: 42, 56 and 69.

A method of assaying the antifungal activity of a substance, which comprises:

(1) culturing the transformed cell as defined in claim 1 in the presence of a test substance;

(2) measuring an amount of intracellular signal transduction from the osmosensing histidine kinase having no transmembrane region or an index value having the correlation therewith; and (3) assessing the antifungal activity of the test substance based on a difference between an amount of intracellular signal transduction or an index value having the correlation therewith measured in (2) and a control.

The method of assaying according to claim 8, wherein the amount of intracellular signal transduction from the osmosensing histidine kinase having no transmembrane region or the index value having the correlation therewith is an amount of growth of the transformed cell.

A method of searching for a potent antifungal compound, which comprises selecting an antifungal compound based on the antifungal activity assessed in the assaying method as defined in claim 8.

A polynucleotide encoding an amino acid sequence selected from the group consisting of:

(a) an amino acid sequence of an osmosensing histidine kinase having no transmembrane region, which has amino acid sequence homology of 95% or more to the amino acid sequence of any of SEQ ID NOs: 41, 55 and 68;

(b) an amino acid sequence of an osmosensing histidine kinase having no transmembrane region, which is encoded by a DNA amplified by a polymerase chain reaction using a cDNA obtained from *Fusarium oxysporum* as a template and using as primers an oligonucleotide comprising the nucleotide sequence of SEQ ID NO: 52 and an oligonucleotide comprising the nucleotide sequence of SEQ ID NO: 53;

(c) an amino acid sequence of an osmosensing histidine kinase having no transmembrane region, which is encoded by a DNA amplified by a polymerase chain reaction using a cDNA obtained from *Mycospharella tritici* as a template and using as primers an oligonucleotide comprising the nucleotide sequence of SEQ ID NO: 64 and an oligonucleotide comprising the nucleotide sequence of SEQ ID NO: 65;

(d) an amino acid sequence of an osmosensing histidine kinase having no transmembrane region, which is encoded by a DNA amplified by a polymerase chain reaction using a cDNA obtained from *Thanatephorus cucumeris* as a template and using as primers an oligonucleotide comprising the nucleotide sequence of SEQ ID NO: 85 and an oligonucleotide comprising the nucleotide sequence of SEQ ID NO: 86;

(e) the amino acid sequence of SEQ ID NO: 41;

(f) the amino acid sequence of SEQ ID NO: 55; and (g) the amino acid sequence of SEQ ID NO: 68.

The polynucleotide according to claim 11, which encodes the amino acid sequence of any of SEQ ID NOs: 41, 55 and 68.

The polynucleotide according to claim 11, which has the nucleotide sequence of any of SEQ ID NOs: 42, 56 and 69.

A method of obtaining from a plant-pathogenic filamentous fungus a polynucleotide encoding an osmosensing histidine kinase having no transmembrane region, which comprises:

amplifying a desired polynucleotide by polymerase chain reaction using as a primer an oligonucleotide comprising the nucleotide sequence of any of SEQ ID NOs: 52, 53, 64, 65, 85 and 86, and recovering the amplified desired polynucleotide.

The method, wherein the plant-pathogenic filamentous fungus may be *Fusarium oxysporum*, and wherein the desired polynucleotide is amplified using as primers an oligonucleotide comprising the nucleotide sequence of SEQ ID NO: 52 and an oligonucleotide comprising the nucleotide sequence of SEQ ID NO: 53.

The method, wherein the plant-pathogenic filamentous fungus may be *Mycospharella tritici*, and wherein the desired polynucleotide is amplified using as primers an oligonucleotide comprising the nucleotide sequence of SEQ ID NO: 64 and an oligonucleotide comprising the nucleotide sequence of SEQ ID NO: 65.

The method, wherein the plant-pathogenic filamentous fungus may be *Thanatephorus cucumeris*, and wherein the desired polynucleotide is amplified using as primers an oligonucleotide comprising the nucleotide sequence of SEQ ID NO: 85 and an oligonucleotide comprising the nucleotide sequence of SEQ ID NO: 86.

An osmosensing histidine kinase having no transmembrane region, which is encoded by the polynucleotide as defined in claim 10.

The osmosensing histidine kinase having no transmembrane region which is encoded by the polynucleotide as defined in claim 10, which has the amino acid sequence of any of SEQ ID NOs: 41, 55 and 68

DETAILED DESCRIPTION OF THE PRESENT INVENTION

The present invention will be explained in detail below.

The "transformed cell in which a polynucleotide having a nucleotide sequence encoding an amino acid sequence of an osmosensing histidine kinase having no transmembrane region is introduced in a functional form into a cell deficient in at least one hybrid-sensor kinase" is obtained by introducing a polynucleotide having a nucleotide sequence encoding an amino acid sequence of an "osmosensing histidine kinase having no transmembrane region" in a functional form into a "cell deficient in at least one hybrid-sensor kinase" which is a host cell. Herein, "introduction of a polynucleotide in a functional form" means that the polynucleotide is introduced so as to complement the deficiency in hybrid-sensor kinase, in other words, that the polynucleotide is introduced in such a form that a phenotype of the cell caused by the deficiency in hybrid-sensor kinase revert to a phenotype without the deficiency in hybrid-sensor kinase. Specifically, for example, in the case of budding yeast (e.g. *Saccharomyces cerevisiae*), when SLN1 which is hybrid-sensor kinase is deleted, the SLN1-deficient yeast cell shows a phenotype that the cell can not grow under the normal growing condition. By introducing a polynucleotide having a nucleotide sequence encoding an amino acid sequence of SLN1 isolated from budding yeast into the SLN1-deficient cell so that SLN1 is expressed (e.g. operably linked to downstream of a promoter), the cell becomes possible to grow under the normal growing condition. The "cell deficient in at least one hybrid-sensor kinase" may be obtained, for example, by deleting at least one intrinsic hybrid-sensor kinase. First, hybrid-sensor kinase will be explained below.

(Two-Component Regulatory System and Hybrid-Sensor Kinase)

Two-component regulatory system is a signal transduction system which is widely used in prokaryotic organisms and, since this system is basically composed of two proteins called a sensor and a regulator, it is called two-component regulatory system. In a typical two-component regulatory system, a sensor is composed of an input region and a histidine kinase region, and a regulator is composed of a receiver region and an output region. When the input region senses an environmental stimulus, a histidine residue in an amino acid sequence in the histidine kinase region which is well conserved among organisms is phosphorylated or dephosphorylated. Herein, phosphorylation of the histidine residue is autophosphorylation utilizing ATP as a substrate. This phosphate group is transferred to an aspartic acid residue in an amino acid sequence in the receiver region in the regulator which is well conserved among organisms, and phosphorylation and dephosphorylation of the aspartic acid residue regulates the activity of the output region in the regulator. In the case of prokaryotic organisms, the output region is a transcription regulating factor in many cases although there are exceptions, and the regulator directly controls gene expression through the aforementioned phosphoryl transfer in response to stimuli sensed by the sensor.

A sensor takes a more complicated structure in some cases unlike the aforementioned typical structure. For example, in addition to a structure composed of an input region and a histidine kinase region, following this, the sensor contains a receiver region, which is observed in a regulator, on its C-terminal side in some cases. In this case, the phosphorylay system of a phosphate group becomes more complicated, and it is known that a phosphate is transferred from the sensor to a regulator called a response regulator via an intervening protein having a transmitter region called a phosphotransmitter. That is, when the input region of the sensor senses stimuli, phospate is transferred to mediate signal transduction from a histidine residue of the histidine kinase region in the same molecule to an aspartic acid residue of the receiver region in the same molecule, then, to a histidine residue of the phosphotransmitter, finally, to an aspartic acid residue of the receiver region in a response regulator. Like this, two-component regulatory system is associated with three proteins in some cases. Such the sensor involved in signal transduction system through phosphoryl transfer composed of three proteins and having the aforementioned structural characteristic is referred to as "hybrid-sensor kinase". Hybrid-sensor kinase is found not only in a prokaryotic organism but also in an eukaryotic microorganism such as yeast, a plant and the like, and is involved in response to a variety of stimuli or stresses.

Herein, an input region of a hybrid-sensor kinase is a region present at the N-terminal of the kinase, and have a transmembrane region in many cases. The transmembrane region can be revealed by a structure prediction analysis using a structure prediction software, for example, TMpred program [K. Hofmann & W. Stoffel, Biol. Chem. Hoppe-Seyler, 374, 166 (1993)] which is available, for example, from http://www.ch.embnet.org/software/TMPRED_form.html. A histidine kinase region of a hybrid-sensor kinase is, for example, a region following the C-terminal of the input region, and is a region characterized in that it has five conserved motifs common to general histidine kinases as described in Parkinson, J. S. & Kofoid, E. C. (1989) Annual Review of Genetics 23:311-336, Stock, J. B. et. al. (1989) Microbiological Reviews 53(4):450-490. For example, in the hybrid-sensor kinase SLN1 of budding yeast, a histidine kinase region is the region from amino acid residues 556 to 908. A receiver region of a hybrid-sensor kinase is, for example, a region following the C-terminal of the histidine kinase region, and is a region characterized in that it has three conserved motifs common to general histidine kinases as described in Parkinson, J. S. & Kofoid, E. C. Annual Review of Genetics 23:311-336 (1989), Stock, J. B. et. al. (1989) Microbiological Reviews 53(4): 450-490. For example, in the hybrid-sensor kinase SLN1 of budding yeast, a receiver region is the region from amino acid residues 1088 to 1197.

As a signal transduction system after a response regulator, in addition to a simple system in which an output region of a regulator is a transcription regulating factor as described above, as a more complicated system, there is known a system in which a signal is transmitted to a transcription regulating factor participating in control of gene expression, via MAP kinase cascade which is associated with various controls in a cell.

Specific examples of a hybrid-sensor kinase and a signal transduction system which involves the hybrid-sensor kinase will be explained below.

(Hybrid-Sensor Kinase of Budding Yeast)

In budding yeast (*Saccharomyces cerrevisiae*), the hybrid-sensor kinase SLN1 is utilized for signal transduction relating to osmolarity response. The SLN1 is a sole histidine kinase found in budding yeast. SLN1 is an osmosensing histidine kinase having a transmembrane region in its input region, and mediates a phosphoryl transfer signal to the response regulator SSK1 via the phosphotransmitter YPD1. Downstream of the signal transduction, MAP kinase cascade composed of three kinases SSK2 (MAPKKK), PBS2 (MAPKK) and HOG1 (MAPK) lies to regulate expression of genes involved in osmolarity adaptation such as glycerol biosynthesis and the like. The output region of the response regulator SSK1 has an activity of phosphorylating SSK2. The SSK1 is negatively controled by phosphorylation of an aspartic acid residue in its receiver region, the phosphorylating activity of whose output region is inhibited. Specifically, at a normal osmolarity, a histidine residue in the histidine kinase region of SLN1 is autophosphorylated, and the phosphate is subsequently transferred to an aspartic acid residue of the receiver region in the same molecule, then, to a histidine residue of YPD1, finally, to an aspartic acid residue in the receiver region of SSK1. By phosphorylation of an aspartic acid residue in the receiver region of SSK1, the phosphorylating activity of the output region of SSK1 is suppressed, and the phosphate is not transferred to a MAP kinase cascade composed of SSK2, PBS2 and HOG1, and then expression of genes involved in osmolarity adaptation such as glycerol biosynthesis and the like are not induced. On the other hand, under a condition of high osmolarity, since autophosphorylation of a histidine residue of the histidine kinase region is inhibited in SLN1, the MAP kinase cascade composed of SSK2, PBS2 and HOG1 is activated, and then expression of genes involved in osmolarity adaptation such as glycerol biosynthesis and the like is induced (Maeda, T. et. al. (1994) Nature 369:242-245).

(Hybrid-Sensor Kinase of Fission Yeast)

In fission yeast (*Scchizosaccharomyces pombe*), three kinds of hybrid-sensor kinases PHK1 (MAK2), PHK2 (MAK3) and PHK3 (MAK1) participate in regulation of cell cycle progression [G(2) to M phase transition] and oxidative stress response. In a fission yeast, there is no histidine kinase other than PHK1, PHK2 and PHK3. PHK1 and PHK2 are histidine kinases responsive to oxidative stress such as hydrogen peroxide and the like (Buck, V. et. al., Mol. Biol. Cell 12:407-419). Three kinds of hybrid-sensor kinases PHK1, PHK2 and PHK3 metiate a phosphoryl transfer signal to the response regulator MCS4 via the phosphotransmitter SPY1 (MPR1). Downstream of this signal transduction, a MAP kinase cascade composed of three kinases WAK1 (MAPKKK), WIS1 (MAPKK) and STY1 (MAPK) lies to regulate expression of genes involved in regulation of cell cycle progression and oxidative stress response. The output region of the response regulator MCS4 has an activity of phosphorylating WAK1. The MCS4 is negatively controled by phosphorylation of an aspartic acid residue in its receiver region, the phosphorylating activity of whose output region is inhibited. Specifically, under a normal condition, each of histidine residues in the histidine kinase regions of PHK1 to PHK3 is autophosphorylated, and the phosphates are transferred to each of aspartic acid residues of receiver regions in the same molecule, then, to a histidine residue of SPY, finally, to an aspartic acid residue in the receiver region of MCS4. By phosphorylation of an aspartic acid residue in the receiver region of MCS4, the phosphorylating activity of the output region of MCS4 is suppressed, and the phosphate is not transferred to a MAP kinase cascade composed of WAK1, WIS1 and STY1, and then expression of genes involved in regulation of cell cycle progression and stress response are not induced. On the other hand, under a stress condition, autophosphorylation of each of histidine residues of the histidine kinase regions in PHK1 to PHK3 is inhibited, a MAP kinase cascade composed of WAK1, WIS1 and STY1 is activated, and expression of genes involved in control of cell cycle progression and oxidative stress response are induced. As a result, it is observed such a phenotype that G(2) to M phase transition in cell cycle progression of the fission yeast is promoted, and that a dividing cell length becomes remarkably shorter than usual (Aoyama, K. et. al. (2001) Boisci. Biotechnol. Biochem. 65:2347-2352).

(Hybrid-Sensor Kinase of Bacterium)

In a prokaryotic organism *Escherichia coli*, the hybrid-sensor kinase RcsC participates in control of expression of the cps operon involved in capsular polysaccharide synthesis. RcsC is a histidine kinase having a transmembrane region, and it is known that it mediates a phosphoryl transfer signal to the response regulator RcsB via the phosphotransmitter YojN. The output region of RcsB has an activity of inducing transcription of the cps operon. Specifically, under a normal condition, a histidine residue in the histidine kinase region of RcsC is autophosphorylated, and the phosphate is transferred to an aspartic acid residue of the receiver region in the same molecule, then, to a histidine residue of YojN, finally, to an aspartic acid residue in the receiver region of RcsB. By phosphorylation of an aspartic acid residue in the receiver region of RcsB, the cps operon transcription inducing activity of the output region of RcsB is suppressed, and expression of genes involved in capsular polysaccharide synthesis are not induced. On the other hand, under a condition of high osmolarity, in RcsC, autophosphorylation of a histidine residue in the histidine kinase region is inhibited, the cps operon transcription inducing activity of the output region of RcsB is activated, and expression of genes involved in capsular polysaccharide synthesis are induced (Clarke, D. J. et. al. (2002) J. Bactriol. 184:1204-1208).

A bioluminescent marine microorganism *Vibrio harveyi* emits fluorescent light generated in luciferase reaction depending on its own cell density. Hybrid-sensor kinases LuxN and LuxQ parcipite in control of expression of a gene involved in this cell density-responsive bioluminescence. LuxN and LuxQ are histidine kinases each having a transmembrane region. To sense its own cell density, *V. harveyi* produces and secrets two kinds of substances (AI-1, AI-2) called autoinducer. AI-1 is sensed by LuxN and AI-2 is sensed by LuxQ to convey cell-density information. LuxN and LuxQ mediate phosphoryl transfer signals to the response regulator LuxO via the phosphotransmitter LuxU. The output region of LuxO has an activity of inducing transcription of the luciferase operon. To specifically explain by referring to LuxN, when a cell density is low, since AI-1 in the environment is at low level and is not sensed by the input region of LuxN, a histidine residue in the histidine kinase region of LuxN is autophosophorylated. The phosphate is transferred to an aspartic acid residue of the receiver region in the same molecule, then, to a histidine residue of LuxU, finally, to an aspartic acid residue in the receiver region of LuxO. By phosphorylation of an aspartic acid residue in the receiver region of LuxO, the luciferase operon transcription inducing activity of the output region of LuxO is suppressed, and expression of genea involved in bioluminescence are not induced. On the other hand, under a high cell density condition, since AI-1 in environment is at high level and is sensed by the input region of LuxN, autophosphorylation of a histidine residue of the histidine kinase region is inhibited in LuxN, the luciferase operon transcription inducing activity of the output region of LuxO is activated, and bioluminescence is induced (Freeman, J. A. et. al. (2000) Mol. Microbiol. 35:139-149).

(Hybrid-Sensor Kinase of Plant)

In a higher plant *Arabadopsis thaliana*, receptor proteins CRE1, AHK2 and AHK3 for a plant hormone cytokinin are hybrid-sensor kinases. Receptor proteins CRE1, AHK2 and AHK3 are all cytokinin-sensitive histidine kinase having a transmembrane region (Inoue, T. et. al. (2001) Nature 409: 1060-1063). CRE1 mediates a phosphoryl transfer signal to response regulators ARR1, ARR2 and ARR10 via phosphotransmitters AHP1 and AHP2. It is considered that output regions of ARR1, ARR2 and ARR10 have an activity of inducing transcription of cytokinin-inducing genes ARR4 to ARR7. Specifically, in the presence of cytokinin, a hisitidine residue in the histidine kinase region of CRE1 is autophosphorylated, and the phosphate is transferred to an aspartic acid residue of the receiver region in the same molecule, then, to histidine residues of AHP1 and AHP2, finally, to aspartic acid residues in receiver regions of ARR1, ARR2 and ARR10. By phosphorylation of aspartic acid residues in receiver regions of ARR1, ARR2 and ARR10, a gene transcription inducing activity of output regions of ARR1, ARR2 and ARR10 are promoted, and expression of cytokinin-responsive genes ARR4 to 7 is induced (Hwang, I. & Sheen J. (2001) Nature 413:383-389).

(Cell Deficient in at Least One Hybrid-Sensor Kinase)

"The cell deficient in at least one hybrid-sensor kinase" means a cell in which function of at least one intrinsic hybrid-sensor kinase is lost. Examples of the cell include a cell in which production of at least one intrinsic hybrid-sensor kinase is deleted, suppressed or inhibited, a cell in which activity of at least one intrinsic hybrid-sensor kinase is deleted, suppressed or inhibited, and the like. More specific examples include budding yeast deficient in SLN1, fission yeast deficient in all of three of PHK1, PHK2 and PHK3, *Escherichia coli* deficient in RcsC, *V. harveyi* deficient in LuxN, *Arabidopsis thaliana* deficient in CRE1, and the like.

In order to prepare the "cell deficient in at least one hybrid-sensor kinase", for example, deletion, addition, substitution or the like of one or more nucleotides are introduced into the whole or a part of a promoter region or a coding region of a gene encoding hybrid-sensor kinase to be deleted. Specifically, for example, the SLN1-deficient budding yeast strain TM182 can be prepared by the method described in Maeda, T. et. al. (1994) Nature 369:242-245, the PHK1, PHK2 and PHK3-deficient fission yeast strain KI011 can be prepared by the method described in Aoyama, K. et. al. (2001) Boisci. Biotechnol. Biochem. 65:2347-2352. In addition, the RcsC-deficient *Escherichia coli* strain SRC122 can be prepared by the method described in Suzuki, T., et. al. (2001) Plant Cell Physiol. 42:107-113, and the LuxN-deficient *V. harveyi* strain BNL63 can be prepared by the method described in Freeman, J. A. et. al. (2000) Mol. Micobiol. 35:139-149. For preparing a CRE1-deficient *Arabidopsis thaliana*, for example, a clone defective in cytokine response is selected from clones obtained by mutagenesis of *Arabidopsis thaliana* according to the method described in Inoue, T. et. al. (2001) Nature 409:1060-1063. Genomic CRE1 gene fragment is amplified by PCR using a primer designed based on the nucleotide sequence of the genomic CRE1 gene listed in Genebank accession AB049934 and using a genomic DNA of the selected clone as a template, and its nucleotide sequence is confirmed, whereby, a CRE1-deficient clone which can not express CRE1 can be selected.

Alternatively, a cell deficient in unknown hybrid-sensor kinase besides the aforementioned kinases may be also prepared, for example, by isolating a hybrid-sensor kinase gene from a desired cell, and deleting the gene harbored by the cell by homologous recombination using the gene. For isolating a hybrid-sensor kinase gene of a desired cell, the structural characteristic of hybrid-sensor kinases can be utilized. For example, amino acid sequences around the histidine residue to be autophosphorylated are conserved among hisitidine kinase regions and amino acid sequences around the aspartic acid residue to which a phosphate to be transferred from the histidine residue are conserved among receiver regions. Then, a hybrid-sensor kinase gene of a desired cell can be isolated by a polymerase chain reaction (hereinafter, referred to as PCR) using an oligonucleotide designed based on a nucleotide sequence encoding the aforementioned conserved amino acid sequences as a primer, or a hybridization method using an oligonucleotide having a nucleotide sequence encoding the aforementioned conserved amino acid sequences as a prove. By examining whether or not the aforementioned structural characteristic is possessed based on an amino acid sequence deduced from a nucleotide sequence of the isolated gene, it can be confirmed that the isolated gene is a gene having a nucleotide sequence encoding an amino acid sequence of a hybrid-sensor kinase. A specific example is a PCR method described in Srilantha, T. et. al. (1998) Microbiology 144:2715-2729. For PCR and hybridization, for example, the experimental conditions using upon isolation of the "polynucleotide having a nucleotide sequence encoding an amino acid sequence of osmosensing hisitidine kinase having no transmembrane region" described later may be used.

Alternatively, a hybrid-sensor kinase gene may be also isolated using, as an index, the functional complementation in budding yeast in which expression of SLN1 is conditionally suppressed, for example, according to the method described in Nagahashi, S. et. al. (1998) Microbiology 144:425-432.

(Osmosensing Histidine Kinase Having No Transmembrane Region)

Then, the "osmosensing histidine kinase having no transmembrane region" to be introduced into the aforementioned "cell deficient in at least one hybrid-sensor kinase" in a functional form will be explained.

In filamentous fungus, a histidine kinase having a structure similar to that of the aforementioned hybrid-sensor kinase is isolated. The histidine kinase has a histidine kinase region and a receiver region which are observed in hybrid-sensor kinases, and has no transmembrane region, which is observed in many hybrid-sensor kinases, in its input region, and further has a characteristic structure in which amino acid sequences composed of about 90 amino acids having the amino acid sequence homology to each other are present repeatedly about six times, in place of the transmembrane region. Although a signal transduction pathway from this histidine kinase has not been completely clarified, it is known that the signal transduction participates in osmolarity response.

In the present invention, "homology" refers to identity of sequences between two genes or two proteins. The "homology" is determined by comparing two sequences aligned in the optimal state, over a region of a sequence of a subject to be compared. Herein, in optimal alignment of nucleotide sequences or amino acid sequences to be compared, addition or deletion (e.g. gap etc.) may be allowable. Such the "homology" can be calculated by homology analysis with making alignment using a program of FASTA [Pearson & Lipman, Proc. Natl. Acad. Sci. USA, 4, 2444-2448 (1998)], BLAST [Altschul et. al. Journal of Molecular Biology, 215, 403-410 (1990)], CLUSTAL W [Thompson, Higgins & Gibson, Nucleic Acid Research, 22, 4673-4680(1994a)] and the like. The above programs are available to the public, for example, in homepage (http://www.ddbj.nig.ac.jp) of DNA Data Bank of Japan [international DNA Data Bank managed in Center for Information Biology and DNA Data Bank of Japan (CIB/DDBJ)). Alternatively, the "homology" may be also obtained by using commercially available sequence analysis software. Specifically, the homology can be calculated, for example, by performing homology analysis with making alignment by the Lipman-Pearson method [Lipman, D. J. and Pearson, W. R., Science, 227, 1435-1441, (1985)] using GENETYX-WIN Ver. 5 (manufactured by Software Development Co., Ltd.).

Herein, as the "structure in which amino acid sequences composed of about 90 amino acids having the amino acid sequence homology to each other are repeatedly present about six times", for example, there is a repeat sequence region described in Alex, L. A. et. al. (1996) Proc. Natl. Acad. Sci. USA 93:3416-3421, Ochiai, N. et. al. (2001) Pest Manag. Sci. 57:437-442, Oshima, M. et. al. (2002) Phytopathology 92:75-80 and the like, and such the structure is present at the N-terminal region of the hisitide kinase. The "amino acid sequences composed of about 90 amino acids are repeatedly present about six times" include an amino acid sequence motif composed of about 90 amino acids is repeated five times followed by a sixth truncated repeat sequence (5.7 times repeat), an amino acid sequence motif composed of about 90 amino acids is repeated six times followed by a seventh truncated repeat sequence (6.7 times repeat), and the like. Specifically, in amino acid sequence of a histidine kinase of the present invention, examples of the "a region in which amino acid sequences composed of about 90 amino acids having the amino acid sequence homology to each other are present repeatedly about six times" include a region from amino acid residues 190 to 707 in an amino acid sequence represented by SEQ ID NO: 1 (5.7 times repeat), a region from amino acid residues 189 to 706 in an amino acid sequence represented by SEQ ID NO: 16 (5.7 times repeat), a region from amino acid residues 176 to 693 in an amino acid sequence represented by SEQ ID NO: 41 (5.7 times repeat), a region from amino acid residues 192 to 709 in an amino acid sequence represented by SEQ ID NO: 55 (5.7 times repeat), and a region from amino acid residues 299 to 911 in an amino acid sequence represented by SEQ ID NO: 68 (6.7 times repeat), and the like.

The "osmosensing histidine kinase having no transmembrane region" is the aforementioned histidine kinase characteristic in filamentous fungus, and refers to a osmosensing protein having a repeat sequence region of amino acid sequences composed of about 90 amino acids having the amino acid sequence homology to each other, a histidine kinase region and a receiver region, and having no transmembrane region.

In order to confirm that a protein has the function of osmosensing histidine kinase, enhancement of the sensitivity of a cell to osmolarity stress may be confirmed when the protein (histidine kinase) is deleted from the cell. Alternatively, it may be also confirmed that a protein (histidine kinase) is osmosensing histidine kinase, by confirming that expression of the protein in an osmosensing hybrid-sensor kinase SLN1-deficient budding yeast cell results in a functional complementation of the SLN1 and the budding yeast cell capable of growing.

Among filamentous fungi, mainly, in *Neurospora crassa* which is a model organism of filamentous fungus, a plant pathogenic filamentous fungus which is a pathogenic microorganism, a host of which is a plant, or the like, the presence of the "osmosensing histidine kinase having no transmembrane region" is reported.

Examples of the "osmosensing histidine kinase having no transmembrane region" of the present invention include an osmosensing histidine kinase having no transmembrane region, which has an amino acid sequence selected from the group consisting of:

(a) an amino acid sequence of an osmosensing histidine kinase having no transmembrane region, which has an amino acid sequence homology of 95% or more to the amino acid sequence represented by any of SEQ ID NOs: 41, 55 and 68;

(b) an amino acid sequence of an osmosensing histidine kinase having no transmembrane region, which is encoded by a DNA amplified by a polymerase chain reaction using a *Fusarium oxysporum*-derived cDNA as a template and using an oligonucleotide having the nucleotide sequence represented by SEQ ID NO: 52 and an oligonucleotide having the nucleotide sequence represented by SEQ ID NO: 53 as primers;

(c) an amino acid sequence of an osmosensing histidine kinase having no transmembrane region, which is encoded by a DNA amplified by a polymerase chain reaction using a *Mycospharella tritici*-derived cDNA as a template and using an oligonucleotide having the nucleotide sequence represented by SEQ ID NO: 64 and an oligonucleotide having the nucleotide sequence represented by SEQ ID NO: 65 as primers;

(d) an amino acid sequence of an osmosensing histidine kinase having no transmembrane region, which is encoded by a DNA amplified by a polymerase chain reaction using a *Thanaphthorus cucumeris*-derived cDNA as a template and using an oligonucleotide having the nucleotide sequence represented by SEQ ID NO: 85 and an oligonucleotide having the nucleotide sequence represented by SEQ ID NO: 86 as primers;

(e) an amino acid sequence of an osmosensing histidine kinase having no transmembrane region, which is derived from *Phytophthora infestans* and has the amino acid sequence represented by SEQ ID NO: 90;

(f) the amino acid sequence represented by SEQ ID NO: 41;

(g) the amino acid sequence represented by SEQ ID NO: 55; and (h) the amino acid sequence represented by SEQ ID NO: 68.

A preferred amino acid sequence homology in the above (a) may for example be about 95%, or higher such as about 98%. The difference from the amino acid sequence represented by any of SEQ ID: 41, 55 and 68 observed in the amino acid sequence of the above (a) may for example be a variation such as the deletion, substitution and addition of amino acids. Such a variation includes a variation which can artificially be introduced by means of a site-directed mutagenesis method or a mutagenic treatment as well as a polymorphic variation which occurs naturally such as a difference in an amino acid sequence resulting from the difference by the species or strains from which the protein is derived. As the site-directed mutagenesis method, for example, there is mentioned the method which utilizes amber mutations (capped duplex method, Nucleic Acids Res., 12, 9441-9456 (1984)), the method by PCR utilizing primers for introducing a mutation and the like.

At least one, specifically one to several (herein "several" means about 2 to about 10), or more amino acid residues may be varied in the above variations. The amino acid residues may be varied in any numbers as far as the effect of the present invention can be observed.

Of the deletion, addition, and substitution, the substitution is particularly preferred in the amino acid variation. Amino acids that are similar to each other in hydrophobicity, charge, pK, stereo-structural characteristic, or the like are more preferably replaced with each other. For example, such substitutable amino acids are in each of the following groups: 1) glycine and alanine; 2) valine, isoleucine, and leucine; 3) aspartic acid, glutamic acid, asparagine, and glutamine; 4) serine and threonine; 5) lysine and arginine; and 6) phenylalanine and tyrosine.

The "osmosensing histidine kinase having no transmembrane region" will be further explained with the specific examples shown below.

(Osmosensing Histidine Kinase Having No Transmembrane Region of *Neurospora crassa*)

A protein OS-1 encoded by an os-1 gene isolated from an osmosensing mutant os-1 of *Neurospora crassa* can be mentioned as the "osmosensing histidine kinase having no transmembrane region" (Schumacher, M. M. et. al. (1997) Current Microbiol. 34:340-347, Alex, L. A. et. al. (1996) Proc. Natl. Acad. Sci. USA 93:3416-3421). Amino acid sequences of OS-1 and nucleotide sequences of the os-1 gene are published (amino acid sequence: Genebank accession AAB03698, AAB01979, nucleotide sequence: Genebank accession U50263, U53189), and utility of OS-1 and os-1 gene in screening system for antifungal compounds is described in U.S. Pat. No. 5,939,306. Since *Neurospora crassa* mutant os-1 has the higher sensitivity to high osmolarity stress than that of a wild strain, it has been found that OS-1 is an osmosensing histidine kinase involved in osmolarity adaptation in *Neurospora crassa*. It is known that OS-1 has the aforementioned structural characteristic based on its amino acid sequence. In addition, it is known that *Neurospora crassa* mutant os-1 has the resistance to fungicides containing, as an active ingredient, a dicarboxyimide antifungal compound, an "aromatic hydrocarbon antifungal compound" or a phenylpyrrole antifungal compound. Further, a gene mutation which leads to an amino acid substitution in a characteristic repeat sequence region of OS-1 was observed in the os-1 mutant gene isolated from *Neurospora crassa* mutant exhibiting the resistance to a fungicide containing a dicarboxyimide antifungal compound as an active ingredient (Miller, T. K. et. al. (2002) Fungl Gen. Biol. 35:147-155). From the foregoing, it is predicted that an antifungal compound contained as an effective ingredient in the aforementioned fungicide targets OS-1 of *Neurospora crassa*.

(Osmosensing Histidine Kinase Having No Transmembrane Region of *Botryotinia fuckeliana*)

Examples of the "osmosensing histidine kinase having no transmembrane region" include BcOS-1 of *Botryotinia fuckeliana*. The BcOS-1 gene was isolated as a gene homologous to *Neurospora crassa* OS-1 gene, and nucleotide sequencez and amino acid sequences are published (nucleotide sequence: GeneBank accession AF396287, AF435964, amino acid sequence: GeneBank accession AAL37947, AAL30826). It is known that BcOS-1 has the aforementioned structural characteristic based on its amino acid sequence. In addition, in the BcOS-1 gene isolated from a *Botryotinia fuckeliana* strain resistant to a fungicide containing a dicarboxyimide antifungal compound as an active ingredient, a mutation which leads to amino acid substitution in the characteristic repeat sequence region of BcOS-1 was observed, as in the OS-1 gene isolated from a *Neurospora crassa* strain resistant to a fungicide containing a dicarboxyimide antifungal compound as an active ingredient. Further, since an antifungal compound-resistant mutant deficient in the BcOS-1 has the higher osmolarity sensitivity than that of a wild strain, it is known that BcOS-1 is osmosensing histidine kinase (Oshima, M. et. al. (2002) Phypotathology 92:75-80).

More specifically, examples of BcOS-1 include BcOS-1 having an amino acid sequence represented by SEQ ID NO: 1 which was isolated from Bc-16 strain described in Example.

(Osmosensing Histidine Kinase Having No Transmembrane Region of *Magnaporthe grisea*)

Example of the "osmosensing histidine kinase having no transmembrane region" include HIK1 of *Magnaporthe grisea*. The hik1 gene is a gene homologous to *Neurospora crass* os-1 gene, and a nucleotide sequence and an amino acid sequence are published (nucleotide sequence: Genebank accession AB041647, amino acid sequence: GeneBank accession BAB40947). It is known that HIK1 has the aforementioned structural characteristics such as lack of the transmembrane region based on its amino acid sequence. In addition, it is observed that *Magnaporthe grisea* deficient in the hik1 gene has the higher osmolarity sensitivity than that of a wild strain, demonstrating that HIK1 is an osmosensing histidine kinase (hppt://www.sci.saitama-u.ac.jp/seitai/iden/Japanese/Abst Symp3.html).

More specifically, examples of HIK1 include HIK1 having an amino acid sequence represented by SEQ ID NO: 16 which was isolated from the P-37 strain described in Example.

(Definition of Filamentous Fungus and Yeast)

In the present invention, the "filamentous fungus" means fungi other than fungi which can be classified as yeast, among fungi consisting of Myxomycota and Eumycota, described in "Revised Edition, Classification and Identification of Microorganisms (Volume 1), edited by Takeharu HASEGAWA, Society Publishing Center, 1984 (ISBN 4-7622-7399-6)". Examples of filamentous fungus classified in Myxomycota include *Plasmodiophora brassicae* belonging to Plasmodiophoromycetes. In addition, examples of filamentous fungus which is classified in Eumycota include *Phytophthora infestans* belonging to Mastigomycotina, *Rhizopus stolonifer* and *Rhizopus oryzae* belonging to Zygomycotina, *Neurospora crassa, Mycospharella tritici, Erysiphe graminis, Linocarpon cariceti, Cochliobolus miyabeanus, Botrytinia fuckeliana* and *Magnaporthe grisea* belonging to Ascomycotina, *Ustilago maydis, Puccinia recondite* and *Thanatephorus cucumeris* belonging to Basidiomycotina, *Cladosporium fulvum, Alternalia kikuchiana* and *Fusarium oxysporum* belonging to Deuteromycotina, and the like.

In addition, yeast means fungi in which they are grown mainly by budding, a single cell generation is long, a colony formed by growth of a single cell does not become hairy, but becomes white bright paste-like" as described in "Revised Edition, Classification and Identification of Microorganisms (Volume 1), edited by Takeharu HASEGAWA, Society Publishing Center, 1984 (ISBN 4-7622-7399-6)". Examples thereof include *Saccharomyces cerevisiae* belonging to genus *Saccharomyces, Schizosaccharomyces pombe* belonging to genus *Schizosaccharomyces, Phichia burtonii* belonging to genus *Phichia, Candida albicans* belonging to genus *Candida*, and the like.

(Osmosensing Histidine Kinase Having Mutation which Confers Resistance to any of Dicarboxylmide Antifungal Compound, Aromatic Hydrocarbon Antifungal Compound and Phenylpyrrole Antifungal Compound, and Having No Transmembrane Region)

As a specific example of the "osmosensing histidine kinase having no transmembrane region", there can also be exemplified "osmosensing histidine kinase having no transmembrane region" having mutation which confers resistance to any of a dicarboxyimide antifungal compound, an "aromatic hydrocarbon antifungal compound" and a phenylpyrrole antifungal compound. Specifically, there can be exemplified BcOS-1 having an amino acid sequence represented by SEQ ID NO: 13 which is described in Example.

Herein, the dicarboxyimide antifungal compound is a generic name of antifungal compounds having dicarboxyimide as a basic structure, and examples thereof include antifungal compounds described in Modern Selective Fungicide-Properties, Applications, Mechanism of Action-$2^{nd}$ revised and enlarged edition Lyr, H. ed. Gustav Fisher Verlag, New York, USA ISBN 3-334-60455-1 Chapter 6, p 99-118. Specifically, there are a compound having a structure represented by the chemical formula (1) (Procymidone: hereinafter, referred to as Compound (1) in some cases), a compound having a structure represented by the chemical formula (2) (Iprodione: hereinafter, referred to as Compound (2) in some cases), a compound having a structure represented by the chemical formula (3) (Vinclozolin: hereinafter, referred to as Compound (3) in some cases) and the like. The "aromatic hydrocarbon antifungal compound" is a generic name of antifungal compounds having a benzene ring as a basic structure, and examples thereof include antifungal compounds described in Modern Selective Fungicide-Properties, Applications, Mechanism of Action-$2^{nd}$ revised and enlarged edition Lyr, H. ed. Gustav Fisher Verlag, New York, USA ISBN 3-334-60455-1 Chapter 5, p 75-98. Specifically, there are a compound having a structure represented by the chemical formula (4) (Quintozene: hereinafter, referred to as Compound (4) in some cases), a compound having a structure represented by the chemical formula (5) (Tolclofos-methyl: hereinafter, referred to as Compound (5) in some cases). In addition, the phenylpyrrole antifungal compound is a generic name of antifungal compounds having phenylpyrrole as a basic structure, and examples thereof include antifungal compounds described in Modern Selective Fungicide-Properties, Applications, Mechanism of Action-$2^{nd}$ revised and enlarged edition Lyr, H. ed. Gustav Fisher Verlag, New York, USA ISBN 3-334-60455-1 Chapter 19, p 405-407. Specifically, there are a compound having a structure represented by the chemical formula (6) (Fludioxonil: hereinafter, referred to as Compound (6) in some cases), a compound having a structure represented by the chemical formula (7) (Fenpiclonil: hereinafter, referred to as Compound (7) in some cases) and the like.

Chemical formulas of the aforementioned dicarboxyimide antifungal compound, "aromatic hydrocarbon antifungal compound" and phenylpyrrole antifungal compounds are shown below.

(1) Compound Having a Structure Represented by the Chemical Formula (1) (Compound (1))

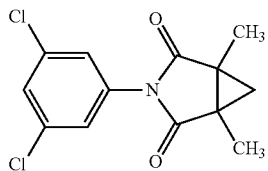

Chemical formula (1)

(2) Compound Having a Structure Represented by the Chemical Formula (2) (Compound (2))

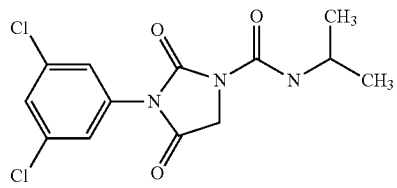

Chemical formula (2)

(3) Compound Having a Structure Represented by the Chemical Formula (3) (Compound (3))

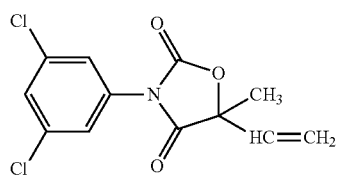

Chemical formula (3)

(4) Compound Having a Structure Represented by the Chemical Formula (4) (Compound (4))

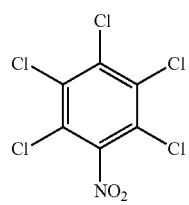

Chemical formula (4)

(5) Compound Having a Structure Represented by the Chemical Formula (5) (Compound (5))

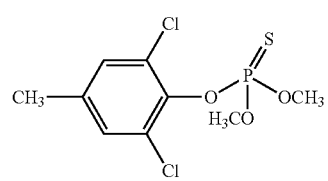

Chemical formula (5)

(6) Compound Having a Structure Represented by the Chemical Formula (6) (Compound (6))

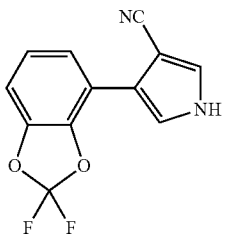

Chemical formula (6)

(7) Compound Having a Structure Represented by the Chemical Formula (7) (Compound (7))

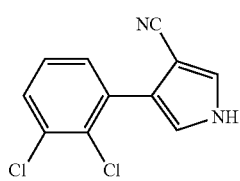

Chemical formula (7)

The "mutation which confers resistance to any of a dicarboxyimide antifungal compound, an aromatic hydrocarbon antifungal compound and a phenylpyrrole antifungal compound" indicates a mutation which can be found in the "osmosensing histidine kinase having no transmembrane region" produced by a filamentous fungus mutant having resistance to any of a dicarboxyimide antifungal compound, an "aromatic hydrocarbon antifungal compound" and a phenylpyrrole antifungal compound, that is, substitution, addition or deletion of one or more amino acids which confer resistance to a dicarboxyimide antifungal compound, an "aromatic hydrocarbon antifungal compound" and a phenylpyrrole antifungal compound, provided that mutation by which the "osmosensing histidine kinase having no transmembrane region" becomes not to function as histidine kinase is eliminated. Herein, a mutant of filamentous fungus having resistance to any of a dicarboxyimide antifungal compound, an "aromatic hydrocarbon antifungal compound" and a phenylpyrrole antifungal compound may be filamentous fungus isolated from the nature to which any of a dicarboxyimide antifungal compound, an "aromatic hydrocarbon antifungal compound" and a phenylpyrrole antifungal compound was applied, or may be resistance-acquired filamentous fungus selected by artificially culturing filamentous fungus in the presence of a dicarboxyimide antifungal compound, an "aromatic hydrocarbon antifungal compound" or phenylpyrrole antifungal compound.

Specifically, in BcOS-1 in the "osmosensing histidine kinase having no transmembrane region" of *Botryotinia fuckeliana*, amino acid-substitution I365S which confers resistance to a dicarboxyimide antifungal compound is reported in Oshima, M. et al. (2002) Phytopathology 92:75-80 (herein, "I365S" means that isoleucine at amino acid residue 365 is substituted with serine. Hereinafter, amino acid substitution is described similarly). As an amino acid substitution which confers resistance to a dicarboxyimide antifungal compound in OS-1 which is the "osmosensing histidine kinase having no transmembrane region" of *Neuorspora crassa*, T368P, Q388S, E418E, L459M, A578V, G580R, 1582M, M639V, A578V, G580G and L625P are reported and, as an amino acid deletion, 680K is reported in Miller, T. K. et al. (2002) Fungal Gen. Biol. 35:147-155 (hereinafter, 680K means that lysine at amino acid residue 680 is deleted. Hereinafter, amino acid deletion is described similarly). In addition, amino acid substitution which confers resistance to a phenylpyrrole antifungal compound in the OS-1 of *Neurospora crassa*, A578V, G580R and L625P are reported in Ochiai, N. et al. (2001) Pest Management Sci. 57:437-442.

Besides the aforementioned resistance mutation, resistance mutation may be found by analyzing an amino acid sequence of the "osmosensing hystidine kinase having no transmembrane region" isolated from a mutant filamentous fungus having resistance to any of a dicarboxyimide antifungal compound, an "aromatic hydrocarbon antifungal compound" and a phenypyrrole antifungal compound, and comparing with an amino acid sequence of the protein in a sensitive wild strain.

(Preparation of Transformed Cell in which a Polynucleotide Having a Nucleotide Sequence Encoding an Amino Acid Sequence of Osmosensing Histidine Kinase Having No Transmembrane Region is Introduced in a Functional Form into a Cell Deficient in at Least One Hybrid-Sensor Kinase)

The transformed cell in which a polynucleotide having a nucleotide sequence encoding an amino acid sequence of osmosensing histidine kinase having no transmembrane region (hereinafter, referred to as present histidine kinase in some cases) is introduced in functional form, can be obtained by introducing a "polynucleotide having a nucleotide sequence encoding an amino acid sequence of the present hystidine kinase" or the like into a "cell deficient in at least one hybrid-sensor kinase" which is to be a host cell, as described below.

Examples of the "polynucleotide having a nucleotide sequence encoding an amino acid sequence of the present hystidine kinase" include a polynucleotide having a nucleotide sequence encoding an amino acid sequence of the present hystidine kinase which is derived from a plant-pathogenic filamentous fungus, more specifically, for example, a polynucleotide having a nucleotide sequence encoding an amino acid sequence selected from the group consisting of:

(a) an amino acid sequence of an osmosensing histidine kinase having no transmembrane region, which has an amino acid sequence homology of 95% or more to the amino acid sequence represented by any of SEQ ID NOs: 41, 55 and 68;

(b) an amino acid sequence of an osmosensing histidine kinase having no transmembrane region, which is encoded by a DNA amplified by a polymerase chain reaction using a *Fusarium oxysporum*-derived cDNA as a template and using an oligonucleotide having the nucleotide sequence represented by SEQ ID NO: 52 and an oligonucleotide having the nucleotide sequence represented by SEQ ID NO: 53 as primers;

(c) an amino acid sequence of an osmosensing histidine kinase having no transmembrane region, which is encoded by a DNA amplified by a polymerase chain reaction using a *Mycospharella tritici*-derived cDNA as a template and using an oligonucleotide having the nucleotide sequence represented by SEQ ID NO: 64 and an oligonucleotide having the nucleotide sequence represented by SEQ ID NO: 65 as primers;

(d) an amino acid sequence of an osmosensing histidine kinase having no transmembrane region, which is encoded by a DNA amplified by a polymerase chain reaction using a *Thanaphthorus cucumeris*-derived cDNA as a template and using an oligonucleotide having the nucleotide sequence represented by SEQ ID NO: 85 and an oligonucleotide having the nucleotide sequence represented by SEQ ID NO: 86 as primers;

(e) an amino acid sequence of an osmosensing histidine kinase having no transmembrane region, which is derived from *Phytophthora infestans* and has the amino acid sequence represented by SEQ ID NO: 90;

(f) the amino acid sequence represented by SEQ ID NO: 41;

(g) the amino acid sequence represented by SEQ ID NO: 55; and (h) the amino acid sequence represented by SEQ ID NO: 68.

One example of a process for producing the transformed cell will be shown below.

(1) Preparation of cDNA

First, total RNA is prepared from filamentous fungus, for example, according to the method described in Molecular Cloning 2nd edition authored by J., Sambrook, E., F., Frisch, T., Maniatis. Specifically, for example, a part of a fungal tissue is collected from *Neurospora crassa, Botrytinia fuckeliana, Magnaporthe grisea, Phytophthora infestans, Thanatephorus cucumeris, Fusarium oxysporum, Mycospharella tritici, Thanatephorus cucumeris, Thanatephorus cucumeris* and the like, the collected tissue is frozen in liquid nitrogen, and is physically ground with a mortar or the like. Then, total RNA may be prepared by the conventional method such as (a) a method of adding a solution containing guanidine hydrochloride and phenol or a solution containing SDS and phenol to the resulting ground material, to obtain total RNA, or (b) a method of adding a solution containing guanidine thiocyanate to the aforementioned ground material, and further adding CsCl, followed by centrifugation, to obtain total RNA. In the procedures, a commercially available kit such as RNeasy Plant Mini Kit (manufactured by QIAGEN) may be also used.

Then, the thus prepared total RNA is used to prepare a cDNA. For example, cDNA may be prepared by reacting a reverse transcriptase on the total RNA after an oligo-dT chain or a random primer is annealed to total RNA. In addition, further, a double-stranded cDNA can be prepared, for example, by reacting RNaseH, DNA Polymerase I on said cDNA. In the procedures, a commercially available kit such as SMART™ PCR cDNA Synthesis Kit (manufactured by Clonech), cDNA Synthesis Kit (manufactured by TAKARA SHUZO Co., Ltd.), cDNA Synthesis Kit (manufactured by Amersham Pharmacia) and ZAP-cDNA Synthesis Kit (manufactured by Stratagene) can be used.

(2) Cloning

When a nucleotide sequence of a desired present histidine kinase is known, a polynucleotide having a nucleotide sequence encoding an amino acid sequence of the present histidine kinase can be obtained, for example, from the cDNA prepared as described above, for example, by PCR using as a primer an oligonucleotide having a partial nucleotide sequence of the known nucleotide sequence, or a hybridization method using as a probe an oligonucleotide having a partial nucleotide sequence of the known nucleotide sequence.

A polynucleotide having a nucleotide sequence encoding an amino acid sequence of BcOS-1 which is the present histidin kinase can be prepared from a cDNA of *Botryotinia fuckeliana*, for example, by PCR using as a primer an oligonucleotide having a partial nucleotide sequence of the nucleotide sequence represented by SEQ ID NO: 2, or a hybridization method using as a probe an oligonucleotide having a partial nucleotide sequence of the nucleotide sequence represented by SEQ ID NO: 2.

In addition, a polynucleotide having a nucleotide sequence encoding an amino acid sequence of HIK1 which is the present histidine kinase can be obtained from a cDNA of *Magnaporthe grisea*, for example, by PCR using as a primer an oligonucleotide having a partial nucleotide sequence of the nucleotide sequence represented by SEQ ID NO: 17, or hybridization method using as a probe an oligonucleotide having a partial nucleotide sequence of the nucleotide sequence represented by SEQ ID NO: 17.

When a nucleotide sequence of a desired present histidine kinase is unknown, a polynucleotide having a nucleotide sequence encoding an amino acid sequence of the present histidine kinase can be obtained by a hybridization method using as a probe an oligonucleotide having a partial nucleotide sequence of the nucleotide sequence of the present histidine kinase, the nucleotide sequence of which is known, or by PCR using as a primer an oligonucleotide designed based on a highly homologous amino acid sequence in plural present histidine kinases, an amino acid sequence of which is known. As the highly homologous amino acid sequence among plural present histidine kinases, amino acid sequences of which are known, for example, there can be exemplified amino acid sequences of a conserved motifs observed in the "repeat sequence region", the "histidine kinase region", the "receiver region" and the like, characterized in the structure of the present histidine kinase.

More specifically, when the BcOS-1 gene of *Botryotinia fuckeliana* is obtained by PCR, for example, oligonucleotides designed and synthesized based on nucleotide sequences of about 20 bp to about 40 bp which are selected from a 5' non-translated region and a 3' non-translated region, respectively, of the nucleotide sequence represented by SEQ ID NO: 2 can be used as a primer set. Examples of the primer set include a set of an oligonucleotide consisting of the nucleotide sequence represented by SEQ ID NO: 3 and an oligonucleotide consisting of the nucleotide sequence represented by SEQ ID NO: 4. A PCR reaction solution to be used may be prepared by adding a reaction solution designated by a commercially available DNA polymerase or kit as described below to 250 ng of a cDNA. The PCR reaction conditions can be appropriately changed depending on a primer set to be used, and examples thereof include the condition of maintaining a temperature at 94° C. for 2 minutes, then maintaining a temperature at about 8° C. for 3 minutes and, thereafter, repeating around 40 cycles of incubation, each cycle comprising maintaining a temperature at 94° C. for 30 seconds, then at 55° C. for 30 seconds, then at 72° C. for 4 minutes, and the condition of repeating 5 to 10 cycles of incubation, each cycle comprising maintaining a temperature at 94° C. for 5 seconds, then at 72° C. for 4 minutes, and further repeating about 20 to 40 cycles of incubation, each cycle comprising maintaining a temperature at 94° C. for 5 seconds, then at 70° C. for 4 minutes. For the procedures, commercially available DNA polymerases contained in Heraculase™ Enhanced DNA Polymerase (manufactured by Toyobo Co., Ltd.), Advantage cDNA PCR Kit (manufactured by Clonetech), and commercially available kits such as TAKARA Ex Taq (manufactured by TAKARA SHUZO Co., Ltd.), PLATINUM™ PCR SUPER Mix (manufactured by Lifetech Oriental), KOD-Plus- (manufactured by Toyobo Co., Ltd.) and the like can be used.

When the hik1 gene of *Magnaporthe grisea* is obtained by PCR, for example, oligonucleotides designed and synthesized based on nucleotide sequences selected from a 5' non-translation region and a 3' non-translation region, respectively, of the nucleotide sequence represented by SEQ ID NO: 17 can be used as a primer set. Examples of the primer set include a set of an oligonucleotide comprising the nucleotide sequence represented by SEQ ID NO: 18 and an oligonucleotide comprising the nucleotide sequence represented by SEQ ID NO: 19. A PCR reaction solution and the reaction conditions as described above can be used to perform PCR, to obtain the hik1 gene.

When a gene of the present histidine kinase, a nucleotide sequence of which is not known, is obtained from *Fusarium oxysporum*, *Mycospharella tritici*, *Thanatephorus cucumeris* or *Phytophthora infestans*, a polynucleotide having a nucleotide sequence encoding a part of an amino acid sequence of the present histidine kinase (hereinafter, referred to as present gene fragment in some cases) can be obtained by the following PCR. As a primer set, for example, a set of oligonucleotides designed and synthesized based on amino acid sequences of a conserved motifs observed in the "repeat sequence region", the "histidine kinase region", the "receiver region" and the like, characterized in the structure of the present histidine kinase, can be used. Examples of the primer set include a primer set of an oligonucleotide having the nucleotide sequence represented by any of SEQ ID NOs: 30 to 34 and an oligonucleotide having the nucleotide sequence represented by any of SEQ ID NOs: 35 to 40.

Specifically, in the case of *Fusarium oxysporum*, for example, using an oligonucleotide primer having the nucleotide sequence represented by SEQ ID NO: 33 and an oligonucleotide primer having the nucleotide sequence represented by SEQ ID NO: 38, and using KOD-Plus- (TOYOBO), amplification is performed under the conditions in which a temperature is maintained at 94° C. for 2 minutes, and then 35 cycles of incubation are repeated, each cycle comprising maintaining a temperature at 94° C. for 15 seconds, then, at 55° C. for 30 seconds and, further, at 68° C. for 5 minutes. In addition, in the case of *Mycospharella tritici*, for example, using an oligonucleotide primer having the nucleotide sequence represented by SEQ ID NO: 31 and an oligonucleotide primer having the nucleotide sequence represented by SEQ ID NO: 40, and using KOD-Plus- (TOYOBO), amplification is performed under the conditions in which a temperature is maintained at 94° C. for 2 minutes, and 35 cycles of incubation are repeated, each cycle comprising maintaining a temperature at 94° C. for 15 seconds, then, at 55° C. for 30 seconds and, further, at 68° C. for 3 minutes. In addition, in the case of *Thanatephorus cucumeris*, for example, using an oligonucleotide primer having the nucleotide sequence represented by SEQ ID NO: 30 and an oligonucleotide primer having the nucleotide sequence represented by SEQ ID NO: 37, and using KOD-Plus- (TOYOBO), amplification is performed under the conditions in which a temperature is maintained at 94° C. for 2 minutes, and 35 cycles of incubation are repeated, each cycle comprising maintaining a temperature at 94° C. for 15 seconds, then, at 55° C. for 30 seconds, further, at 68° C. for 1 minute. In addition, in the case of *Phytophthora infestans*, for example, using an oligonucleotide primer having the nucleotide sequence represented by SEQ ID NO: 31 and an oligonucleotide primer having the nucleotide sequence represented by SEQ ID NO: 37, and using KOD-Plus- (TOYOBO), amplification is performed under the conditions in which a temperature is maintained at 94° C. for 2 minutes, and 35 cycles of incubation are repeated, each cycle comprising maintaining a temperature at 94° C. for 15 seconds, then, at 55° C. for 30 seconds and, further, at 68° C. for 1 minute. By such the PCR, a polynucleotide having a nucleotide sequence encoding a part of an amino acid sequence of the present hisitidine kinase is amplified. A polynucleotide having a nucleotide sequence encoding a full length amino acid sequence of the present histidine kinase can be obtained by RACE method by using, for example, SMART RACE cDNA Amplification Kit (CLONTECH) and primers designed based on a nucleotide sequence of the amplified polynucleotide (present gene fragment).

When the polynucleotide obtained as described above has revealed a nucleotide sequence encoding a full length amino acid sequence of the present histidine kinase, by PCR using an oligonucleotide having a partial nucleotide sequence of the sequence as a primer, a polynucleotide having a nucleotide sequence encoding an amino acid sequence of the present histidine kinase may be also obtained.

Specifically, when a gene of the present histidine kinase of *Fusarium oxysporum* (hereinafter, referred to FoOS-1 gene in some cases) is obtained by PCR, for example, oligonucleotides designed and synthesized based on nucleotide sequences selected from a 5'-terminal region and a 3'-terminal region, respectively, of the nucleotide sequence represented by SEQ ID NO: 42 can be used as a primer set. Examples of the primer set include a set of an oligonucleotide comprising the nucleotide sequence represented by SEQ ID NO: 52 and an oligonucleotide comprising the nucleotide sequence represented by SEQ ID NO: 53. A PCR reaction solution and the reaction conditions as described above are used to perform PCR, whereby, a polynucleotide having a nucleotide sequence encoding an amino acid sequence of the present histidine kinase derived from *Fusarium oxysporum* can be obtained.

In addition, when a gene of the present histidine kinase of *Mycospharella tritici* (hereinafter, referred to StOS-1 gene in some cases) is obtained by PCR, for example, oligonucleotides designed and synthesized based on nucleotide sequences selected from a 5'-teminal region and a 3'-terminal region, repectively, of the nucleotide sequence represented by SEQ ID NO: 56 can be used as a primer set. Examples of the primer set include a set of an oligonuceleotide comprising the nucleotide sequence represented by SEQ ID NO. 64 and an oligonucleotide comprising the nucleotide sequence represented by SEQ ID NO: 65. A PCR reaction solution and the reaction conditions as described above are used to perform PCR, whereby, a polynucleotide having a nucleotide sequence encoding an amino acid sequence of the present histidine kinase derived from *Mycospharella tritici* can be obtained.

In addition, when a gene of the present histidine kinase of *Thanatephorus cucumeris* (hereinafter, referred to RsOS-1 gene in some cases) is obtained by PCR, for example, oligonucleotides designed and synthesized based on nucleotide sequences selected from a 5'-terminal region and a 3'-terminal region, respectively, of the nucleotide sequence represented by SEQ ID NO: 69 can be used as a primer set. Examples of the primer set include a set of an oligonucleotide comprising the nucleotide sequence represented by SEQ ID NO: 85 and an oligonucleotide comprising the nucleotide sequence represented by SEQ ID NO: 86. A PCR reaction solution and the reaction conditions as described above are used to perform PCR, whereby, a polynucleotide having a nucleotide sequence encoding an amino acid sequence of the present histidine kinase derived from *Thanatephorus cucumeris* can be obtained.

When a hybridization method is used, cloning can be performed, for example, according to the method described in Molecular Cloning 2nd edition, authored by J., Sambrook, E., F., Frisch, T., Maniatis.

A probe used to obtain a gene of the present histidine kinase can be obtained by synthesizing a DNA (around about 200 bases to about 500 bases in length) having a partial nucleotide sequence of the nucleotide sequence represented by SEQ ID NO: 2, followed by radioisotope-labeling or fluorescently labeling the DNA according to the conventional method. In such the labeling of a DNA, commercially available kits such as Random Primed DNA Labelling Kit (manufactured by Boehringer), Random Primer DNA Labelling Kit Ver. 2 (manufactured by TAKARA SHUZO Co., Ltd.), ECL Direct Nucleic acid Labelling and Detection System (manufactured by Amersham Pharmacia), Megaprime DNA-labelling system (manufactured by Amersham Pharmacia) and the like may be utilized. The thus obtained probe can be used for cloning a gene of the histidine kinase such as the BcOS1-gene of *Botrytinia fuckeliana*, a nucleotide sequence of which is known, or a gene of the present histidine kinase, a nucleotide sequence of which is unknown.

Examples of the hybridization condition include the stringent condition, specifically, the condition under which, in the presence of 6×SSC (0.9 M NaCl, 0.09 M trisodium citrate), 5×Denhart's solution (0.1% (w/v) Ficoll 400, 0.1% (w/v) polyvinylpyrrolidone, 0.1% BSA), 0.5% (w/v) SDS and 100 µg/ml denatured salmon sperm DNA, or in DIG EASY Hyb solution (Boehringer Manheim) containing 100 µg/ml denatured salmon sperm DNA, a temperature is maintained at 65° C., then a temperature is maintained at room temperature for 15 minutes twice in the presence of 1×SSC (0.15 M NaCl, 0.015 M trisodium citrate) and 0.5% SDS, further, a temperature is maintained at 68° C. for 30 minutes in the presence of 0.1×SSC (0.015 M NaCl, 0.0015M trisodium citrate) and 0.5% SDS.

Specifically, for example, for obtaining the BcOS-1 gene of *Botrytinia fuckeliana*, PCR is performed by using a *Botrytinia fuckeliana* cDNA library phage solution (about 1,000,000 pfu) as a template, and using TAKARA LA Taq™ (manufactured by TAKARA SHUZO Co., Ltd.), and using an oligonucleotide comprising the nucleotide sequence represented by SEQ ID NO: 9 and an oligonucleotide comprising a nucleotide sequence complementary to the nucleotide sequence represented by SEQ ID NO: 10 as a primer set, whereby, a DNA for a probe is amplified, which may be collected. A PCR reaction solution to be used may be prepared by adding a reaction solution designated by a kit as described above to 250 ng of a DNA library. Examples of the PCR reaction condition include the condition under which amplification is performed by maintaining a temperature at 94° C. for 2 minutes, then at 8° C. for 3 minutes, and repeating 40 cycles of incubation, each cycle comprising maintaining a temperature at 94° C. for 30 seconds, then, at 55° C. for 30 seconds and, then, at 68° C. for 5 minutes. Then, a probe labeled with $^{32}$P can be prepared by using the amplified and obtained DNA as a template, and using Megaprime DNA-labelling system (Amersham Pharmacia) and using a reaction solution designated by the kit. The thus prepared probe is used to perform colony hybridization according to the conventional method, in which a temperature is maintained at 65° C. in the presence of 6×SSC (0.9 M NaCl, 0.09M trisodium citrate, 5×Denharp's solution (0.1% (w/v) Ficoll 400, 0.1% (w/v) polyvinylpyrrolidone, 0.1% BSA), 0.5% (w/v) SDS and 100 µg/ml denatured Salmon sperm DNA, or in DIG EASY Hyb solution (Boehringer Mannheim), containing 100 µg/ml denated Salmon sperm DNA, then, a temperature is maintained at room temperature for 15 minutes twice in the presence of 1×SSC (0.15 M NaCl, 0.015M trisodium citrate) and 0.5% SDS and, further, a temperature is maintained at 68° C. for 30 minutes in the presence of 0.1×SSC (0.015 M NaCl, 0.0015 M sodium citrate) and 0.5% SDS, whereby, a clone which hybridizes with the probe can be obtained.

In addition, a gene of the present histidine kinase having a known nucleotide sequence may be also prepared by performing chemical synthesis of a nucleic acid, for example, according to the conventional method such as a phosphite triester method (Hunkapiller, M. et al, Nature 310, 105, 1984), based on the known nucleotide sequence.

The thus obtained polynucleotide having a nucleotide sequence encoding an amino acid sequence of the present histidine kinase may be cloned into a vector according to the conventional method described in "Molecular Cloning: A Laboratory Manual 2nd edition" (1989), Cold Spring Harbor Laboratory Press, "Current Protocols In Molecular Biology" (1987), John Wiley & Sons, Inc. ISBNO-471-50338-X or the like. Examples of the vector to be used include pBlueScript II vector (manufactured by Stratagene), pUC18/19 vector (manufactured by TAKARA SHUZO Co., Ltd.), TA Cloning vector (manufactured by Invitrogen) and the like.

A nucleotide sequence of the cloned gene may be confirmed by the Maxam Gilbert method (described in Maxam, A. M. & W. Gilbert, Proc. Natl. Acad. Sci. USA, 74, 560, 1977 etc.) or the Sanger method (described in Sanger, F.& A. R. Coulson, J. Mol. Biol., 94, 441, 1975, Sanger, F, & Nicklen and A. R. Coulson., Proc. Natl. Acad. Sci. USA, 74, 5463, 1977 etc.). For the procedures, commercially available kits such as Termo Seqenase II dye terminator cycle sequencing kit (manufactured by Amersham Pharmacia), Dye Terminator Cycle Sequencing FS Ready Reaction Kit (manufactured by PE Biosystems Japan) and the like can be used.

(3) Construction of Expression Vector

An expression vector of a polynucleotide having a nucleotide sequence encoding an amino acid sequence of the present histidine kinase may be constructed by a conventional method (for example, method described in J. Sambrook, E., F., Frisch, T., Maniatis, Molecular Cloning 2nd edition, published by Cold Spring Harbor Laboratory Press etc.).

For example, A polynucleotide having a nucleotide sequence encoding an amino acid sequence of the present histidine kinase may be incorporated into a vector which can be utilized in a host cell to be transformed, for example, a vector which contains genetic information required to be replicable in a host cell, can replicates autonomously, can be isolated and purified from a host cell, and has a detectable marker (hereinafter referred to as basic vector in some cases). As the basic vector, specifically, when a bacterium such as *Escherichia coli* is used as a host cell, for the example, a plasmid pUC119 (manufacture d by TAKARA SHUZO Co., Ltd.), phagemid pBluescriptII (manufactured by Stratagene) and the like may be used. When yeast is used as a host cell, for example, plasmids pACT2 (manufactured by Clontech), p415 CYC (ATCC87382), p415 ADH (ATCC87374) and the like may be used. When a plant cell is used as a host cell, for the example, a plasmid pBI221 (Clontech) and the like may be used.

An expression vector which can express a polynucleotide having a nucleotide sequence encoding an amino acid sequence of the present histidine kinase in a host cell can be constructed by incorporating into a basic vector a polynucleotide having a nucleotide sequence encoding an amino acid sequence of the present histidine kinase upstream of which a promoter functional in a host cell is operably linked. Herein, the "operably linked" means that the promoter and a polynucleotide having a nucleotide sequence encoding an amino acid sequence of the present histidine kanase are ligated so that the polynucleotide having a nucleotide sequence encoding an amino acid sequence of the present histidine kinase is expressed under control of the promoter in a host cell. Examples of a promoter functional in a host cell include, when a host cell is *Escherichia coli*, a promoter of a lactose operon (lacP) a promoter of tryptphan operon (trpP), a promoter of an arginine operon (argP), a promoter of a galactose operon (galP), tac promoter, T7 promoter, T3 promoter of *Escherichia coli*, a promoter of λ phage (λ-pL, λ-pR) and the like. In addition, when a host cell is yeast, examples include an ADH1 promoter, a CYC1 promoter and the like. The ADH1 promoter can be prepared, for example, by the conventional genetic engineering method from a yeast expression vector p415 ADH (ATCC87374) harboring an ADH1 promoter and a CYC1 terminator. The CYC1 promoter can be prepared by the conventional genetic engineering method from p415CYC (ATCC87382). Examples of the promoter include, when a host cell is a plant cell, a nopaline synthase gene (NOS) promoter, an octopine synthase gene (OCT) promoter, a cauliflower mosaic virus (CaMV)-derived 19S promoter, a CaMV-derived 35S promoter and the like.

In addition, when a polynucleotide having a nucleotide sequence encoding an amino acid sequence of the present histidine kinase is incorporated into a vector already harboring a promoter functional in a host cell, a gene of the present histidine kinase may be inserted into downstream of the promoter so that a promoter harbored by the vector and a gene of the present histidine kinase are operably linked. For the example, the aforementioned yeast plasmid p415 ADH has an ADH1 promoter and, when a gene of the present histidine kinase is inserted downstream of an ADH1 promoter of the plasmid, an expression vector which can express a gene of the present histidine kinase in a budding yeast such as *Saccharomyces cerevisiae* AH22 (IFO10144) and TM182 (Maeda, T. et al. (1994) Nature 369:242-245) can be constructed.

(4) Preparation of Transformed Cell

By introducing the constructed expression vector into a host cell according to the conventional method, a transformed cell expressing the present histidine kinase can be prepared. As a host cell used for preparing such the transformed cell, for example, there are bacterium, yeast, plant cell and the like. As the bacterium, for example, there are *Escherichia coli*, *Vibrio harveiy* and the like. As the yeast, there are budding yeast and diving yeast. More specifically, for example, there are yeasts belonging to genus *Saccharomyces*, genus *Shizosaccharomycess* the like. As a plant cell, for example, there is a plant cell such as *Arabidopsis thaliana* and the like.

As a method of introducing an expression vector into the aforementioned host cell, the conventional introducing method can be applied depending on a host cell to be transformed. For example, when bacterium is used as a host cell, the expression vector can be introduced into a host cell by the conventional introducing method such as a calcium chloride method and an electroporation method described in Moleculer Cloning (J. Sambrook et al., Cold spring Harbor, 1989). When yeast is used as a host cell, for example, the expression vector can be introduced into a host cell using Yeast transformation kit (Clontech) based on a lithium method. In addition, when a plant cell is used as a host cell, for example, the expression vector can be introduced into a host cell using the conventional introducing method such as an *Agrobacterium* infection method (JP-B No. 2-58917 and JP-A No. 60-70080), an electroporation method into a propoplast (JP-A No. 60-251887 and JP-A No. 5-68575) and a particle gun method (JP-A No. 5-508316 and JP-A No. 63-258525).

(Intracellular Signal Transduction System Regarding Present Histidine Kinase)

In the present invention, in order to measure an amount of intracellular signal transduction from the present histidine kinase expressed in the transformed cell prepared as described above or an index value having the correlation therewith, an intracellular signal transduction system originally contained in a host cell used for preparing the transformed cell may be utilized. Examples of the intracellular signal transduction system which can be utilized include an intracellular signal transduction system regarding osmolarity responses of the aforementioned budding yeast, an intracellular signal transduction system regarding cell cycle progression and oxidative stress response of fission yeast, an intracellular signal transduction system regarding control of expression of capsular polysaccharide biosynthesis operon in *Escherichia coli*, an intracellular signal transduction system regarding control of cell density-sensitive luminescence of bioluminescent marine microorganism *Vibrio harveyi*, an intracellular signal transduction system regarding cytokinin response of *Arabidopsis thaliana* and the like.

When the aforementioned expression vector of the present histidine kinase is introduced using the "cell deficient in at least one hybrid-sensor kinase" as a host cell used for preparing such the transformed cell, the produced present histidine kinase functions in place of deleted hybrid-sensor kinase, and intracellular signal is transmitted. In the case where a test substance is contacted with the transformed cell, when signal transduction from the present histidine kinase is inhibited by the test substance, change in an amount of growth of the transformed cell, change in morphology of the transformed cell, change in a shape of the transformed cell, change in an amount of biosynthesis of a particular substance in the cell, change in an amount of metabolism of a particular substance in the cell and the like occur in some cases. In such the cases, an antifungal activity of the test substance acting on the present histidine kinase can be measured using change in an amount of growth of the transformed cell, change in morphology, change in shape, change in an amount of biosynthesis of a particular substance in a cell, change in an amount of metabolism of a particular substance and the like as an index.

On the other hand, when at least one intrinsic hybrid-sensor kinase is not deleted in a host cell used for preparing a transformed cell, there are both of signal transduction from intrinsic hybrid-sensor kinases and intracellular signal transduction from the introduced present histidine kinase in intracellular signal transduction of the transformed cell. Change in an amount of growth of the transformed cell, change in morphology, change in shape, change in am amount of biosynthesis of a particular substance in the cell, change in an amount in metabolism of a particular substance in the cell and the like reflecting an amount of intracellular signal transduction from the introduced present histidine kinase become smaller by the influence of an amount of intracellular signal transduction from intrinsic hybrid-sensor kinase. In the present invention, by using a host cell deficient in at least one intrinsic hybrid-sensor kinase, since change in an amount of growth of the transformed cell, change in morphology, change in shape, change in an amount of biosynthesis of a particular substance in the cell, change in an amount of metabolism of particular substance in the cell and the like reflecting an amount of intracellular signal transduction from the introduced present histidine kinase become larger, the sensitivity of the transformed cell to an antifungal compound is enhanced. Like this, the transformed cell with the enhanced sensitivity to an antifungal compound is useful for assaying the antifungal activity of a test substance and searching an antifungal compound using the assay.

Specifically, when the present histidine kinase is introduced in a *Saccharomyces cerevisiae* strain deficient in hybrid-sensor kinase SLN1 (Maeda, T. et al. Nature: 369 242-245 (1994)), the present histidine kinase performs signal transduction in place of deficient SLN1, whereby, an amount of intracellular signal transduction from the introduced present histidine kinase can be detected more clearly using an amount of growth of host cell as an index. That is, when the test substance acts on the present histidine kinase, and an amount of signal transduction from the present histidine kinase in a host cell is changed, it can be clearly measured as change in an amount of growth of the transformed budding yeast. In addition, an *Escherichia coli* strain deficient in a hybrid-sensor kinase RcsC, a fission yeast strain deficient in PHK1 to PHK3 involved in control of cell cycle progression, a *Vibrio harveyi* strain deficient in LuxN associated with control of cell density-sensitive luminescence and an *Arabidopsis thaliana* strain deficient in cytokinin receptor CRE1 can be exemplified as one preferable aspect of the "cell deficient in at least one hybrid-sensor kinase".

(Method of Assaying Antifungal Activity of Test Substance)

In a method of assaying the antifungal activity of a test substance, an embodiment of a first step of culturing a transformed cell in which a polynucleotide having a nucleotide sequence encoding an amino acid sequence of the present histidine kinase introduced in the presence of a test substance includes a method of contacting a test substance with the transformed cell by culturing the transformed cell in a medium containing the test substance. Culturing the transformed cell may be any form of liquid culturing in which the cell is cultured in a liquid medium, solid culturing in which the cell is cultured on a solid medium prepared by adding agar or the like to liquid medium, and the like. The concentration of a test substance in the medium is, for example, about 1 nm to about 1 mM, preferably about 10 nm to about 100 µM. A culturing time is, for example, about 1 hour or longer and around 3 days, preferably about 25 hours to around 2 days. When the antifungal activity of a test substance is assayed, as a medium containing a test substance, an antifungal compound-free medium may be used.

An amount of intracellular signal transduction from the present histidine kinase expressed in a transformed cell cultured in the first step or an index value having the correlation therewith is measured. And, the antifungal activity of a test substance is assayed based on a difference between an amount of intracellular signal transduction or an index value having the correlation therewith measured in the second step and a control. For example, the antifungal activity of the test substance can be assessed based on a difference obtained by comparing amounts of intracellular signal transduction or index values having the correlation therewith, which are measured as described above in sections in which different two or more substances (for example, it is preferable that among different two or more substances, at least one substance has no antifungal activity) are independently used, respectively, as a test substance.

Specifically, for example, when a transformed cell prepared by using, as a host cell, the TM182 (SLN1A) strain (Maeda T. et al. Nature: 369 242-245 (1994)) which is a SLN1 gene-deficient strain in which the PTP2 Tyrosine phosphatase gene (Ota et al, Proc. N. A. sic. USA, 89, 2355-2359 (1992)) introduced (that is, a transformed cell having the function that cell growth is directly controlled by transduction of an intracellular signal from the present histidine kinase) is used, the antifungal activity can be measured by using, as an index, an amount of growth of the transformed cell in a medium (agar medium or liquid medium) using glucose as a carbon source, for example, Glu-Ura-Leu medium. When a medium in which a test substance is added to the Glu-Ura-Leu medium (medium containing no antifungal compound) is used, a test substance inhibiting growth of the transformed cell can be assessed to have the antifungal activity. In addition, as a control, it is enough to examine that growth of the transformed cell in a medium using galactose in place of glucose as a carbon source, for example, Gal-Ura-Leu medium is observed regardless of the presence or the absence of test substance.

When a transformed cell prepared by using, as a host cell, fission yeast which is PHK1, PHK2 and PHK3 gene-deficient strain (that is, a transformed cell in which cell cycle progression is directly regulated by transduction of an intracellular signal from the histidine kinase) is used, cell diviision of the fission yeast may be observed under a microscope. When a medium in which a test substance is added to a medium containing no substance having the antifungal activity is used, a test substance which shortens a cell length of a dividing cell of the transformed cell can be assessed to have the antifungal activity.

When a transformed cell prepared by using, as a host cell, RcsC gene-deficient *Escherichia coli* in which cps-LacZ introduced is used, color development of X-Gal may be observed in an agar medium or a liquid medium (Suzuki et al. Plant Cell Physiol. 42:107-113 (2001)). When a medium in which a test substance is added to a medium containing no substance having the antifungal activity is used, a test substance which can make the transformed cell develop blue can be assessed to have the antifungal activity.

In addition, when a transformed cell prepared by using, as a host cell, LuxN gene-deficient *V. harveyi* (i.e. a transformed cell in which bioluminescence is directly regulated by transduction of an intracellular signal from the present histidine kinase) is used, the fluorescent light emitted by the transformed microorganism may be observed. When a medium containing a test substance and not containing a substance having the antifungal activity is used, a test substance which make the transformed cell possible to emit the fluorescent light can be assessed to have the antifungal activity.

Further, a substance having the antifungal activity can be also searched by selecting an antifungal compound based on the antifungal activity assessed by the aforementioned assaying method.

Effects of the Invention

The present invention can provide a transformed cell with the enhanced sensitivity to an antifungal compound, a method of assaying the antifungal activity of a test substance using the transformed cell, and a method of searching an antifungal compound using the method.

EXAMPLES

The present invention is further described in the following Examples, which are not intended to restrict the invention.

Example 1

Isolation of *Botryotinia fuckeliana* BcOS-1 Gene

Total RNA was prepared from *Botryotinia fuckeliana*. 100 mg of a hypha of *Botryotinia fuckeliana* strain Bc-16 grown on a potato dextrose agar medium (PDA medium manufactured by NISSUI Pharmaceutical Co., Ltd.) was scratched off, and this was ground in liquid nitrogen using a mortar and a pestle. A RNA was prepared from frozen ground powder using RNeasy Plant Mini Kit (QIAGEN). A frozen ground powder together with liquid nitrogen was transferred to a 50 ml sample tube and, after liquid nitrogen was all volatilized, a solution obtained by adding 10 µL of mercaptoethanol per 1 ml of a buffer RLC attached to kit was added, followed by stirring. Further, ground powder was well dispersed by a few of pipettings, and was incubated at 56° C. for 3 minutes. Thereafter, the solution containing ground powder was supplied to QIAshredder spin column attached to the kit, and centrifuged at 8,000×g for 2 minutes. The filtration supernatant was transferred to a fresh sample tube, a 0.5-fold volume of 99.5% ethanol was added thereto, and the material was well mixed by pipetting. This mixture was supplied to RNeasy mini spin column attached to the kit, and centrifuged at 8,000×g for 1 minute. The filtrate was discarded, the residue was added 700 µL of a buffer RW1 attached to the kit, and centrifuged at 8,000×g for 1 minute, and the filtrate was discarded. Further, the residue was added 500 µL of a buffer RPE attached to the kit, centrifuged at 8,000×g for 1 minute, and the filtrate was discarded. This procedure was repeated twice. Finally, an upper filter part was transferred to a fresh sample tube, supplied 30 µL of RNase-free sterilized water attached to the kit, and centrifuged at 8,000×g for 1 minute, and total RNA was dissolved out into the filtrate. This dissolution procedure was repeated twice. The concentration of the resulting total RNA solution was obtained from the absorbance at 260 nm to be 322 µg/ml.

Then, a cDNA was synthesized using ThermoScript RT-PCR System (Invitrogen) while employing total RNA as a template. A solution in which 2.7 µl, of total RNA and 6.3 µL of sterilized distilled water were mixed into 1.0 µL of 50 mM Oligo(dt)$_{20}$ attached to the kit and 2.0 µL of 10 mM dNTP Mix was treated at 65° C. for 5 minute, and then rapidly cooled on ice. To this solution were added 4 µL of 5×cDNA Synthesis Buffer attached to the kit, 1 µL of 0.1M DTT, 1 µL of RNase OUT, 1 µL of ThermoScript RT and 1 µL of sterilized distilled water, to react them at 50° C. for 60 minutes and, thereafter, the reaction was stopped by heating treatment at 85° C. for 5 minutes. Further, a RNA of a template was degraded by adding 1 µL of RNaseH attached to the kit to this reaction solution and maintained a temperature at 37° C. for 20 minutes, to obtain a cDNA.

A DNA having a nucleotide sequence encoding an amino acid sequence of *Botryotinia fuckiliana* BcOS-1 (hereinafter, referred to as BcOS-1 DNA in some cases) was amplified by PCR using this cDNA as a template. Using an oligonucleotide comprising the nucleotide sequence represented by SEQ ID NO: 3 and an oligonucleotide consisting of the nucleotide sequence represented by SEQ ID NO: 4 as a primer, a PCR was performed to amplify a DNA having the nucleotide sequence represented by SEQ ID NO: 2. The PCR was performed using KOD-Plus- (TOYOBO) under the amplifying conditions that a temperature was maintained at 94° C. for 2 minutes and, thereafter, 35 cycles of incubation were repeated, each cycle comprising maintaining a temperature at 94° C. for 15 seconds, then, at 55° C. for 30 seconds, then, at 68° C. for 6 minutes. The PCR reaction solution (50 µL) was prepared by adding 2 µL of the aforementioned cDNA, 5 µL of 10× Buffer, 5 µL of 2 mM dNTPs, 2 µL of 25 mM MgSO$_4$, each 1 µL of 10 µM oligonucleotide primers, 33 µL of sterilized distilled water and 1 µL of KOD-Plus-. After the reaction, a part of the reaction solution was separated by 0.8% agarose gel electrophoresis, and stained with ethidium bromide. It was confirmed that about 4 kb of a DNA (BcOS-1 DNA) was amplified.

Example 2

Construction of Expression Plasmid of *Botryotinia fuckeliana* BcOS-1 Gene and Preparation of Transformed Budding Yeast BcOS-1 DNA was cloned into a shuttle vector p415ADH (ATCC87312) replicable in yeast and *Escherichia coli*. About 4 kb of the aforementioned DNA (BcOS-1 DNA) was purified from the PCR reaction solution prepared in Example 1 using QIAquick PCR Purification Kit (QIAGEN) according to the attached manual. About 4 kb of the purified DNA (BcOS-1 DNA) was digested with restriction enzymes SpeI and PstI and, on the other hand, the shuttle vector p415ADH was also digested with restriction enzymes SpeI and PstI and, thereafter, each of which was separated by 0.8% agarose gel electrophoresis, and a part of the gel containing a desired DNA was excised. The BcOS-1 DNA digested with SpeI and PstI and the shuttle vector digested with SpeI and PstI were recovered from the gel using QIAquick Gel Extraction Kit (QIAGEN) according to the attached manual. The aforementioned BcOS-1 DNA was inserted between SpeI site and PstI site in the multicloning site of the shuttle vector using Ligation Kit Ver. 2 (TaKaRa) according to the attached manual, to construct an expression plasmid pADHBcOS1. A nucleotide sequence of the resulting expression plasmid was analyzed with a DNA sequencer (Model 3100, Applied Biosystems) after a sequencing reaction using BigDye terminator v3.0 Cycle Sequencing Ready Reaction Kit (Applied Biosystems) according to the attached manual. The sequencing reaction was performed using an oligonucleotide consisting of the nucleotide sequence represented by any of SEQ ID NOs: 5 to 12 as a primer under the amplifying conditions that 30 cycles were repeated, each cycle comprising maintaining a temperature at 96° C. for 10 seconds, then, at 50° C. for 5 seconds, then, at 60° C. for 4 minutes. As a result, the nucleotide sequence represented by SEQ ID NO: 2 was obtained, and it was confirmed that the expression plasmid pADHBcOS1 harbored a DNA having a nucleotide sequence encoding an amino acid sequence of BcOS-1.

The prepared expression plasmid pADHBcOS1 was introduced into each of budding yeast (*Saccharomyces cerevisiae*) AH22 strain (IFO10144) and TM182 strain (Maeda T. et al. (1994) Nature vol. 369, pp 242-245) according to the method described in Geitz R D & Woods R A (1994) Molecular Genetics of Yeast: Practical Approaches ed. Johnson J A, Oxford University Press pp 124-134. By utilizing disappearance of leucine auxotrophy in the resulting transformed budding yeast, the transformed budding yeast AH 22 strain (AH22-BcOS1) was selected on a Glu-Leu agar medium, and the transformed budding yeast TM182 strain (TM182-BcOS1) was selected on a Gal-Ura-Leu agar medium. It was confirmed that the resulting TM182-BcOS1 grows even when transplanted to a Glu-Ura-Leu medium.

Example 3

Antifungal Compound Sensitivity Test of Transformed Budding Yeast TM182-BcOS1

The transformed budding yeast AH22-BcOS1 prepared in Example 2 was cultured while shaking at 30° C. for 18 hours in a Glu-Leu medium. As a control, the AH22 strain was similarly cultured while shaking at 30° C. for 18 hours in a Glu medium. The absorbance at 600 nm of each of the grown transformed budding yeasts in a cell suspension was measured, and a cell suspension diluted with sterilized distilled water to the absorbance of 0.1 was prepared. Further, a cell suspension in which the aforementioned cell suspension of the transformed budding yeast AH22-BcOS1 was diluted 200-fold with a Glu-Leu medium, and a cell suspension in which the aforementioned cell suspension of the AH22 strain was diluted 200-fold with a Glu medium were prepared. A solution in which each of Compounds (1) to (3) was dissolved in dimethylsulfoxide (DMSO) to the concentration of 60 ppm, a solution in which each of Compounds (4) and (5) was dissolved in dimethylsulfoxide (DMSO) to the concentration of 2000 ppm, and a solution in which each of Compounds (6) and (7) was dissolved in dimethylsulfoxide (DMSO) to the concentration of 20 ppm were prepared, and two microplates were prepared in which each 2.0 µL per well of the Compound solution and DMSO as a control were dispensed into two wells. In one microplate among them, each 200 µL of cell suspensions of the transformed budding yeast AH22-BcOS1 which had been prepared by dilution as described above was dispensed, and cultured by allowing to stand at 30° C. for 48 hours. In another microplate, each 200 µL of the cell suspensions of the control yeast AH22 strain which had been prepared by dilution as described above was dispensed, and cultured by allowing to stand at 30° C. for 48 hours. After culturing, the absorbance at 600 nm of each well was measured with a microplate reader.

Similarly, the transformed budding yeast TM182-BcOS1 prepared in Example 2 was cultured at 30° C. for 18 hours in a Glu-Ura-Leu medium. The absorbance at 600 nm of the grown transformed budding yeast in a cell suspension was measured, and a cell suspension diluted with sterilized distilled water to the absorbance of 0.1 was prepared. Further, a cell suspension in which the aforementioned cell suspension of the transformed budding yeast TM182-BcOS1 was diluted 200-fold with a Glu-Ura-Leu medium and, as a control, a cell suspension in which the aforementioned cell suspension was diluted 200-fold with a Gal-Ura-Leu medium were prepared. A suspension in which each of Compounds (1) to (3) was dissolved in dimethylsulfoxide (DMSO) to the concentration of 60 ppm, a solution in which each of Compounds (4) and (5) was dissolved in dimethylsulfoxide (DMSO) to the concentration of 2000 ppm, and a solution in which each of Compounds (6) and (7) was dissolved in dimethylsulfoxide (DMSO) to the concentration of 20 ppm were prepared, and two microplates were prepared in which each 2.0 µL per well of the Compound solution and DMSO as a control were dispensed into two wells. In one microplate among them, each 200 µL of cell suspensions of the transformed budding yeast TM182-BcOS1 which had been prepared by dilution with a Glu-Ura-Leu medium as described above was dispensed, and cultured by allowing to stand at 30° C. for 67 hours. In another microplate, as described above, as a control, each 200 µL of the cell suspensions of the transformed budding yeast TM182-BcOS1 which had been prepared by dilution with a Gal-Ura-Leu medium was dispensed, and cultured by allowing to stand at 30° C. for 67 hours. After culturing, the absorbance at 600 nm of each well was measured with a microplate reader.

Degree of growths of both of the transformed budding yeasts cultured under the presence of each of Compound (1) to (7) and budding yeast as a control therefor are shown in Table 1. Degree of growths of both of the transformed budding yeasts and budding yeasts as a control therefor are expressed by a relative value in percentage, letting the absorbance at 600 nm in a well having the concentration of the aforementioned Compound of 0 ppm to be 100. It was confirmed that an inhibiting degree of growth of TM182-BcOS1 by each test substance was grater than an inhibiting degree of growth of AH22-BcOS1 by each test substance, and the TM182-BcOS1 was a transformed cell with the enhanced sensitivity to an antifungal compound as compared with AH22-BcOS1.

TABLE 1

| | Degree of growth of budding yeast (%) | | | |
|---|---|---|---|---|
| | AH22 | AH22-BcOS1 | TM182-BcOS1 | |
| Test substance (final concentration) | Glu medium | Glu-Leu medium | Gal-Ura-Leu medium | Gal-Ura-Leu medium |
| Compound (1) (0.6 ppm) | 99 | 90 | 99 | 9 |
| Compound (2) (0.6 ppm) | 99 | 92 | 98 | 11 |
| Compound (3) (0.6 ppm) | 98 | 93 | 98 | 10 |
| Compound (4) (20 ppm) | 96 | 45 | 102 | 10 |
| Compound (5) (20 ppm) | 97 | 79 | 103 | 48 |
| Compound (6) (0.2 ppm) | 99 | 81 | 99 | 8 |
| Compound (7) (0.2 ppm) | 101 | 94 | 99 | 11 |

Example 4

Isolation of *Botryotinia fuckeliana* Mutant BcOS-1 Gene Exhibiting Resistance to Dicarboxyimide Antifungal Compound A DNA having a nucleotide sequence encoding an amino acid sequence of *Botryotinia fuckeliana* mutant BcOS-1 (Oshima, M. et al. (2002) Phytopathology 92, pp 75-80) exhibiting resistance to a dicarboxyimide antifungal compound (hereinafter, referred to as mutant BoOS1 DNA in some cases) was prepared by PCR using the cDNA prepared in Example 1 as a template. A first time PCR was performed using, as a primer, an oligonucleotide consisting of the nucleotide sequence represented by SEQ ID NO: 15 and an oligonucleotide consisting of the nucleotide sequence represented by SEQ ID NO: 4, and a DNA having a nucleotide sequence represented by base numbers 1081 to 3948 of the nucleotide sequence represented by SEQ ID NO: 14 was amplified. The PCR was performed using KOD-Plus- (TOYOBO) under the amplifying conditions that a temperature was maintained at 94° C. for 2 minutes and, thereafter, 35 cycles were repeated, each cycle comprising maintaining a temperature at 94° C. for 15 seconds, then, at 55° C. for 30 seconds, then, at 68° C. for 6 minutes. The PCR reaction solution (50 µl) was prepared by adding 2 µL of the aforementioned cDNA, 5 µL of 10× Buffer, 5 µL of 2 mM dNTPs, 2 µL of 25 mM MgSO₄, each 1 µL of 10 µM oligonucleotide primers, 33 µL of sterilized distilled water and 1 µL of KOD-Plus-. After the reaction, a second PCR was performed using an oligonucleotide consisting of the nucleotide sequence represented by SEQ ID NO: 3 and 1 µL of the first time PCR reaction solution while using the cDNA prepared in Example 1 as a template. The reaction conditions were the same as those of the first time PCR and after the reaction, a part of the reaction solution was separated by 0.8% agarose gel electrophoresis, and stained with ethidium bromide. It was confirmed that about 4 kb of the DNA (mutant BcOS-1 DNA) was amplified.

Example 5

Construction of Expression Plasmid of *Botryotinia fuckeliana* BcOS-1 Mutant Gene Exhibiting Resistance to Dicarboxyimde Antifungal Compound and Preparation of Transformed Budding Yeast First, the mutant BcOS-1 DNA was cloned into a vector pBluescript II SK(+) (TOYOBO). About 4 kb of the DNA (mutant BcOS-DNA) was purified from the second time PCR reaction solution prepared in Example 4 using QIAquick PCR Purification Kit (QIAGEN) according to the attached manual. About 4 kb of the purified DNA (mutant BcOS-1 DNA) was digested with restriction enzymes SpeI and PstI and, on the other hand, the vector pBluescript II SK(+) was also digested with restriction enzymes SpeI and PstI, each of which was separated by 0.8% agarose gel electrophoresis, and a part of the gel containing a desired DNA was excised. The mutant BcOS-1 DNA digested with SpeI and PstI and the vector pBluescript II SK(+) digested with SpeI and PstI were recovered from the gel using QIAquick Gel Extraction Kit (QIAGEN) according to the attached manual. The aforementioned mutant BcOS-1 DNA was inserted between SpeI site and PstI site in the multicloning site of the vector pBluescript II SK(+) using Ligation Kit Ver. 2 (TaKaRa) according to the attached manual, to construct a plasmid pBcOS1-I 365S. A nucleotide sequence of the resulting plasmid was analyzed with a DNA sequencer (Model 3100, Applied Biosystems) after a sequencing reaction using BigDye terminator v3.0 Cycle Sequence FS Ready Reaction Kit (Applied Biosystems) according to the attached manual. The sequencing reaction was performed by using an oligonucleotide consisting of the nucleotide sequences represented by any of SEQ ID NOs: 7 to 12 as a primer under the amplifying conditions that 30 cycles were repeated, each cycle comprising maintaining a temperature at 96° C. for 10 seconds, then, at 50° C. for 5 seconds, then, at 60° C. for 4 minutes. As a result, the nucleotide sequence represented by SEQ ID NO: 14 was obtained and it was confirmed that the plasmid pBcOS1-I 365S harbored the mutant BcOS-1 DNA.

The mutant BcOS-1 DNA contained in the thus prepared plasmid pBcOS1-I365S was cloned into a shuttle vector p415ADH replicable in yeast and *Escherichia coli*, to construct an expression plasmid. The plasmid pBcOS1-I365S was digested with restriction enzymes SpeI and PstI and, on the other hand, the shuttle vector p415ADH was also digested with restriction enzymes SpeI and PstI. These were separated by 0.8% agarose gel electrophoresis, respectively, each of gel parts containing the mutant BcOS-1 DNA digested with SpeI and PstI and the shuttle vector p415ADH digested with SpeI and PstI was excised, and the mutant BcOS-1 DNA and the shuttle vector were recovered from the gel using QIAquick-Gel Extraction Kit (QIAGEN) according to the attached manual. The mutant BcOS-1 DNA was inserted between SpeI site and PstI site in the multicloning site of the shuttle vector using Ligation Kit Ver. 2 (TaKaRa) according to the attached manual, to construct an expression plasmid pADHBcOS1-I365S. A nucleotide sequence of the resulting expression plasmid was analyzed with a DNA sequencer (Model 3100, Applied Biosystems) after a sequencing reaction using BigDye terminator v3.0 Cycle Sequence FS Ready Reaction Kit (Applied Biosystems) according to the attached manual. The sequencing reaction was performed by using an oligonucleotide consisting of the nucleotide sequence represented by any of SEQ ID NOs: 5 to 12 as a primer under the amplifying conditions that 30 cycles of incubation were repeated, each cycle comprising maintaining a temperature at 96° C. for 10 seconds, then, at 50° C. for 5 seconds, then, at 60° C. for 4 minutes. As a result, the nucleotide sequence represented by SEQ ID NO: 14 was obtained, and it was confirmed that the expression plasmid pADHBcOS1-I365S harbored a DNA having a nucleotide sequence encoding an amino acid sequence of the mutant BcOS-1.

The prepared expression plasmid pADHBcOS1-I 365S was introduced into the budding yeast TM182 strain according to the method described in Example 2. By utilizing disappearance of leucine auxotrophy in the resulting transformed budding yeast, the transformed budding yeast TM182 strain (TM182-BcOS1-I365s) was selected on a Gal-Ura-Leu agarose medium. It was confirmed that the resulting TM182-BcOS1-I365S grows even when transplanted to a Glu-Ura-Leu medium.

Example 6

Antifungal Compound Sensitivity Test of Transformed Budding Yeast TM182-BcOS1-I-365S The transformed budding yeast TM182-BcOS1-I365S prepared in Example 5 was cultured at 30° C. for 18 hours in a Glu-Ura-Leu medium. The absorbance at 600 nm of a cell suspension of the grown transformed budding yeast was measured, and a cell suspension diluted with sterilized distilled water to the absorbance of 0.1 was prepared. Further, a cell suspension in which the aforementioned cell suspension of the transformed budding yeast TM182-BcOS1-I 365S was diluted 200-fold with a Glu-Ura-Leu medium and, as a control, a cell suspension in which the cell suspension was diluted 200-fold with a Gal-Ura-Leu medium were prepared. A solution in which each of Compound (1) to (3) was dissolved in dimethylsulfoxide (DMSO) to the concentration of 60 ppm, a solution in which each of Compounds (4) and (5) was dissolved in dimethylsulfoxide (DMSO) to the concentration of 2000 ppm, and a solution in which each of Compounds (6) and (7) was dissolved in dimethylsulfoxide (DMSO) to the concentration of 20 ppm were prepared, and two microplates were prepared in which each 2.0 µL per well of the Compound solution and DMSO as a control were dispensed into two wells. In one microplate among them, each 200 µL of cell suspensions of the transformed budding yeast TM182-BcOS1-I365S which had been prepared by dilution with a Glu-Ura-Leu medium as described above was dispensed, and cultured by allowing to stand at 30° C. for 67 hours. In another microplate, as a control, each 200 µL of cell suspensions of the transformed budding yeast TM182-BcOS1-I 365S which had been prepared by dilution with a Gal-Ura-Leu medium was dispensed, and cultured by allowing to stand at 30° C. for 67 hours. After culturing, the absorbance at 600 nm of each well was measured with a microplate reader.

Degrees of growths of both of the transformed budding yeasts cultured under the presence of Compounds (1) to (7) and budding yeast as a control therefor are shown in Table 2. Degrees of growths of both of the transformed budding yeasts and budding yeast as a control are expressed by a relative value in percentage, letting the absorbance at 600 nm at the concentration of 0 ppm to be 100. It was confirmed that an inhibiting degree of growth of the transformed budding yeast TM182-BcOS1-I 365S by each test substance was grater than an inhibiting degree of growth of the transformed budding yeast AH22-BcOS1-I 365S by each test substance, and the transformed budding yeast TM182-BcOS1-I 365S was a transformed cell with the enhanced sensitivity to an antifungal compound as compared with the transformed budding yeast AH22-BcOS1-I365S.

TABLE 2

| | Degree of growth of budding yeast (%) | | | |
|---|---|---|---|---|
| | | AH22-BcOS1-I365S | TM182-BcOS1-I365S | |
| | AH22 | | | |
| Test substance (final concentration) | Glu medium | Glu-Leu medium | Gal-Ura-Leu medium | Glu-Ura-Leu medium |
| Compound (1) (6 ppm) | 88 | 68 | 99 | 9 |
| Compound (2) (6 ppm) | 91 | 81 | 88 | 11 |
| Compound (3) (6 ppm) | 87 | 75 | 92 | 9 |

TABLE 2-continued

| | Degree of growth of budding yeast (%) | | | |
|---|---|---|---|---|
| | | AH22-BcOS1-I365S | TM182-BcOS1-I365S | |
| | AH22 | | | |
| Test substance (final concentration) | Glu medium | Glu-Leu medium | Gal-Ura-Leu medium | Glu-Ura-Leu medium |
| Compound (4) (20 ppm) | 96 | 83 | 101 | 41 |
| Compound (5) (20 ppm) | 80 | 64 | 76 | 13 |
| Compound (6) (0.2 ppm) | 92 | 67 | 93 | 7 |
| Compound (7) (0.2 ppm) | 91 | 79 | 90 | 22 |

Example 7

Isolation of *Magnaporthe grisea* HIK1 Gene

Total RNA was prepared from *Magnaporthe grisea*. 100 mg of a hypha of *Magnaporthe grisea* P-37 strain which had been grown on a potato dextrose agar medium (PDA medium manufactured by NISSUI Pharmaceutical Co., Ltd.) was scratched off, and this was ground using a mortar and a pestle in liquid nitrogen. A RNA was prepared from frozen ground powder using RNeasy Plant Mini Kit (QIAGEN). A frozen ground powder together with liquid nitrogen was transformed to a 50 ml sample tube and, after liquid nitrogen was all volatilized off, a solution obtained by adding 10 μL of mercaptoethanol was added per 1 ml of a buffer RLC attached to the kit was added, followed by stirring. Further, after ground powder was well dispersed by a few pipettings, a temperature was maintained at 56° C. for 3 minutes. Thereafter, a solution containing ground powder was supplied to QIAshredder spin column attached to the kit, and centrifuged at 8,000×g for 2 minutes. The filtration supernatant was transferred to a fresh sample tube, a 0.5-fold volume of 99.5% ethanol was added, and the material was well mixed by pipetting. This mixtured solution was supplied to RNeasy mini spin column attached to the kit, and centrifuged at 8,000×g for 1 minute. The filtrate was discarded, 700 μL of Buffer RW1 attached to the kit was added, centrifuged at 8,000×g for 1 minute, and the filtrate was discarded. Further, the residue was added 500 μL of Buffer RPE attached to the kit, and centrifuged at 8,000×g for 1 minute, and the filtrate was discarded. This procedure was repeated twice. Finally, an upper filter part was transferred to a fresh sample tube, supplied 30 μL of RNase-free sterilized water, and centrifuged at 8,000×g for 1 minute, and total RNA was dissolved into the filtrate. This dissolution procedure was repeated twice.

Then, a cDNA was synthesized using ThermoScript RT-PCR System (Invitrogen) while using total RNA as a template. A solution in which 9.0 μL of total RNA was mixed into 1.0 μL of 50 mM Oligo$(dt)_{20}$ attached to the kit and 2.0 μL of 10 mM dNTP Mix was treated at 65° C. for 5 minutes, and rapidly cooled on ice. To this solution were added 4 μL of 5×cDNA Synthesis Buffer attached to the kit, 1 μL of 0.1M DTT, 1 μL of RNase OUT, 1 μL of ThermoScript RT and 1 μl of sterilized distilled water, to react them at 50° C. for 60 minutes and, thereafter, the reaction was stopped by heating treatment at 85° C. for 5 minutes. Further, 1 μL of RNaseH attached to the kit was added to this reaction solution, the materials were reacted at 37° C. for 20 minutes, and a RNA as a template was degraded to obtain a cDNA.

A DNA having a nucleotide sequence encoding an amino acid sequence of *Magnaporthe grisea* HIK1 (hereinafter, referred to as HIK1 DNA in some cases) was amplified by PCR using this cDNA as a template. A PCR was performed using an oligonucleotide consisting of the nucleotide sequence represented by SEQ ID NO: 18 and an oligonucleotide consisting of the nucleotide sequence represented by SEQ ID NO: 19, to amplify a DNA having the nucleotide sequence represented by SEQ ID NO: 17. The PCR was performed using KOD-Plus- (TOYOBO) under the amplifying conditions that a temperature was maintained at 94° C. for 2 minutes and, thereafter, 35 cycles of incubation were repeated, each cycle comprising maintaining a temperature at 94° C. for 15 seconds, then, at 55° C. for 30 seconds, then, at 68° C. for 6 minutes. The PCR reaction solution (50 μL) was prepared by adding 2 μL of the aforementioned cDNA, 5 μL of 10× Buffer, 5 μL of 2 mM dDNPs, 2 μL of 25 mM MgSO$_4$, each 1 μL of 10 μM oligonucleotide primers, 33 μL of sterilized distilled water and 1 μL of KOD-Plus-. After the reaction, a part of the reaction solution was separated with 1.0% agarose gel electrophoresis, and stained with ethidium bromide. It was confirmed that about 4 kb of the DNA (HIK1 DNA) was amplified.

Example 8

Construction of an Expression Plasmid of *Magnaporthe grisea* HIK1 Gene and Preparation of Transformed Budding Yeast The HIK1 DNA was cloned into a cloning vector pBluesripit SK II(+). About 4 kb of the aforementioned. DNA (HIK1 DNA) was purified from the PCR reaction solution prepared in Example 7 using QIAquick PCR Purification Kit (QIAGEN) according to the attached manual. About 4 kb of the purified DNA (HIK1 DNA) was digested with restriction enzymes of SpeI and HindIII and, on the other hand, after the cloning vector pBluescript SK II (t) (manufactured by Stratagene) was also digested with restriction enzymes SpeI and HindIII, each of which was separated with 1.0% agarose gel electrophoresis, and a part of the gel containing a desired DNA was excised. The NIK1 DNA digested with SpeI and HindIII and the cloning vector digested with SpeI and HindIII were recovered form the gel using QIAquick Gel Extraction Kit (QIAGEN) according to the attached manual. The HIK1 DNA was inserted between SpeI site and HindIII site in the multicloning site of the cloning vector using Ligation Kit Ver. 2 (TaKaRa) according to the attached manual, to construct a plasmid pBlueHIK1. A nucleotide sequence of the resulting plasmid was analyzed with a DNA sequencer (Model 3100, Applied Biosystems) after a sequencing reaction using BigDye terminator v3.0 Cycle Sequence FS Ready Reaction Kit (Applied Biosystems) according to the attached manual. The sequencing reaction was performed using an oligonucleotide consisting of the nucleotide sequence represented by any of SEQ ID NOs:20 to 29 as a primer under the amplifying conditions that 35 cycles of incubation were repeated, each cycle comprising maintaining a temperature at 96° C. for 10 seconds, then, at 50° C. for 5 seconds, then, at 60° C. for 2 minutes. As a result, the nucleotide sequence represented by SEQ ID NO: 17 was obtained, and it was confirmed that the plasmid pBlueHIK1 harbored a DNA having a nucleotide sequence encoding an amino acid sequence of HIK1.

Then, the HIK1 DNA was inserted into a shuttle vector p415ADH (ATCC87312) replicable in yeast and *Escherichia coli*. The plasmid pBlueHIK1 prepared as described above was digested with restriction enzymes SpeI and HindIII and, on the other hand, after the shuttle vector p415ADH (ATCC87312) was also digested with restriction enzymes SpeI and HindIII, each of which was separated with 1.0% agarose gel electrophoresis, and a part of the gel containing a desired DNA was excised. The HIK1 DNA digested with SpeI and HindIII and the shuttle vector digested with SpeI and HindIII were recovered from the gel using QIAquick Gel Extraction Kit (QIAGEN) according to the attached manual. The HIK1 DNA was inserted between SpeI site and HindIII site in the multicloning site of the shuttle vector using Ligation Kit Ver. 2 (TaKaRa) according to the attached manual, to construct an expression plasmid pADHHIK1.

The prepared expressed plasmid pADHHIK1 was introduced into budding yeast (*Saccharomyces cerevisiae*) AH22 strain (IFO10144) and TM182 strain (Maeda T. et al. (1994) Nature vol. 369, pp 242-245) according to the method described in Geitz R D & Woods R A (1994) Molecular Genetics of Yeast: Practical Approaches ed. Johnson J A, Oxford University Press pp 124-134. By utilizing disappearance of leucine auxotrophy in the resulting transformed budding yeast, the transformed budding yeast AH22 strain (AH21-HIK1) was selected on a Glu-Leu agar medium, and the transformed budding yeast TM182 strain (TM182-HIK1) was selected on a Glu-Ura-Leu agar medium. It was confirmed that the resulting TM182-HIK1 grows even transferred to a Glu-Ura-Leu medium.

Example 9

Antifungal Compound Sensitivity Test of Transformed Budding Yeast TM182-HIK1

The transformed budding yeast AH22-HIK1 prepared in Example 8 was cultured while shaking at 30° C. for 24 hours in a Glu-Leu medium. As a control, the AH22 strain was similarly cultured while shaking at 30° C. for 24 hours in a Glu medium. The absorbance at 600 nm of a cell suspension of each of the grown transformed budding yeasts was measured, and a cell suspension diluted with each medium to the absorbance of 0.1 was prepared. Further, a cell suspension in which the aforementioned cell suspension of the transformed budding yeast AH22-HIK1 was diluted 50-fold with a GluLeu medium, and a cell suspension in which the aforementioned cell suspension of AH22 strain was diluted 50-fold with a Glu medium were prepared. A suspension in which each of compounds (1) to (3) was dissolved in dimethylsulfoxide (DMSO) to the concentration of 200 ppm, a solution in which each of Compounds (4) to (5) was dissolved in dimethylsulfoxide (DMSO) to the concentration of 600 ppm, and a solution in which each of Compounds (6) and (7) was dissolved in dimethylsulfoxide (DMSO) to the concentration of 20 ppm were prepared, and two microplates were prepared in which each 1.0 μL per well of the Compound solution and DMSO as a control were dispensed into two wells. In one microplate among them, each 100 of a cell suspension of the transformed budding yeast AH22-hiki which had been prepared by dilution as described above was dispensed, and cultured by allowing to stand at 30° C. for 23 hours. In another microplate, each 100 μL of the cell suspensions of control yeast AH22 strain which had been prepared by dilution as described above was dispensed, and cultured by allowing to stand at 30° C. for 27 hours. After culturing, the absorbance at 600 nm of each well was measured with a microplate reader.

Similarly, the transformed budding yeast TM182-HIK1 prepared in Example 8 was cultured at 30° C. for 24 hours in a Glu-Ura-Leu medium. The absorbance at 600 nm of a cell suspension of the grown transformed budding yeast was measured, and a cell suspension diluted with each medium to the absorbance of 0.1 was prepared. Further, a cell suspension in which the aforementioned cell suspension of the transformed budding yeast TM182-HIK1 was diluted 50-fold with a Glu-Ura-Leu medium and, as a control, a cell suspension in which the suspension was diluted 50-fold with a Glu-Ura-Leu medium were prepared. A suspension in which each of Compounds (1) to (3) was dissolved in dimethylsulfoxide (DMSO) to the concentration of 200 ppm, a solution in which each of Compounds (4) and (5) was dissolved in dimethylsulfoxide (DMSO) to the concentration of 600 ppm, and a solution in which each of Compounds (6) and (7) was dissolved in dimethylsulfoxide (DMSO) to the concentration of 20 ppm were prepared, and two microplates were prepared in which each 1.0 µL per well of the Compound DMSO solution and DMSO as a control were dispensed into two wells. In one microplate among them, each 100 µL of cell suspensions of the transformed budding yeast TM182-HIK1 which had been prepared by dilution with a Glu-Ura-Leu medium as described above was dispensed, and cultured by allowing to stand at 30° C. for 27 hours. In another microplate, as described above, as a control, each 100 µL of cell suspensions of the transformed budding yeast TM182-HIK1 which had been prepared by dilution with a Gal-Ura-Leu medium was dispensed, and cultured by allowing to stand at 30° C. for 27 hours. After culturing, the absorbance at 600 nm of each well was measured with a microplate reader.

Degree of growths of both of the transformed budding yeasts cultured in the presence of Compounds (1) to (7) and budding yeast as a control therefor are shown in Table 3. Degrees of growths of both of the transformed budding yeasts and budding yeast as a control thereofor are shown by a relative value in percentage, letting the absorbance of 600 nm at the concentration of the Compound of 0 ppm to be 100. It was confirmed that an inhibiting degree of growth of TM182-HIK1 by each test substance was greater than an inhibiting degree of growth of AH22-HIK1 by each test substance, and the TM182-HIK1 was a transformed cell with the enhanced sensitivity to an antifungal compound as compared with AH22-HIK1.

TABLE 3

| Test substance (final concentration) | Degree of growth of budding yeast (%) | | | |
|---|---|---|---|---|
| | AH22 Glu medium | AH22-HIK1 Glu-Leu medium | TM182-HIK1 Gal-Ura-Leu medium | TM182-HIK1 Glu-Ura-Leu medium |
| Compound (1) (2.0 ppm) | 85 | 89 | 100 | 62 |
| Compound (2) (2.0 ppm) | 96 | 84 | 94 | 79 |
| Compound (3) (2.0 ppm) | 99 | 104 | 100 | 30 |
| Compound (4) (6.0 ppm) | 97 | 92 | 97 | 63 |
| Compound (5) (6.0 ppm) | 93 | 99 | 106 | 22 |
| Compound (6) (0.2 ppm) | 101 | 98 | 104 | 11 |
| Compound (7) (0.2 ppm) | 89 | 102 | 87 | 9 |

Example 10

Amplification of Osmosensitivie Histidine Kinase Gene Fragment from Other Filamentas Fungus (1) Preparation of Total RNA of *Fusarium oxysporum*

Total RNA was prepared from *Fusarium oxysporum*. 100 mg of a hypha of *Fusarium oxysporum* RJN1 strain grown on a potato dextrose agarose medium (PDA medium, manufactured by NISSUI Pharmaceutical Co., Ltd.) was collected, and this was ground using a mortar and a pestle in liquid nitrogen. Total RNA was prepared from frozen ground powder using RNeasy Plant Mini Kit (QIAGEN) according to the method described in Example 1.

(2) Preparation of Total RNA of *Mycospharella tritici*

Total RNA was prepared from *Mycospharella tritici*. Spore of *Mycospharella tritici* St-8 strain grown on a potato dextrose agarose medium (PDA medium, manufactured by NISSUI Pharmaceutical Co., Ltd.) was added to 100 ml of PD broth (DIFCO), and this was cultured at 20° C. and 150 rpm for 4 days using a 500 ml volume Erlenmeyer flask. 8 ml of the culture solution was centrifuged to remove the supernatant, and 300 mg of a wet weight of cells were transferred to a mortar and ground in liquid nitrogen using a pestle. Total RNA was prepared from frozen ground powder according to the method described in Example 1.

(3) Preparation of Total RNA of *Thanatephorus cucumeris*

Total RNA was prepared from *Thanatephorus cucumeris*. Hypha of *Thanatephorus cucumeris* Rs-18 strain grown on a potato dextrose agar medium (PDA medium, manufactured by NISSUI Pharmaceutical Co., Ltd.) was added to 100 ml of PD broth (DIFCO), and cultured by allowing to stand at 25° C. for 4 days using a 500 ml volume Erlenmeyer flask. 8 ml of the culture solution was centrifuged to remove the supernatant, 300 mg of a wet weight of hypha were transferred to a mortar, and ground in liquid nitrogen using a pestle. Total RNA was prepared from frozen ground powder using Rneasy Plant Mini Kit (QIAGEN) according to the method described in Example 1.

(4) Preparation of Total RNA of *Phytophthora infestans*

Total RNA was prepared from *Phytophthora infestans*. Hypha of *Phytophthora infestans* Pi-5 strain grown on a rye agar medium (rye 60 g, sucrose 15 g, agar 20 g/1 L) was added to 20 ml of a rye medium (rye 60 g, sucrose 15 g/1 L), and cultured at 20° C. and 150 rpm for 5 days using a 300 ml of volume Erlenmeyer flask. 20 ml of the culture solution was centrifuged to remove the supernatant, a wet weight of 200 mg of cells were transferred to a mortar, and ground using a pestle in liquid nitrogen. Total RNA was prepared from frozen ground powder using RNeasy Plant Mini Kit (QIAGEN) according to the method described in Example 1.

(5) Amplification of Osmosensing Histidine Kinase Gene Fragment by PCR

Using the total RNA of *Magnaporthe grisea* prepared in Example 7, the total RNA of *Fusarium oxysporum* prepared in Example 10 (1), the total RNA of *Mycospharella tritici* prepared in Example 10 (2), the total RNA of *Thanatephorus cucumeris* prepared in Example 10 (3), or the total RNA of *Phytophthora infestans* prepared in Example 10 (4), amplification of a DNA having a nucleotide sequence encoding a part of an amino acid sequence of osmosensing histidine kinase was performed.

First, a cDNA was synthesized using ThermoScript RT-PCR System (Invitrogen) and using each of total RNAs as a template. A solution in which 4.0 µL of each of total RNAs and 5.0 µL of sterilized distilled water were mixed into 1.0 µL of 50 mM Oligo(dT)$_{20}$ attached to the kit and 2.0 µL of 10 mM dNTP Mix was prepared, and a cDNA was synthesized according to the method described in Example 1.

A PCR was performed using each cDNA as a template. As primers, a primer pair shown in Table 4 was used. A size of a DNA which is predicted to be amplified by PCR using each primer pair based on the nucleotide sequence represented by SEQ ID NO: 2 is shown in Table 4.

TABLE 4

| Primer Pair | Primer | Primer | DNA to be amplified |
|---|---|---|---|
| 1 | SEQ ID NO: 30 | SEQ ID NO: 35 | 368 bp |
| 2 | SEQ ID NO: 30 | SEQ ID NO: 36 | 374 bp |
| 3 | SEQ ID NO: 30 | SEQ ID NO: 37 | 383 bp |
| 4 | SEQ ID NO: 31 | SEQ ID NO: 35 | 359 bp |
| 5 | SEQ ID NO: 31 | SEQ ID NO: 36 | 365 bp |
| 6 | SEQ ID NO: 31 | SEQ ID NO: 37 | 374 bp |
| 7 | SEQ ID NO: 32 | SEQ ID NO: 38 | 3019 bp |
| 8 | SEQ ID NO: 32 | SEQ ID NO: 40 | 3052 bp |
| 9 | SEQ ID NO: 33 | SEQ ID NO: 38 | 2927 bp |
| 10 | SEQ ID NO: 33 | SEQ ID NO: 40 | 2960 bp |
| 11 | SEQ ID NO: 34 | SEQ ID NO: 38 | 2867 bp |
| 12 | SEQ ID NO: 34 | SEQ ID NO: 40 | 2900 bp |
| 13 | SEQ ID NO: 30 | SEQ ID NO: 39 | 1424 bp |
| 14 | SEQ ID NO: 30 | SEQ ID NO: 40 | 1442 bp |
| 15 | SEQ ID NO: 31 | SEQ ID NO: 39 | 1415 bp |
| 16 | SEQ ID NO: 31 | SEQ ID NO: 40 | 1433 bp |

A PCR was performed using KOD-Plus- (TOYOBO) under the amplifying conditions that a temperature was maintained at 94° C. for 2 minutes and, thereafter, 35 cycles of incubation were repeated, each cycle comprising maintaining a temperature at 94° C. for 15 seconds, then, at 55° C. for 30 seconds further, at 68° C. for 1 minutes. When primer pairs 1 to 6 were used, the incubation at 68° C. in the cycle was for 1 minutes. When the primer pairs 7 to 12 were used, the incubation at 68° C. in the cycle was for 5 minutes. When the primer pairs 13 to 16 were used, the incubation at 68° C. in the cycle was for 3 minutes. The PCR reaction solution (25 µL) was prepared by adding 0.5 µL of the cDNA, 2.5 µL of 10× buffer, 2.5 µL of 8 mM dNTPs, 1.0 µL of 25 mM MgSO$_4$, each 0.5 µL of 10 µM oligonucleotide primers, 17 µL of sterilized distilled water and 0.5 µL of KOD-Plus-. The PCR reaction solution after the reaction was analyzed with 1% or 4% agarose gel electrophoresis.

When primer pairs 1, 2, 3, 4, 5 or 6 were used and a cDNA of *Magnaporthe grisea* was used as a template, amplification of predicted size of DNA was observed. When primer pairs 2, 3, 7, 8, 9, 10, 11 or 12 were used, and a cDNA of *Fusarium oxysporum* was used as a template, amplification of a predicted size of DNA was observed. When the primer pairs 3, 5, 6, 13, 14, 15 or 16 were used, and cDNA of *Mycospharella Tritici* was used as a template, amplification of predicted size of DNA was observed. When primer pairs 2, 3, 5 or 6 were used, and cDNA of *Thanatephorus cucumeris* was used as a template, amplification of a predicted size of a DNA was observed. When the primer pairs 5 or 6 were used, and cDNA of *Phytophthora infestans* was used as a template, amplification of predicted size of DNA was observed.

Example 11

Isolation of *Fusarium oxysporum* FoOS-1 Gene (1) Analysis of *Fusarium oxysporum* FoOS-1 Gene Fragment The amplified DNA was purified from the reaction solution of PCR which had been performed by using a cDNA of *Fusarium oxysporum* as a template and using a primer pair 9 in Example 10 (5), using QIAquick PCR Purification Kit (QIAGEN) according to the attached instruction.

Adenine was added to the 3'-terminal of the purified DNA using Ex Taq (TaKaRa) (hereinafter, referred to as 3'A addition). The reaction solution (20 µL) for 3'A addition was prepared by adding 15.3 µL of a solution of the aforementioned purified DNA, 2.0 µL of 10× buffer, 2.5 µL of 10 mM dNPTs and 0.2 µL of Ex Taq, and this was maintained at 72° C. for 30 minutes.

Thus the 3'A-added DNA and the pCR2.1-TOPO cloning vector (Invitrogen) were ligated according to the instruction attached to the cloning vector, after that, which was introduced into *Escherichia coli* JM109 (TaKaRa). A plasmid DNA was purified from the resulted *Escherichia coli* transformant using QIAprep Spin Miniprep Kit (QIAGEN). A nucleotide sequence of the plasmid DNA was analyzed with a DNA sequencer (Model 3100, Applied Biosystems) after a sequencing reaction employing the resulting plasmid DNA as a template, and using an oligonucleotide consisting of the nucleotide sequence represented by any of SEQ ID NOs: 28, 29, and 45 to 48 as a primer, and using BigDye Terminator v3.0 Cycle Sequencing Ready Reaction Kit (Applied Biosystems Japan) according to the instruction attached to the kit. The sequencing reaction was performed under the amplifying conditions that 35 cycles of incubation were repeated, each cycle comprising maintaining a temperature at 96° C. for 10 seconds, then, at 50° C. for 5 seconds, further, at 60° C. for 2 minutes. As a result, a nucleotide sequence represented by base numbers 663 to 3534 of the nucleotide sequence represented by SEQ ID NO: 42 was read.

(2) Analysis of Full Length FoOS-1 Gene of *Fusarium oxysporum*

A DNA having a nucleotide sequence extending toward to the 5' upstream region from a nucleotide number 663 of the nucleotide sequence represented by SEQ ID Mo. 42 was cloned using SMART RACE cDNA Amplification Kit (CLONTECH) according to the instruction attached to the kit. 1.0 µL of CDS-primer attached to the kit, and 1.0 µL of SMART IIA Oligo were mixed into 3 µL (230 ng) of the total RNA prepared in Example 10 (1) to prepare a reaction solution. The reation solution was maintained at 70° C. for 2 minutes and maintained on ice for 2 minutes. To the reaction solution were added 2 µL of 5× First-Strand buffer attached to the kit, 1 µL of 20 mM DTT, 1 µL of 10 mM dNPT Mix and 1 µL of PowerScript Reverse Transcriptase and mixed, and the mixture was maintained at 42° C. for 1.5 hours. To the reaction solution after temperature maintenance was added 100 µL of Tricine-EDTA buffer attached to the kit, and a temperature was maintained at 72° C. for 7 minutes to prepare 5' RACE ready cDNA. PCR amplifying 5' upstream region was performed by using this 5' RACE ready cDNA as a template. A PCR reaction solution was obtained by adding 5.0 µL of 10× Advantage 2 buffer, 1.0 µL of 10 mM dNTP Mix and 1.0 µL of 50× Advantage 2 Polymerase Mix attached to the kit to 2.5 µL of 5' RACE ready cDNA and mixing them, and adding 5.0 µL of 10× Universal Primer A Mix attached to the kit as a primer, and 1.0 µL of a 10 µM solution of an oligonucleotide consisting of the nucleotide sequence represented by SEQ ID NO: 43, and adding sterilized distilled water to a total amount of 50 µL. This reaction solution was subjected to repetition of 5 cycles of incubation, each cycle comprising maintaining a temperature at 94° C. for 5 seconds, then, at 72° C. for 2 minutes, further repetition of 5 cycles of incubation, each cycle comprising a maintaining a temperature at 94° C. for 5 seconds, then, at 70° C. for 10 seconds, then, at 72° C. for 2 minutes, further repetition of 25 cycles of incubation, each cycle comprising maintaining a temperature at 94° C. for 5 seconds, then, at 68° C. for 10 seconds, then, at 72° C. for 2 minutes, followed by maintaining a temperature at 72° C. for 7 minutes. The PCR reaction solution and the pCR2.1-TOPO cloning vector (Invitrogen) were ligated according to the instruction attached to the cloning vector, after that, which was introduced into *Escherichia coli* JM109

(TaKaRa). A plasmid DNA was purified from the resulting *Escherichia coli* transformant using QIAprep Spin Miniprep Kit (QIAGEN). A nucleotide sequence was analyzed using the resulting plasmid DNA as a template, and using a primer consisting of the nucleotide sequence represented by any of SEQ ID NOs: 29, 49 and 54 according to the method described in Example 11 (1). As a result, a nucleotide sequence represented by nucleotide numbers 1 to 662 of the nucleotide sequence represented by SEQ ID NO: 42 was read.

Further, a DNA having a nucleotide sequence extending toward to the 3' downstream region from nucleotide number 3534 of the nucleotide sequence represented by SEQ ID NO: 42 was cloned. 1.0 µL of CDS-primer attached to the kit and 1.0 µL of sterilized distilled water were mixed into 3 µL (230 ng) of the total RNA prepared in Example 10 (1), the mixture was maintained at 70° C. for 2 minutes, and maintained on ice for 2 minutes. 3' RACE ready cDNA was prepared using the reaction solution as in preparation of 5' RACE ready cDNA. PCR amplifying 3' downstream region was performed using this 3' RACE ready cDNA as a template. A PCR reaction solution was prepared by mixing 5.0 µL of 10× Advantage 2 buffer attached to the kit, 1.0 µL of 10 mM dNTP Mix and 1.0 µL of 50× Advantage 2 Polymerase Mix into 2.5 µL of 3' RACE ready cDNA, adding 5.0 µL of 10× Universal Primer A Mix attached to the kit as a primer, and 1.0 µL of a 10 µM solution of an oligonucleotide consisting of the nucleotide sequence represented by SEQ ID NO: 42, and adding sterilized distilled water to a total amount of 50 µL. This reaction solution was subjected to repetition of 5 cycles of incubation, each cycle comprising maintaining a temperature at 94° C. for 5 seconds, then, at 72° C. for 2 minutes, further repetition of 5 cycles of incubation, each cycle comprising maintaining a temperature at 94° C. for 5 seconds, then, at 70° C. for 10 seconds, then, at 72° C. for 2 seconds, further repetition of 25 cycles of incubation, each cycle comprising maintaining a temperature at 94° C. for 5 seconds, then, at 68° C. for 10 seconds, then, at 72° C. for 2 minutes, followed by maintaining a temperature at 72° C. for 7 minutes. The PCR reaction solution and the pCR2.1-TOPO cloning vector (Invitrogen) were ligated to the vector according to the instruction attached to the kit, after that, which was introduced into *Escherichia coli* JM109 (TaKaRa). A plasmid DNA was purified from the resulting *Escherichia coli* transformant using QIAprep Spin Miniprep Kit (QIAGEN). A nucleotide sequence was analyzed using the resulting plasmid DNA as a template, and using a primer consisting of the nucleotide sequence represented by any of SEQ ID NOs: 29, 50 and 54, according to the method described in Example 11 (1). As a result, a nucleotide sequence represented by nucleotide numbers 3535 to 3882 of the nucleotide sequence represented by SEQ ID NO: 42 was read.

All analyzed nucleotide sequences were joined and, as a result, the nucleotide sequence represented by SEQ ID NO: 42 was obtained. The nucleotide sequence represented by SEQ ID NO: 42 consists of 3882 bases (including termination codon), and was a nucleotide sequence encoding 1293 amino acid residues (SEQ ID NO: 41). A molecular weight of a protein having the amino acid sequence represented by SEQ ID NO: 41 was calculated to be 141818 Da.

(3) Isolation of Full Length *Fusarium oxysporum* FoOS1 Gene

A DNA having a nucleotide sequence encoding an amino acid sequence of *Fusarium oxysporum* FoOS1 (hereinafter, referred to as FoOS-1 DNA in some cases) was amplified by PCR using the 5' RACE ready cDNA prepared in Example 11 (2) as a template. By performing a PCR using, as a primer, an oligonucleotide consisting of the nucleotide sequence represented by SEQ ID NO: 52 and an oligonucleotide consisting of the nucleotide sequence represented by SEQ ID NO: 53, a DNA having the nucleotide sequence represented by SEQ ID NO: 42 was amplified. The PCR was performed using KOD-Plus- (TOYOBO) under the amplifying conditions that a temperature was maintained at 94° C. for 2 minutes and, thereafter, 35 cycles of incubation were repeated, each cycle comprising maintaining a temperature at 94° C. for 15 seconds, then, at 55° C. for 30 seconds, further, at 68° C. for 6 minutes. The PCR reaction solution (50 µL) was prepared by adding 2.5 µL of 5' a RACE ready cDNA, 5.0 µL of 10× buffer, 5.0 µL of 2 mM dNTPs, 2.0 µL of 25 mM MgSO$_4$, each 1.0 µL of 10 µM oligonucleotide primers, 32.5 µL of sterilized distilled water and 1.0 µL of KOD Plus-. After the reaction, a part of the PCR reaction solution was separated by 1% agarose gel electrophoresis, and stained with ethidium bromide. It was confirmed that about 4 kb of the DNA (FoOS1 DNA) was amplified.

Example 12

Construction of Expression Plasmid of *Fusarium oxysporum* FoOS1 Gene and Preparation of Transformed Budding Yeast The FoOS1 DNA was cloned into a pCR2.1-TOPO cloning vector (Invitrogen). About 4 kb of the DNA (FoOS-1 DNA) was purified from the PCR reaction solution prepared in Example 11 (3) using QIAquick PCR Purification Kit (QIAGEN) according to the instruction attached to the kit. 3'A addition was performed on about 4 kb of the purified DNA (FoOS-1 DNA) according to the method described in Example 11 (1). The 3'A-added about 4 kb DNA (FoOS-1 DNA) and the pCR2.1-TOPO cloning vector (Invitrogen) were ligated according to the manual attached to the cloning vector to construct a plasmid pCRFoOS1. A nucleotide sequence of the resulting plasmid was analyzed according to the method described in Example 11(1). As a primer, an oligonucleotide consisting of the nucleotide sequence represented by any of SEQ ID NOs: 29, 43 to 51, and 54 was used. As a result, the nucleotide sequence represented by SEQ ID NO: 42 was obtained, and it was confirmed that the plasmid pCRFoOS1 was a plasmid containing the FoOS-1 DNA.

The FoOS-1 DNA contained in the thus prepared plasmid pCRFoOS1 was cloned into a shuttle vector p415ADH replicable in yeast and *Escherichia coli* to construct an expression plasmid. The plasmid pCRFoOS1 was digested with restriction enzymes SpeI and PstI and, on the other hand, the shuttle vector p415ADH was also digested with restriction enzymes SpeI and PstI. Each of them was separated by 0.8% agarose gel electrophoresis, a part of the gel containing the FoOS-1 DNA digested with SpeI and PstI and the shuttle vector p415ADH digested with SpeI and PstI was excised, and the FoOS-1 DNA and the shuttle vector were recovered from the gel using QIAquick Gel Extraction Kit (QIAGEN) according to the attached manual. The FoOS-1 DNA was inserted between SpeI site and PstI site in the multicloning site of the shuttle vector using Ligation Kit Ver. 2 (TaKaRa) according to the manual attached to the kit, whereby, an expression plasmid pADHFoOS1 was constructed. A nucleotide sequence of the resulting expression plasmid was analyzed according to the method described in Example 11 (1). As a primer, an oligonucleotide consisting of the nucleotide sequence represented by any of SEQ ID NO: 43 to 53 was used. As a result, the nucleotide sequence represented by SEQ ID NO: 42 was obtained, and it was confirmed that the expression plasmid pADHFoOS1 harbored a DNA having a nucleotide sequence encoding an amino acid sequence of FoOS-1.

The prepared expression plasmid pADHFoOS1 was introduced into budding yeast AH22 strain and TM182 strain according to the method described in Example 2. By utilizing the disappearance of leucine auxotrophy in the resulting transformed budding yeast, the transformed budding yeast AH22 strain (AH22-FoOS1) was selected on a Glu-Leu agar medium, and the transformed budding yeast TM182 strain (TM182-FoOS1) was selected on a Gal-Ura-Leu agar medium. It was confirmed that the resulting TM182-FoOS1 grows even when transplanted to a Glu-Ura-Leu medium.

Example 13

Antifungal Compound Sensitivity Test of Transformed Budding Yeast TM182-FoOS1

The transformed budding yeast AH22-FoOS1 prepared in Example 12 was cultured while shaking at 30° C. for 18 hours in a Glu-Leu medium. As a control, the AH22 strain was similarly cultured while shaking at 30° C. for 18 hours in a Glu medium. The absorbance at 600 nm of each grown transformed budding yeast in a cell suspension was measured, and cell suspension diluted with sterilized distilled water to the absorbance of 0.1 was prepared. Further, a cell suspension in which the aforementioned cell suspension of the transformed budding yeast AH22-FoOS1 was diluted 50-fold with a Glu-Leu medium, and a cell suspension in which the aforementioned cell suspension of the AH22 strain was diluted 50-fold with a Glu medium were prepared.

A solution in which each of Compounds (1) to (3) was dissolved in dimethylsulfoxide (DMSO) to the concentration of 600 ppm, a solution in which each of Compounds (4) and (5) was dissolved in dimethylsulfoxide (DMSO) to the concentration of 2000 ppm, and a solution in which Compounds (6) and (7) was dissolved in dimethylsulfoxide (DMSO) to the concentration of 20 ppm were prepared, and two microplates were prepared in which each 1.0 µL per well of the Compound solution and DMSO as a control were dispensed. In one microplate among them, each 100 µL of cell suspensions of the transformed budding yeast AH22-FoOS1 which had been prepared by dilution as described above was dispensed, and cultured by allowing to stand at 30° C. for 26.5 hours. In another microplate, each 100 µL of cell suspensions of the control yeast AH22 strain which had been prepared by dilution as described above was dispensed, and cultured by allowing to stand at 30° C. for 24.5 hours. After culturing, the absorbance at 600 nm of each well was measured with a microplate reader.

Similarly, the transformed budding yeast TM182-FoOS1 prepared in Example 12 was cultured at 30° C. for 18 hours in a Glu-Ura-Leu medium. The absorbance at 600 nm of the grown transformed budding yeast in a cell suspension was measured, and a cell suspension diluted with sterilized distilled water to the absorbance of 0.1 was prepared. Further, a cell suspension in which the transformed budding yeast TM182-FoOS1 was diluted 50-fold with a Glu-Ura-Leu medium and, as a control, a cell suspension in which the yeast was diluted 50-fold with a Gal-Ura-Leu medium were prepared.

A solution in which each of Compounds (1) to (3) was dissolved in dimethylsulfoxide (DMSO) to the concentration of 600 ppm, a solution in which each of Compounds (4) and (5) was dissolved in dimethylsulfoxide (DMSO) to the concentration of 2000 ppm, and a solution in which each of Compounds (6) and (7) was dissolved in dimethylsulfoxide (DMSO) to the concentration of 20 ppm were prepared, and two microplates were prepared in which each 2.0 µL per well of the Compound-DMSO solution and DMSO as a control were dispensed into 2 wells. In one microplate among them, each 100 µL of cell suspensions of the transformed budding yeast TM182-FoOS1 which had been prepared by dilution with a Glu-Ura-Leu medium as described above was dispensed, and cultured by allowing to stand at 30° C. for 25 hours. In another microplate, as described above, as a control, each 100 µL of cell suspensions of the transformed budding yeast TM182-FoOS1 which had been prepared by dilution with a Gal-Ura-Leu medium was dispensed, and cultured at 30° C. for 51 hours. After culturing, the absorbance at 600 nm of each well was measured with a microplate reader.

A degree of growth of each transformed budding yeast cultured in the presence of Compounds (1) to (7) is shown in Table 5. A degree of growth of the transformed budding yeast is expressed as a relative value in percentage, letting the absorbance at 600 nm at the concentration of the Compound of 0 ppm to be 100. It was confirmed that an inhibiting degree of growth of the transformed budding yeast TM182-FoOS1 by each test substance was grater than an inhibiting degree of growth of the transformed budding yeast AH22-FoOS1 by each test substance, and the transformed budding yeast TM182-FoOS1 was a transformed cell with the enhanced sensitivity to an antifungal compound as compared with the transformed budding yeast AH22-FoOS1.

TABLE 5

| | Degree of growth of budding yeast | | | |
|---|---|---|---|---|
| Test substance (final concentration) | AH22 Glu medium | AH22-FoOS1 Glu-Leu medium | TM182-FoOS1 Gal-Ura-Leu medium | TM182-FoOS1 Gul-Ura-Leu medium |
| Compound (1) (6 ppm) | 88 | 81 | 116 | 26 |
| Compoud (2) (6 ppm) | 91 | 91 | 87 | 55 |
| Compound (3) (6 ppm) | 87 | 86 | 99 | 22 |
| Compound (4) (20 ppm) | 96 | 90 | 104 | 20 |
| Compound (5) (20 ppm) | 80 | 71 | 80 | 57 |
| Compound (6) (0.2 ppm) | 92 | 69 | 99 | 7 |
| Compound (7) (0.2 ppm) | 91 | 88 | 89 | 21 |

Example 14

Isolation of *Mycospharella tritici* StOS-1 Gene (1) Analysis of *Mycospharella tritici* StOS-1 Gene Fragment The amplified DNA was purified from the reaction solution of PCR which had been performed using a primer pair 16 and using a cDNA of *Mycospharella tritici* as a template in Example 10 (4), using QIAquick PCR Purification Kit (QIAGEN) according to the instruction attached to the kit. 3'A addition was performed on the purified DNA according to the method described in Example 11 (1). The 3'A-added DNA and the pCR2.1-TOPO cloning vector (Invitrogen) were ligated according to the instruction attached to the cloning vector, and this was introduced into *Escherichia coli* JM109 (TaKaRa).

DNA was purified from the resulting *Escherichia coli* transformant by colony PCR using Ex Taq HS (TaKaRa). The PCR reaction solution (15 μL) was prepared by mixing 1.5 μL of 10× buffer, 2.25 μL of 10 mM dNTPs, 0.15 μL of Ex Taq HS, each 0.4 μL of a 10 μM solution of an oligonucleotide consisting of the nucleotide sequence represented by SEQ ID NO: 66 and a 10 µM solution of an oligonucleotide consisting of the nucleotide sequence represented by SEQ ID NO: 67, and 10.3 µL of sterilized distilled water, and adding a part of the *Escherichia coli* transformant colony thereto. PCR was performed under the amplifying conditions that this reaction solution was maintained at 97° C. for 2 minutes and, thereafter, 35 cycles of incubation were repeated, each cycle comprising maintaining a temperature at 97° C. for 15 seconds, then, at 55° C. for 15 seconds, then, at 72° C. for 3 minutes. The amplified DNA was purified from the PCR reaction solution after temperature maintenance using QIAquick PCR Purification Kit (QIAGEN) according to the instruction attached to the kit. A nucleotide sequence was analyzed using oligonucleotides consisting of nucleotide sequences represented by SEQ ID NOs: 29 and 54 as a primer and employing the purified DNA as a template according to the method described in Example 11 (1). As a result, a nucleotide sequence represented by base numbers 2241 to 3603 of the nucleotide sequence represented by SEQ ID NO: 56 was read.

(2) Analysis of Full Length *Mycospharella tritici* StOS-1 Gene

A DNA having a nucleotide sequence extending toward to 5' upstream region of a base number 2241 of the nucleotide sequence represented by SEQ ID NO: 56 was cloned using SMART RACE cDNA Amplification Kit (CLONTECH) according to the instruction attached to the kit. A reaction solution was prepared by mixing 1.0 µL of CDS-primer and 1.0 µL of SMART IIA Oligo attached to the kit into 3 µL (230 ng) of total RNA prepared in Example 10 (2), a temperature was maintained at 70° C. for 2 minutes, and maintained on ice for 2 minutes. To the reaction solution were added 2 µL of 5× First-Strand buffer attached to the kit, 1 µL of 20 mM DTT, 1 µL of 10 mM dNTP Mix and 1 µL of PowerScript Reverse Transcriptase, to mix them, and the mixture was maintained at 42° C. for 1.5 hours. To the reaction solution after temperature maintenance was added 100 µL of Tricine-EDTA buffer attached to the kit, a temperature was maintained at 72° C. for 7 minutes, thus 5' RACE ready cDNA was prepared. PCR amplifying 5' upstream region was performed using this 5' RACE ready cDNA as a template and using KOD-plus- (TOYOBO). The PCR reaction solution was prepared by mixing 2.5 µL of 5' RACE ready cDNA, 5.0 µL of 10× buffer, 5.0 µL of 2 mM dNTPs, 2.0 µL of 25 mM MgSO$_4$ and 1.0 µL of KOD-Plus, adding 5.0 µL of 10× Universal Primer A Mix attached to the kit and 1.0 µL of a 10 µM solution of an oligonucleotide consisting of the nucleotide sequence represented by SEQ ID NO: 43 as primers, and adding sterilized distilled water to a total amount of 50 µL. This reaction solution was maintained at 94° C. for 2 minutes, and 35 cycles of incubation were repeated, each cycle comprising maintaining a temperature at 94° C. for 15 seconds, then, at 68° C. for 5 minutes. The amplified DNA was purified from the PCR reaction solution using QIAquick PCR Purification Kit (QIAGEN) according to the instruction attached to the kit, and then, 3'A addition was performed on the DNA according to the method described in Example 11(1). The 3'A-added DNA and the pCR2.1-TOPO cloning vector (Invitrogen) were ligated according to the instruction attached to the cloning vector, after that, which was introduced into *Escherichia coli* JM109 (TaKaRa). A plasmid DNA was purified from the resulting *Escherichia coli* transformant using QIAprep Spin Miniprep Kit (QIAGEN). A nucleotide sequence was analyzed using the resulting plasmid DNA as a template and using primers consisting of nucleotides sequences represented by SEQ ID NOs: 29, 54, and 59 to 61 according to the method described in Example 11(1). As a result, a nucleotide sequence represented by base numbers 1 to 2240 of the nucleotide sequence represented by SEQ ID NO: 56 was read.

Further, a DNA having a nucleotide sequence extending toward to the 3' downstream region from nucleotide number 3603 of the nucleotide sequence represented by SEQ ID NO: 56 was cloned. 1.0 µL of CDS-primer attached to the kit and 1.0 µL of sterilized distilled water were mixed into 3 µL (230 ng) of the total RNA prepared in Example 10 (2), the mixture was maintained at 70° C. for 2 minutes, and maintained on ice for 2 minutes. 3' RACE ready cDNA was prepared using the reaction solution as in preparation of 5' RACE ready cDNA. PCR amplifying 3' downstream region was performed using this 3' RACE ready cDNA as a template. A PCR reaction solution was prepared by mixing 5.0 µL of 10× Advantage 2 buffer attached to the kit, 1.0 µL of 10 mM dNTP Mix and 1.0 µL of 50× Advantage 2 Polymerase Mix into 2.5 µL of 3' RACE ready cDNA, adding 5.0 µL of 10× Universal Primer A Mix attached to the kit as a primer, and 1.0 µL of a 10 µM solution of an oligonucleotide consisting of the nucleotide sequence represented by SEQ ID NO: 58, and adding sterilized distilled water to a total amount of 50 µL. This reaction solution was subjected to repetition of 5 cycles of incubation, each cycle comprising maintaining a temperature at 94° C. for 5 seconds, then, at 72° C. for 4 minutes, further repetition of 5 cycles of incubation, each cycle comprising maintaining a temperature at 94° C. for 5 seconds, then, at 70° C. for 10 seconds, then, at 72° C. for 4 minutes, further repetition of 25 cycles of incubation, each cycle comprising maintaining a temperature at 94° C. for 5 seconds, then, at 68° C. for 10 seconds, then, at 72° C. for 4 minutes, followed by maintaining a temperature at 72° C. for 7 minutes. The PCR reaction solution and the pCR2.1-TOPO cloning vector (Invitrogen) were ligated to the vector according to the instruction attached to the kit, after that, which was introduced into *Escherichia coli* JM109 (TaKaRa). A plasmid DNA was purified from the resulting *Escherichia coli* transformant using QIAprep Spin Miniprep Kit (QIAGEN). A nucleotide sequence was analyzed using the resulting plasmid DNA as a template, and using a primer consisting of the nucleotide sequence represented by any of SEQ ID NOs: 29 and 54, according to the method described in Example 11 (1). As a result, a nucleotide sequence represented by nucleotide numbers 3604 to 3924 of the nucleotide sequence represented by SEQ ID NO: 56 was read.

All analyzed nucleotide sequences were joined and, as a result, the nucleotide sequence represented by SEQ ID NO: 56 was obtained. The nucleotide sequence represented by SEQ ID NO: 56 consists of 3924 bases (including termination codon), and was a nucleotide sequence encoding 1307 amino acid residues (SEQ ID NO: 55). A molecular weight of a protein having the amino acid sequence represented by SEQ ID NO: 55 was calculated to be 143276 Da.

(3) Isolation of Full Length *Mycospharella tritici* StOS-1 Gene

A DNA having a nucleotide sequence encoding an amino acid sequence of *Mycospharella tritici* StOS-1 (hereinafter, referred to as StOS-1 DNA in some cases) was amplified by PCR using the 5' RACE ready cDNA prepared in Example 14 (2) as a template. By performing a PCR using, as a primer, an oligonucleotide consisting of the nucleotide sequence represented by SEQ ID NO: 64 and an oligonucleotide consisting of the nucleotide sequence represented by SEQ ID NO: 65, a DNA having the nucleotide sequence represented by SEQ ID NO: 56 was amplified, according to the method described in Example 11 (3). After the reaction, a part of the PCR reaction solution was separated by 1% agarose gel electrophoresis, and stained with ethidium bromide. It was confirmed that about 4 kb of the DNA (StOS-1 DNA) was amplified.

Example 15

Construction of Expression Plasmid of *Mycosphaerella tritici* StOS-1 Gene and Preparation of Transformed Budding Yeast The StOS-1 DNA was cloned into a pCR2.1-TOPO cloning vector (Invitrogen). About 4 kb of the DNA (StOS-1 DNA) was purified from the PCR reaction solution prepared in Example 14 (3) using QIAquick PCR Purification Kit (QIAGEN) according to the instruction attached to the kit. 3'A addition was performed on about 4 kb of the purified DNA (StOS-1 DNA) according to the method described in Example 11 (1). The 3'A-added about 4 kb DNA (StOS-1 DNA) and the pCR2.1-TOPO cloning vector (Invitrogen) were ligated according to the manual attached to the cloning vector to construct a plasmid pCRStOS1. A nucleotide sequence of the resulting plasmid was analyzed according to the method described in Example 11(1). As a primer, an oligonucleotide consisting of the nucleotide sequence represented by any of SEQ ID NOs: 29, 54, and 58 to 63 was used. As a result, the nucleotide sequence represented by SEQ ID NO: 56 was obtained, and it was confirmed that the plasmid pCRStOS1 was a plasmid containing the StOS-1 DNA.

The StOS-1 DNA contained in the thus prepared plasmid pCRStOS1 was cloned into a shuttle vector p415ADH replicable in yeast and *Escherichia coli* to construct an expression plasmid. The plasmid pCRStOS1 was digested with restriction enzymes SpeI and HindIII and, on the other hand, the shuttle vector p415ADH was also digested with restriction enzymes SpeI and HindIII. Each of them was separated by 0.8% agarose gel electrophoresis, a part of the gel containing the StOS-1 DNA digested with SpeI and HindIII and the shuttle vector p415ADH digested with SpeI and HindIII was excised, and the StOS-1 DNA and the shuttle vector were recovered from the gel using QIAquick Gel Extraction Kit (QIAGEN) according to the attached manual. The StOS-1 DNA was inserted between SpeI site and HindIII site in the multicloning site of the shuttle vector using Ligation Kit Ver. 2 (TaKaRa) according to the manual attached to the kit, whereby, an expression plasmid pADHStOS1 was constructed. A nucleotide sequence of the resulting expression plasmid was analyzed according to the method described in Example 11 (1). As a primer, an oligonucleotide consisting of the nucleotide sequence represented by any of SEQ ID NO: 58 to 65 was used. As a result, the nucleotide sequence represented by SEQ ID NO: 56 was obtained, and it was confirmed that the expression plasmid pADHStOS1 harbored a DNA having a nucleotide sequence encoding an amino acid sequence of StOS-1.

The prepared expression plasmid pADHStOS1 was introduced into budding yeast AH22 strain and TM182 strain according to the method described in Example 2. By utilizing the disappearance of leucine auxotrophy in the resulting transformed budding yeast, the transformed budding yeast AH22 strain (AH22-StOS1) was selected on a Glu-Leu agar medium, and the transformed budding yeast TM182 strain (TM182-StOS1) was selected on a Gal-Ura-Leu agar medium. It was confirmed that the resulting TM182-StOS1 grows even when transplanted to a Glu-Ura-Leu medium.

Example 16

Antifungal Compound Sensitivity Test of Transformed Budding Yeast TM182-StOS1

The transformed budding yeast AH22-StOS1 prepared in Example 15 was cultured while shaking at 30° C. for 18 hours in a Glu-Leu medium. As a control, the AH22 strain was similarly cultured while shaking at 30° C. for 18 hours in a Glu medium. The absorbance at 600 nm of each grown transformed budding yeast in a cell suspension was measured, and cell suspension diluted with sterilized distilled water to the absorbance of 0.1 was prepared. Further, a cell suspension in which the aforementioned cell suspension of the transformed budding yeast AH22-StOS1 was diluted 50-fold with a Glu-Leu medium, and a cell suspension in which the aforementioned cell suspension of the AH22 strain was diluted 50-fold with a Glu medium were prepared.

A solution in which each of Compounds (1) to (3) was dissolved in dimethylsulfoxide (DMSO) to the concentration of 6 ppm, a solution in which each of Compounds (4) and (5) was dissolved in dimethylsulfoxide (DMSO) to the concentration of 2000 ppm, and a solution in which Compounds (6) and (7) was dissolved in dimethylsulfoxide (DMSO) to the concentration of 20 ppm were prepared, and two microplates were prepared in which each 1.0 μL per well of the Compound solution and DMSO as a control were dispensed. In one microplate among them, each 100 μL of cell suspensions of the transformed budding yeast AH22-StOS1 which had been prepared by dilution as described above was dispensed, and cultured by allowing to stand at 30° C. for 28 hours. In another microplate, each 100 μL of cell suspensions of the control yeast AH22 strain which had been prepared by dilution as described above was dispensed, and cultured by allowing to stand at 30° C. for 24.5 hours. After culturing, the absorbance at 600 nm of each well was measured with a microplate reader.

Similarly, the transformed budding yeast TM182-StOS1 prepared in Example 15 was cultured at 30° C. for 18 hours in a Glu-Ura-Leu medium. The absorbance at 600 nm of the grown transformed budding yeast in a cell suspension was measured, and a cell suspension diluted with sterilized distilled water to the absorbance of 0.1 was prepared. Further, a cell suspension in which the transformed budding yeast TM182-StOS1 was diluted 50-fold with a Glu-Ura-Leu medium and, as a control, a cell suspension in which the yeast was diluted 50-fold with a Gal-Ura-Leu medium were prepared.

A solution in which each of Compounds (1) to (3) was dissolved in dimethylsulfoxide (DMSO) to the concentration of 6 ppm, a solution in which each of Compounds (4) and (5) was dissolved in dimethylsulfoxide (DMSO) to the concentration of 2000 ppm, and a solution in which each of Compounds (6) and (7) was dissolved in dimethylsulfoxide (DMSO) to the concentration of 20 ppm were prepared, and two microplates were prepared in which each 2.0 μL per well of the Compound-DMSO solution and DMSO as a control were dispensed into 2 wells. In one microplate among them, each 100 μL of cell suspensions of the transformed budding yeast TM182-StOS1 which had been prepared by dilution with a Glu-Ura-Leu medium as described above was dispensed, and cultured by allowing to stand at 30° C. for 26.5 hours. In another microplate, as described above, as a control, each 100 μL of cell suspensions of the transformed budding yeast TM182-StOS1 which had been prepared by dilution with a Gal-Ura-Leu medium was dispensed, and cultured at 30° C. for 49.5 hours. After culturing, the absorbance at 600 nm of each well was measured with a microplate reader.

A degree of growth of each transformed budding yeast cultured in the presence of Compounds (1) to (7) is shown in Table 6. A degree of growth of the transformed budding yeast is expressed as a relative value in percentage, letting the absorbance at 600 nm at the concentration of the Compound of 0 ppm to be 100. It was confirmed that an inhibiting degree of growth of the transformed budding yeast TM182-StOS1 by each test substance was grater than an inhibiting degree of growth of the transformed budding yeast AH22-StOS1 by each test substance, and the transformed budding yeast TM182-StOS1 was a transformed cell with the enhanced sensitivity to an antifungal compound as compared with the transformed budding yeast AH22-StOS1.

TABLE 6

| Test substance (final concentration) | Degree of growth of budding yeast | | | |
|---|---|---|---|---|
| | AH22 Glu medium | AH22-StOS1 Glu-Leu medium | TM182-StOS1 Gal-Ura-Leu medium | TM182-StOS1 Gul-Ura-Leu medium |
| Compoud (1) (0.6 ppm) | 99 | 101 | 101 | 67 |
| Compoud (2) (0.6 ppm) | 94 | 100 | 97 | 23 |
| Compoud (3) (0.6 ppm) | 96 | 98 | 94 | 19 |
| Compoud (4) (20 ppm) | 96 | 91 | 99 | 7 |
| Compoud (5) (20 ppm) | 80 | 76 | 74 | 6 |
| Compoud (6) (0.2 ppm) | 92 | 93 | 97 | 6 |
| Compoud (7) (0.2 ppm) | 91 | 91 | 91 | 9 |

Example 17

Isolation of *Thanatephorus cucumeris* RsOS-1 Gene (1) Analysis of *Thanatephorus cucumeris* RsOS-1 Gene Fragment The amplified DNA was purified from the reaction solution of PCR which had been performed using a primer pair 3 and using a cDNA of *Thanatephorus cucumeris* as a template in Example 10 (5), using QIAquick PCR Purification Kit (QIAGEN) according to the instruction attached to the kit. 3'A addition was performed on the purified DNA according to the method described in Example 11 (1). The 3'A-added DNA and the pCR2.1-TOPO cloning vector (Invitrogen) were ligated according to the instruction attached to the cloning vector, and this was introduced into *Escherichia coli* JM109 (TaKaRa).

DNA was purified from the resulting *Escherichia coli* transformant by colony PCR using Ex Taq HS (TaKaRa). The PCR reaction solution (15 μL) was prepared by mixing 1.5 μL of 10× buffer, 2.25 μL of 10 mM dNTPs, 0.15 μL of Ex Taq HS, each 0.4 μL of a 10 μM solution of an oligonucleotide consisting of the nucleotide sequence represented by SEQ ID NO: 28 and a 10 μM solution of an oligonucleotide consisting of the nucleotide sequence represented by SEQ ID NO: 29, and 10.3 μL of sterilized distilled water, and adding a part of the *Escherichia coli* transformant colony thereto. PCR was performed under the amplifying conditions that this reaction solution was maintained at 97° C. for 2 minutes and, thereafter, 35 cycles of incubation were repeated, each cycle comprising maintaining a temperature at 97° C. for 15 seconds, then, at 55° C. for 15 seconds, then, at 72° C. for 3 minutes.

The amplified DNA was purified from the PCR reaction solution after temperature maintenance using QIAquick PCR Purification Kit (QIAGEN) according to the instruction attached to the kit. A nucleotide sequence was analyzed using oligonucleotides consisting of nucleotide sequences represented by SEQ ID NOs: 28 and 29 as a primer and employing the purified DNA as a template according to the method described in Example 11 (1). As a result, a nucleotide sequence represented by base numbers 2838 to 3165 of the nucleotide sequence represented by SEQ ID NO: 69 was read.

(2) Analysis of Full Length *Thanatephorus cucumeris* RsOs-1 Gene

A DNA having a nucleotide sequence extending toward to 3' downstream region of a base number 3165 of the nucleotide sequence represented by SEQ ID NO: 69 was cloned using SMART RACE cDNA Amplification Kit (CLONTECH) according to the instruction attached to the kit. A reaction solution was prepared by mixing 1.0 μL of CDS-primer and 1.0 μL of sterilized distilled water attached to the kit into 3 μL (253 ng) of total RNA prepared in Example 10 (3), a temperature was maintained at 70° C. for 2 minutes, and maintained on ice for 2 minutes. To the reaction solution were added 2 μL of 5× First-Strand buffer attached to the kit, 1 μL of 20 mM DTT, 1 μL of 10 mM dNTP Mix and 1 μL of PowerScript Reverse Transcriptase, to mix them, and the mixture was maintained at 42° C. for 1.5 hours. To the reaction solution after temperature maintenance was added 100 μL of Tricine-EDTA buffer attached to the kit, a temperature was maintained at 72° C. for 7 minutes, thus 3' RACE ready cDNA was prepared. PCR amplifying 3' downstream region was performed using this 3' RACE ready cDNA as a template and using KOD-plus- (TOYOBO). The PCR reaction solution was prepared by mixing 2.5 μL of 3' RACE ready cDNA, 5.0 μL of 10× buffer, 5.0 μL of 2 mM dNTPs, 2.0 μL of 25 mM MgSO$_4$ and 1.0 μL of KOD-Plus, adding 5.0 μL of 10× Universal Primer A Mix attached to the kit and 1.0 μL of a 10 μM solution of an oligonucleotide consisting of the nucleotide sequence represented by SEQ ID NO: 70 as primers, and adding sterilized distilled water to a total amount of 50 μL. This reaction solution was maintained at 94° C. for 2 minutes, and 35 cycles of incubation were repeated, each cycle comprising maintaining a temperature at 94° C. for 15 seconds, then, at 68° C. for 6 minutes. The amplified DNA was purified from the PCR reaction solution using QIAquick PCR Purification Kit (QIAGEN) according to the instruction attached to the kit, and then, 3'A addition was performed on the DNA according to the method described in Example 11(1). The 3'A-added DNA and the pCR2.1-TOPO cloning vector (Invitrogen) were ligated according to the instruction attached to the cloning vector, after that, which was introduced into *Escherichia coli* JM109 (TaKaRa). A plasmid DNA was purified from the resulting *Escherichia coli* transformant using QIAprep Spin Miniprep Kit (QIAGEN). A nucleotide sequence was analyzed using the resulting plasmid DNA as a template and using primers consisting of nucleotide sequences represented by SEQ ID NOs: 28, 29, and 73 to 76 according to the method described in Example 11(1). As a result, a nucleotide sequence represented by base numbers 3119 to 4317 of the nucleotide sequence represented by SEQ ID NO: 69 was read.

Further, a DNA having a nucleotide sequence extending toward to the 5' upstream region from nucleotide number 2838 of the nucleotide sequence represented by SEQ ID NO: 69 was cloned. 1.0 μL of CDS-primer attached to the kit and 1.0 μL of SMART IIA Oligo were mixed into 3 μL (253 ng) of the total RNA prepared in Example 10 (3), the mixture was maintained at 70° C. for 2 minutes, and maintained on ice for 2 minutes. 5' RACE ready cDNA was prepared using the reaction solution as in preparation of 3' RACE ready cDNA. PCR amplifying 5' upstream region was performed using this 5' RACE ready cDNA as a template and using KOD-plus- (TOYOBO). The PCR reaction solution was prepared by mixing 2.5 μL of 5' RACE ready cDNA, 5.0 μL of 10× buffer, 5.0 μL of 2 mM dNTPs, 2.0 μL of 25 mM MgSO$_4$ and 1.0 μL of KOD-Plus, adding 5.0 μL of 10× Universal Primer A Mix attached to the kit and 1.0 μL of a 10 μM solution of an oligonucleotide consisting of the nucleotide sequence represented by SEQ ID NO: 71 as primers, and adding sterilized distilled water to a total amount of 50 μL. This reaction solution was maintained at 94° C. for 2 minutes, and 35 cycles of incubation were repeated, each cycle comprising maintaining a temperature at 94° C. for 15 seconds, then, at 68° C. for 6 minutes. Using the resulting PCR reaction solution as a template, the PCR reaction solution for a further PCR was prepared by adding 5.0 μL of 10× buffer, 5.0 μL of 2 mM dNTPs, 2.0 μL of 25 mM MgSO$_4$ and 1.0 μL of KOD-Plus, 1.0 μL of 10 μM Nested universal primer attached to the kit and 1.0 μL of a 10 μM solution of an oligonucleotide consisting of the nucleotide sequence represented by SEQ ID NO: 72 as primers, and adding sterilized distilled water to a total amount of 50 μL. This reaction solution was maintained at 94° C. for 2 minutes, and 20 cycles of incubation were repeated, each cycle comprising maintaining a temperature at 94° C. for 15 seconds, then, at 68° C. for 6 minutes. The PCR reaction solution and the pCR2.1-TOPO cloning vector (Invitrogen) were ligated to the vector according to the instruction attached to the kit, after that, which was introduced into *Escherichia coli* JM109 (TaKaRa). A plasmid DNA was purified from the resulting *Escherichia coli* transformant using QIAprep Spin Miniprep Kit (QIAGEN). A nucleotide sequence was analyzed using the resulting plasmid DNA as a template, and using a primer consisting of the nucleotide sequence represented by any of SEQ ID NOs: 28, 29, and 77 to 82, according to the method described in Example 11 (1). As a result, a nucleotide sequence represented by nucleotide numbers 1 to 3042 of the nucleotide sequence represented by SEQ ID NO: 69 was read.

All analyzed nucleotide sequences were joined and, as a result, the nucleotide sequence represented by SEQ ID NO: 69 was obtained. The nucleotide sequence represented by SEQ ID NO: 69 consists of 4317 bases (including termination codon), and was a nucleotide sequence encoding 1438 amino acid residues (SEQ ID NO: 68). A molecular weight of a protein having the amino acid sequence represented by SEQ ID NO: 68 was calculated to be 155296 Da.

(3) Isolation of Full Length *Thanatephorus cucumeris* RsOS-1 Gene

A DNA having a nucleotide sequence encoding an amino acid sequence of *Thanatephorus cucumeris* RsOs-1 (hereinafter, referred to as RsOS-1 DNA in some cases) was amplified by PCR using a cDNA of *Thanatephorus cucumeris* prepared in Example 10 (5) as a template. By performing a PCR using, as a primer, an oligonucleotide consisting of the nucleotide sequence represented by SEQ ID NO: 85 and an oligonucleotide consisting of the nucleotide sequence represented by SEQ ID NO: 86, a DNA having the nucleotide sequence represented by SEQ ID NO: 69 was amplified, according to the method described in Example 11 (3). After the reaction, a part of the PCR reaction solution was separated by 1% agarose gel electrophoresis, and stained with ethidium bromide. It was confirmed that about 4 kb of the DNA (RsOS-1 DNA) was amplified.

Example 18

Construction of Expression Plasmid of *Thanatephorus cucumeris* RsOS-1 Gene and Preparation of Transformed Budding Yeast The RsOS-1 DNA was cloned into a pCR2.1-TOPO cloning vector (Invitrogen). About 4 kb of the DNA (RsOS-1 DNA) was purified from the PCR reaction solution prepared in Example 17 (3) using QIAquick PCR Purification Kit (QIAGEN) according to the instruction attached to the kit. 3'A addition was performed on about 4 kb of the purified DNA (StOS-1 DNA) according to the method described in Example 11 (1). The 3'A-added about 4 kb DNA (RsOS-1 DNA) and the pCR2.1-TOPO cloning vector (Invitrogen) were ligated according to the manual attached to the cloning vector to construct a plasmid pCRRsOS1. A nucleotide sequence of the resulting plasmid was analyzed according to the method described in Example 11(1). As a primer, an oligonucleotide consisting of the nucleotide sequence represented by any of SEQ ID NOs: 28, 29, 70 to 73, 75, 77, 78, and 81 to 84 was used. As a result, the nucleotide sequence represented by SEQ ID NO: 69 was obtained, and it was confirmed that the plasmid pCRRsOS1 was a plasmid containing the RsOS-1 DNA.

The RsOS-1 DNA contained in the thus prepared plasmid pCRRsOS1 was cloned into a shuttle vector p415ADH replicable in yeast and *Escherichia coli* to construct an expression plasmid. The plasmid pCRRsOS1 was digested with restriction enzymes SpeI and HindIII and, on the other hand, the shuttle vector p415ADH was also digested with restriction enzymes SpeI and HindIII. Each of them was separated by 0.8% agarose gel electrophoresis, a part of the gel containing the RsOS-1 DNA digested with SpeI and HindIII and the shuttle vector p415ADH digested with SpeI and HindIII was excised, and the RsOS-1 DNA and the shuttle vector were recovered from the gel using QIAquick Gel Extraction Kit (QIAGEN) according to the attached manual. The RsOS-1 DNA was inserted between SpeI site and HindIII site in the multicloning site of the shuttle vector using Ligation Kit Ver. 2 (TaKaRa) according to the manual attached to the kit, whereby, an expression plasmid pADHRsOS1 was constructed. A nucleotide sequence of the resulting expression plasmid was analyzed according to the method described in Example 11 (1). As a primer, an oligonucleotide consisting of the nucleotide sequence represented by any of SEQ ID NO: 70 to 73, 75, 77, 78, 81 to 84, 87 and 88 was used. As a result, the nucleotide sequence represented by SEQ ID NO: 69 was obtained, and it was confirmed that the expression plasmid pADHRsOS1 harbored a DNA having a nucleotide sequence encoding an amino acid sequence of RsOS-1.

The prepared expression plasmid pADHRsOS1 was introduced into budding yeast AH22 strain and TM182 strain according to the method described in Example 2. By utilizing the disappearance of leucine auxotrophy in the resulting transformed budding yeast, the transformed budding yeast AH22 strain (AH22-RsOS1) was selected on a Glu-Leu agar medium, and the transformed budding yeast TM182 strain (TM182-RsOS1) was selected on a Gal-Ura-Leu agar medium. It was confirmed that the resulting TM182-RsOS1 grows even when transplanted to a Glu-Ura-Leu medium.

Example 19

Antifungal Compound Sensitivity Test of Transformed Budding Yeast TM182-RsOS1

The transformed budding yeast AH22-RsOS1 prepared in Example 18 was cultured while shaking at 30° C. for 18 hours in a Glu-Leu medium. As a control, the AH22 strain was similarly cultured while shaking at 30° C. for 18 hours in a Glu medium. The absorbance at 600 nm of each grown transformed budding yeast in a cell suspension was measured, and cell suspension diluted with sterilized distilled water to the absorbance of 0.1 was prepared. Further, a cell suspension in which the aforementioned cell suspension of the transformed budding yeast AH22-RsOS1 was diluted 50-fold with a Glu-Leu medium, and a cell suspension in which the aforementioned cell suspension of the AH22 strain was diluted 50-fold with a Glu medium were prepared.

A solution in which each of Compounds (1) to (5) was dissolved in dimethylsulfoxide (DMSO) to the concentration of 600 ppm, and a solution in which Compounds (6) and (7) was dissolved in dimethylsulfoxide (DMSO) to the concentration of 60 ppm were prepared, and two microplates were prepared in which each 1.0 µL per well of the Compound solution and DMSO as a control were dispensed. In one microplate among them, each 100 µL of cell suspensions of the transformed budding yeast AH22-RsOS1 which had been prepared by dilution as described above was dispensed, and cultured by allowing to stand at 30° C. for 29.8 hours. In another microplate, each 100 µL of cell suspensions of the control yeast AH22 strain which had been prepared by dilution as described above was dispensed, and cultured by allowing to stand at 30° C. for 24.8 hours. After culturing, the absorbance at 600 nm of each well was measured with a microplate reader.

Similarly, the transformed budding yeast TM182-RsOS1 prepared in Example 18 was cultured at 30° C. for 18 hours in a Glu-Ura-Leu medium. The absorbance at 600 nm of the grown transformed budding yeast in a cell suspension was measured, and a cell suspension diluted with sterilized distilled water to the absorbance of 0.1 was prepared. Further, a cell suspension in which the transformed budding yeast TM182-RsOS1 was diluted 50-fold with a Glu-Ura-Leu medium. As a control, the transformed budding yeast TM182-RsOS1 was cultured at 30° C. for 18 hours in a Gal-Ura-Leu medium. The absorbance at 600 nm of the grown transformed budding yeast in a cell suspension was measured, and a cell suspension diluted with sterilized distilled water to the absorbance of 0.1 was prepared. Further, a cell suspension in which the transformed budding yeast TM182-RsOS1 was diluted 50-fold with a Gal-Ura-Leu medium.

A solution in which each of Compounds (1) to (5) was dissolved in dimethylsulfoxide (DMSO) to the concentration of 600 ppm, and a solution in which each of Compounds (6) and (7) was dissolved in dimethylsulfoxide (DMSO) to the concentration of 60 ppm were prepared, and two microplates were prepared in which each 2.0 µL per well of the Compound-DMSO solution and DMSO as a control were dispensed into 2 wells. In one microplate among them, each 100 µL of cell suspensions of the transformed budding yeast TM182-RsOS1 which had been prepared by dilution with a Glu-Ura-Leu medium as described above was dispensed, and cultured by allowing to stand at 30° C. for 26.8 hours. In another microplate, as described above, as a control, each 100 µL of cell suspensions of the transformed budding yeast TM182-RsOS1 which had been prepared by dilution with a Gal-Ura-Leu medium was dispensed, and cultured at 30° C. for 42.5 hours. After culturing, the absorbance at 600 nm of each well was measured with a microplate reader.

A degree of growth of each transformed budding yeast cultured in the presence of Compounds (1) to (7) is shown in Table 7. A degree of growth of the transformed budding yeast is expressed as a relative value in percentage, letting the absorbance at 600 nm at the concentration of the Compound of 0 ppm to be 100. It was confirmed that an inhibiting degree of growth of the transformed budding yeast TM182-RsOS1 by each test substance was grater than an inhibiting degree of growth of the transformed budding yeast AH22-RsOS1 by each test substance, and the transformed budding yeast TM182-RsOS1 was a transformed cell with the enhanced sensitivity to an antifungal compound as compared with the transformed budding yeast AH22-RsOS1.

TABLE 7

| | Degree of growth of budding yeast | | | |
|---|---|---|---|---|
| | AH22 | AH22-RsOS1 | TM182-RsOS1 | |
| Test substance (final concentration) | Glu medium | Glu-Leu medium | Gal-Ura-Leu medium | Gul-Ura-Leu medium |
| Compoud (1) (6.0 ppm) | 88 | 103 | 108 | 15 |
| Compoud (2) (6.0 ppm) | 92 | 101 | 96 | 11 |
| Compoud (3) (6.0 ppm) | 82 | 101 | 101 | 27 |
| Compoud (4) (6.0 ppm) | 83 | 89 | 88 | 17 |
| Compoud (5) (6.0 ppm) | 78 | 85 | 101 | 9 |
| Compoud (6) (0.6 ppm) | 79 | 79 | 100 | 12 |
| Compoud (7) (0.6 ppm) | 85 | 101 | 99 | 31 |

Example 20

Isolation of a Gene of the Present Histidine Kinase of *Phytophthora infestans* (Hereinafter, Referred to PiOS-1 Gene)

(1) Analysis of *Phytophthora infestans* PiOS-1 Gene Fragment

The amplified DNA was purified from the reaction solution of PCR which had been performed using a primer pair 6 and using a cDNA of *Phytophthora infestans* as a template in Example 10(5), using QIAquick PCR Purification Kit (QIAGEN) according to the instruction attached to the kit. 3'A addition was performed on the purified DNA according to the method described in Example 11 (1). The 3'A added DNA and the pCR2.1-TOPO cloning vector (Invitrogen) were ligated according to the instruction attached to the cloning vector, after that, which was introduced into *Escherichia coli* JM109 (TaKaRa).

A DNA was amplified from the resulting *Escherichia coli* transformant by colony PCR using Ex Taq HS (TaKaRa). The PCR reaction solution (15 μL) was prepared by mixing 1.5 μL of 10× buffer, 2.25 μL of 10 mM dNTPs, 0.15 μL of Ex Taq HS, each 0.4 μL of a 10 μM solution of an oligonucleotide consisting of the nucleotide sequence represented by SEQ ID NO: 28 and a 10 μM solution of an oligonucleotide consisting of the nucleotide sequence represented by SEQ ID NO: 29, and 10.3 μL of sterilized distilled water, and adding a part of the *Escherichia coli* transformant colony thereto. PCR was performed under the amplifying conditions that this reaction solution was maintained at 97° C. for 2 minutes, and 35 cycles of incubation were repeated, each cycle comprising maintaining a temperature at 97° C. for 15 seconds, then, at 55° C. for 15 seconds, further, at 72° C. for 3 minutes. The amplified DNA was purified from the PCR reaction solution after temperature maintenance using QIAquick PCR purification Kit (QIAGEN) according to the manual attached to the kit. A nucleotide sequence was analyzed using the purified DNA as a template and using oligonucleotides consisting of the nucleotide sequence represented by any of SEQ ID NOs: 28 and 29 as primers according to the method described in Example 11(1). As a result, a nucleotide sequence represented by SEQ ID NO: 89 containing a nucleotide sequence of an oligonucleotide used as a primer pair 6 was read.

(2) Analysis of Full Length *Phytophthora infestans* PiOS-1 Gene

A DNA having a nucleotide sequence extending toward to 5' upstream region of a nucleotide sequence represented by SEQ ID NO: 89 is cloned using SMART RACE cDNA Amplification Kit (CLONTECH) according to the instruction attached to the kit. A reaction solution is prepared by mixing 1.0 μL of CDS-primer attached to the kit and 1.0 μL of SMART IIA Oligo into 3 μL (200 ng) of the total RNA prepared in Example 10 (4), a temperature is maintained at 70° C. for 2 minutes, and is maintained on ice for 2 minutes. To the reaction solution are added 2 μL of 5× First-Strand buffer attached to the kit, 1 μL of 20 mM DTT, 1 μL of 10 mM dNTP Mix and 1 μL of PowerScript Reverse Transcriptase to mix them, and the mixture is maintained at 42° C. for 1.5 hours. To the reaction solution after temperature maintenance is added 100 μL of Tricine-EDTA buffer attached to the kit, a temperature is maintained at 72° C. for 7 minutes, and 5' RACE ready cDNA is prepared. PCR amplifying 5' upstream region is performed using this 5' RACE ready cDNA as a template and using KOD-plus- (TOYOBO). The PCR reaction solution is prepared by mixing 2.5 μL of 5' RACE ready cDNA, 5.0 μL of 10× buffer, 5.0 μL of 2 mM dNTPs, 2.0 μL of 25 mM $MgSO_4$ and 1.0 μL of KOD-Plus-, adding 5.0 μL of 10× Universal primer A Mix attached to the kit as a primer and 1.0 μL of a 10 μM solution of an oligonucleotide consisting of 20 to 30 bases selected from complementary sequences of the nucleotide sequence represented by SEQ ID NO: 89, and adding sterilized distilled water to a total amount of 50 μL. This reaction solution is maintained at 94° C. for 2 minutes, and further 35 cycles of incubation are repeated, each cycle comprising maintaining a temperature at 94° C. for 15 seconds, then, at 68° C. for 5 minutes. The amplified DNA is purified from the PCR reaction solution using QIAquick PCR Purification Kit (QIAGEN) according to the instruction attached to the kit, and 3'A addition is performed on the DNA according to the method described in Example 11 (1). 3'A added DNA and the pCR2.1-TOPO cloning vector (Invitrogen) are ligated according to the instruction attached to the cloning vector, after that, which is introduced into *Escherichia coli* JM109 (TaKaRa). A plasmid DNA is purified from the resulting *Escherichia coli* transformant using QIAprep Spin Miniprep Kit (QIAGEN). A nucleotide sequence is analyzed using the resulting plasmid DNA as a template and using primers consisting of the nucleotide sequence represented by any of SEQ ID NOs: 28, 29, and the like according to the method described in Example 11(1). As a result, a nucleotide sequence of the 5'-terminal region including a translation initiation codon of an os-1 homologous gene of *Phytophthora infestans*, that is, gene of *Phytophthora infestans* encoding osmosensing histidine kinase having no transmembrane region (PiOS1) can be read.

Further, a DNA having a nucleotide sequence extending to 3' downstream region of the nucleotide sequence represented by SEQ ID NO: 89 is cloned. 1.0 μL of CDS-primer attached to the kit and 1.0 μL of sterilized distilled water are mixed into 3 μL (200 ng) of the total RNA prepared in Example 10 (4), a temperature is maintained at 70° C. for 2 minutes, and is maintained on ice for 2 minutes. 3' RACE ready cDNA is prepared using the reaction solution as in preparation of 5' RACE ready cDNA. PCR amplifying 3' downstream region is performed using this 3' RACE ready cDNA as a template. The PCR reaction solution is prepared by mixing 5.0 μL of 10× Advantage 2 buffer attached to the kit, 1.0 μL it of 10 mM dNTP Mix and 1.0 μL of 50× Advantage 2 polymerase Mix into 2.5 μL of 5' RACE ready cDNA, adding 5.0 μL of 10× Universal Primer A Mix attached to the kit, and 1.0 μL of a 10 μM solution of an oligonucleotide consisting of 20 to 30 bases selected from the nucleotide sequence represented by SEQ ID NO: 89 as primers, and adding sterilized distilled water to a total amount of 50 μL. This reaction solution is subjected to repetition of 5 cycles of incubation, each cycle comprising maintaining a temperature at 94° C. for 5 seconds, then, at 72° C. for 4 minutes, further repetition of 5 cycles of incubation, each cycle comprising maintaining a temperature at 94° C. for 5 seconds, then, at 70° C. for 10 seconds then, at 72° C. for 4 minutes, further repetition of 25 cycles of incubation, each cycle comprising maintaining a temperature at 94° C. for 5 seconds, then, at 68° C. for 10 seconds, then, at 72° C. for 4 minutes, followed by maintaining a temperature at 72° C. for 7 minutes. The PCR reaction solution and the pCR2.1-TOPO cloning vector (Invitrogen) are ligated according to the instruction attached to the cloning vector, after that, which is introduced into *Escherichia coli* JM109 (TaKaRa). A plasmid DNA is purified from the resulting *Escherichia coli* transformant using QIAprep Spin Miniprep Kit (QIAGEN). A nucleotide sequence is analyzed using the resulting plasmid DNA as a template and using primers consisting of the nucleotide sequence represented by any of SEQ ID NOs: 28, 29, and the like according to the method described in Example 11 (1). As a result, a nucleotide sequence of the 3'-terminal region including a translation termination codon of a *Phytophthora infestans* PiOS1 gene is read.

By ligating all analyzed nucleotide sequences, full nucleotide sequence of *Phytophthora infestans* PiOS-1 gene including nucleotide sequence represented by SEQ ID NO: 89 is confirmed.

(3) Isolation of Full Length *Phytophthora infestans* PiOS1 Gene

A DNA having a nucleotide sequence encoding an amino acid sequence of *Phytophthora infestans* PiOS1 (hereinafter, referred to as PiOS-1 DNA) is amplified by PCR using the cDNA prepared in Example 10 (4) as a template. Using as primers an oligonucleotide comprising a nucleotide sequence in which a nucleotide sequence ACGACAGT is added to the 5'-terminal end of a nucleotide sequence from the 5'-terminal end to the 20$^{th}$ base including the initiation codon of a nucleotide sequence of *Phytophthora infestans* PiOS-1 gene obtained in Example 20 (2), and an oligonucleotide having a nucleotide sequence complementary to a nucleotide sequence in which a nucleotide sequence AAGCTTCAG is added to the 3'-terminal end of a nucleotide sequence of from the 3'-terminal end to the 20$^{th}$ base including the termination codon of a nucleotide sequence of *Phytophthora infestans* PiOS-1 gene obtained in Example 20 (2), a PCR is performed according to the method described in Example 11 (3). DNA containing a nucleotide sequence encoding an amino acid sequence of *Phytophthora infestans* PiOS-1, and having a recognition sequence of a restriction enzyme SpeI immediately before an initiation codon, and having a recognition sequence of a restriction enzyme HindIII immediately after a termination codon is amplified. A part of the PCR reaction solution after the reaction is separated by 1% agarose gel electrophoresis, and stained with ethidium bromide. It is confirmed that the about 4 kb PiOS-1 DNA is amplified.

Example 21

Construction of Expression Plasmid of *Phytophthora infestans* PiOS-1 Gene and Preparation of Transformed Budding Yeast The PiOS-1 DNA is cloned into the pCR2.1-TOPO cloning vector (Invitrogen). An about 4 kb DNA (PiOS-1 DNA) is purified from the PCR reaction solution prepared in Example 20 (3) using QIAquick PCR Purification Kit (QIAGEN) according to the manual attached to the kit. 3'A addition is performed on the about 4 kb purified DNA according to the method described in Example 11 (3). The about 4 kb 3'A-added DNA (PiOS-1 DNA) and the pCR2.1-TOPO cloning vector (Invitrogen) are ligated according to the instruction attached to the cloning vector, whereby, the plasmid pCR-PiOS1 is constructed. A nucleotide sequence of the resulting plasmid is analyzed by the method described in Example 11 (1). As a primer, oligonucleotides consisting of the nucleotide sequence represented by any of SEQ ID NOs: 28 and 29 are used. As a result, it is confirmed that the plasmid pCRPiOS1 is a plasmid harboring PiOS-1 DNA containing the nucleotide sequence represented by SEQ ID NO: 89.

The *Phytophthora infestans* PiOS-1 gene contained in the thus prepared plasmid pCR PiOS1 is cloned into a shuttle vector p415ADH replicable in yeast and *Escherichia coli*, whereby, an expression plasmid is constructed. The plasmid pCRPiOS1 is digested with restriction enzymes SpeI and HindIII and, on the other hand, the shuttle vector p415ADH is also digested with restriction enzymes SpeI and HindIII. These are separated by 0.8% agarose gel electrophoresis, respectively, thereafter, a part of the gel containing the PiOS-1 DNA digested with restriction enzymes SpeI and HindIII and the shuttle vector p415ADH digested with SpeI and HindIII is excised, and the PiOS-1 DNA and the shuttle vector are recovered from the gel using QIAquick Gel Extraction Kit (QUAGEN) according to the manual attached to the kit. Using Ligation Kit Ver. 2 (TaKaRa) according to the manual attached to the kit, the PiOS-1 DNA is inserted between SpeI site and HindIII site in the multicloning site of the shuttle vector, whereby, the expression plasmid pADH-PiOS1 is constructed. A nucleotide sequence of the resulting expression plasmid is analyzed according to the method described in Example 11 (1). As a primer, oligonucleotides consisting of the nucleotide sequence represented by any of SEQ ID NOs: 28 and 29 are used. As a result, it is confirmed that the expression plasmid pADHPiOS1 is a plasmid harboring the PiOS-1 DNA containing the nucleotide sequence represented by SIQ ID NO: 89.

The prepared expression plasmid pADH PiOS1 is gene-introduced into budding yeast AH22 strain and TM182 strain according to the method described in Example 2. By utilizing disappearance of leucine auxotrophy in the resulting transformed budding yeast, the transformed budding yeast AH22 strain (AH22-PiOS1) is selected on a Glu-Leu agar medium, and the transformed budding yeast TM182 strain (TN182-PiOS1) is selected on a Gal-Ura-Leu agar medium. It is confirmed that the resulting TM182-PiOS1 grows even when transplanted to a Glu-Ura-Leu medium.

Example 22

Antifungal Compound Sensitivity Test of Transformed Budding Yeast TM182-PiOS1

The transformed budding yeast AH22-PiOS1 prepared in Example 21 is cultured while shaking at 30° C. in a Glu-Leu medium. As a control, the AH22 strain is similarly cultured while shaking at 30° C. in a Glu medium. The absorbance at 600 nm of each of grown transformed budding yeasts in a cell suspension is measured, and a cell suspension diluted with sterilized distilled water to the absorbance of 0.1 is prepared. Further, a cell suspension in which the aforementioned suspension of the transformed budding yeast AH22-PiOS1 is diluted 50-fold with a Glu-Leu medium, and a cell suspension in which the aforementioned suspension of the AH22 strain is diluted 50-fold with a Glu medium are prepared.

A solution in which each of Compounds (1) to (7) is dissolved in dimethylsulfoxide (DMSO) is prepared, and two microplates are prepared in which each 1.0 μL per well of each of the Compound Solution and DMSO as a control are dispensed into two wells. In one microplate among them, each 100 μL of cell suspensions of the transformed budding yeast AH22-PiOS1 which has been prepared by dilution as described above is dispensed, and is cultured by allowing to stand at 30° C. In another microplate, each 100 μL of cell suspensions of the control yeast AH22 strain which has been prepared by dilution as described above is dispensed, and is cultured by allowing to stand at 30° C. After culturing, the absorbance at 600 nm of each well is measured with a microplate reader.

Similarly, the transformed budding yeast TM182-PiOS1 prepared in Example 21 is cultured at 30° C. in a Glu-Ura-Leu medium. The absorbance at 600 nm of a cell suspension of the grown transformed budding yeast is measured, and a cell suspension diluted with sterilized distilled water to the absorbance of 0.1 is prepared. Further, a cell suspension in which the aforementioned cell suspension of the transformed budding yeast TM182-PiOS1 is diluted 50-fold with a Glu-Ura-Leu medium and, as a control, a cell suspension in which the aforementioned cell suspension is diluted 50-fold with a Gal-Ura-Leu medium are prepared.

A solution in which each of Compounds (1) to (7) is dissolved in dimethylsulfoxide (DMSO) is dissolved is prepared, and two microplates are prepared in which each 1.0 μL per well of the Compound solution and DMSO as a control are dispensed. In one microplate among them, each 100 μL of cell suspensions of the transformed budding yeast TM182-PiOS1 which has been prepared by dilution with a Glu-Ura-Leu medium as described above is dispensed, and is cultured by allowing to stand at 30° C. In another microplate as described above, as a control, each 100 μL of cell suspensions of the transformed budding yeast TM182-PiOS1 which has been prepared by dilution with a Gal-Ura-Leu medium is dispensed, and is cultured by allowing to stand at 30° C. After culturing, the absorbance at 600 nm of each well is measured with a microplate reader.

It is confirmed that an inhibiting degree of growth of the transformed budding yeast TM182-PiOS1 by each test substance is greater than an inhibiting degree of growth of the transformed budding yeast AH22-PiOS1 by each test substance, and the transformed budding yeast TM182-PiOS1 is a transformed cell with the enhanced sensitivity to an antifungal compound as compared with the transformed budding yeast AH2-PiOS1.

The compositions of media used in the present invention are described below.

(a) Glu-Medium

Becto-yeast nitrogen base without amino acids 6.7 g, Glucose 20 g, Drop-out mix (1) 2.0 g, Distilled water 1000 ml (b) Glu-Leu Medium Bacto-yeast nitrogen base without amino acids 6.7 g, Glucose 20 g, Drop-out mix (2) 2.0 g, Distilled water 1000 ml (c) Glu-Ura-Leu Medium Bacto-yeast nitrogen base without amino acids 6.7 g, Glucose 20 g, Drop-out mix (3) 2.0 g, Distilled water 1000 ml (d) Gal-Ura-Leu Medium Bacto-yeast nitrogen base without amino acids 6.7 g, Galactose 20 g Drop-out mix (3) 2.0 g, Distilled water 1000 ml Drop-out mix (1):

Adenine 0.5 g, Lysine 2.0 g, Alanine 2.0 g, Methionine 2.0 g, Arginine 2.0 g, para-Aminobenzoic acid 0.2 g, Asparagine 2.0 g. Phenylalanine 2.0 g, Aspartic acid 2.0 g, Proline 2.0 g, Cysteine 2.0 g, Serine 2.0 g, Glutamine 2.0 g, Threonine 2.0 g, Glutamic acid 2.0 g, Tryptophan 2.0 g, Glycine 2.0 g, Tyrosine 2.0 g, Histidine 2.0 g, Valine 2.0 g, Inositol 2.0 g, Isoleucine 2.0 g, Uracil 2.0 g, Leucine 10.0 g, Distilled water 1000 ml Drop-out mix (2): Drop-out mix (1) except for leucine (10.0 g)

Drop-out mix (3): Drop-out mix (1) except for uracil (2.0 g) and leucine (10.0 g)

(e) Glu-agar Medium

Solid medium in which 2% (W/V) agar is added to a medium (a)

(f) Glu-Leu agar Medium

Solid medium in which 2% (W/V) agar is added to a medium (b)

(g) Glu-Ura-Leu Agar Medium

Solid medium in which 2% (W/V) agar is added to a medium (c)

(h) Gal-Ura-Leu Agar Medium

Solid medium in which 2% (W/V) agar is added to a medium (d)

Free text in Sequence Listing

SEQ ID NO:3

Designed oligonucleotide primer for PCR

SEQ ID NO:4

Designed oligonucleotide primer for PCR

SEQ ID NO:5

Designed oligonucleotide primer for sequencing

SEQ ID NO:6

Designed oligonucleotide primer for sequencing

SEQ ID NO:7

Designed oligonucleotide primer for sequencing

SEQ ID NO:8

Designed oligonucleotide primer for sequencing

SEQ ID NO:9

Designed oligonucleotide primer for sequencing

SEQ ID NO:10

Designed oligonucleotide primer for sequencing

SEQ ID NO:11

Designed oligonucleotide primer for sequencing

SEQ ID NO:12

Designed oligonucleotide primer for sequencing

SEQ ID NO:15

Designed oligonucleotide primer for PCR

SEQ ID NO:18

Designed oligonucleotide primer for PCR

SEQ ID NO:19

Designed oligonucleotide primer for PCR

SEQ ID NO:20

Designed oligonucleotide primer for sequencing

SEQ ID NO:21

Designed oligonucleotide primer for sequencing

SEQ ID NO:22

Designed oligonucleotide primer for sequencing

SEQ ID NO:23

Designed oligonucleotide primer for sequencing

SEQ ID NO:24

Designed oligonucleotide primer for sequencing

SEQ ID NO:25

Designed oligonucleotide primer for sequencing

SEQ ID NO:26

Designed oligonucleotide primer for sequencing

SEQ ID NO:27

Designed oligonucleotide primer for sequencing

SEQ ID NO:28

Designed oligonucleotide primer for sequencing

SEQ ID NO:29

Designed oligonucleotide primer for sequencing

SEQ ID NO:30

Designed oligonucleotide primer for PCR

SEQ ID NO:31

Designed oligonucleotide primer for PCR

SEQ ID NO:32

Designed oligonucleotide primer for PCR

SEQ ID NO:33

Designed oligonucleotide primer for PCR

SEQ ID NO:34

Designed oligonucleotide primer for PCR

SEQ ID NO:35
Designed oligonucleotide primer for PCR
SEQ ID NO:36
Designed oligonucleotide primer for PCR
SEQ ID NO:37
Designed oligonucleotide primer for PCR
SEQ ID NO:38
Designed oligonucleotide primer for PCR
SEQ ID NO:39
Designed oligonucleotide primer for PCR
SEQ ID NO:40
Designed oligonucleotide primer for PCR
SEQ ID NO:43
Designed oligonucleotide primer for PCR
SEQ ID NO:44
Designed oligonucleotide primer for PCR
SEQ ID NO:45
Designed oligonucleotide primer for DNA sequencing
SEQ ID NO:46
Designed oligonucleotide primer for DNA sequencing
SEQ ID NO:47
Designed oligonucleotide primer for DNA sequencing
SEQ ID NO:48
Designed oligonucleotide primer for DNA sequencing
SEQ ID NO:49
Designed oligonucleotide primer for DNA sequencing
SEQ ID NO:50
Designed oligonucleotide primer for DNA sequencing
SEQ ID NO:51
Designed oligonucleotide primer for DNA sequencing
SEQ ID NO:52
   Designed oligonucleotide primer for PCR
SEQ ID NO:53
Designed oligonucleotide primer for PCR
SEQ ID NO:54
Designed oligonucleotide primer for DNA sequencing
SEQ ID NO:57
Designed oligonucleotide primer for PCR
SEQ ID NO:58
Designed oligonucleotide primer for PCR
SEQ ID NO:59
Designed oligonucleotide primer for DNA sequencing
SEQ ID NO:60
Designed oligonucleotide primer for DNA sequencing
SEQ ID NO:61
Designed oligonucleotide primer for DNA sequencing
SEQ ID NO:62
Designed oligonucleotide primer for DNA sequencing
SEQ ID NO:63
Designed oligonucleotide primer for DNA sequencing
SEQ ID NO:64
Designed oligonucleotide primer for PCR
SEQ ID NO:65
Designed oligonucleotide primer for PCR
SEQ ID NO:66
Designed oligonucleotide primer for DNA sequencing
SEQ ID NO:67
Designed oligonucleotide primer for DNA sequencing
SEQ ID NO:70
Designed oligonucleotide primer for PCR
SEQ ID NO:71
Designed oligonucleotide primer for PCR
SEQ ID NO:72
Designed oligonucleotide primer for PCR
SEQ ID NO:73
Designed oligonucleotide primer for PCR
SEQ ID NO:74
Designed oligonucleotide primer for PCR
SEQ ID NO:75
Designed oligonucleotide primer for PCR
SEQ ID NO:76
Designed oligonucleotide primer for PCR
SEQ ID NO:77
Designed oligonucleotide primer for PCR
SEQ ID NO:78
Designed oligonucleotide primer for PCR
SEQ ID NO:79
Designed oligonucleotide primer for PCR
SEQ ID NO:80
Designed oligonucleotide primer for PCR
SEQ ID NO:81
Designed oligonucleotide primer for PCR
SEQ ID NO:82
Designed oligonucleotide primer for PCR
SEQ ID NO:83
Designed oligonucleotide primer for PCR
SEQ ID NO:84
Designed oligonucleotide primer for PCR

SEQ ID NO:85

Designed oligonucleotide primer for PCR

SEQ ID NO:86

Designed oligonucleotide primer for PCR

SEQ ID NO:87

Designed oligonucleotide primer for PCR

SEQ ID NO:88

Designed oligonucleotide primer for PCR

What is claimed is:

1. A transformed cell in which a polynucleotide encoding an osmosensing histidine kinase having no transmembrane region is introduced in a functional form into a cell that is deficient in at least one hybrid-sensor kinase, wherein the osmosensing histidine kinase having no transmembrane region has an amino acid sequence homology of 98% or more to the amino acid sequence of SEQ ID NO: 55.

2. The transformed cell according to claim 1, wherein the polynucleotide complements the hybrid-sensor kinase deficiency.

3. The transformed cell according to claim 1, wherein the cell is a microorganism cell.

4. The transformed cell according to claim 1, wherein the cell is a budding yeast cell.

5. The transformed cell according to claim 1, wherein the osmosensing histidine kinase having no transmembrane region has the amino acid sequence of SEQ ID NO: 55.

6. The transformed cell according to claim 1, wherein the polynucleotide has the nucleotide sequence of SEQ ID NO: 56.

7. A method of assaying the antifungal activity of a substance, which comprises:

(1) culturing the transformed cell as defined in claim 1 in the presence of a test substance;

(2) measuring an amount of intracellular signal transduction from the osmosensing histidine kinase having no transmembrane region or an index value having the correlation therewith; and (3) assessing the antifungal activity of the test substance based on a difference between an amount of intracellular signal transduction or an index value having the correlation therewith measured in (2) and a control.

8. The method of assaying according to claim 7, wherein the amount of intracellular signal transduction from the osmosensing histidine kinase having no transmembrane region or the index value having the correlation therewith is an amount of growth of the transformed cell.

9. A method of searching for a potent antifungal compound, which comprises selecting an antifungal compound based on the antifungal activity assessed in the assaying method as defined in claim 7.

10. An isolated polynucleotide encoding an amino acid sequence selected from the group consisting of:

(a) an amino acid sequence of an osmosensing histidine kinase having no transmembrane region, which has amino acid sequence homology of 98% or more to the amino acid sequence of any of SEQ ID NO: 55 and (b) the amino acid sequence of SEQ ID NO: 55.

11. The polynucleotide according to claim 10, which encodes the amino acid sequence of SEQ ID NO: 55.

12. The polynucleotide according to claim 10, which has the nucleotide sequence of SEQ ID NO: 56.

13. The transformed cell according to claim 1, wherein the polynucleotide encodes an osmosensing histidine kinase having no transmembrane region is obtained from *Mycospharella tritici*.

* * * * *